US011773170B2

(12) United States Patent
Geuijen et al.

(10) Patent No.: US 11,773,170 B2
(45) Date of Patent: Oct. 3, 2023

(54) ANTIBODIES THAT BIND EGFR AND CMET

(71) Applicant: MERUS N.V., Utrecht (NL)

(72) Inventors: Cecilia Anna Wilhelmina Geuijen, Utrecht (NL); Robertus Cornelis Roovers, Utrecht (NL); Mark Throsby, Utrecht (NL); Cornelis Adriaan De Kruif, Utrecht (NL); Ton Logtenberg, Utrecht (NL)

( * ) Notice: Subject to any disclaimer, the term of this patent is extended or adjusted under 35 U.S.C. 154(b) by 274 days.

(21) Appl. No.: 16/637,464

(22) PCT Filed: Aug. 9, 2018

(86) PCT No.: PCT/NL2018/050537
§ 371 (c)(1),
(2) Date: Feb. 7, 2020

(87) PCT Pub. No.: WO2019/031965
PCT Pub. Date: Feb. 14, 2019

(65) Prior Publication Data
US 2020/0247892 A1    Aug. 6, 2020

(30) Foreign Application Priority Data

Aug. 9, 2017  (EP) .................................... 17185572

(51) Int. Cl.
*C07K 16/28* (2006.01)
*A61P 35/00* (2006.01)
*C07K 16/40* (2006.01)
*A61K 39/00* (2006.01)

(52) U.S. Cl.
CPC .......... *C07K 16/2863* (2013.01); *A61P 35/00* (2018.01); *C07K 16/40* (2013.01); *A61K 2039/505* (2013.01); *C07K 2317/21* (2013.01); *C07K 2317/31* (2013.01); *C07K 2317/33* (2013.01); *C07K 2317/35* (2013.01); *C07K 2317/526* (2013.01); *C07K 2317/565* (2013.01); *C07K 2317/732* (2013.01); *C07K 2317/76* (2013.01)

(58) Field of Classification Search
CPC ............................ C07K 16/2863; C07K 16/40; C07K 2317/21; C07K 2317/31; C07K 2317/33; C07K 2317/35; C07K 2317/526; C07K 2317/565; C07K 2317/732; C07K 2317/76; A61K 2039/505; A61P 35/00
See application file for complete search history.

(56) References Cited

U.S. PATENT DOCUMENTS

| | | | |
|---|---|---|---|
| 4,801,687 A | 1/1989 | Ngo | |
| 4,816,567 A | 3/1989 | Cabilly et al. | |
| 5,151,504 A | 9/1992 | Croze | |
| 5,731,168 A | 3/1998 | Carter et al. | |
| 7,642,228 B2 | 1/2010 | Carter et al. | |
| 7,705,103 B2 | 4/2010 | Sherman et al. | |
| 8,349,574 B2 | 1/2013 | Bates et al. | |
| 8,592,562 B2 | 11/2013 | Kannan et al. | |
| 8,628,774 B2 | 1/2014 | Gurney et al. | |
| 9,220,775 B2 | 12/2015 | Chowdhury et al. | |
| 9,248,181 B2 | 2/2016 | De Kruif et al. | |
| 9,248,182 B2 | 2/2016 | De Kruif et al. | |
| 9,358,286 B2 | 6/2016 | De Kruif et al. | |
| 9,551,208 B2 | 1/2017 | Ma et al. | |
| 9,758,805 B2 | 9/2017 | De Kruif et al. | |
| 9,914,777 B2 | 3/2018 | Bakker et al. | |
| 9,968,676 B2 | 5/2018 | Adler et al. | |
| 10,208,354 B2 | 2/2019 | Fernandez-Cuesta et al. | |
| 10,358,492 B2 | 7/2019 | Bakker et al. | |
| 10,416,162 B2 | 9/2019 | Huang et al. | |
| 10,844,127 B2 | 11/2020 | Logtenberg et al. | |
| 2003/0078385 A1 | 4/2003 | Arathoon et al. | |
| 2004/0071696 A1 | 4/2004 | Adams et al. | |
| 2006/0212956 A1 | 9/2006 | Crocker et al. | |
| 2009/0181022 A1 | 7/2009 | Nielsen et al. | |
| 2009/0182127 A1 | 7/2009 | Kjaergaard et al. | |

(Continued)

FOREIGN PATENT DOCUMENTS

| AU | 2014212081 A1 | 8/2015 |
|---|---|---|
| EP | 0120694 A2 | 10/1984 |

(Continued)

OTHER PUBLICATIONS

Liu et al., A novel MET-EGFR bispecific antibody LY3164530 shows advantage over combining MET and EGFR antibodies in tumor inhibition and overcome resistance. Cancer Res. 76 (14) Supplement, Abstract 873, Jul. 15, 2016.*
Vajdos et al., Comprehensive Functional Maps of the Antigen-binding Site of an Anti-ErbB2 Antibody Obtained with Shotgun Scanning Mutagenesis. J. Mol. Biol. 320:415-428, 2002.*
Rudikoff et al., Single amino acid substitution altering antigen-binding specificity. Proc. Natl. Acad. Sci. USA 79:1979-1983, 1982.*
Brown et al., Tolerance of single, but not multiple, amino acid replacements in antibody VH CDR 2: a means of minimizing B cell wastage from somatic hypermutation? J. Immunology 156: 3285-3291, 1996.*

(Continued)

*Primary Examiner* — Ruixiang Li
(74) *Attorney, Agent, or Firm* — STERNE, KESSLER, GOLDSTEIN & FOX P.L.L.C.; Paul Calvo

(57) ABSTRACT

The invention as disclosed herein relates to bispecific antibodies that comprises a first variable domain that can bind an extracellular part of epidermal growth factor receptor (EGFR) and a second variable domain that can bind an extracellular part of MET Proto-Oncogene, Receptor Tyrosine Kinase (cMET). The antibody may comprise a common light chain. It may be a human antibody. The antibody may be a full length antibody. In some embodiments the bispecific antibody is an IgG1 format antibody having an anti-EGFR, anti-cMET stoichiometry of 1:1. In some embodiment the antibody has one variable domain that can bind EGFR and one variable domain that can bind cMET.

16 Claims, 27 Drawing Sheets
Specification includes a Sequence Listing.

(56) References Cited

U.S. PATENT DOCUMENTS

| | | |
|---|---|---|
| 2009/0191559 A1 | 7/2009 | Huang et al. |
| 2010/0015133 A1 | 1/2010 | Igawa et al. |
| 2010/0183615 A1 | 7/2010 | Kufer et al. |
| 2010/0286374 A1 | 11/2010 | Kannan et al. |
| 2011/0077163 A1 | 3/2011 | Doranz |
| 2011/0195454 A1 | 8/2011 | McWhirter et al. |
| 2012/0107234 A1 | 5/2012 | Pedersen et al. |
| 2012/0107306 A1 | 5/2012 | Elis et al. |
| 2012/0270801 A1 | 10/2012 | Frejd et al. |
| 2012/0328623 A1 | 12/2012 | Takahashi |
| 2013/0071859 A1 | 3/2013 | Bates et al. |
| 2013/0084297 A1 | 4/2013 | Daly et al. |
| 2013/0095116 A1 | 4/2013 | Gurney et al. |
| 2013/0115208 A1 | 5/2013 | Ho et al. |
| 2013/0156779 A1 | 6/2013 | Clarke et al. |
| 2013/0185821 A1 | 7/2013 | Babb et al. |
| 2013/0251703 A1 | 9/2013 | Elis et al. |
| 2013/0259867 A1 | 10/2013 | Amler et al. |
| 2013/0336885 A1 | 12/2013 | Hongo et al. |
| 2013/0336981 A1 | 12/2013 | De Kruif et al. |
| 2013/0344093 A1 | 12/2013 | Daly et al. |
| 2014/0056898 A1 | 2/2014 | Zhang et al. |
| 2014/0072579 A1 | 3/2014 | De Kruif et al. |
| 2014/0120096 A1 | 5/2014 | Bakker et al. |
| 2014/0140999 A1 | 5/2014 | De Kruif et al. |
| 2014/0141019 A1 | 5/2014 | Kharrat et al. |
| 2014/0378664 A1 | 12/2014 | Suh et al. |
| 2015/0013996 A1 | 1/2015 | Davies et al. |
| 2015/0139996 A1 | 5/2015 | De Kruif et al. |
| 2015/0196637 A1 | 7/2015 | De Kruif et al. |
| 2015/0259423 A1 | 9/2015 | Kirshner et al. |
| 2016/0031984 A1 | 2/2016 | Reyes et al. |
| 2016/0229920 A1 | 8/2016 | Ward et al. |
| 2016/0367699 A1 | 12/2016 | Jackson et al. |
| 2017/0037145 A1 | 2/2017 | Geuijen et al. |
| 2017/0166653 A1 | 6/2017 | Garner et al. |

FOREIGN PATENT DOCUMENTS

| | | |
|---|---|---|
| EP | 0314161 A1 | 5/1989 |
| EP | 0481790 A2 | 4/1992 |
| EP | 0523949 A1 | 1/1993 |
| EP | 0870459 A2 | 10/1998 |
| EP | 2604625 A1 | 6/2013 |
| JP | H11500915 A | 1/1999 |
| JP | 2008531557 A | 8/2008 |
| JP | 2011508604 A | 3/2011 |
| JP | 2012509259 A | 4/2012 |
| JP | 2014508782 A | 4/2014 |
| JP | 2014511383 A | 5/2014 |
| JP | 2017507944 A | 3/2017 |
| WO | WO-9627011 A1 | 9/1996 |
| WO | WO-9850431 A2 | 11/1998 |
| WO | WO-0063403 A2 | 10/2000 |
| WO | WO-0120694 A1 | 3/2001 |
| WO | WO-03004704 A2 | 1/2003 |
| WO | WO-03107218 A1 | 12/2003 |
| WO | WO-2004009618 A2 | 1/2004 |
| WO | WO-2004061104 A2 | 7/2004 |
| WO | WO-2005000894 A2 | 1/2005 |
| WO | WO-2005118635 A2 | 12/2005 |
| WO | WO-2006028936 A2 | 3/2006 |
| WO | WO-2006044908 A2 | 4/2006 |
| WO | WO-2006091209 A2 | 8/2006 |
| WO | WO-2006106105 A1 | 10/2006 |
| WO | WO-2007110205 A2 | 10/2007 |
| WO | WO-2007147901 A1 | 12/2007 |
| WO | WO-2008027236 A2 | 3/2008 |
| WO | WO-2008100624 A2 | 8/2008 |
| WO | WO-2008119353 A1 | 10/2008 |
| WO | WO-2008140493 A2 | 11/2008 |
| WO | WO-2009051974 A1 | 4/2009 |
| WO | WO-2009080251 A1 | 7/2009 |
| WO | WO-2009080252 A1 | 7/2009 |
| WO | WO-2009080253 A1 | 7/2009 |
| WO | WO-2009089004 A1 | 7/2009 |
| WO | WO-2009098596 A2 | 8/2009 |
| WO | WO-2009157771 A2 | 12/2009 |
| WO | WO-2010022736 A2 | 3/2010 |
| WO | WO-2010059315 A1 | 5/2010 |
| WO | WO-2010084197 A1 | 7/2010 |
| WO | WO-2010108127 A1 | 9/2010 |
| WO | WO-2010129304 A2 | 11/2010 |
| WO | WO-2010151792 A1 | 12/2010 |
| WO | WO-2011022727 A2 | 2/2011 |
| WO | WO-2011028952 A1 | 3/2011 |
| WO | WO-2011028953 A1 | 3/2011 |
| WO | WO-2011143545 A1 | 11/2011 |
| WO | WO-2012023053 A2 | 2/2012 |
| WO | WO-2012058768 A1 | 5/2012 |
| WO | WO-2012116317 A2 | 8/2012 |
| WO | WO-2012125573 A2 | 9/2012 |
| WO | WO-2012125864 A2 | 9/2012 |
| WO | WO-2012131555 A2 | 10/2012 |
| WO | WO-2012140274 A9 | 3/2013 |
| WO | WO-2013048883 A2 | 4/2013 |
| WO | WO-2013084151 A2 | 6/2013 |
| WO | WO-2013107218 A1 | 7/2013 |
| WO | WO-2013134686 A1 | 9/2013 |
| WO | WO-2013149159 A1 | 10/2013 |
| WO | WO-2013157953 A1 | 10/2013 |
| WO | WO-2013157954 A1 | 10/2013 |
| WO | WO-2014051433 A1 | 4/2014 |
| WO | WO-2014060365 A1 | 4/2014 |
| WO | WO-2014101954 A1 | 5/2014 |
| WO | WO-2014159580 A1 | 10/2014 |
| WO | WO-2014165855 A1 | 10/2014 |
| WO | WO-2014182970 A1 | 11/2014 |
| WO | WO-2015130172 A1 | 9/2015 |
| WO | WO-2015130173 A1 | 9/2015 |
| WO | WO-2016077734 A2 | 5/2016 |
| WO | WO-2016090024 A2 | 6/2016 |
| WO | WO-2017069628 A2 | 4/2017 |
| WO | WO-2018182422 A1 | 10/2018 |

OTHER PUBLICATIONS

Castoldi, R., et al., "A Novel Bispecific EGFR/Met Antibody Blocks Tumor-promoting Phenotypic Effects Induced by Resistance to EGFR Inhibition and Has Potent Antitumor Activity," Oncogene, 32(50):5593-5601, Nature Publishing Group, England (Jul. 1, 2013).

International Search Report and Written Opinion for Application No. PCT/NL2018/050537, dated Jan. 30, 2019, European Patent Office, Rijswijk, Netherlands, 19 pages.

Labrijn, A.F., et al., "Efficient Generation of Stable Bispecific IgG1 by Controlled Fab-arm Exchange," Proceedings of the National Academy of Sciences of the United States of America, 110(13):5145-5150, United States (Mar. 26, 2013).

Moores, S.L., et al., "A Novel Bispecific Antibody Targeting EGFR and cMet Is Effective against EGFR Inhibitor-Resistant Lung Tumors," Cancer Research, 76(13):3942-3953, United States (May 23, 2016).

Mosmi, S., et al., "Role of MetMAb (OA-5D5) in c-MET Active Lung Malignancies," Expert Opinion on Biological Therapy, 11(12):1655-1662, Taylor & Francis, England (Dec. 1, 2011).

Noh Jin Park., et al., "Measurement of Cetuximab and Panitumumab-Unbound Serum EGFR Extracellular Domain Using an Assay Based on Slow Off-Rate Modified Aptamer (SOMAmer) Reagents," PloS One, 8(8):e71703, Public Library of Science, United States (Aug. 21, 2013).

Pan, D.S., et al., "Binding Characteristic of Fully Human Anti-EGFR Monoclonal Antibody to EGFR in Skin Tissues of Different Species of Animals," Chinese Journal of New Drugs Co. Ltd, 21(1):26-30, China (Jan. 2012).

Agus, D.B., et al., "Targeting ligand-activated ErbB2 signaling inhibits breast and prostate tumor growth," Cancer Cell, 2(2):127-137, Cell Press, United States (2002).

Appella, E, and IT Weber, F Blasi, "Structure and Function of Epidermal Growth Factor-Like Regions In Proteins," FEBS Letters 231(1):1-4, John Wiley & Sons Ltd, United Kingdom (Apr. 1988).

(56) References Cited

OTHER PUBLICATIONS

Ardeshirpour, Y., et al., "In vivo assessment of HER2 receptor density in HER2-positive tumors by near-infrared imaging, using repeated injections of the fluorescent probe," Technology In Cancer Research & Treatment 13(5):427-434, SAGE, United States (Oct. 2014).

Arteaga, C.L., et al., "Treatment of Her2-positive Breast Cancer: Current Status and Future Perspectives," Nature Reviews Clinical Oncology 9(1):16-32, Nature Publishing Group, United Kingdom (Nov. 2011).

Bakker, A.B., et al., "C-type Lectin-like Molecule-1: a Novel Myeloid Cell Surface Marker Associated With Acute Myeloid Leukemia," Cancer Research 64(22):8443-8450, American Association for Cancer Research, United States (Nov. 2004).

Balko, J.M., et al., The receptor tyrosine kinase ErbB3 maintains the balance between luminal and basal breast epithelium PNAS, 109(1): 221-226, U.S. National Academy of Science, United States (2012).

Birchmeier, C., et al., "Met, Metastasis, Motility and More," Nature Reviews Molecular Cell Biology 4(12):915-925, Nature Publishing Group, United Kingdom (Dec. 2003).

Buday, L. et al., "Epidermal growth factor regulates the exchange rate of guanine nucleotides on p21ras in fibroblasts," Molecular and Cellular Biology 13(3):1903-1910, American Society for Microbiology, United States (1993).

Chames, P., and Baty, D., "Bispecific Antibodies for Cancer Therapy: The Light at the End of the Tunnel?" MAbs 1(6):539-547, Taylor & Francis, United States (Nov.-Dec. 2009).

Chandra A., "The Role of ERBB3 Inhibitors as Cancer Therapeutics," pp. 1-78, Boston University School of Medicine, United States (May 2015).

Chen, C.T., et al., "MET activation mediates resistance to lapatinib inhibition of HER2-amplified gastric cancer cells," Molecular Cancer Therapeutics 11(3):650-669, American Association for Cancer Research, Inc., United States (Mar. 2012).

Chernomordik, V., et al., "Quantitative Analysis of HER2 Receptor Expression in Vivo By Near-Infrared Optical Imaging," Molecular Imaging 9(4):192-200, SAGE Publications, United States (Aug. 2010).

Chien, N.C., et al., "Significant Structural and Functional Change of an Antigen-Binding Site by a Distant Amino Acid Substitution: Proposal of a Structural Mechanism," Proceedings of the National Academy of Sciences USA 86(14):5532-5536, National Academy of Sciences, United States (1989).

Conforti, F., et al., "Dissecting Breast Cancer Complexity: Specific Biological Features and Vulnerabilities of Triple Positive Breast Cancer Tumors," Clinic of Oncology 2(1288):1-3, Remedy Publications LLC, United States (May 2017).

Corona S.P., et al., "CDK4/6 Inhibitors in HER2-positive Breast Cancer," Critical Reviews in Oncology/Hematology 118:208-214, Elsevier, Netherlands (2017).

Cui, H., et al., "Chemically Programmed Bispecific Antibodies That Recruit and Activate T Cells," The Journal of Biological Chemistry 287(34):28206-28214, American Society for Biochemistry and Molecular Biology, United States (Aug. 2012).

Curley, M.D., et al., "Seribantumab, An Anti-ERBB3 Antibody, Delays the Onset of Resistance and Restores Sensitivity to Letrozole in an Estrogen Receptor-Positive Breast Cancer Model," Molecular Cancer Therapeutics 14(11):2642-2652, American Association for Cancer Research, Inc., United States (Nov. 2015).

De Kruif, J., et al., "Selection and Application of Human Single Chain Fv Antibody Fragments from a Semi-Synthetic Phage Antibody Display Library with Designed CDR3 Regions," Journal of Molecular Biology 248(1):97-105, Elsevier, United Kingdom (Apr. 1995).

De Kruif, J., et al., "Generation of Stable Cell Clones Expressing Mixtures of Human Antibodies," Biotechnology and Bioengineering 106(5):741-750, Wiley, United States (Aug. 2010).

Dreier, T., et al., "Extremely Potent, Rapid and Costimulation-Independent Cytotoxic T-Cell Response against Lymphoma Cells Catalyzed By a Single-Chain Bispecific Antibody," International Journal of Cancer 100(6):690-697, Wiley-Liss, United States (2002).

Fong, J.T., et al., "Alternative signaling pathways as potential therapeutic targets for overcoming EGFR and c-Met inhibitor resistance in non-small cell lung cancer," PLoS One 8(11):e78398, Public Library of Science, United States (Nov. 2013).

Fu, W., et al., "Insights into HER2 signaling from step-by-step optimization of anti-HER2 antibodies," MAbs 6(4):978-990, Taylor & Francis, United Kingdom (2014).

Gaborit, N., et al., "Emerging anti-cancer antibodies and combination therapies targeting HER3/ERBB3," Human Vaccines and Immunotherapies, 12(3): 576-592, Taylor & Francis, United Kingdom (2015).

Geuijen, C., et al., "Abstract LB-261: Mechanism of action of MCLA-128, a humanized bispecific IgG1 antibody targeting the HER2: HER3 heterodimer," Cancer Research; 106th Annual Meeting of The American Association for Cancer Research (AACR) 75(Suppl. 15): LB-261, Philadelphia, United States (2015).

Geuijen, C.A.W., et al., "Unbiased Combinatorial Screening Identifies a Bispecific IgG1 that Potently Inhibits HER3 Signaling via HER2-Guided Ligand Blockade," Cancer Cell 33(5):922-936, Elsevier, Netherlands (2018).

Gulli, L.F., et al., "Epidermal Growth Factor-induced Apoptosis in A431 Cells Can Be Reversed by Reducing the Tyrosine Kinase Activity," Cell Growth & Differentiation 7(2):173-178, The Association, United States (Feb. 1996).

Harms B., et al., "Understanding the Role of Cross-arm Binding Efficiency in the Activity of Monoclonal and Multispecific Therapeutic Antibodies", Methods 65(1):95-104, Elsevier, Netherlands (Jan. 2014).

Hathaway, H.J., et al., "Detection of breast cancer cells using targeted magnetic nanoparticles and ultra-sensitive magnetic field sensors," Breast Cancer Research 13(5):R108, BioMed Central, United Kingdom (Nov. 2011).

Hommel, U., et al., "Human Epidermal Growth Factor. High Resolution Solution Structure and Comparison With Human Transforming Growth Factor Alpha," Journal of Molecular Biology 227(1):271-282, Elsevier, United Kingdom (Sep. 1992).

Howarth, K.D., et al., "Nrg1 Fusions in Breast Cancer," Breast Cancer Research 23(1):3, BioMed Central Ltd, United Kingdom (Jan. 2021).

Hu, T., and Li, C., "Convergence between Wnt-B-catenin and EGFR signaling in cancer," Molecular Cancer 236: 1-7, BioMed Central, United States (2010).

Huang W, et al., "Comparison of Central HER2 Testing With Quantitative Total HER2 Expression and HER2 Homodimer Measurements Using a Novel Proximity-Based Assay," American Journal of Clinical Pathology 134(2):303-311, Oxford University Press, United Kingdom (Aug. 2010).

Huhalov, A., et al., "MM-111, an ErbB2/ErbB3 Bispecific Antibody with Potent Activity in ErbB2-Overexpressing Cells, Positively Combines with Trastuzumab to Inhibit Growth of Breast Cancer Cells Driven by the ErbB2/ErbB3 Oncogenic Unit", Cancer Research 51:845-846, American Association for Cancer Research, United States (Apr. 2010).

International Search Report And Written Opinion for International Application No. PCT/NL2016/050726, European Patent Office, Netherlands, dated Jun. 2, 2017, 20 pages.

Jackson, C., et al., "Clinical Significance of HER-2 Splice Variants in Breast Cancer Progression and Drug Resistance," International Journal of Cell Biology 2013: 973584, Hindawi, United Kingdom (2013).

Jelovac, D., et al., "HER2-Directed Therapy for Metastatic Breast Cancer," Oncology (Williston Park) 27(3):166-175, CMP Healthcare Media, United States (Mar. 2013).

Ji, H., et al., "Epidermal growth factor receptor variant III mutations in lung tumorigenesis and sensitivity to tyrosine kinase inhibitors," PNAS 103(20):7817-7822, United States National Academy of Sciences, United States (May 2006).

Jin, H., et al., "Metmab, the One-Armed 5D5 Anti-C-Met Antibody, Inhibits Orthotopic Pancreatic Tumor Growth and Improves Survival," Cancer Research 68(11):4360-4368, American Association for Cancer Research, United States (Jun. 2008).

(56) References Cited

OTHER PUBLICATIONS

Jorissen, R.N., et al., "Epidermal Growth Factor Receptor: Mechanisms of Activation and Signaling," Experimental Cell Research 284(1):31-53, Academic Press, United States (Mar. 2003).

Jung, Y., et al., "VAMP2-NRG1 Fusion Gene is a Novel Oncogenic Driver of Non-Small-Cell Lung Adenocarcinoma," J Thor Oncol 10(7): 1107-1111, International Association for the Study of Lung Cancer, United States (2015).

Junttila, T.T., et al., "Ligand-Independent HER2/HER3/PI3K Complex Is Disrupted by Trastuzumab and Is Effectively Inhibited by the PI3K Inhibitor GDC-0941," Cancer Cell, 15(5):429-440, Elsevier, Netherlands (2009).

Kang J.C., et al., "Engineering Multivalent Antibodies to Target Heregulin-Induced HER3 Signaling in Breast Cancer Cells," MAbs 6(2):340-353, Taylor & Francis, United Kingdom (Apr. 2014).

Kim, G.P., et al. "Targeting Colorectal Cancer with Human Anti-EGFR Monoclonocal Antibodies: Focus on Panitumumab," Biologies 2(2):223-228, Dove Medical Press, New Zealand (Jun. 2008).

Kim, K.H., et al., "Progress of Antibody-Based Inhibitors of the Hgf-Cmet Axis in Cancer Therapy," Experimental & Molecular Medicine 49(3):e307, Nature Publishing Group, United States (Mar. 2017).

Kodack D.P., et al., "Combined Targeting of HER2 and VEGFR2 for Effective Treatment of HER2-amplified Breast Cancer Brain Metastases," Proceedings of the National Academy of Sciences 109(45):E3119-E3127, National Academy of Sciences, United States (Nov. 2012).

Koide, A., et al., "The Fibronectin Type III Domain as a Scaffold for Novel Binding Proteins," Journal of Molecular Biology 284(4):1141-1151, Academic Press, United States (Dec. 1998).

Kol, A., et al., "HER3, Serious Partner in Crime: Therapeutic Approaches and Potential Biomarkers for Effect of HER3-targeting," Pharmacology & Therapeutics 143(1):1-11, Pergamon Press, United Kingdom (Jul. 2014).

Kontermann, R.E., "Dual Targeting Strategies with Bispecific Antibodies," MAbs 4(2):182-197, Taylor and Francis, United States (2012).

Landgraf, R., et al., "HER2 Therapy. HER2 (ERBB2): Functional Diversity from Structurally Conserved Building Blocks," Breast Cancer Research 9(1):202, BioMed Central Ltd, United Kingdom (2007).

Lanzavecchia, A. and Staerz, U.D., "Lysis of Nonnucleated Red Blood Cells by Cytotoxic T Lymphocytes," European Journal of Immunology 17(7):1073-1074, Wiley-VCH, Germany (Jul. 1987).

Lazrek, Y., et al., "Anti-HER3 Domain 1 and 3 Antibodies Reduce Tumor Growth by Hindering HER2/HER3 Dimerization and AKT-Induced MDM2. XIAP, and Fox1 Phosphorylation," Neoplasia 15(3):335-347, Neoplasia Press, United States (Mar. 2013).

Le Clorennec, C., et al., "Neuregulin 1 Allosterically Enhances the Antitumor Effects of the Noncompeting Anti-HER3 Antibody 9 F7-F11 by Increasing Its Binding to HER3," Molecular Cancer Therapeutics, 16(7): 1312-1323, American Association for Cancer Research, United States (2017).

Lee, D., et al., "Development of antibody-based c-Met inhibitors for targeted cancer therapy," Immunotargets and Therapy 9(4):34-44, Dove Medical Press, New Zealand (2015).

Lee-Hoeflich, S.T., et al., "A Central Role for HER3 in HER2-Amplified Breast Cancer: Implications for Targeted Therapy," Cancer Research, 68(14): 5878-5887, American Association for Cancer Research, United States (2008).

Lumachi F., et al., "Endocrine Therapy of Breast Cancer," Current Medicinal Chemistry 18(4):513-522, Bentham Science Publishers, United Arab Emirates (2011).

Luo, H., et al., "Noninvasive Brain Cancer Imaging With a Bispecific Antibody Fragment, Generated via Click Chemistry," Proceedings of the National Academy of Sciences of the United States of America 112(41):12806-12811, National Academy of Sciences, United States (Oct. 2015).

Ma, P.C., et al., "C-Met: Structure, Functions and Potential for Therapeutic Inhibition," Cancer and Metastasis Reviews 22:309-325, Kluwer Academic, Netherlands (Dec. 2003).

Malm, M., et al., "Engineering of a Bispecific Affibody Molecule Towards HER2 and HER3 by Addition of an Albumin-Binding Domain Allows for Affinity Purification and in Vivo Half-Life Extension," Biotechnology Journal 9(9):1215-1222, Wiley-VCH Verlag, Germany (Sep. 2014).

Malm, M., et al., "Targeting HER3 using mono- and bispecific antibodies or alternative scaffolds," mABS 8(7): 1195-1209, Taylor & Francis, United Kingdom (2016).

Maulik, G., et al., Role of the hepatocyte growth factor receptor, c-Met, in oncogenesis and potential for therapeutic inhibition, Cytokine & Growth Factor Reviews 13(1):41-59, Elsevier Science, United Kingdom (Feb. 2002).

Maussang-Detaille, D., et al., "The binding mode of the bispecific anti-HER2xHER3 antibody MCLA-128 is responsible for its potent inhibition of HRG-driven tumorigenesis," Abstract 33, Research Poster Presentation Design, Retrieved from the Internet: (URL: http://www.merus.nl/wordpress/wp-content/uploads/2017/04/MCLA-128-poster-AACR2017-final-.pdf). (Apr. 1, 2017).

May, C., et al., "Advances in Bispecific Biotherapeutics for the Treatment of Cancer," Biochemical Pharmacology 84:1105-1112, Elsevier, Netherlands (2012).

McDonagh, C.F., et al., "Antitumor Activity of a Novel Bispecific Antibody that Targets the ErbB2/ErbB3 Oncogenic Unit And Inhibits Heregulin-Induced Activation of ErbB3," Molecular Cancer Therapeutics 11(3):582-593, American Association for Cancer Research, United States (Mar. 2012).

Merchant, M.A., et al., "An efficient route to human bispecific IgG," Nature Biotechnology, 16: 677-681, Nature Publishing Group, United States (1998).

Merlino, G.T., et al., "Amplification and Enhanced Expression of the Epidermal Growth Factor Receptor Gene in A431 Human Carcinoma Cells," Science 224(4647): 417-419, American Association for the Advancement of Science, United States (1984).

Merus, "Merus selects clinical candidate for the treatment of acute myeloid leukemia (AML)," www.merus.nl, press release, 2 pages, dated Jan. 7, 2013.

Merus, "Merus presents preclinical data on its novel bispecific antibody MCLA-117 at EHA 2013," www.merus.nl, press release, 3 pages, dated Jun. 17, 2013.

Momeny M., et al., "Heregulin-HER3-HER2 signaling promotes matrix metalloproteinase-dependent blood-brain-barrier transendothelial migration of human breast cancer cell lines," Oncotarget 6(6):3932-3946, Impact Journals LLC, United States (Feb. 2015).

Moore, P.A., et al., "Application of Dual Affinity Retargeting Molecules to Achieve Optimal Redirected T-cell killing of B-cell Lymphoma," Blood 117(17):4542-4551, American Society of Hematology, United States (Apr. 2011).

Morgillo, F., et al., "Mechanisms of resistance to EGFR targeted drugs: lung cancer," ESMO Open 2016 1:e000060, 13 pages, Biomedical Journal, United States (2016).

Morrison, M.M., et al., "ErbB3 Downregulation Enhances Luminal Breast Tumor Response to Antiestrogens," The Journal of Clinical Investigation 123(10):4329-4343, American Society for Clinical Investigation, United States (Oct. 2013).

Musolino, A., et al., "Immunoglobulin G Fragment C Receptor Polymorphisms and Clinical Efficacy of Trastuzumab-based Therapy in Patients With Her-2/neu-positive Metastatic Breast Cancer," Journal of Clinical Oncology 26(11):1789-1796, American Society of Clinical Oncology, United States (2008).

Nakade, J., et al., "Triple Inhibition of EGFR, MET, and VEGF Suppresses Regrowth of HGF-Triggered, Erlotinib-Resistant Lung Cancer Harboring an EGFR Mutation," Journal of Thoracic Oncology 9(6):775-783, Elsevier, United States (Jun. 2014).

Nieba, L., et al., "Disrupting the Hydrophobic Patches at the Antibody Variable/constant Domain Interface: Improved in Vivo Folding and Physical Characterization of an Engineered Scfv Fragment," Protein Engineering 10(4):435-444, Oxford University Press, United Kingdom (Apr. 1997).

(56) References Cited

OTHER PUBLICATIONS

Ocana, A., et al., "HER3 Overexpression and Survival in Solid Tumors: A Meta-Analysis," J. Natl Cancer Inst., 105(4): 266-273, Oxford University Press, United Kingdom (2013).

Omenn, G.S., et al., "A New Class of Protein Cancer Biomarker Candidates: Differentially-Expressed Splice Variants of ERBB2 (HER2/neu) and ERBB1 (EGFR) in Breast Cancer Cell Lines," Journal of Proteomics 107:103-112, Elsevier, Netherlands (Jul. 2014).

Organ, S.L., et al., "An Overview of the C-Met Signaling Pathway," Therapeutic Advances in Medical Oncology 3(1 Suppl):S7-S19, Sage, United Kingdom (2011).

Osborne K.C., et al., "Mechanisms of Endocrine Resistance in Breast Cancer," Annual review of medicine 62:233-247, Annual Reviews Inc., United States (2011).

Panke, C., et al., "Quantification of Cell Surface Proteins with Bispecific Antibodies," Protein Engineering Design and Selection 26(10):645-654, Oxford University Press, United Kingdom (Aug. 2013).

Pastore, S., et al., "Erk1/2 Regulates Epidermal Chemokine Expression and Skin Inflammation," Journal of Immunology 174:5047-5056, American Association of Immunologists, United States (2005).

Patel, D.K., "Clinical Use of Anti-epidermal Growth Factor Receptor Monoclonal Antibodies in Metastatic Colorectal Cancer," Pharmacotherapy 28(11):31S-41S, Wiley, United States (2008).

Paul, I., et al., "Current Understanding on EGFR and Wnt/Beta-Catenin Signaling in Glioma and Their Possible Crosstalk," Genes & Cancer 4(11-12):427-446, SAGE, United States (2013).

Pedersen, M.W., et al., "Targeting Three Distinct HER2 Domains with a Recombinant Antibody Mixture Overcomes Trastuzumab Resistance," Molecular Cancer Therapeutics 14(3):669-680, American Association for Cancer Research, United States (Jan. 2015).

Prigent, S., et al., "Identification of C-erbB-3 Binding Sites for Phosphatidylinositol 3'-kinase and SHC Using an EGF Receptor/c-erbB-3 Chimera," The EMBO Journal 13(12):2831-2841, National Center for Biotechnology Information, United States (Jun. 1994).

Regina, A., et al., "ANG4043, a Novel Brain-Penetrant peptide-mAb Conjugate, Is Efficacious Against HER2-positive Intracranial Tumors in Mice," Molecular Cancer Therapeutics 14(1):129-140, American Association for Cancer Research, Inc., United States (Jan. 2015).

Reusch, U., and Knackmuss, S., "Beyond mAbs with T and Abs," Innovations in Pharmaceutical Technology, 4 pages, IPT Online, United Kingdom (2011).

Richards, D.A., et al., "A Phase 1 Study of Mm-111, a Bispecific HER2/HER3 Antibody Fusion Protein, Combined with Multiple Treatment Regimens in Patients with Advanced HER2-Positive Solid Tumors," Journal of Clinical Oncology 32(15):651, American Society of Clinical Oncology, United States (2014).

Riemer, A.B., et al., "Matching of Trastuzumab (Herceptin) Epitope Mimics Onto the Surface of Her-2/neu—a New Method of Epitope Definition," Molecular Immunology 42(9):1121-1124, Pergamon Press, United Kingdom (2005).

Robinson, M.K., et al., "Targeting ErbB2 and ErbB3 with a bispecific single-chain FV Enhances targeting selectivity and induces a therapeutic effect in Vitro", British Journal of CA 99(9):1415-1425, Nature Publishing Group, United Kingdom (Oct. 2008).

Roskoski, R., "The ErbB/HER Family of Protein-Tyrosine Kinases and Cancer," Pharmacological Research 79:34-74, Elsevier, Netherlands (Jan. 2014).

Sanchez-Valdivieso, E.A., et al., "y-Heregulin has no biological significance in primary breast cancer," British Journal of Cancer, 86(8): 1362-1366, Cancer Research UK, United Kingdom (2002).

Schaefer, G., et al., "A Two-in-one Antibody Against Her3 and Egfr Has Superior Inhibitory Activity Compared With Monospecific Antibodies," Cancer Cell 20(4):472-486, Cell Press, United States (Oct. 2011).

Schmitz, K., and Ferguson K.M., "Interaction of Antibodies With ErbB Receptor Extracellular Regions," Experimental Cell Research 315(4):659-670, Academic Press, United States (Feb. 2009).

Schoeberl, B., et al., "AnErB3 Antibody, MM-121, Is Active in Cancers with Ligand-Dependent Activation," Cancer Research, 70(6): 2485-2494, American Association for Cancer Research, United States (2010).

Seidel, C., et al., "Role of hepatocyte growth factor and its receptor c-met in multiple myeloma," Medical Oncology 15:145-153, Springer Nature, Switzerland (Sep. 1998).

Sergina, N.V., et al., "Escape from HER-family tyrosine kinase inhibitor therapy by the kinase-inactive HER3," Nature, 445(7126): 437-441, Springer, United Kingdom (2007).

Seshagiri, S., et al., "Recurrent R-spondin Fusions in Colon Cancer," Nature 488(7413):660-664, Nature Publishing Group, United Kingdom (2012).

Shames, D.S., et al., "High Heregulin Expression Is Associated with Activated HER3 and May Define an Actionable Biomarker in Patients with Squamous Cell Carcinomas of the Head and Neck," PLoS One 8(2):e56765, Public Library of Science, United States (2013).

Sheridan, C., "Amgen Swallows Micromet to BiTE Into All Market," Nature Biotechnology 30(4):300-301, Nature America Publishing, United States (Apr. 2012).

Soltoff, S.P., et al., "ErbB3 is involved in activation of phosphatidylinositol 3-kinase by epidermal growth factor," Molecular and Cellular Biology 14(6):3550-3558, American Society for Microbiology, United States (Jun. 1994).

Sorkin, A., "Internalization of the Epidermal Growth Factor Receptor: Role In Signaling," Biochemical Society Transactions 29(Pt 4):480-484, Portland Press On The Behalf Of The Biochemical Society, United Kingdom (Aug. 2001).

Staerz, U.D., and Bevan, M.J., "Hybrid Hybridoma Producing a Bispecific Monoclonal Antibody that can Focus Effector T-cell Activity," Proceedings of the National Academy of Sciences USA 83(5):1453-1457, National Academy of Sciences, United States (1986).

Stancovski, I., et al., "Mechanistic aspects of the opposing effects of monoclonal antibodies to the ERBB2 receptor on tumor growth," Proceedings of the National Academy of Sciences USA 88(19):8691-8695, National Academy of Sciences, United States (1991).

Strelkauskas, A., et al., "Human Monoclonal Antibody: 2. Simultaneous Expression of lgG and lgM with Similar Binding Specificities by a Human Hybrid Clone," Hybridoma 6(5):479-488, Mary Ann Liebert, United states (Oct. 1987).

Thery, J.C., et al., "Resistance to Human Epidermal Growth Factor Receptor Type 2-targeted Therapies," European Journal of Cancer 50(5):892-901, Elsevier, Netherlands (Mar. 2014).

Troise, F., et al., "A novel ErbB2 epitope targeted by human antitumor immunoagents," FEBS Journal 278:1156-1166, John Wiley & Sons, United States (2011).

Uberall, I., et al.,"The status and role of ErbB receptors in human cancer," Experimental and Molecular Pathology 84:79-89, Elsevier, Netherlands (2008).

Vajdos, F.F., et al., "Comprehensive Functional Maps of The Antigen-binding Site of an Anti-Erbb2 Antibody Obtained with Shotgun Scanning Mutagenesis," Journal of Molecular Biology 320(2):415-428, Academic Press, United Kingdom (Jul. 2002).

Vecchione, L., et al., "EGFR-targeted therapy," Experimental Cell Research 317(19): 2765-2771, Academic Press, United States (Nov. 2011).

Wadhwa, D., et al., "Trastuzumab Mediated Cardiotoxicity in the Setting of Adjuvant Chemotherapy for Breast Cancer: a Retrospective Study," Breast Cancer Research and Treatment 117(2):357-364, Kluwer Academic, Netherlands (Sep. 2009).

Wehrman, T.S., et al., "A System for Quantifying Dynamic Protein Interactions Defines a Role for Herceptin in Modulating ErbB2 Interactions," Proceedings of the National Academy of Sciences of the United States of America 103(50):19063-19068, National Academy of Sciences, United States (Dec. 2006).

Weidle, U. H., et al., "The intriguing options of multispecific antibody formats for treatment of cancer," Cancer Genomics Proteomics 10(1):1-18, International Institute of Anticancer Research, Greece (Jan.-Feb. 2013).

(56) References Cited

OTHER PUBLICATIONS

Weinstein, E.J., et al., "The oncogene heregulin induces apoptosis in breast epithelial cells and tumors," Oncogene 17(16):2107-2113, Nature Publishing Group, United Kingdom (1998).
Wick, M.J., et al., "Establishment and Characterization of a HER2-positive, TDM1-Resistant PDX Breast Model," Abstract C74 at AACR-NC1-EORTC International Conference: Molecular Targets and Cancer Therapeutics (Nov. 5-9, 2015 in Boston, MA), Drug Resistance and Modifiers 14(12): Supplement 2, 4 pages (Dec. 2015).
Wilson, T.R., et al., "Neuregulin-1-Mediated Autocrine Signaling Underlies Sensitivity to HER2 Kinase Inhibitors in a Subset of Human Cancer," Cancer Cells, 20(2): 158-172, Elsevier, Inc., Netherlands (2011).
Wilson, T.R., et al., "Widespread potential for growth-factor-driven resistance to anticancer kinase inhibitors," Nature, 487(7408): 505-509, Springer, United Kingdom (2012).
Winkler, K., et al., "Changing the Antigen Binding Specificity by Single Point Mutations of an Anti-p24 (HIV-1) Antibody," The Journal of Immunology 165(8):4505-4514, The American Association of Immunologists, United States (2000).
Wolff, A.C., et al., "Recommendations for Human Epidermal Growth Factor Receptor 2 Testing in Breast Cancer: American Society of Clinical Oncology/College of American Pathologists Clinical Practice Guideline Update," Journal of Clinical Oncology 31(31):3997-4013, Grune & Stratton, United States (Nov. 2013).
Woning, S.V.D., et al., "Quantification of ErbB3 Receptor Density on Human Breast Cancer Cells, Using a Stable Radio-Labeled Mutant of Nrg1beta," Biochemical and Biophysical Research Communications, 378(2):285-289, Elsevier, United States (Jan. 2009).
Xu, F., et al., "Antibody-Induced Growth Inhibition is Mediated Through Immunochemically and Functionally Distinct Epitopes on the Extracellular Domain of the c-erB-2 (HER-2/neu) Gene Product p185," International Journal of Cancer 53(3):401-408, Wiley-Liss, United States (1993).
Yano, S. et al., "Hepatocyte Growth Factor Induces Gefitinib Resistance of Lung Adenocarcinoma With Epidermal Growth Factor Receptor-activating Mutations," Cancer Research 68(22):9479-9487, American Association for Cancer Research, United States (Nov. 2008).
Yano, S., et al.,"Molecular Mechanism of EGFR-TK1 Resistance," Japanese Journal of Lung Cancer 49(6):939-943, The Japan Lung Cancer Society, Japan (Oct. 2009).
Yarden, Y. et al., "The EGFR family and its ligands in human cancer: signaling mechanisms and therapeutic opportunities," European Journal of Cancer 37(Supp4):S3-S8, Research Gate GmbH, Netherlands (Sep. 2001).
Yarden, Y., et al., "The ERBB Network: At Last, Cancer Therapy Meets Systems Biology," Nature Reviews Cancer 12(8):553-563, Nature Publishing Group, United Kingdom (Jul. 2012).
Yonesaka, K., et al., "Activation of ERBB2 Signaling Causes Resistance to the Egfr-Directed Therapeutic Antibody Cetuximab," Science Translational Medicine 3(99):99ra86, American Association for the Advancement of Science, United States (Sep. 2011).
Zeidler, R., et al., "Simultaneous Activation of T Cells and Accessory Cells by a New Class of Intact Bispecific Antibody Results in Efficient Tumor Cell Killing," Journal of Immunology 163(3):1246-1252, American Association of Immunologists, United States (1999).
Zhang, H., et al., "ErbB receptors: from oncogenes to targeted cancer therapies," J. Clin Invest., 117(8): 2051-2058, The American Society for Clinical Investigations, United States (2007).
Zhang, Y.W., et al., "MET kinase inhibitor SGX523 synergizes with epidermal growth factor receptor inhibitor erlotinib in a hepatocyte growth factor-dependent fashion to suppress carcinoma growth," Cancer Research 70(17):6880-6890, American Association for Cancer Research, United States (Sep. 2010).
Zhang, B., et al., "Abstract 655: Combination of Mm-111, an Erbb2/erbb3 Bispecific Antibody, With Endocrine Therapies as an Effective Strategy for Treatment of Er+/her2+ Breast Cancer," Cancer Research 71(8):655-655, American Association of Cancer Research, United States (Jul. 2011).
Zhao, X., et al., "Targeting C-type Lectin-like Molecule-1 for Antibody-mediated Immunotherapy in Acute Myeloid Leukemia," Haematologica 95(1):71-78, Ferrata Storti Foundation, Italy (Jan. 2010).
Ahmed, M., et al., "Lack of in Vivo Antibody Dependent Cellular Cytotoxicity with Antibody Containing Gold Particles," Bioconjugate Chem. 26:812-816, American Chemical Society, United States (2015).
Almagro, J.C., et al., "Humanization of antibodies," Front Biosci. 13:1619-1633, IMR Press, Singapore (2008).
Bardelli, A., et al., "Amplification of the MET receptor drives resistance to anti-EGFR therapies in colorectal cancer," Cancer Discov. 3(6):658-673, American Association for Cancer Research, United States (2013).
Elliott, B.E., et al., "The role of hepatocyte growth factor (scatter factor) in epithelial-mesenchymal transition and cancer," Can. J. Physiol. Pharmacol. 80(2):91-102, Canadian Science Publishing, Canada (2002).
Ferguson, K.M., "Structure-based view of epidermal growth factor receptor regulation," Annu. Rev. Biophys. 37:353-373, Annual Reviews, United States (2008).
Gale, N.W., et al., "Grb2 mediates the EGF-dependent activation of guanine nucleotide exchange on Ras," Nature 363:88-92, Nature Publishing Group, United Kingdom (1993).
Kubota, T., et al., "Engineered therapeutic antibodies with improved effector functions," Cancer Sci. 100(9):1566-1572, Wiley, United States (2009).
Olayioye, M.A., et al., "The ErbB signaling network: receptor heterodimerization in development and cancer," EMBO J. 19(13):3159-3167, EMBO Press, United Kingdom (2000).
Park, N.J., et al., "Measurement of Cetuximab and Panitumumab-Unbound Serum EGFR Extracellular Domain Using an Assay Based on Slow Off-Rate Modified Aptamer (SOMAmer) Reagents," PLOS One 8(21):e71703, PLOS, United States (2013).
Robertson, S.C., et al., "RTK mutations and human syndromes: when good receptors turn bad," Trends Genet. 16(6):265-271, Elsevier, Netherlands (2000).
Siegfried, J.M., et al., "The clinical significance of hepatocyte growth factor for non-small cell lung cancer," Ann Thoracic Surg. 66(6):1915-1918, Elsevier, Netherlands (1998).
Vecchione, L., et al., "EGFR-targeted therapy," Experimental Cell Research 317(19):2765-2771, Elsevier, Netherlands (2011).

* cited by examiner

Figure 1

| MF nr | Specificity | VH Sequence |
|---|---|---|
| 1337 | TT | EVQLVETGAEVKKPGASVKVSCKASDYIFTKYEHNWVRQAPGQGLEWMGWMSAANTGNTGYAQKFQGRVTMTRDTSINTAYMELSSLTSGDTAVYFCARSSLFKTETAPYYHPALDYWGQGTTVTVSS (SEQ ID NO:69) |
| 3370 | EGFR | QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCAKDRHWHWWLLDAFDYWGQGTLVTVSS (SEQ ID NO:70) |
| 3755 | EGFR | QVQLVQSGSELKKPGASVKISCKASGYTFTNYAMKWVRQAPKHGLEWMGWINANTGDFTYAQGFTYSLDTSVSTAYLQSSLAEDSAVYYCTRREFLEWLHFTYWGQGTLVTVSS (SEQ ID NO:71) |
| 4297 | cMet | EVQLVESGGGLVKPGGSLRLSCAASGFTFSKAWMNWVRQAPIKGLEWVGRIKSKTDGGTTDYAAPVKGRFTISRDDSKNTLYLQMNSLKPEDTAVYYCTTASSMTKHGVIVSWFDPWGQGTLVTVSS (SEQ ID NO:72) |
| 4356 | cMet | QVQLVQSGSELKKPGASVKVSCKASGYTFTSSMNWVRQAPGQGLEWMGWINTYTGDPTYAQGFTGKVFSLDTSVNTAYLQSSLKABDTAVYYCAARETYYIDRGGYPPDPWGQGTLVTVSS (SEQ ID NO:73) |
| 2708 | RSV-G | EVQLVESGGGVVQPGRSLRLSCAASGFTFSNYGMHWVRQAPGKGLEWVAVISYDGSTKYSADSLKGRFTISRDNSKNTLYLQMNSLRADDTAVYYCAKEGWSFDSSCYRSWFDSWGQGTLVTVSS (SEQ ID NO:74) |

| MF nr | Specificity | FR1 | CDR1 | FR2 | CDR2 | FR3 | CDR3 | FR4 |
|---|---|---|---|---|---|---|---|---|
| 1337 | TT | EVQLVETGAEVKKPGASVKVSCKAS (SEQ ID NO:104) | KYEH (SEQ ID NO:105) | WVRQAPGQGLEWMG (SEQ ID NO:106) | WMSAANTGNTGYAQKFQG (SEQ ID NO:107) | RVTMTRDTSINTAYMELSSLTSGDTAVYFCAR (SEQ ID NO:108) | SSLFKTETAPYYHPALDY (SEQ ID NO:109) | WGQGTTVTVSS (SEQ ID NO:110) |
| 3370 | EGFR | QVQLVQSGAEVKKPGASVKVSCKASGYTFT (SEQ ID NO:111) | SYGIS (SEQ ID NO:112) | WVRQAPGQGLEWMG (SEQ ID NO:113) | WISAYNGNTNYAQKLQG (SEQ ID NO:114) | RVTMTTDTSTSTAYMELRSLRSDDTAVYYCAK (SEQ ID NO:115) | DRHWHWWLLDAFDY (SEQ ID NO:116) | WGQGTLVTVSS (SEQ ID NO:117) |
| 3755 | EGFR | QVQLVQSGSELKKPGASVKISCKASGYTFT (SEQ ID NO:118) | NYAMK (SEQ ID NO:119) | WVRQAPKHGLEWMG (SEQ ID NO:120) | WINANTGDFTYAQGFTG (SEQ ID NO:121) | KVFSLDTSVSTAYLQSSLAEDSAVYYCTR (SEQ ID NO:122) | REFLEWLHFTY (SEQ ID NO:123) | WGQGTLVTVSS (SEQ ID NO:124) |
| 4297 | cMet | EVQLVESGGGLVKPGGSLRLSCAASGFTFS (SEQ ID NO:125) | KAWMN (SEQ ID NO:126) | WVRQAPGKGLEWVG (SEQ ID NO:127) | RIKSKTDGGTTDYAAPVKG (SEQ ID NO:128) | RFTISRDDSKNTLYLQMNSLKPEDTAVYYCTT (SEQ ID NO:129) | ASSMTKHGVIVSWFDP (SEQ ID NO:130) | WGQGTLVTVSS (SEQ ID NO:131) |
| 4356 | cMet | QVQLVQSGSELKKPGASVKVSCKASGYTFT (SEQ ID NO:132) | SSMNW (SEQ ID NO:133) | WVRQAPGQGLEWMG (SEQ ID NO:134) | WINTYTGDPTYAQGFTG (SEQ ID NO:135) | KVFSLDTSVNTAYLQSSLKABDTAVYYCAA (SEQ ID NO:136) | RETYYIDRGGYPPDP (SEQ ID NO:137) | WGQGTLVTVSS (SEQ ID NO:138) |
| 2708 | RSV-G | EVQLVESGGGVVQPGRSLRLSCAASGFTFS (SEQ ID NO:139) | NYGMH (SEQ ID NO:140) | WVRQAPGKGLEWVA (SEQ ID NO:141) | VISYDGSTKYSADSLKG (SEQ ID NO:142) | RFTISRDNSKNTLYLQMNSLRADDTAVYYCAK (SEQ ID NO:143) | EGWSFDSSCYRSWFDS (SEQ ID NO:144) | WGQGTLVTVSS (SEQ ID NO:145) |

Figure 7

| | | |
|---|---|---|
| MF3353 | (SEQ ID NO:75) | QVQLVQSGAEVKKPGASVKVSCKASGYTFTSYGISWVRQAPGQGLEWMGW |
| MF8229 | (SEQ ID NO:76) | QVQLVQSGAEVKKPGASVKVSCKASGYTFTSYGISWVRQAPGQGLEWMGW |
| MF8228 | (SEQ ID NO:77) | QVQLVQSGAEVKKPGASVKVSCKASGYTFTSYGISWVRQAPGQGLEWMGW |
| MF3370 | (SEQ ID NO:78) | QVQLVQSGAEVKKPGASVKVSCKASGYTFTSYGISWVRQAPGQGLEWMGW |
| MF8233 | (SEQ ID NO:79) | QVQLVQSGAEVKKPGASVKVSCKASGYTFTSYGISWVRQAPGQGLEWMGW |
| MF8232 | (SEQ ID NO:80) | QVQLVQSGAEVKKPGASVKVSCKASGYTFTSYGISWVRQAPGQGLEWMGW |
| MF3393 | (SEQ ID NO:81) | QVQLVQSGAEVKKPGASVKVSCKASGYTFTSYGISWVRQAPGQGLEWMGW |
| MF8227 | (SEQ ID NO:82) | QVQLVQSGAEVKKPGASVKVSCKASGYTFTSYGISWVRQAPGQGLEWMGW |
| MF8226 | (SEQ ID NO:83) | QVQLVQSGAEVKKPGASVKVSCKASGYTFTSYGISWVRQAPGQGLEWMGW |

```
                  **************************************************
```

| | |
|---|---|
| MF3353 | ISAYNGNTNYAQKLQGRVTMTTDTSTSTAYMELRSLRSDDTAVYYCARDS |
| MF8229 | ISAYNANTNYAQKLQGRVTMTTDTSTSTAYMELRSLRSDDTAVYYCARDS |
| MF8228 | ISAYSGNTNYAQKLQGRVTMTTDTSTSTAYMELRSLRSDDTAVYYCARDS |
| MF3370 | ISAYNGNTNYAQKLQGRVTMTTDTSTSTAYMELRSLRSDDTAVYYCAKDR |
| MF8233 | ISAYNANTNYAQKLQGRVTMTTDTSTSTAYMELRSLRSDDTAVYYCAKDR |
| MF8232 | ISAYSGNTNYAQKLQGRVTMTTDTSTSTAYMELRSLRSDDTAVYYCAKDR |
| MF3393 | ISAYNGNTNYAQKLQGRVTMTTDTSTSTAYMELRSLRSDDTAVYYCARGY |
| MF8227 | ISAYNANTNYAQKLQGRVTMTTDTSTSTAYMELRSLRSDDTAVYYCARGY |
| MF8226 | ISAYSGNTNYAQKLQGRVTMTTDTSTSTAYMELRSLRSDDTAVYYCARGY |

```
                  ****..********************************************:.
```

| | |
|---|---|
| MF3353 | YWHWWLGAFDYWGQGTLVTVSS |
| MF8229 | YWHWWLGAFDYWGQGTLVTVSS |
| MF8228 | YWHWWLGAFDYWGQGTLVTVSS |
| MF3370 | HWHWWLDAFDYWGQGTLVTVSS |
| MF8233 | HWHWWLDAFDYWGQGTLVTVSS |
| MF8232 | HWHWWLDAFDYWGQGTLVTVSS |
| MF3393 | LDHWWLGAFDYWGQGTLVTVSS |
| MF8227 | LDHWWLGAFDYWGQGTLVTVSS |
| MF8226 | LDHWWLGAFDYWGQGTLVTVSS |

```
MF8225 (SEQ ID NO:1)  QVQLVQSGSELKKPGASVKVSCKASGYTFTTYSLNWVRQAPGQGLEWMGW
MF8243 (SEQ ID NO:2)  QVQLVQSGSELKKPGASVKVSCKASGYTFTSYAMNWVRQAPGQGLEWMGW
MF8224 (SEQ ID NO:3)  QVQLMQSGSELKKPGASVKVSCKASGYTFTTYSMNWVRQAPGQGLEWMGW
MF8239 (SEQ ID NO:4)  QVQLVQSGSELKKPGASVKVSCKASGYTFTDYAMNWVRQVPGQGLEWMGW
MF8242 (SEQ ID NO:5)  QVQLVQSGSELKKPGASVKVSCKASGYTFTNYAMNWVRQAPGQGLEWMGW
MF8237 (SEQ ID NO:6)  QVQLVQSGSELKKPGASVKVSCKASGYTFTSFGMSWVRQAPGQGLEWMGW
MF8240 (SEQ ID NO:7)  QVQLVQSGSELKKPGASVKVSCKASGYTFTTYSMNWVRQAPGQGLEWMGW
MF8234 (SEQ ID NO:8)  QVQLVQSGSELEKPGASVKVSCKASGYTFISYAMNWVRQAPGQGLEWMGW
MF8245 (SEQ ID NO:9)  QVQLVQSGSELKKPGASVKVSCKASGYTFTSYAVNWVRQAPGQGLEWMGW
MF8231 (SEQ ID NO:10) QVQVVQSGSEVKKPGASVKVSCKASGYTFTTYSMNWVRQAPGQGLEWMGW
MF8247 (SEQ ID NO:11) QVQLVQSGSELKKPGASVKVSCKASGYTFTDYAMNWVRQAPGQGLEWMGW
MF8238 (SEQ ID NO:12) QVQLVQSGSELEKPGASVKVSCKASGYTFTTYSMNWVRQAPGQGLEWMGW
MF8230 (SEQ ID NO:13) QVQLVQSGSELKKPGASVKVSCKASGYTFTTYSMNWVRQAPGQGLEWMGW
MF8248 (SEQ ID NO:14) QVQLVQSGSELKKPGASVKVSCKASGYTFTTYAINWVRQAPGQGLEWMGW
MF8246 (SEQ ID NO:15) QVQLVQSGSELKKPGASVKVSCKASGYTFTTYAMNWVRQAPGQGLEWMGW
MF8223 (SEQ ID NO:16) QVQLVQSGSELKKPGASVKVSCKASGYTFTTYAMNWVRQAPGQGLEWMGW
MF8222 (SEQ ID NO:17) QVELVQSGSELKKPGASVKVSCKASGYTFTTYSMNWVRQAPGQGLEWMGW
MF8235 (SEQ ID NO:18) QVQLVQSGSELKKPGASVKVSCKASGYTFTTYSMNWVRQAPGQGLEWMGW
MF8236 (SEQ ID NO:19) QVQLVQSGSELKKPGASVKVSCKASGYTFTTYSMNWVRQAPGQGLEWMGW
MF8241 (SEQ ID NO:20) QVQLVQSGSELEKPGASVKVSCKASGYTFTTYSMNWVRQAPGQGLEWMGW
MF8244 (SEQ ID NO:21) QVQLVQSGSELEKPGASVKVSCKASGYTFTTYSMNWVRQAPGQGLEWMGW
MF8221 (SEQ ID NO:22) QVQLVQSGSELKKPGASVKVSCKASGYTFTDYAMNWVRQAPGQGLEWMGW
MF4356 (SEQ ID NO:23) QVQLVQSGSELKKPGASVKVSCKASGYTFTSYSMNWVRQAPGQGLEWMGW
                      **:::****::*****************    :::.****.*********

MF8225      INTYTGNPTYAQGFTGRFVFFLDTSVSTAYLQISSLKAEDTAVYYCARET
MF8243      INTNTGNPTYAQGFTGRFVFSLDTSVSTAYLQISSLKAEDTAVYYCARET
MF8224      INTNTGNPTYAQDFTGRFVFSLDTSVSTAYLQISSLKAEDTAVYYCARET
MF8239      INTYTGNPTYVQGFTGRFVFSLDTSVSTAYLQISSLKAEDTAVYYCARET
MF8242      INTNTGNPTYAQGFTGRFVFPLDTSVSTTYLQISSLKAEDTAVYYCARET
MF8237      INTNTGNPTYAQGFTGRFVFSLDTSVSTAYLQINSLKAEDTAVYYCARES
MF8240      INTNTGNPTYAQGFTGRFVFSLDTSVSTAYLQISSLNTEDTAVYYCARET
MF8234      INTYTGNPTYAQGFTGRFVFSLDTSVSTAYLQISSLKAEDTAVYYCARET
MF8245      INTYTGNPTYAQGFTGRFVFSSDTSVNTAYLQISSLKAEDTAVYYCARET
MF8231      INTYTGDPTYVQGFTGRFVFSLDTSVSTAYLQISSLKAEDTAVYYCARET
MF8247      INTYTGNPTYVQGFTGRFVFSLDTSVSTAYLQISSLKAEDTAVYYCARET
MF8238      INTYTGSPTYAQGFTGRFVFSLDTSVSTAYLQISSLKAEDTAIYYCARET
MF8230      INTYTGDPTYAQGFTGRFVFSLDTSVSTAYLQISSLKAEDTAVYYCARET
MF8248      INTNTGNPTYAQGFTGRFVFSLDTSVSTAHLQISSLKAEDTAVYYCARET
MF8246      INTYTGDPTYAQGFTGRFVFSLDTSVNTAYLQISSLKAEDTAVYYCARET
MF8223      INTNTGNPTYAQGFTGRFVFSLDTSDSTAFLQISSLKAEDTAVYYCARET
MF8222      INTNTGTPTYAQGFTGRFVFSLDTSVSTAYLQISSLKAEDTAVYYCARET
MF8235      INTNTGTPTYAQGFTGRFVFSLDTSVSTAYLQISSLKAEDTAVYYCARET
MF8236      INTYTGNPTYAQGFTGRFVFSLDTSVSTAYLQISSLTTEDTAVYYCARET
MF8241      INTYTGSPTYAQGFTGRFVFSLDTSVSTAYLQISSLKAEDTAVYYCARET
MF8244      INTYTGSPTYAQGFTGRFVFSLDTSVSTAYLQISSLKAEDTAVYYCARET
```

Figure 8, continued

```
MF8221     INTYTGNPTYVQGFTGRFVFSLDTSVSTAYLQISSLKAEDTAVYYCARET
MF4356     INTYTGDPTYAQGFTGRYVFSLDTSVNTAYLQISSLKAEDTAVYYCARET
           *** ** *** * **** ** ***  * **** ** ****.*******

MF8225     YYYDSSGYPFDPWGQGTLVTVSS (SEQ ID NO: 1)
MF8243     YYYDRGGYPFDPWGQGTLVTVSS (SEQ ID NO: 2)
MF8224     YYYDSSGYPFDPWGQGTLVTVSS (SEQ ID NO: 3)
MF8239     YYYDSSGFPFDPWGQGTLVTVSS (SEQ ID NO: 4)
MF8242     YYYQSSGYLFDPWGQGTLVTVSS (SEQ ID NO: 5)
MF8237     YYYDRNDYPFDPWGQGTLVTVSS (SEQ ID NO: 6)
MF8240     YYYDVGGYPFDPWGQGTLVTVSS (SEQ ID NO: 7)
MF8234     YYYDSGGYPFDPWGQGTLVTVSS (SEQ ID NO: 8)
MF8245     YFYDSSGYPFDPWGQGTLVTVSS (SEQ ID NO: 9)
MF8231     YFYDRGGYPFDPWGQGTLVTVSS (SEQ ID NO: 10)
MF8247     YYYDSSAYPFDPWGQGTLVTVSS (SEQ ID NO: 11)
MF8238     FYFDSGGYPFDPWGQGTLVTVSS (SEQ ID NO: 12)
MF8230     YFYDRGGYPFDPWGQGTLVTVSS (SEQ ID NO: 13)
MF8248     YYYATSGYPFDPWGQGALVTVSS (SEQ ID NO: 14)
MF8246     SYYDRTGYPFDPWGQGTLVTVSS (SEQ ID NO: 15)
MF8223     YYYDSSGYPFDPWGQGTLVTVSS (SEQ ID NO: 16)
MF8222     YYYDSSGYPFDPWGQGTLVTVSS (SEQ ID NO: 17)
MF8235     YYYGSSGYPFAPWGQGTLVTVSS (SEQ ID NO: 18)
MF8236     YYYESSGYPFDPWGQGTLVTVSS (SEQ ID NO: 19)
MF8241     YYFDSGDYPFDPWGQGTLVTVSS (SEQ ID NO: 20)
MF8244     YYFDSGGYPFDPWGQGTLVTVSS (SEQ ID NO: 21)
MF8221     YYYDSSGYPFDPWGQGTLVTVSS (SEQ ID NO: 22)
MF4356     YYYDRGGYPFDPWGQGTLVTVSS (SEQ ID NO: 23)
            :   :  * *****:******
```

Figure 9A:

DIQMTQSPSSLSASVGDRVTITCRASQSISSYLNWYQQKPGKAPKLLIYAASSLQSGVPSRFSGSGSGTDFTLTI
SSLQPEDFATYYCQQSYSTPPTFGQGTKVEIK (SEQ ID NO: 84)
RTVAAPSVFIFPPSDEQLKSGTASVVCLLNNFYPREAKVQWKVDNALQSGNSQESVTEQDSKDSTYSLSSTLTLS
KADYEKHKVYACEVTHQGLSSPVTKSFNRGEC (SEQ ID NO: 85)

Figure 9B:

gacatccagatgacccagtctccatcctccctgtctgcatctgtaggagacagagtcacc
  D  I  Q  M  T  Q  S  P  S  S  L  S  A  S  V  G  D  R  V  T
atcacttgccggggcaagtcagagcattagcagctacttaaattggtatcagcagaaacca
  I  T  C  R  A  S  Q  S  I  S  S  Y  L  N  W  Y  Q  Q  K  P
gggaaagcccctaagctcctgatctatgctgcatccagtttgcaaagtggggtcccatca
  G  K  A  P  K  L  L  I  Y  A  A  S  S  L  Q  S  G  V  P  S
aggttcagtggcagtggatctgggacagatttcactctcaccatcagcagtctgcaacct
  R  F  S  G  S  G  S  G  T  D  F  T  L  T  I  S  S  L  Q  P
gaagattttgcaacttactactgtcaacagagttacagtaccccctccaacgttcggccaa
  E  D  F  A  T  Y  Y  C  Q  Q  S  Y  S  T  P  P  T  F  G  Q
gggaccaaggtggagatcaaa (SEQ ID NO: 86)
  G  T  K  V  E  I  K (SEQ ID NO: 87)

Figure 9C:

cgaactgtggctgcaccatctgtcttcatcttcccgccatctgatgagcagttgaaatct
  R  T  V  A  A  P  S  V  F  I  F  P  P  S  D  E  Q  L  K  S
ggaactgcctctgttgtgtgcctgctgaataacttctatcccagagaggccaaagtacag
  G  T  A  S  V  V  C  L  L  N  N  F  Y  P  R  E  A  K  V  Q
tggaaggtggataacgccctccaatcgggtaactcccaggagagtgtcacagagcaggac
  W  K  V  D  N  A  L  Q  S  G  N  S  Q  E  S  V  T  E  Q  D
agcaaggacagcacctacagcctcagcagcaccctgacgctgagcaaagcagactacgag
  S  K  D  S  T  Y  S  L  S  S  T  L  T  L  S  K  A  D  Y  E
aaacacaaagtctacgcctgcgaagtcacccatcagggcctgagctcgcccgtcacaaag
  K  H  K  V  Y  A  C  E  V  T  H  Q  G  L  S  S  P  V  T  K
agcttcaacaggggagagtgttag (SEQ ID NO: 88)
  S  F  N  R  G  E  C  - (SEQ ID NO: 89)

Figure 9D

DIQMTQSPSSLSASVGDRVTITCRASQSISSYLNWYQQKPGKAPKLLIYAASSLQSGVPSRFSGSGSG
TDFTLTISSLQPEDFATYYCQQSYSTPPITFGQGTRLEIK (SEQ ID NO: 90)

Figure 9E

DIQMTQSPSSLSASVGDRVTITCRASQSISSYLNWYQQKPGKAPKLLIYAASSLQSGVPSRFSGSGSG
TDFTLTISSLQPEDFATYYCQQSYSTP (SEQ ID NO: 91)

Figure 10A
CH1:
```
gctagcaccaagggcccatcggtcttccccctggcaccctcctccaagagcacctctggg
 A   S   T   K   G   P   S   V   F   P   L   A   P   S   S   K   S   T   S   G
ggcacagcggccctgggctgcctggtcaaggactacttccccgaaccggtgacggtgtcg
 G   T   A   A   L   G   C   L   V   K   D   Y   F   P   E   P   V   T   V   S
tggaactcaggcgccctgaccagcggcgtgcacaccttcccggctgtcctacagtcctca
 W   N   S   G   A   L   T   S   G   V   H   T   F   P   A   V   L   Q   S   S
ggactctactccctcagcagcgtcgtgaccgtgccctccagcagcttgggcacccagacc
 G   L   Y   S   L   S   S   V   V   T   V   P   S   S   S   L   G   T   Q   T
tacatctgcaacgtgaatcacaagcccagcaacaccaaggtggacaagagagtt (SEQ ID NO: 92)
 Y   I   C   N   V   N   H   K   P   S   N   T   K   V   D   K   R   V  (SEQ ID NO: 93)
```

Figure 10B
Hinge:
```
gagcccaaatcttgtgacaaaactcacacatgcccaccgtgccca (SEQ ID NO: 94)
 E   P   K   S   C   D   K   T   H   T   C   P   P   C   P  (SEQ ID NO: 95)
```

Figure 10C
CH2:
```
gcacctgaactcctggggggaccgtcagtcttcctcttccccccaaaacccaaggacacc
 A   P   E   L   L   G   G   P   S   V   F   L   F   P   P   K   P   K   D   T
ctcatgatctcccggacccctgaggtcacatgcgtggtggtggacgtgagccacgaagac
 L   M   I   S   R   T   P   E   V   T   C   V   V   V   D   V   S   H   E   D
cctgaggtcaagttcaactggtacgtggacggcgtggaggtgcataatgccaagacaaag
 P   E   V   K   F   N   W   Y   V   D   G   V   E   V   H   N   A   K   T   K
ccgcgggaggagcagtacaacagcacgtaccgtgtggtcagcgtcctcaccgtcctgcac
 P   R   E   E   Q   Y   N   S   T   Y   R   V   V   S   V   L   T   V   L   H
caggactggctgaatggcaaggagtacaagtgcaaggtctccaacaaagccctcccagcc
 Q   D   W   L   N   G   K   E   Y   K   C   K   V   S   N   K   A   L   P   A
cccatcgagaaaaccatctccaaagccaaa (SEQ ID NO: 96)
 P   I   E   K   T   I   S   K   A   K (SEQ ID NO: 97)
```

Figure 10D
CH2 containing L235G and G236R silencing substitutions:
gcacctgaactcggcaggggaccgtcagtcttcctcttccccccaaaacccaaggacacc
 A   P   E   L   G   R   G   P   S   V   F   L   F   P   P   K   P   K   D   T
ctcatgatctcccggaccctgaggtcacatgcgtggtggtggacgtgagccacgaagac
 L   M   I   S   R   T   P   E   V   T   C   V   V   V   D   V   S   H   E   D
cctgaggtcaagttcaactggtacgtggacggcgtggaggtgcataatgccaagacaaag
 P   E   V   K   F   N   W   Y   V   D   G   V   E   V   H   N   A   K   T   K
ccgcgggaggagcagtacaacagcacgtaccgtgtggtcagcgtcctcaccgtcctgcac
 P   R   E   E   Q   Y   N   S   T   Y   R   V   V   S   V   L   T   V   L   H
caggactggctgaatggcaaggagtacaagtgcaaggtctccaacaaagccctcccagcc
 Q   D   W   L   N   G   K   E   Y   K   C   K   V   S   N   K   A   L   P   A
cccatcgagaaaaccatctccaaagccaaa (SEQ ID NO: 98)
 P   I   E   K   T   I   S   K   A   K (SEQ ID NO: 99)

Figure 10E
CH3: KK of DEKK
gggcagccccgagaaccacaggtgtacaccaagccccatcccgggaggagatgaccaag
 G   Q   P   R   E   P   Q   V   Y   T   K   P   P   S   R   E   E   M   T   K
aaccaggtcagcctgaagtgcctggtcaaaggcttctatcccagcgacatcgccgtggag
 N   Q   V   S   L   K   C   L   V   K   G   F   Y   P   S   D   I   A   V   E
tgggagagcaatgggcagccggagaacaactacaagaccacgcctcccgtgctggactcc
 W   E   S   N   G   Q   P   E   N   N   Y   K   T   T   P   P   V   L   D   S
gacggctccttcttcctctatagcaagctcaccgtggacaagagcaggtggcagcagggg
 D   G   S   F   F   L   Y   S   K   L   T   V   D   K   S   R   W   Q   Q   G
aacgtcttctcatgctccgtgatgcatgaggctctgcacaaccactacacgcagaagagc
 N   V   F   S   C   S   V   M   H   E   A   L   H   N   H   Y   T   Q   K   S
ctctccctgtctccgggttga (SEQ ID NO: 100)
 L   S   L   S   P   -  (SEQ ID NO: 101)

Figure 10F
CH3: DE of DEKK
gggcagccccgagaaccacaggtgtacaccgacccccatcccgggaggagatgaccaag
 G   Q   P   R   E   P   Q   V   Y   T   D   P   P   S   R   E   E   M   T   K
aaccaggtcagcctgacctgcgaggtcaaaggcttctatcccagcgacatcgccgtggag
 N   Q   V   S   L   T   C   E   V   K   G   F   Y   P   S   D   I   A   V   E
tgggagagcaatgggcagccggagaacaactacaagaccacgcctcccgtgctggactcc
 W   E   S   N   G   Q   P   E   N   N   Y   K   T   T   P   P   V   L   D   S
gacggctccttcttcctctatagcaagctcaccgtggacaagagcaggtggcagcagggg
 D   G   S   F   F   L   Y   S   K   L   T   V   D   K   S   R   W   Q   Q   G
aacgtcttctcatgctccgtgatgcatgaggctctgcacaaccactacacgcagaagagc
 N   V   F   S   C   S   V   M   H   E   A   L   H   N   H   Y   T   Q   K   S
ctctccctgtctccgggttga (SEQ ID NO: 102)
 L   S   L   S   P   -  (SEQ ID NO: 103)

ANTIBODIES THAT BIND EGFR AND CMET

CROSS-REFERENCE TO RELATED APPLICATIONS

This application is a U.S. national stage filing of International Application No. PCT/NL2018/050537, filed Aug. 9, 2018; which claims priority to EP Application No. 17185572.9, filed Aug. 9, 2017. The entire contents of International Application No. PCT/NL2018/050537 are hereby incorporated herein by reference.

REFERENCE TO SEQUENCE LISTING SUBMITTED ELECTRONICALLY

The content of the electronically submitted sequence listing (Name: "4096_0310001_Seqlisting_ST25.txt"; Size: 162,882 bytes; and Date of Creation: Apr. 18, 2023) is herein incorporated by reference in its entirety.

The invention relates to the field of antibodies. In particular it relates to the field of therapeutic antibodies, including human antibodies, for the treatment of diseases involving aberrant cells. Further, it relates to antibodies that bind EGFR and cMET, including multispecific antibodies, and their use in the binding of EGFR and cMET positive cells, particularly tumor cells.

The epidermal growth factor (EGF) receptor (EGFR) is a cell-surface receptor for members of the epidermal growth factor family (EGF-family) of extracellular protein ligands. EGFR is also known as the ErbB-1 receptor. The receptor has been given various names in the past (EGFR; ERBB; ERBB1; HER1; PIG61; mENA). In the present invention the names ErbB-1, EGFR or HER1 in humans will be used interchangeably. EGFR is a member of the ErbB family of receptors, a subfamily of four closely related receptor tyrosine kinases: ErbB-1 (EGFR), ErbB-2 (HER2/c-neu; Her2), ErbB-3 (Her 3) and ErbB-4 (Her 4).

EGFR exists on a cell surface and may be activated by binding of its specific ligands, including epidermal growth factor and transforming growth factor α (TGFα). Upon activation by its growth factor ligands, the receptor may undergo a transition from an inactive mostly monomeric form to an active homodimer. In addition to forming homodimers after ligand binding, EGFR may pair with another member of the ErbB receptor family, such as ErbB2, to create an activated heterodimer. Dimers may also form in the absence of ligand-binding and clusters of activated EGFRs may form after ligand binding.

EGFR dimerization stimulates intrinsic intracellular protein-tyrosine kinase (PTK) activity. This activity induces several signal transduction cascades that lead to cell proliferation and differentiation. The kinase domain of EGFR can cross-phosphorylate tyrosine residues of other receptors it is complexed with, and can itself be activated in that manner.

Mutations involving EGFR have been identified in several types of cancer. It is the target of an expanding class of anticancer therapies. Such therapies include EGFR tyrosine kinase inhibitors (EGFR-TKIs) such as gefitinib and erlotinib for lung cancer, and antibodies as cetuximab and panitumumab for colon cancer and head and neck cancer.

Cetuximab and panitumumab are monoclonal antibodies that inhibit the receptor. Other monoclonals in clinical development are zalutumumab, nimotuzumab, and matuzumab. The monoclonal antibodies aim to block the extracellular ligand-induced receptor activation, mostly by blocking ligand binding to the receptor. With the binding site blocked, signal-inducing molecules may not attach effectively and thereby also not activate downstream signaling. Ligand-induced receptor activation may also be inhibited by stabilization of the inactive receptor conformation (matuzumab).

To date, EGFR targeted therapies have been associated with the development of treatment resistance over time. Various mechanisms for the resistance to EGFR-TKIs have been described. In patients with advanced non-small cell lung cancer (NSCLC) the mechanisms of resistance include the occurrence of secondary mutations (e.g., T790M, C797S), the activation of alternative signaling (e.g., Met, HGF, AXL, Hh, IGF-1R), aberrant downstream pathways (e.g., AKT mutations, loss of PTEN), the impairment of the EGFR-TKIs-mediated apoptosis pathway (e.g., BCL2-like 11/BIM deletion polymorphism) and histological transformation. Although some mechanisms of resistance have been identified others remain to be identified. Similarly, patients with colorectal cancer that are treated with EGFR antibodies also develop resistance over time. This may occur through emergence of KRAS mutations. Of those without KRAS mutations; amplification of the MET proto-oncogene may be associated with acquired resistance during anti-EGFR therapy (Bardelli et al., 2013; Cancer Discov. June; 3(6): 658-73. doi: 10.1158/2159-8290.CD-12-0558). The tumor can be resistant ab initio or develop resistance during treatment. Resistance to EGFR-targeted therapy is seen in many EGFR positive cancers and has demonstrated a need in the art for more efficacious EGFR cancer treatments that improve the standard of care, and are superior in terms of the capacity to address EGFR-targeted therapy resistance.

Dysregulation of MET Proto-Oncogene, Receptor Tyrosine Kinase (cMET) and hepatocyte growth factor (HGF) have been reported in a variety of tumors. Ligand-driven cMET activation has been observed in several cancers. Elevated serum and intra-tumoral HGF is observed in lung, breast cancer, and multiple myeloma (J. M. Siegfried et al., Ann Thorac Surg 66, 1915 (1998); P. C. Ma et al., Anticancer Res 23, 49 (2003); B. E. Elliott et al. Can J Physiol Pharmacol 80, 91 (2002); C. Seidel, et al, Med Oncol 15, 145 (1998)). Overexpression of cMET, cMET amplification or mutation has been reported in various cancers such as colorectal, lung, gastric, and kidney cancer and may drive ligand-independent receptor activation (C. Birchmeier et al, Nat Rev Mol Cell Biol 4, 915 (2003); G. Maulik et al., Cytokine Growth Factor Rev 13, 41 (2002)). Expression of HGF is also associated with the activation of the HGF/cMET signaling pathway and is also one of the escape mechanisms of tumors under selection by EGFR targeted therapy.

The cMET receptor is formed by proteolytic processing of a common precursor into a single-pass, disulphide-linked α/β heterodimer. The extracellular portion of cMET is composed of three domain types. The N-terminal region fold forms a large semaphorin (Sema) domain, which encompasses the whole α-subunit and part of the β-subunit. The plexin-semaphorin-integrin (PSI) domain follows the Sema domain, and includes four disulphide bonds. This domain is connected to the transmembrane helix via four immunoglobulin-plexin-transcription (IPT) domains, which are related to immunoglobulin-like domains. Intracellularly, the cMET receptor contains a tyrosine kinase catalytic domain flanked by distinctive juxtamembrane and carboxy-terminal sequences (Organ and Tsao. Therapeutic advances in medical oncology 3.1_suppl (2011): S7-S19 which is incorporated herein by reference in its entirety).

The ligand of cMET, hepatocyte growth factor (HGF; also known as scatter factor) and its splicing isoforms (NK1, NK2) are known ligands of the cMET receptor. HGF was identified in 1991 as a potent mitogen/morphogen. The HGF/cMET signaling pathway plays important roles in the development and progression of various cancers. Dysregulation and/or hyperactivation of HGF or cMET in human cancers are linked to poor prognosis, cMET can be activated via overexpression, amplification, or mutation. Activation may promote development, progression, invasive growth, and metastasis of cancers, cMET can be activated in an HGF associated and HGF independent fashion. HGF independent activation occurs in cases of cMET over-expression. Abundance of cMET also may trigger (hetero)dimerization and intra-cellular signaling in the absence of ligand. Additional ligand does not appear to affect the function of such cMET over-expression cells. cMET amplification is associated with cMET over-expression and has emerged as a biomarker of tumor subtypes.

HGF is expressed ubiquitously throughout the body, showing this growth factor to be a systemically available cytokine as well as coming from the tumor stroma. A positive paracrine and/or autocrine loop of cMET activation can lead to further cMET expression. The HGF specific antibody Rilotumumab (AMG102) was developed for gastric cancer. Phase I and Phase II trials appeared promising but a phase III study with cisplatin and capecitabine as a first-line therapy in gastric cancer (RILOMET-2) was terminated following a pre-planned data monitoring committee safety review of study 20070622.

The relevance of cMET/HGF signaling in resistance to EGFR-targeted therapies has stimulated the development of ways to deal with the resistance. To date, antibody based approaches include anti-HGF antibodies; anti cMET or cMET antibodies and cMET/EGFR (reviewed in Lee et al., 2015; Immunotargets and Therapy 4: 35-44) have not been clinically effective. The cMET antibodies Onartuzumab (MetMab™) and Emibetuzumab (LY-2875358) have been evaluated in phase II clinical trials. Of these Onartuzumab appeared to be effective against colorectal cancer in a combination treatment together with the EGFR-inhibitor erlotinib. These results could, however, not be repeated in a randomized phase III clinical trial. MetMAb is a monovalent monoclonal antibody (mAb) against cMET, which blocks HGF binding to cMET and subsequent pathway activation (Jin et al., 2008 Cancer Research Vol. 68: pp 4360-68).

Overcoming a problem with anti-EGFR, cMET and HGF immunotherapies, the present invention provides novel bispecific antibodies that comprise a first variable domain that can bind an extracellular part of epidermal growth factor receptor (EGFR) and a second variable domain that can bind an extracellular part of cMET Proto-Oncogene, Receptor Tyrosine Kinase (cMET).

To date, certain bispecific EGFR x cMET antibodies have been described in the art. Castoldi R. et al. (2013) describe a bispecific EGFR x cMET antibody designated MetHer1 with the cMET binding site of the antibody 5D5 (or MetMab) and the EGFR binding site of cetuximab. The bispecific antibody has a fixed EGFR and cMET binding stoichiometry of 2:1 (see Supplemental Figures)

US20140378664 describes a cMET x EGFR bispecific antibody among various other bispecific antibodies. The complete bispecific antibody is produced as a single protein which is later proteolytically cleaved. The two VH/VL domains are produced as single chain Fv fragments. Binding of the antibody induces cMET degradation and Akt phosphorylation in a gastric cancer cell line. Moores et al (2016) describe a bispecific cMET x EGFR antibody designated JNJ-61186372 produced by controlled Fab-arm exchange (cFAE) having mutations at position 405 and 409 according to EU numbering, which may have potential for immunogenicity. JNJ-61186372 was shown to be active in vivo using a xenograft model with tumor cell line H1975 that expresses the cMET ligand HGF. This tumor model is known to be dependent on the ADCC activity of the antibody (Ahmed et al., 2015). JNJ-61186372 has a reported affinity imbalance of approximately 40× greater affinity for cMET than EGFR (Moores et al. (2016)), and the anti-EGFR arm derived from zalutumumab is known to cause infusion related reaction, skin disorders, among other issues.

LY3164530 is a bispecific cMET x EGFR antibody, which contains the EGFR binding domain of cetuximab as a single chain Fv fragment fused to the heavy chain variable domain of the cMET binding antibody LY2875358 (Emibetuzumab; Kim and Kim 2017). It is a so-called dual variable domain antibody that comprises two binding sites for each of the antigens. No data are provided on HGF inhibition for the antibody. The antibody reportedly binds and internalizes cMET and EGFR without agonistic activity. The authors review various cMET, EGFR and cMET x EGFR targeted therapies and draw the conclusion that to date none of these inhibitors have shown significant efficacy in clinical trials.

There is thus a need for novel bispecific cMET x EGFR antibodies, including those which may have superior characteristics as described herein.

SUMMARY OF THE INVENTION

In one aspect the invention provides a bispecific antibody that comprises a first variable domain that can bind an extracellular part of human epidermal growth factor receptor (EGFR) and a second variable domain that can bind an extracellular part of human MET Proto-Oncogene, Receptor Tyrosine Kinase (cMET).

The bispecific antibody may comprise a common light chain. The first and second variable domains preferably comprise the same or substantially the same (common) light chain variable region. Said common light chain variable region may be one that is known to pair well with a diversity of human variable region gene segments that have undergone recombination. More preferably said common light chain is preferably a variable region encoded by a germline Vk gene segment, preferably the O12/IgV$_K$1-39*01 variable region gene segment. The preferred light chain variable region comprises the rearranged IgV$_K$1-39*01/IGJ$_K$1*01 or IgV$_K$1-39*01/IGJ$_K$5*01. The light chain of the cMET binding arm and the light chain of the EGFR binding arm is preferably the same (common) light chain. The common light chain is preferably the rearranged kappa light chain IgV$_K$1-39*01/IGJ$_K$1*01 or IgV$_K$1-39*01/IGJ$_K$5*01 joined to a human light chain constant region. The bispecific antibody can be a human antibody. The bispecific antibody can be a full length antibody. It may have one variable domain that can bind EGFR and one variable domain that can bind cMET. In one aspect the variable domain that can bind human EGFR can also beneficially bind mouse EGFR and/or cynomolgus EGFR. The variable domain that can bind human EGFR may bind to domain III of human EGFR. The variable domain that can bind cMET may block the binding of antibody 5D5 to cMET. The variable domain that can bind cMET may block the binding of HGF to cMET. The Kd of the antibody for cMET can be at least 10 times less than the Kd of the antibody for EGFR. The amino acids at positions 405 and 409 in one CH3 domain may be the same as the amino acids at the corresponding positions in the other CH3 domain (EU-numbering).

The first variable domain may comprise a heavy chain variable region with a CDR1 sequence SYGIS (SEQ ID NO: 24); a CDR2 sequence WISAYX$_1$X$_2$NTNYAQKLQG (SEQ ID NO: 25) and a CDR3 comprising the sequence X$_3$X$_4$X$_5$X$_6$HWWLX$_7$A (SEQ ID NO: 26)

wherein X$_1$=N or S; X$_2$=A or G; X$_3$=D or G; X$_4$=R, S or Y; X$_5$=H, L or Y; X$_6$=D or W and X$_7$=D or G; with 0-5 amino acid insertions, deletions, substitutions, additions or a combination thereof at a position other than X$_1$-X$_7$.

The second variable domain may comprise a heavy chain variable region with the amino acid sequence of one of the sequences of SEQ ID NO: 1-23 with 0-10 preferably 0-5 amino acid insertions, deletions, substitutions, additions or a combination thereof.

Bispecific antibodies are described wherein

X$_1$=N; X$_2$=G; X$_3$=D; X$_4$=S; X$_5$=Y; X$_6$=W and X$_7$=G; WISAYNGNTNYAQKLQG (SEQ ID NO:113) and DSYWHWWLGA (SEQ ID NO:153), X$_1$=N; X$_2$=A; X$_3$=D; X$_4$=; X$_5$=Y; X$_6$=W and X$_7$=G;
WISAYNANTNYAQKLQG (SEQ ID NO:25) and DSYWHWWLGA (SEQ ID NO:153), X$_1$=S; X$_2$=G; X$_3$=D; X$_4$=; X$_5$=Y; X$_6$=W and X$_7$=G;
WISAYSGNTNYAQKLQG (SEQ ID NO:140) and DSYWHWWLGA (SEQ ID NO:153),
X$_1$=N; X$_2$=G; X$_3$=D; X$_4$=R; X$_5$=H; X$_6$=W and X$_7$=D; WISAYNGNTNYAQKLQG (SEQ ID NO:113) and DRHWHWWLDA (SEQ ID NO:139),
X$_1$=N; X$_2$=A; X$_3$=D; X$_4$=R; X$_5$=H; X$_6$=W and X$_7$=D; WISAYNANTNYAQKLQG (SEQ ID NO:25) and DRHWHWWLDA (SEQ ID NO:139), X$_1$=S; X$_2$=G; X$_3$=D; X$_4$=R; X$_5$=H; X$_6$=W and X$_7$=D;
WISAYSGNTNYAQKLQG (SEQ ID NO:140) and DRHWHWWLDA (SEQ ID NO:139),
X$_1$=N; X$_2$=G; X$_3$=G; X$_4$=Y; X$_5$=L; X$_6$=D and X$_7$=G; WISAYNGNTNYAQKLQG (SEQ ID NO:113) and GYLDHWWLGA (SEQ ID NO:154),
X$_1$=N; X$_2$=A; X$_3$=G; X$_4$=Y; X$_5$=L; X$_6$=D and X$_7$=G; WISAYNANTNYAQKLQG (SEQ ID NO:25) and GYLDHWWLGA (SEQ ID NO:154), or
X$_1$=S; X$_2$=G; X$_3$=G; X$_4$=Y; X$_5$=L; X$_6$=D and X$_7$=G, WISAYSGNTNYAQKLQG (SEQ ID NO:140) and GYLDHWWLGA (SEQ ID NO:154).

In some embodiments

X$_1$=N; X$_2$=G; X$_3$=D; X$_4$=R; X$_5$=H; X$_6$=W and X$_7$=D; WISAYNGNTNYAQKLQG (SEQ ID NO:113) and DRHWHWWLDA (SEQ ID NO:139), X$_1$=N; X$_2$=A; X$_3$=D; X$_4$=R; X$_5$=H; X$_6$=W and X$_7$=D;
WISAYNANTNYAQKLQG (SEQ ID NO:25) and DRHWHWWLDA (SEQ ID NO:139), or
X$_1$=S; X$_2$=G; X$_3$=D; X$_4$=R; X$_5$=H; X$_6$=W and X$_7$=D WISAYSGNTNYAQKLQG (SEQ ID NO:140) and DRHWHWWLDA (SEQ ID NO:139).

In a preferred embodiment X$_3$-X$_7$=DRHWD (SEQ ID NO: 27) and X$_1$ and X$_2$ are NG; SG or NA.

Bispecific antibodies are described wherein the heavy chain variable region of the second variable domain comprises the amino acid sequence of one of the sequences of SEQ ID NO: 1-3; 7; 8; 10; 13; 15; 16; 17; 21; 22 or 23 with 0-10 preferably 0-5 amino acid insertions, deletions, substitutions, additions or a combination thereof.

The invention also provides a method of treatment of a subject that has a tumor the method comprising administering the bispecific antibody as described herein to the individual in need thereof. Typically, the individual is one suffering from a disease involving aberrant cells, for examples the individual may be suffering from a tumor.

The invention also provides a bispecific antibody that comprises a first variable domain that can bind an extracellular part of epidermal growth factor receptor (EGFR) and a second variable domain that can bind an extracellular part of MET Proto-Oncogene, Receptor Tyrosine Kinase (cMET), wherein the first variable domain comprises a heavy chain variable region with a CDR1 sequence SYGIS (SEQ ID NO: 24); a CDR2 sequence WISAYX$_1$X$_2$NTNYAQKLQG (SEQ ID NO: 25) and a CDR3 comprising the sequence X$_3$X$_4$X$_5$X$_6$HWWLX$_7$A (SEQ ID NO: 26) wherein X$_1$=N or S; X$_2$=A or G; X$_3$=D or G; X$_4$=R, S or Y; X$_5$=H, L or Y; X$_6$=D or W and X$_7$=D or G with 0-5 amino acid insertions, deletions, substitutions, additions or a combination thereof at a position other than X$_1$-X$_7$ and wherein the second variable domain comprises a heavy chain variable region with the amino acid sequence of one of the sequences of SEQ ID NO: 1-23 with 0-10 preferably 0-5 amino acid insertions, deletions, substitutions, additions or a combination thereof.

The first variable domain preferably comprises a heavy chain variable region with a CDR1 sequence SYGIS (SEQ ID NO: 24); a CDR2 sequence WISAYNGNTNYAQKLQG (SEQ ID NO: 113) and a CDR3 comprising the sequence DRHWHWWLDAFDY (SEQ ID NO: 37) and the second variable domain preferably comprises a heavy chain variable region with a CDR1 sequence SYSMN (SEQ ID NO: 28); a CDR2 sequence WINTYTGDPTYAQGFTG (SEQ ID NO: 29) and a CDR3 sequence ETYYYDRGGYPFDP (SEQ ID NO: 30).

The invention also provides a bispecific antibody of an invention as disclosed herein for use in the treatment of a subject that has a disease involving abserrant cells, such as a tumor.

Also provided is a use of a bispecific antibody of an invention as disclosed herein in the manufacture of a medicament for the treatment of a disease involving aberrant cells, such as a tumor or cancer.

Also provided is a method of treatment of a subject that has a tumor, preferably an EGFR positive tumor, a cMET positive tumor or an EGFR and cMET positive tumor, the method comprising administering the bispecific antibody to the individual in need thereof.

An antibody of an invention as disclosed herein preferably inhibits HGF induced migration of EBC1 cells in a wound healing assay. Preferably the inhibition is better than the combination of cetuximab and MetMab. For example, it is preferred to achieve inhibition via prevention of wound closure in the presence of HGF with or without EGF (HGF is present at 15 ng/ml and EGF, when present, is present in amount of 12.5 ng/ml).

An antibody of an invention disclosed herein inhibits HGF and EGF/HGF induced growth of the EGFR TKI resistant tumor cell lines PC-9 and HCC827 when used in combination with a TKI. The TKI is preferably gefitinib.

An antibody of an invention disclosed herein inhibits HGF induced growth of an HGF responsive cell, preferably of the EGFR TKI resistant tumor cell line PC-9 or HCC827.

An antibody of an invention disclosed herein inhibits EGF induced growth of an EGF responsive cell, without inducing the toxicities such as rash and diarrhea associated with high affinity bivalent EGFR antibodies. This renders the antibody ideally suited for combination with TKI which have its own toxicity profile.

The invention further comprises a pharmaceutical composition that comprises a bispecific antibody disclosed herein.

An antibody of the invention may be used to treat a tumor which is resistant to treatment with an EGFR tyrosine kinase inhibitor, for example resistant to erlotinib, gefitinib, or afatinib, an analogue of erlotinib, gefitinib or afatinib or a combination of one or more of the respective compounds and/or analogues thereof.

Treatment according to the invention may further comprise treatment with an EGFR tyrosine kinase inhibitor for example wherein the EGFR tyrosine kinase inhibitor is erlotinib.

Accordingly, the bispecific antibody of the invention may be administered simultaneously, sequentially or separately with an EGFR tyrosine kinase inhibitor.

The invention further comprises a nucleic acid molecule or a group of nucleic acid molecules that alone or together encode a heavy chain(s) or a heavy chain variable region(s) of a bispecific antibody disclosed herein or a variant thereof. Also provided is a nucleic acid molecule or group of nucleic acid molecules that encode an antibody disclosed herein.

In a preferred embodiment the heavy chain comprises a constant region of an IgG1 antibody, preferably a human IgG1 antibody. The CH2 region of said IgG1 constant region can be engineered to alter ADCC and/or CDC activity of the antibody, or not. In a preferred embodiment, said alteration results in enhanced ADCC and/or CDC activity. In a preferred embodiment the CH3-region of the antibody is engineered to facilitate heterodimerization of heavy chains comprising a first heavy chain that binds EGFR and a second heavy chain binds cMET.

The invention further comprises is a cell comprising one or more nucleic acid molecules that alone or together encode a bispecific antibody or a variant thereof as disclosed herein. Also provided are methods of producing a bispecific antibody or a variant thereof disclosed herein using a cell as described, preferably together with the harvesting of the bispecific antibody or variant thereof from a culture of the cells.

The invention further comprises a cell system that comprises a bispecific antibody or variant thereof disclosed herein.

The invention further provides a cell that expresses the bispecific antibody and/or comprises the nucleic acid molecule(s) that encode said bispecific antibody.

The invention further comprises a bispecific antibody as disclosed herein that further comprises a label, preferably a label for in vivo imaging.

DETAILED DESCRIPTION OF THE INVENTION

EGFR is a member of a family of four receptor tyrosine kinases (RTKs), named Her- or cErbB-1, -2, -3 and -4. The EGFR has an extracellular domain (ECD) that is composed of four sub-domains, two of which are involved in ligand binding and one of which is involved in homo-dimerization and hetero-dimerization Ferguson (2008). The reference numbers used in this section refer to the numbering of the references in the list headed "cited in the specification", which are each incorporated by reference. EGFR integrates extracellular signals from a variety of ligands to yield diverse intracellular responses (Yarden at al. 2001; and Jorrisen et al. 2003). The EGFR is implicated in several human epithelial malignancies, notably cancers of the breast, bladder, non-small cell lung cancer lung, colon, ovarian head and neck and brain. Activating mutations in the gene have been found, as well as over-expression of the receptor and of its ligands, giving rise to autocrine activation loops (for review, see Robertson et al. 2000). This RTK has therefore been extensively used as target for cancer therapy. Both small-molecule inhibitors targeting the RTK and monoclonal antibodies (mAbs) directed to the extracellular ligand-binding domains have been developed and have shown hitherto several clinical successes, albeit mostly for a select group of patients. Database accession numbers for the human EGFR protein and the gene encoding it are (GenBank NM_005228.3). Other database identifiers for the gene and/or protein are HGNC: 3236; Entrez Gene: 1956; Ensembl: ENSG00000146648; OMIM: 131550 and UniProtKB: P00533. The accession numbers are primarily given to provide a further method of identification of EGFR protein as a target, the actual sequence of the EGFR protein bound by an antibody may vary, for instance because of a mutation in the encoding gene such as those occurring in some cancers or the like. Where reference herein is made to EGFR, the reference refers to human EGFR unless otherwise stated. The antigen-binding site that binds EGFR, binds EGFR and a variety of variants thereof such as those expressed on some EGFR positive tumors.

The term "EGFR ligand" as used herein refers to polypeptides which bind and activate EGFR. Examples of EGFR ligands include, but are not limited to EGF, TGF-α, HB-EGF, amphiregulin, betacellulin and epiregulin (for review Olayioye M A et al.; EMBO J (2000) Vol 19: pp 3159-3167). The term includes biologically active fragments and/or variants of a naturally occurring polypeptide cMET, also called tyrosine-protein kinase MET or hepatocyte growth factor receptor (HGFR), is a protein that in humans is encoded by the MET gene. The protein possesses tyrosine kinase activity. The primary single chain precursor protein is post-translationally cleaved to produce the alpha and beta subunits, which are disulfide linked to form the mature receptor.

Aberrantly activated cMET may induce tumor growth, the formation of new blood vessels (angiogenesis) that supply the tumor with nutrients, and cancer spread to other organs (metastasis). cMET is deregulated in many types of human malignancies, including cancers of kidney, liver, stomach, breast, and brain. The cMET gene is known under a number of different names such as MET Proto-Oncogene, Receptor Tyrosine Kinase; Hepatocyte Growth Factor Receptor; Tyrosine-Protein Kinase Met; Scatter Factor Receptor; Proto-Oncogene C-Met; HGF/SF Receptor; HGF Receptor; SF Receptor; EC 2.7.10.1; Met Proto-Oncogene; EC 2.7.10; DFNB97; AUTS9; RCCP2; C-Met; MET; HGFR; External Ids for cMET are HGNC: 7029; Entrez Gene: 4233; Ensembl: ENSG00000105976; OMIM: 164860 and UniProtKB: P08581. The accession numbers are primarily given to provide a further method of identification of cMET protein as a target, the actual sequence of the cMET protein bound by an antibody may vary, for instance because of a mutation in the encoding gene such as those occurring in some cancers or the like. Where reference herein is made to cMET, the reference refers to human cMET unless otherwise stated. The antigen-binding site that binds cMET, binds cMET and a variety of variants thereof such as those expressed on some cMET positive tumors.

An antibody typically recognizes only a part of an antigen. The antigen is typically but not necessarily a protein. The recognition or binding site on an antigen, bound by an antibody is referred to as the epitope, where an epitope may be linear or conformational. Binding of an antibody to an antigen is typically specific. The 'specificity' of an antibody refers to its selectivity for a particular epitope, whereas 'affinity' refers to the strength of the interaction between the antibody's antigen binding site and the epitope it binds.

Exemplary antibodies of an invention disclosed herein binds to EGFR and cMET, preferably human EGFR and human cMET. An EGFR/cMET bispecific antibody of an invention disclosed herein binds to EGFR and, under otherwise identical conditions, at least 100-fold less to the homologous receptors ErbB-2 and ErbB-4 of the same species. An EGFR/cMET bispecific antibody of an invention as disclosed herein binds to cMET and, under otherwise identical conditions, at least 100-fold less to the receptors ErbB-2 and ErbB-4 of the same species. Considering that the receptors are cell surface receptors, the binding may be assessed on cells that express the receptor(s). A bispecific antibody of an invention disclosed herein preferably binds to human, cynomolgus EGFR and/or to mouse EGFR.

An antibody that binds EGFR and cMET may bind other proteins as well if such other proteins contain the same epitope. Hence, the term "binding" does not exclude binding of the antibodies to another protein or protein(s) that contain the same epitope. Such binding is typically referred to as cross-reactivity. An EGFR/cMET bispecific antibody typically does not bind to other proteins than EGFR and/or cMET on the membrane of cells in a post-natal, preferably adult human. An antibody according to an invention disclosed herein is typically capable of binding EGFR with a binding affinity (i.e. equilibrium dissociation constant Kd) of at least $1 \times 10e-6$ M, as outlined in more detail below.

The term "antibody" as used herein means a proteinaceous molecule preferably belonging to the immunoglobulin class of proteins. An antibody typically contains two variable domains that bind an epitope on an antigen. Such domains are derived from or share sequence homology with the variable domain of an antibody. A bispecific antibody of an invention as disclosed herein preferably comprises two variable domains. Antibodies for therapeutic use are preferably as close to natural antibodies of the subject to be treated as possible (for instance human antibodies for human subjects). Antibody binding can be expressed in terms of specificity and affinity. The specificity determines which antigen or epitope thereof is specifically bound by the binding domain. Typically, antibodies for therapeutic applications can have affinities of up to $1 \times 10e-10$ M or higher. Antibodies such as bispecific antibodies of an invention disclosed herein preferably comprise the constant domains (Fc part) of a natural antibody. An antibody of invention as disclosed herein is typically a bispecific full length antibody, preferably of the human IgG subclass. Preferably, the antibodies of the present invention are of the human IgG1 subclass. Such antibodies of invention as disclosed herein can have good ADCC properties, have a favorable half-life upon in vivo administration to humans and CH3 engineering technology exists that can provide for modified heavy chains that preferentially form hetero-dimers over homo-dimers upon co-expression in clonal cells. ADCC activity of an antibody can also be improved through techniques known to persons of skill in the art.

An antibody of an invention as disclosed herein is preferably a "full length" antibody. The term 'full length' according to an invention as disclosed herein is defined as comprising an essentially complete antibody, which however does not necessarily have all functions of an intact antibody. For the avoidance of doubt, a full length antibody contains two heavy and two light chains. Each chain contains constant (C) and variable (V) regions, which can be broken down into domains designated CH1, CH2, CH3, VH, and CL, VL. Typically, an antibody binds to antigen via the variable domains contained in the Fab portion, and after binding can interact with molecules and cells of the immune system through the constant domains, mostly through the Fc portion. Full length antibodies according to an invention disclosed herein encompasses antibodies wherein mutations may be present that provide desired characteristics. Antibodies wherein one or several amino acid residues are deleted, without essentially altering the specificity and/or affinity characteristics of the resulting antibody are embraced within the term "full length antibody". For instance, an IgG antibody can have 1-20 amino acid residue insertions, deletions, or substitutions or a combination thereof in the constant region.

An antibody of an invention as disclosed herein is preferably a bispecific IgG antibody, preferably a bispecific full length IgG1 antibody and more preferably a human IgG1. Full length IgG antibodies are preferred because of their typically favorable half-life and the desire to stay as close to fully autologous (human) molecules for reasons of immunogenicity. In some embodiments, an antibody of the invention is a full length IgG1, a full length IgG2, a full length IgG3 or a full length IgG4 antibody.

An invention disclosed herein includes a bispecific antibody that comprises a first variable domain that can bind an extracellular part of EGFR and a second variable domain that can bind an extracellular part of cMET wherein the first variable domain binds EGFR with an affinity that is less than cetuximab which has a Kd of 0.39 nM (Kim et al 2008). The first variable domain preferably binds EGFR with a Kd that is between 10e-6 M and 10e-9 M. The Kd is preferably between 10e-7 M and 10e-9 M, preferably between 10e-8 M and 10e-9 M. The second variable domain preferably binds cMET with a Kd that is 10e-7 M or less. The Kd is preferably between 10e-7 M and 10e-11 M. The second variable domain preferably has a higher affinity for cMET than the first variable domain has for EGFR. In other words in this preferred embodiment the Kd of the antibody for cMET is less than the Kd of the antibody for EGFR. In a preferred embodiment the Kd of the antibody for cMET is at least 5 and preferably at least 10× less than the Kd of the antibody for EGFR. In this embodiment the values for the Kd for the respective antigens are preferably as indicated in this paragraph. This appropriate imbalance of affinity permits the bispecific antibody of an invention disclosed herein to dock on a cell preferably via binding to EGFR and block the binding the ligand HGF to cMET.

The variable domain that can bind EGFR is preferably a variable domain that, in the context of a bivalent monospecific antibody, inhibits EGF induced death of A431 cells. Inhibition of EGF induced cell death is preferably measured at a concentration of 10 nM EGF and 10 µg/ml antibody. Inhibition of EGF induced cell death is detectable by comparing the number of cells with and without the antibody after a 3-7 of day of culture of the A431 under conditions that are permissive (but for the EGF) for A431cell growth. Without being bound by theory it is believed that the binding of the antibody to EGFR blocks the binding of EGF to EGFR. The variable domain that can bind EGFR is preferably a variable domain that, in the context of a bivalent monospecific antibody, inhibits EGF induced proliferation of BxPC3 or BxPC3-luc2 cells.

An antibody of an invention as disclosed herein preferably inhibits HGF induced migration of EBC1 cells in a wound healing assay. The wound healing assay is preferably an assay as described in the examples. The inhibition of wound healing is better than the combination of cetuximab and MetMab. The inhibition is typically not 100%. Some wound healing also occurs in the presence of an inhibitory antibody.

An antibody of an invention as disclosed herein inhibits HGF and EGF/HGF induced growth of the EGFR TKI resistant tumor cell lines PC-9 and HCC827 when used in combination with a TKI. The TKI is preferably gefitinib.

An antibody of an invention as disclosed herein inhibits HGF induced growth of an HGF responsive cell, preferably of the EGFR TKI resistant tumor cell line PC-9 or HCC827.

An antibody of an invention as disclosed herein inhibits EGF induced growth of an EGF responsive cell, without inducing significant common toxicities such as rash and diarrhea, etc. associated with high affinity bivalent EGFR antibodies. This renders the antibody ideally suited for combination with TKIs which have their own toxicity profile.

The induced growth is preferably measured using an assay as described in the examples. The inhibition is typically not 100%. Some growth occurs also in the context of an inhibitory antibody.

The variable domain that can bind EGFR and that comprises the amino acid sequence of the MF3370 or variant thereof as indicated herein, preferably binds to EGFR domain III (see table 4 of international patent application PCT/NL2015/050124; WO2015/130172 which is incorporated by reference herein). The binding of the variable domain to EGFR can be inhibited by cetuximab. The variable domain binds an epitope that is different from the epitope that is recognized by cetuximab and zalutumumab. For example, the variable domain binds to mouse EGFR whereas cetuximab and zalutumumab do not, indicating that one or more of the residues that differ between mouse and human EGFR domain III play a role in cetuximab and zalutumumab binding, but not in an antibody of an invention described herein. An advantage of a bispecific antibody of an invention described herein having human, mouse, cynomolgus EGFR cross-reactivity is that it permits the use of xenograft studies with human cancer models, which may be more predictive with respect to effectivity and toxicity as the antibody also binds to the normal mouse cells that have the receptor, while also being capable of use in cynomolgus toxicology studies. In one aspect the invention provides a bispecific antibody that comprises a first variable domain that can bind an extracellular part of human epidermal growth factor receptor (EGFR) and a second variable domain that can bind an extracellular part of human MET Proto-Oncogene, Receptor Tyrosine Kinase (cMET), wherein said first variable domain can also bind mouse EGFR, cynomolgus EGFR or both.

A cMET variable domain preferably comprises an amino acid sequence of the MF4356 or variant thereof as indicated herein, and preferably blocks the binding of the antibody MetMab to cMET. The variable domain preferably blocks the binding of the ligand HGF to cMET. The variable domain blocks the binding of the antibody MetMab to cMET when the binding of MetMab to cMET at half-maximum binding conditions is reduced by at least 40% and preferably at least 60% in the presence of a saturating amount of said variable domain. The variable domain is preferably provided in the context of a bivalent monospecific antibody. The cMET variable domain can preferably bind the sema domain of cMET. The cMET variable domain of the invention may compete with 5D5 for binding cMET or not compete with reported anti-cMET reference antibodies, such as 5D5. See Table 2.

A variable domain of an invention disclosed herein can bind EGFR (the first variable domain) and preferably comprises a heavy chain variable region with a CDR1 sequence SYGIS (SEQ ID NO: 24); a CDR2 sequence WISAYX$_1$X$_2$NTNYAQKLQG (SEQ ID NO: 25) and a CDR3 comprising the sequence X$_3$X$_4$X$_5$X$_6$HWWLX$_7$A (SEQ ID NO: 26) wherein X$_1$=N or S; X$_2$=A or G; X$_3$=D or G; X$_4$=R, S or Y; X$_5$=H, L or Y; X$_6$=D or W and X$_7$=D or G.

X$_{1-7}$ is preferably:
X$_1$=N; X$_2$=G; X$_3$=D; X$_4$=S; X$_5$=Y; X$_6$=W and X$_7$=G; WISAYNGNTNYAQKLQG (SEQ ID NO:113) and DSYWHWWLGA (SEQ ID NO:153),
X$_1$=N; X$_2$=A; X$_3$=D; X$_4$=S; X$_5$=Y; X$_6$=W and X$_7$=G; WISAYNANTNYAQKLQG (SEQ ID NO:25) and DSYWHWWLGA (SEQ ID NO:153),
X$_1$=S; X$_2$=G; X$_3$=D; X$_4$=S; X$_5$=Y; X$_6$=W and X$_7$=G; WISAYSGNTNYAQKLQG (SEQ ID NO:140) and DSYWHWWLGA (SEQ ID NO:153),
X$_1$=N; X$_2$=G; X$_3$=D; X$_4$=R; X$_5$=H; X$_6$=W and X$_7$=D; WISAYNGNTNYAQKLQG (SEQ ID NO:113) and DRHWHWWLDA (SEQ ID NO:139),
X$_1$=N; X$_2$=A; X$_3$=D; X$_4$=R; X$_5$=H; X$_6$=W and X$_7$=D; WISAYNANTNYAQKLQG (SEQ ID NO:25) and DRHWHWWLDA (SEQ ID NO:139),
X$_1$=S; X$_2$=G; X$_3$=D; X$_4$=R; X$_5$=H; X$_6$=W and X$_7$=D; WISAYSGNTNYAQKLQG (SEQ ID NO:140) and DRHWHWWLDA (SEQ ID NO:139),
X$_1$=N; X$_2$=G; X$_3$=G; X$_4$=Y; X$_5$=L; X$_6$=D and X$_7$=G; WISAYNGNTNYAQKLQG (SEQ ID NO:113) and GYLDHWWLGA (SEQ ID NO:154),
X$_1$=N; X$_2$=A; X$_3$=G; X$_4$=Y; X$_5$=L; X$_6$=D and X$_7$=G; WISAYNANTNYAQKLQG (SEQ ID NO:25) and GYLDHWWLGA (SEQ ID NO:154), or
X$_1$=S; X$_2$=G; X$_3$=G; X$_4$=Y; X$_5$=L; X$_6$=D and X$_7$=G WISAYSGNTNYAQKLQG (SEQ ID NO:140) and GYLDHWWLGA (SEQ ID NO:154).

In a preferred embodiment
X$_1$=N; X$_2$=G; X$_3$=D; X$_4$=R; X$_5$=H; X$_6$=W and X$_7$=D; WISAYNGNTNYAQKLQG (SEQ ID NO: 113) and DRHWHWWLDA (SEQ ID NO: 139),
X$_1$=N; X$_2$=A; X$_3$=D; X$_4$=R; X$_5$=H; X$_6$=W and X$_7$=D; WISAYNANTNYAQKLQG (SEQ ID NO:25) and DRHWHWWLDA (SEQ ID NO: 139),
or
X$_1$=S; X$_2$=G; X$_3$=D; X$_4$=R; X$_5$=H; X$_6$=W and X$_7$=D; WISAYSGNTNYAQKLQG (SEQ ID NO: 140) and DRHWHWWLDA (SEQ ID NO: 139).

Preferably X$_1$=N; X$_2$=G; X$_3$=D; X$_4$=R; X$_5$=H; X$_6$=W and X$_7$=D;
WISAYNGNTNYAQKLQG (SEQ ID NO: 113) and DRHWHWWLDA (SEQ ID NO: 139).

The amino acids following the amino acid A in the sequence X$_3$X$_4$X$_5$X$_6$HWWLX$_7$A (SEQ ID NO: 26) in the CDR3 sequence of the first variable domain can vary. The amino acid sequence following the sequence X$_3$X$_4$X$_5$X$_6$HWWLX$_7$A (SEQ ID NO: 26) can be FDY. The CDR3 of the first variable domain preferably comprises the sequence X$_3$X$_4$X$_5$X$_6$HWWLX$_7$AF (SEQ ID NO: 32), preferably X$_3$X$_4$X$_5$X$_6$HWWLX$_7$AFD (SEQ ID NO: 33), more preferably X$_3$X$_4$X$_5$X$_6$HWWLX$_7$AFDY (SEQ ID NO: 34).

The first variable domain preferably comprises a heavy chain variable region with a CDR1 sequence SYGIS (SEQ ID NO: 24); a CDR2 sequence WISAYNGNTNYAQKLQG (SEQ ID NO: 113) and a CDR3 sequence X$_3$X$_4$X$_5$X$_6$HWWLX$_7$A (SEQ ID NO: 26).

The first variable domain preferably comprises a heavy chain variable region with a CDR1 sequence SYGIS (SEQ ID NO: 24); a CDR2 sequence WISAYNGNTNYAQKLQG (SEQ ID NO: 113) and a CDR3 comprising the sequence DRHWHWWLDA (SEQ ID NO: 139). The amino acids following the sequence LDA in the CDR3 sequence of the first variable domain can vary. The amino acid sequence following the sequence LDA can be FDY. The CDR3 of the first variable domain preferably comprises the sequence DRHWHWWLDAF (SEQ ID NO: 35), preferably DRHWHWWLDAFD (SEQ ID NO: 36), more preferably DRHWHWWLDAFDY (SEQ ID NO: 37).

The first variable domain preferably comprises a heavy chain variable region with the amino acid sequence of MF3353; MF8229; MF8228; MF3370; MF3233; MF8232; MF3393; MF8227 or MF8226 as depicted in FIG. 7 having at most 10, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the indicated sequence. In a preferred embodiment the first variable domain comprises a heavy chain variable region with the amino acid sequence of MF3353; MF8229; MF8228; MF3370; MF3233; MF8232; MF3393; MF8227 or MF8226 as depicted in FIG. 7.

The variable domain that can bind cMET (the second variable domain) preferably comprises a heavy chain variable region that comprises the amino acid sequence of one of the sequences of SEQ ID NO: 1-23 with 0-10 preferably 0-5 amino acid insertions, deletions, substitutions, additions or a combination thereof. The heavy chain variable region of the second variable domain preferably comprises the amino acid sequence of one of the sequences of SEQ ID NO: 1-3; 7; 8; 10; 13; 15; 16; 17; 21; 22 or 23 with 0-10 preferably 0-5 amino acid insertions, deletions, substitutions, additions or a combination thereof. The heavy chain variable region of the second variable domain preferably comprises the amino acid sequence of one of the sequences of SEQ ID NO: 2; 7; 8; 10; 13 or 23 with 0-10 preferably 0-5 amino acid insertions, deletions, substitutions, additions or a combination thereof. The heavy chain variable region of the second variable domain preferably comprises the amino acid sequence of the sequence of SEQ ID NO: 13 or SEQ ID NO: 23 with 0-10, preferably 0-5 amino acid insertions, deletions, substitutions, additions or a combination thereof.

In a preferred embodiment the first variable domain comprises a heavy chain variable region with a CDR1 sequence SYGIS (SEQ ID NO: 24); a CDR2 sequence WISAYNGNTNYAQKLQG (SEQ ID NO: 113) and a CDR3 comprising the sequence DRHWHWWLDA (SEQ ID NO: 35), preferably DRHWHWWLDAFDY (SEQ ID NO: 37) and wherein the second variable domain comprises a heavy chain variable region with a CDR1 sequence SYSMN (SEQ ID NO: 28); a CDR2 sequence WINTYTGDPTYAQGFTG (SEQ ID NO: 29) and a CDR3 sequence ETYYYDRGGYPFDP (SEQ ID NO: 30). The CDR1, CDR2 and CDR3 of a light chain of the first and second variable domain preferably comprises respectively the amino acid sequence CDR1-QSISSY (SEQ ID NO: 38), CDR2-AAS, CDR3-QQSYSTP (SEQ ID NO: 39), i.e. the CDRs of IGKV1-39 (according to IMGT).

In a preferred embodiment the first variable domain comprises a heavy chain variable region with a CDR1 sequence SYGIS (SEQ ID NO: 24); a CDR2 sequence WISAYNGNTNYAQKLQG (SEQ ID NO: 113) and a CDR3 comprising the sequence DRHWHWWLDA (SEQ ID NO: 139) and wherein the second variable domain comprises a heavy chain variable region with a CDR1 sequence TYSMN (SEQ ID NO:152); a CDR2 sequence WINTYTGDPTYAQGFTG (SEQ ID NO: 29) and a CDR3 comprising the sequence ETYFYDRGGYPFDP (SEQ ID NO: 31). The CDR1, CDR2 and CDR3 of a light chain of the first and second variable domain preferably comprises respectively the amino acid sequence CDR1-QSISSY (SEQ ID NO: 38), CDR2-AAS, CDR3-QQSYSTP (SEQ ID NO: 39), i.e. the CDRs of IGKV1-39 (according to IMGT).

A bispecific antibody that comprises a first variable domain that can bind an extracellular part of EGFR and a second variable domain that can bind an extracellular part of cMET wherein the first variable domain comprises a heavy chain variable region with a CDR1 sequence SYGIS (SEQ ID NO: 24); a CDR2 sequence WISAYNANTNYAQKLQG (SEQ ID NO: 25) and a CDR3 comprising the sequence DRHWHWWLDA (SEQ ID NO: 139) and wherein the second variable domain comprises a heavy chain variable region with a CDR1 sequence SYSMN (SEQ ID NO: 28); a CDR2 sequence WINTYTGDPTYAQGFTG (SEQ ID NO: 29) and a CDR3 sequence ETYYYDRGGYPFDP (SEQ ID NO: 30). The CDR1, CDR2 and CDR3 of a light chain of the first and second variable domain preferably comprises respectively the amino acid sequence CDR1-QSISSY (SEQ ID NO: 38), CDR2-AAS, CDR3-QQSYSTP (SEQ ID NO: 39), i.e. the CDRs of IGKV1-39 (according to IMGT).

A bispecific antibody that comprises a first variable domain that can bind an extracellular part of EGFR and a second variable domain that can bind an extracellular part of cMET wherein the first variable domain comprises a heavy chain variable region with a CDR1 sequence SYGIS (SEQ ID NO: 24); a CDR2 sequence WISAYNANTNYAQKLQG (SEQ ID NO: 25) and a CDR3 comprising the sequence DRHWHWWLDA (SEQ ID NO: 139) and wherein the second variable domain comprises a heavy chain variable region with a CDR1 sequence TYSMN (SEQ ID NO: 152); a CDR2 sequence WINTYTGDPTYAQGFTG (SEQ ID NO: 29) and a CDR3 comprising the sequence ETYFYDRGGYPFDP (SEQ ID NO: 31). The CDR1, CDR2 and CDR3 of a light chain of the first and second variable domain preferably comprises respectively the amino acid sequence CDR1-QSISSY (SEQ ID NO: 38), CDR2-AAS, CDR3-QQSYSTP (SEQ ID NO: 39), i.e. the CDRs of IGKV1-39 (according to IMGT).

A bispecific antibody that comprises a first variable domain that can bind an extracellular part of EGFR and a second variable domain that can bind an extracellular part of cMET wherein the first variable domain comprises a heavy chain variable region with a CDR1 sequence SYGIS (SEQ ID NO: 24); a CDR2 sequence WISAYSGNTNYAQKLQG (SEQ ID NO: 140) and a CDR3 comprising the sequence DRHWHWWLDA (SEQ ID NO: 139) and wherein the second variable domain comprises a heavy chain variable region with a CDR1 sequence SYSMN (SEQ ID NO: 28); a CDR2 sequence WINTYTGDPTYAQGFTG (SEQ ID NO: 29) and a CDR3 sequence ETYYYDRGGYPFDP (SEQ ID NO: 30). The CDR1, CDR2 and CDR3 of a light chain of the first and second variable domain preferably comprises respectively the amino acid sequence CDR1-QSISSY (SEQ ID NO: 38), CDR2-AAS, CDR3-QQSYSTP (SEQ ID NO: 39), i.e. the CDRs of IGKV1-39 (according to IMGT).

A bispecific antibody that comprises a first variable domain that can bind an extracellular part of EGFR and a second variable domain that can bind an extracellular part of cMET wherein the first variable domain comprises a heavy chain variable region with a CDR1 sequence SYGIS (SEQ ID NO: 24); a CDR2 sequence WISAYSGNTNYAQKLQG (SEQ ID NO: 140) and a CDR3 comprising the sequence DRHWHWWLDA (SEQ ID NO: 139) and wherein the second variable domain comprises a heavy chain variable region with a CDR1 sequence TYSMN (SEQ ID NO: 152); a CDR2 sequence WINTYTGDPTYAQGFTG (SEQ ID NO: 29) and a CDR3 comprising the sequence ETYFYDRGGYPFDP (SEQ ID NO: 31). The CDR1, CDR2 and CDR3 of a light chain of the first and second variable domain preferably comprises respectively the amino acid sequence CDR1-QSISSY (SEQ ID NO: 38), CDR2-AAS, CDR3-QQSYSTP (SEQ ID NO: 39), i.e. the CDRs of IGKV1-39 (according to IMGT).

The CDR1, CDR2 and CDR3 of a light chain of the first and second variable domain as described herein preferably comprises respectively the amino acid sequence CDR1-QSISSY (SEQ ID NO: 38), CDR2-AAS, CDR3-QQSYSTP (SEQ ID NO: 39), i.e. the CDRs of IGKV1-39 (according to IMGT). In some embodiments of a bispecific antibody as described herein the first and second variable domain comprise a common light chain, preferably a light chain of FIG. 9B.

In another preferred embodiment an EGFR/cMET bispecific antibody comprises a first variable domain that can bind an extracellular part of human EGFR that comprises the CDR1, CDR2 and CDR3 of the heavy chain variable region of MF3755 depicted in FIG. 1 and a second variable domain that can bind an extracellular part of human cMET that comprises the CDR1, CDR2 and CDR3 of the heavy chain variable region of MF4297 depicted in FIG. 1. The light chain variable region in said first and second variable domain is preferably a common light chain variable region as described herein. The CDR1, CDR2 and CDR3 of a light chain of the first and second variable domain preferably comprises respectively the amino acid sequence CDR1-QSISSY (SEQ ID NO: 38), CDR2-AAS, CDR3-QQSYSTP (SEQ ID NO: 39), i.e. the CDRs of IGKV1-39 (according to IMGT). In a preferred embodiment the antibody comprises a heavy chain variable region with the amino acid sequence of MF3755 as depicted in FIG. 1 having at most 10, preferably 0, 1, 2, 3, 4, 5, 6, 7, 8, 9 or 10 and preferably having 0, 1, 2, 3, 4 or 5 amino acid insertions, deletions, substitutions or a combination thereof with respect to the indicated sequence. In a preferred embodiment the first variable domain comprises a heavy chain variable region with the amino acid sequence of MF3755 as depicted in FIG. 1. The variable domain that can bind cMET (the second variable domain) preferably comprises a heavy chain variable region that comprises the amino acid sequence of MF4297 as depicted in FIG. 1 with 0-10 preferably 0-5 amino acid insertions, deletions, substitutions, additions or a combination thereof. The heavy chain variable region of the second variable domain preferably comprises the amino acid sequence of MF4297 as depicted in FIG. 1.

The term 'bispecific' (bs) in the context of the present invention means that an antibody is capable of binding two different targets or two epitopes on the same target, for example, where one variable domain of the antibody (as defined above) binds to an epitope on EGFR and a second variable domain binds to an epitope on cMET. Depending on the expression level, (sub-)cellular localization and stoichiometry of the two antigens recognized by a bispecific antibody, both Fab arms of the antibody may or may not simultaneously bind their epitope. One arm of the bispecific antibody typically contains the variable domain of one antibody and the other arm contains the variable domain of another antibody (i.e. one arm of the bispecific antibody is formed by one heavy chain paired with one light chain whereas the other arm is formed by a different heavy chain paired with a light chain). Thus, the stoichiometry of a preferred bispecific antibody of an invention disclosed herein is 1:1, EGFR:cMET binding.

The heavy chain variable regions of the bispecific antibody of an invention as disclosed herein are typically different from each other, whereas the light chain variable regions are preferably the same. A bispecific antibody wherein the different heavy chain variable regions are associated with the same light chain variable region is also referred to as a bispecific antibody with a common light chain variable region (cLcv). It is preferred that the light chain constant region is also the same. Such bispecific antibodies are referred to as having a common light chain (cLc). Further provided is therefore a bispecific antibody according to an invention as disclosed herein, wherein both arms comprise a common light chain.

The term 'common light chain' according to an invention disclosed herein refers to two or more light chains in a bispecific antibody which may be identical or have some amino acid sequence differences while the binding specificity of the full length antibody is not affected. It is for instance possible within the scope of the definition of common light chains as used herein, to prepare or find light chains that are not identical but still functionally equivalent, e.g., by introducing and testing conservative amino acid changes, changes of amino acids in regions that do not or only partly contribute to binding specificity when paired with the heavy chain, and the like. The terms 'common light chain', 'common LC', 'cLC', 'single light chain' with or without the addition of the term 'rearranged' are all used herein interchangeably. The terms 'common light chain variable region', 'common VL', 'common LCv', 'cLCv', 'single VL' with or without the addition of the term 'rearranged' are all used herein interchangeably. It is a preferred aspect of the present invention that a bispecific antibody has a common light chain (variable region) that can combine with at least two, and preferably a plurality of heavy chains (variable regions) of different binding specificity to form antibodies with functional antigen binding domains (e.g., WO2009/157771). The common light chain (variable region) is preferably a human light chain (variable region). A common light chain (variable region) preferably has a germline sequence. A preferred germline sequence is a light chain variable region that has good thermodynamic stability, yield and solubility. A preferred germline light chain is O12. A common light chain preferably comprises the light chain encoded by a germline human Vk gene segment, and is preferably the rearranged germline human kappa light chain IgV$_K$1-39*01/IGJ$_K$1*01 (FIG. 9A). The common light chain variable region is preferably the variable region of the rearranged germline human kappa light chain IgV$_K$1-39*01/IGJ$_K$1*01. A common light chain preferably comprises a light chain variable region as depicted in FIG. 9B, or 9D with 0-5 amino acid insertions, deletions, substitutions, additions or a combination thereof. The common light preferably further comprises a light chain constant region, preferably a kappa light chain constant region. A nucleic acid that encodes the common light chain can be codon optimized for the cell system used to express the common light chain protein. The encoding nucleic acid can deviate from a germ-line nucleic acid sequence.

In a preferred embodiment the light chain comprises a light chain region comprising the amino acid sequence of an O12/IgV$_K$1-39*01 gene segment as depicted in FIG. 9A with 0-10, preferably 0-5 amino acid insertions, deletions, substitutions, additions or a combination thereof. The phrase "O12 light chain" will be used throughout the specification as short for "a light chain comprising a light chain variable region comprising the amino acid sequence of an O12/IgV$_K$1-39*01 gene segment as depicted in FIG. 9A with 0-10, preferably 0-5 amino acid insertions, deletions, substitutions, additions or a combination thereof. IgV$_K$1-39 is short for Immunoglobulin Variable Kappa 1-39 Gene. The gene is also known as Immunoglobulin Kappa Variable 1-39; IGKV139; IGKV1-39; 012a or O12. External Ids for the gene are HGNC: 5740; Entrez Gene: 28930; Ensembl: ENSG00000242371. A preferred amino acid sequence for IgV$_K$1-39 is given in FIG. 9E. This lists the sequence of the V-region. The V-region can be combined with one of five J-regions. FIGS. 9B and 9D describe two preferred sequences for IgV$_K$1-39 in combination with a J-region. The joined sequences are indicated as IGKV1-39/jk1 and IGKV1-39/jk5; alternative names are IgV$_K$1-39*01/IGJ$_K$1*01 or IgV$_K$1-39*01/IGJ$_K$5*01 (nomenclature according to the IMGT database worldwide web at imgt.org).

It is preferred that the O12/IgV$_K$1-39*01 comprising light chain variable region is a germline sequence. It is further preferred that the IGJ$_K$1*01 or/IGJ$_K$5*01 comprising light chain variable region is a germline sequence. In a preferred embodiment, the IGKV1-39/jk1 or IGKV1-39/jk5 light chain variable regions are germline sequences.

In a preferred embodiment the light chain variable region comprises a germline O12/IgV$_K$1-39*01. In a preferred embodiment the light chain variable region comprises the kappa light chain IgV$_K$1-39*01/IGJ$_K$1*01 or IgV$_K$1-39*01/IGJ$_K$5*01. In a preferred embodiment a IgV$_K$1-39*01/IGJ$_K$1*01. The light chain variable region preferably comprises a germline kappa light chain IgV$_K$1-39*01/IGJ$_K$1*01 or germline kappa light chain IgV$_K$1-39*01/IGJ$_K$5*01, preferably a germline IgV$_K$1-39*01/IGJ$_K$1*01.

Mature B-cells that produce an antibody with an O12 light chain often produce a light chain that has undergone one or more mutations with respect to the germline sequence, i.e. the normal sequence in non-lymphoid cells of the organism. The process that is responsible for these mutations is often referred to as somatic (hyper)mutation. The resulting light chain is referred to as an affinity matured light chain. Such light chains, when derived from an O12 germline sequence are O12-derived light chains. In this specification, the phrase "common light chain" will include "common light chain derived light chains and the phrase "O12 light chains" will include O12-derived light chains. The mutations that are introduced by somatic hypermutation can also be introduced artificially in the lab. In the lab also other mutations can be introduced without affecting the properties of the light chain in kind, not necessarily in amount. A light chain is at least an O12 light chain if it comprises a sequence as depicted in FIG. 9A, FIG. 9B; FIG. 9D or FIG. 9E with 0-10, preferably 0-5 amino acid insertions, deletions, substitutions, additions or a combination thereof. In a preferred embodiment the O12 light chain is a light chain comprising a sequence as depicted in FIG. 9A; 9B; 9D or 9E with 0-9, 0-8, 0-7, 0-6, 0-5, 0-4 amino acid insertions, deletions, substitutions, additions or a combination thereof. In a preferred embodiment the O12 light chain is a light chain comprising a sequence as depicted in FIG. 9A, FIG. 9B; FIG. 9D or FIG. 9E with 0-5, preferably 0-4, more preferably 0-3 amino acid insertions, deletions, substitutions, additions or a combination thereof. In a preferred embodiment the O12 light chain is a light chain comprising a sequence as depicted in FIG. 9A, FIG. 9B; FIG. 9D or FIG. 9E with 0-2, more preferably 0-1, most preferably 0 amino acid insertions, deletions, substitutions, additions or a combination thereof. In a preferred embodiment the O12 light chain is a light chain comprising a sequence as depicted in FIG. 9A or FIG. 9B with the mentioned amino acid insertions, deletions, substitutions, additions or a combination thereof. In a preferred embodiment the light chain comprises the sequence of FIG. 9A. In a preferred embodiment the light chain variable region comprises the sequence of FIG. 9B. The mentioned 1, 2, 3, 4 or 5 amino acid substitutions are preferably conservative amino acid substitutions, the insertions, deletions, substitutions or combination thereof are preferably not in the CDR3 region of the VL chain, preferably not in the CDR1, CDR2 or CDR3 region or FR4 region of the VL chain.

The common light chain can have a lambda light chain and this is therefore also provided in the context of an invention as disclosed herein, however a kappa light chain is preferred. The constant part of a common light chain of an invention as disclosed herein can be a constant region of a kappa or a lambda light chain. It is preferably a constant region of a kappa light chain, preferably wherein said common light chain is a germline light chain, preferably a rearranged germline human kappa light chain comprising the IgVK1-39 gene segment, most preferably the rearranged germline human kappa light chain IgVK1-39*01/IGJK1*01 (FIG. 9). The terms rearranged germline human kappa light chain IgV$_K$1-39*01/IGJ$_K$1*01, IGKV1-39/IGKJ1, huV$_K$1-39 light chain or in short huV$_K$1-39, or simply 1-39 are used interchangeably throughout the application.

A cell that produces a common light chain can produce for instance rearranged germline human kappa light chain IgV$_K$1-39*01/IGJ$_K$1*01 and a light chain comprising the variable region of the mentioned light chain fused to a lambda constant region.

In a preferred embodiment the light chain variable region comprises the amino acid sequence DIQMT QSPSS LSASV GDRVT ITCRA SQSIS SYLNW YQQKP GKAPK LLIYA ASSLQ SGVPS RFSGS GSGTD FTLTI SSLQP EDFAT YYCQQ SYSTP PTFGQ GTKVE IK (SEQ ID NO: 40) or DIQMT QSPSS LSASV GDRVT ITCRA SQSIS SYLNW YQQKP GKAPK LLIYA ASSLQ SGVPS RFSGS GSGTD FTLTI SSLQP EDFAT YYCQQ SYSTP PITFG QGTRL EIK (SEQ ID NO: 41) with 0-10, preferably 0-5 amino acid insertions, deletions, substitutions, additions or a combination thereof. In a preferred embodiment the light chain variable region comprises 0-9, 0-8, 0-7, 0-6, 0-5, 0-4, preferably 0-3, preferably 0-2, preferably 0-1 and preferably 0 amino acid insertions, deletions, substitutions, additions with respect to the indicated amino acid sequence, or a combination thereof. A combination of an insertion, deletion, addition or substitution is a combination as claimed if aligned sequences do not differ at more than 5 positions. In a preferred embodiment the light chain variable region comprises the amino acid sequence DIQMT QSPSS LSASV GDRVT ITCRA SQSIS SYLNW YQQKP GKAPK LLIYA ASSLQ SGVPS RFSGS GSGTD FTLTI SSLQP EDFAT YYCQQ SYSTP PTFGQ GTKVE IK (SEQ ID NO: 40) or DIQMT QSPSS LSASV GDRVT ITCRA SQSIS SYLNW YQQKP GKAPK LLIYA ASSLQ SGVPS RFSGS GSGTD FTLTI SSLQP EDFAT YYCQQ SYSTP PITFG QGTRL EIK (SEQ ID NO: 41). In a preferred embodiment the light chain variable region comprises the amino acid sequence DIQMT QSPSS LSASV GDRVT ITCRA SQSIS SYLNW YQQKP GKAPK LLIYA ASSLQ SGVPS RFSGS GSGTD FTLTI SSLQP EDFAT YYCQQ SYSTP PTFGQ GTKVE IK (SEQ ID NO: 40). In another preferred embodiment the light chain variable region comprises the amino acid sequence DIQMT QSPSS LSASV GDRVT ITCRA SQSIS SYLNW YQQKP GKAPK LLIYA ASSLQ SGVPS RFSGS GSGTD FTLTI SSLQP EDFAT YYCQQ SYSTP PITFG QGTRL EIK (SEQ ID NO: 41).

The amino acid insertions, deletions, substitutions, additions or combination thereof are preferably not in the CDR3 region of the light chain variable region, preferably not in the CDR1 or CDR2 region of the light chain variable region. In a preferred embodiment the light chain variable region does not comprise a deletion, addition or insertion with respect to the sequence indicated. In this embodiment the heavy chain variable region can have 0-5 amino acid substitutions with respect to the indicated amino acid sequence. An amino acid substitution is preferably a conservative amino acid substitution. The CDR1, CDR2 and CDR3 of a light chain of an antibody of the invention preferably comprises respectively the amino acid sequence CDR1-QSISSY (SEQ ID NO: 38), CDR2-AAS, CDR3-QQSYSTP (SEQ ID NO: 39), i.e. the CDRs of IGKV1-39 (according to IMGT).

Bispecific antibodies as described herein preferably have one heavy chain variable region/light chain variable region (VH/VL) combination that binds an extracellular part of EGFR and a second VH/VL combination that binds an extracellular of cMET. In a preferred embodiment the VL in said first VH/VL combination is similar to the VL in said second VH/VL combination. In a more preferred embodiment, the VLs in the first and second VH/VL combinations are identical. In a preferred embodiment, the bispecific antibody is a full length antibody which has one heavy/light (H/L) chain combination that binds an extracellular part of EGFR and one H/L chain combination that binds an extracellular part of cMET. In a preferred embodiment the light chain in said first H/L chain combination is similar to the light chain in said second H/L chain combination. In a more preferred embodiment, the light chains in the first and second H/L chain combinations are identical.

Several methods have been published to produce a host cell whose expression favors the production of the bispecific antibody or vice versa, the monospecific antibodies. In the present invention it is preferred that the cellular expression of the antibody molecules is favored toward the production of the bispecific antibody over the production of the respective monospecific antibodies. Such is typically achieved by modifying the constant region of the heavy chains such that they favor heterodimerization (i.e. dimerization with the heavy chain of the other heavy/light chain combination) over homodimerization. In a preferred embodiment the bispecific antibody of an invention as disclosed herein comprises two different immunoglobulin heavy chains with compatible heterodimerization domains. Various compatible heterodimerization domains have been described in the art. The compatible heterodimerization domains are preferably compatible immunoglobulin heavy chain CH3 heterodimerization domains. When wildtype CH3 domains are used, co-expression of two different heavy chains (A and B) and a common light chain will result in three different antibody species, AA, AB and BB. AA and BB are designations for the two mono-specific, bivalent antibodies, and AB is a designation for the bispecific antibody. To increase the percentage of the desired bispecific product (AB) CH3 engineering can be employed, or in other words, one can use heavy chains with compatible hetero-dimerization domains, as defined hereunder. The art describes various ways in which such hetero-dimerization of heavy chains can be achieved. One way is to generate 'knob into hole' bispecific antibodies.

The term 'compatible hetero-dimerization domains' as used herein refers to protein domains that are engineered such that engineered domain A' will preferentially form heterodimers with engineered domain B' and vice versa, homo-dimerization between A'-A' and B'-B' is diminished.

In U.S. Ser. No. 13/866,747 (now issued as U.S. Pat. No. 9,248,181), U.S. Ser. No. 14/081,848 (now issued as U.S. Pat. No. 9,358,286) and PCT/NL2013/050294 (published as WO2013/157954; incorporated herein by reference) methods and means are disclosed for producing bispecific antibodies using compatible heterodimerization domains. These means and methods can also be favorably employed in the present invention. Specifically, a bispecific antibody of an invention as disclosed herein preferably comprises mutations to produce substantial expression of bispecific full length IgG molecules in host cells. Preferred mutations are the amino acid substitutions L351K and T366K in the first CH3 domain (the 'KK-variant' heavy chain) and the amino acid substitutions L351D and L368E in the second domain (the 'DE-variant' heavy chain), or vice versa. U.S. Pat. Nos. 9,248,181 and 9,358,286 patents as well as the WO2013/157954 PCT application (which are incorporated by reference herein) demonstrate that the DE-variant and KK-variant preferentially pair to form heterodimers (so-called 'DEKK' bispecific molecules). Homodimerization of DE-variant heavy chains (DEDE homodimers) are disfavored due to repulsion between the charged residues in the CH3-CH3 interface between identical heavy chains.

Bispecific antibodies can be generated by (transient) transfection of plasmids encoding a light chain and two different heavy chains that are CH3 engineered to ensure efficient hetero-dimerization and formation of the bispecific antibodies. The production of these chains in a single cell leads to the favored formation of bispecific antibodies over the formation of monospecific antibodies. Preferred mutations to produce essentially only bispecific full length IgG1 molecules are amino acid substitutions at positions 351 and 366, e.g. L351K and T366K (numbering according to EU numbering) in the first CH3 domain (the 'KK-variant' heavy chain) and amino acid substitutions at positions 351 and 368, e.g. L351D and L368E in the second CH3 domain (the 'DE-variant' heavy chain), or vice versa (see for instance FIGS. 10E and 10F).

In one embodiment the heavy chain/light chain combination that comprises the variable domain that binds EGFR, comprises a DE variant of the heavy chain. In this embodiment the heavy chain/light chain combination that comprises the variable domain that can bind to cMET comprises a KK variant of the heavy chain. The KK variant of the heavy chain that binds cMET do not produce homodimers thereby rendering the observed effect of HGF induced cMET activation inhibition by the bispecific antibody very precise. It avoids activation of cMET sometimes observed with bivalent cMET antibodies (agonism).

The Fc region mediates effector functions of an antibody, such as complement-dependent cytotoxicity (CDC), antibody-dependent cellular cytotoxicity (ADCC) and antibody-dependent cell phagocytosis (ADCP). Depending on the therapeutic antibody or Fc fusion protein application, it may be desired to either reduce or increase the effector function. Reduced effector function can be desired when an immune response is to be activated, enhanced or stimulated as in some of the embodiments of an invention as disclosed herein. Antibodies with reduced effector functions can be used to target cell-surface molecules of immune cells, among others.

Antibodies with reduced effector functions are preferably IgG antibodies comprising a modified CH2/lower hinge region, for instance to reduce Fc-receptor interaction or to reduce C1q binding. In some embodiments the antibody of the invention is an IgG antibody with a mutant CH2 and/or lower hinge domain such that interaction of the bispecific IgG antibody to a Fc-gamma receptor is reduced. An antibody comprising a mutant CH2 region is preferably an IgG1 antibody. Such a mutant IgG1 CH2 and/or lower hinge domain preferably comprise an amino substitution at position 235 and/or 236 (EU-numbering), preferably an L235G and/or G236R substitution (FIG. 10D).

An antibody of an invention as disclosed herein preferably has effector function. A bispecific antibody of an invention as disclosed herein preferably comprises antibody-dependent cell-mediated cytotoxicity (ADCC). The antibody can be engineered to enhance the ADCC activity (for review, see Cancer Sci. 2009 September; 100(9):1566-72. Engineered therapeutic antibodies with improved effector functions. Kubota T, Niwa R, Satoh M, Akinaga S, Shitara K, Hanai N). Several in vitro methods exist for determining the efficacy of antibodies or effector cells in eliciting ADCC. Among these are chromium-51 [Cr51] release assays, europium [Eu] release assays, and sulfur-35 [S35] release assays. Usually, a labeled target cell line expressing a certain surface-exposed antigen is incubated with antibody specific for that antigen. After washing, effector cells expressing Fc receptor CD16 are co-incubated with the antibody-labeled target cells. Target cell lysis is subsequently measured by release of intracellular label by a scintillation counter or spectrophotometry. In one aspect a bispecific antibody of an invention as disclosed herein exhibits ADCC activity. In such aspect the bispecific antibody can have improved ADCC activity. In another aspect a bispecific antibody of an invention as disclosed herein does not exhibit ADCC activity. In such aspect the antibody can have reduced ADCC by means of one or more CH2 mutations as described elsewhere herein and by techniques known to in the art. One technique for enhancing ADCC of an antibody is afucosylation. (See for instance Junttila, T. T., K. Parsons, et al. (2010). "Superior In vivo Efficacy of Afucosylated Trastuzumab in the Treatment of HER2-Amplified Breast Cancer." Cancer Research 70(11): 4481-4489). Further provided is therefore a bispecific antibody according to an invention as disclosed herein, which is afucosylated. Alternatively, or additionally, multiple other strategies can be used to achieve ADCC enhancement, for instance including glycoengineering (Kyowa Hakko/Biowa, GlycArt (Roche) and Eureka Therapeutics) and mutagenesis, all of which seek to improve Fc binding to low-affinity activating FcγRIIIa, and/or to reduce binding to the low affinity inhibitory FcγRIIb. A bispecific antibody of an invention as disclosed herein is preferably afucosylated in order to enhance ADCC activity. A bispecific antibody of an invention as disclosed herein preferably comprises a reduced amount of fucosylation of the N-linked carbohydrate structure in the Fc region, when compared to the same antibody produced in a normal CHO cell.

A variant of an antibody or bispecific antibody as described herein comprises a functional part, derivative and/or analogue of the antibody or bispecific antibody. The variant maintains the binding specificity of the (bispecific) antibody. The functional part, derivative and/or analogue maintains the binding specificity of the (bispecific) antibody. Binding specificity is defined by capacity to bind an extracellular part of a first membrane protein and a second membrane protein as described herein.

A bispecific antibody of an invention disclosed herein is preferably used in humans. A preferred antibody of the invention is a human or humanized antibody. The constant region of a bispecific antibody of an invention disclosed herein is preferably a human constant region. The constant region may contain one or more, preferably not more than 10, preferably not more than 5 amino-acid differences with the constant region of a naturally occurring human antibody. It is preferred that the constant part is entirely derived from a naturally occurring human antibody. Various antibodies produced herein are derived from a human antibody variable domain library. As such these variable domains are human. The unique CDR regions may be derived from humans, be synthetic or derived from another organism. The variable region is considered a humanized variable region when it has an amino acid sequence that is identical to an amino acid sequence of the variable region of a naturally occurring human antibody, but for the CDR regions. In such embodiments, the VH of a variable domain of an antibody that binds EGFR or cMET of an invention as disclosed herein may contain one or more, preferably not more than 10, preferably not more than 5 amino-acid differences with the variable region of a naturally occurring human antibody, not counting possible differences in the amino acid sequence of the CDR regions. The light chain variable region of an EGFR binding domain and/or a cMET binding domain in an antibody of invention as disclosed herein may contain one or more, preferably not more than 10, preferably not more than 5 amino-acid differences with the variable region of a naturally occurring human antibody, not counting possible differences in the amino acid sequence of the CDR regions. The light chain in an antibody of an invention as disclosed herein may contain one or more, preferably not more than 10, preferably not more than 5 amino-acid differences with the variable region of a naturally occurring human antibody, not counting possible differences in the amino acid sequence of the CDR regions. Such mutations also occur in nature in the context of somatic hypermutation.

Antibodies may be derived from various animal species, at least with regard to the heavy chain variable region. It is common practice to humanize such e.g. murine heavy chain variable regions. There are various ways in which this can be achieved among which there are CDR-grafting into a human heavy chain variable region with a 3D-structure that matches the 3-D structure of the murine heavy chain variable region; deimmunization of the murine heavy chain variable region, preferably done by removing known or suspected T- or B-cell epitopes from the murine heavy chain variable region. The removal is typically by substituting one or more of the amino acids in the epitope for another (typically conservative) amino acid, such that the sequence of the epitope is modified such that it is no longer a T- or B-cell epitope.

Deimmunized murine heavy chain variable regions are less immunogenic in humans than the original murine heavy chain variable region. Preferably a variable region or domain of an invention as disclosed herein is further humanized, such as for instance veneered. By using veneering techniques, exterior residues which are readily encountered by the immune system are selectively replaced with human residues to provide a hybrid molecule that comprises either a weakly immunogenic or substantially non-immunogenic veneered surface. An animal as used in an invention as disclosed herein is preferably a mammal, more preferably a primate, most preferably a human.

A bispecific antibody according to an invention as disclosed herein preferably comprises a constant region of a human antibody. According to differences in their heavy chain constant domains, antibodies are grouped into five classes, or isotypes; IgG, IgA, IgM, IgD, and IgE. These classes or isotypes comprise at least one of said heavy chains that is named with a corresponding Greek letter. A preferred embodiment comprises an antibody wherein said constant region is selected from the group of IgG, IgA, IgM, IgD, and IgE constant regions, more preferably said constant region comprises an IgG constant region, i.e. selected from the group consisting of IgG1, IgG2, IgG3 and IgG4. Preferably, said constant region is an IgG1 or IgG4 constant region, more preferably a mutated IgG1 constant region. Some variation in the constant region of IgG1 occurs in nature and/or is allowed without changing the immunological properties of the resulting antibody. Variation can also be introduced artificially to install certain preferred features on the antibody or parts thereof. Such features are for instance described herein in the context of CH2 and CH3. Typically between about 1-10 amino acid insertions, deletions, substitutions or a combination thereof are allowed in the constant region.

A VH chain of FIG. 1, 7 or 8 preferably has at most 15, preferably 0, 1, 2, 3, 4, 5, 6, 7, 8, 9 or 10 amino acid insertions, deletions, substitutions or a combination thereof with respect to the VH chain depicted in FIG. 1, 7 or 8, preferably has 0, 1, 2, 3, 4 or 5 amino acid insertions, deletions, substitutions or a combination thereof with respect to the VH chain depicted in FIG. 1, 7 or 8, preferably 0, 1, 2, 3 or 4 insertions, deletions, substitutions or a combination thereof, preferably 0, 1, 2 or 3 insertions, deletions, substitutions or a combination thereof, more preferably 0; 1 or 2 insertions, deletions, substitutions or a combination thereof, and preferably 0 or 1 insertion, deletion, substitution or a combination thereof with respect to the VH chain depicted in FIG. 1, 7 or 8. The one or more amino acid insertions, deletions, substitutions or a combination thereof are preferably not in the CDR1, CDR2 and/or CDR3 region of the VH chain. They are also preferably not present in the Fr4 region. An amino acid substitution is preferably a conservative amino acid substitution.

Rational methods have evolved toward minimizing the content of non-human residues in the human context. Various methods are available to successfully graft the antigen-binding property of an antibody onto another antibody. The binding properties of antibodies may rest predominantly in the exact sequence of the CDR3 region, often supported by the sequence of the CDR1 and CDR2 regions in the variable domain combined with the appropriate structure of the variable domain as a whole. The amino acid sequence of a CDR region as depicted herein determined with the Kabat definition. Various methods are presently available to graft CDR regions onto a suitable variable domain of another antibody. Some of these methods are reviewed in J. C. Almagrol and J. Fransson (2008) Frontiers in Bioscience 13, 1619-1633, which is included by reference herein. An invention as disclosed herein therefore further provides a human or humanized bispecific antibody comprising a first antigen-binding site that binds EGFR and a second antigen-binding site that binds cMET, wherein the variable domain comprising the EGFR binding site comprises a VH CDR3 sequence as depicted for MF3370 in FIG. 1, and wherein the variable domain comprising the cMET binding site comprises a VH CDR3 region as depicted for MF4356 in FIG. 1. The VH variable region comprising the EGFR binding site preferably comprises the sequence of the CDR1 region, CDR2 region and the CDR3 region of a VH chain as depicted for MF3370 in FIG. 1. The VH variable region comprising the cMET binding site preferably comprises the sequence of the CDR1 region, CDR2 region and the CDR3 region of a VH chain as depicted for MF4356 in FIG. 1. CDR grafting may also be used to produce a VH chain with the CDR regions of a VH of FIG. 1, but having a different framework. The different framework may be of another human VH, or of a different mammal. An invention as disclosed herein therefore further provides a human or humanized bispecific antibody comprising a first antigen-binding site that binds EGFR and a second antigen-binding site that binds cMET, wherein the variable domain comprising the EGFR binding site comprises a VH CDR3 sequence as depicted for MF8233 in FIG. 7, and wherein the variable domain comprising the cMET binding site comprises a VH CDR3 region as depicted for MF8230 in FIG. 8. The VH variable region comprising the EGFR binding site preferably comprises the sequence of the CDR1 region, CDR2 region and the CDR3 region of a VH chain as depicted for MF8233 in FIG. 7. The VH variable region comprising the cMET binding site preferably comprises the sequence of the CDR1 region, CDR2 region and the CDR3 region of a VH chain as depicted for MF8230 in FIG. 8. CDR grafting may also be used to produce a VH chain with the CDR regions of a VH of FIG. 7 or FIG. 8, but having a different framework. The different framework may be of another human VH, or of a different mammal.

An invention as disclosed herein therefore further provides a human or humanized bispecific antibody comprising a first antigen-binding site that binds EGFR and a second antigen-binding site that binds cMET, wherein the variable domain comprising the EGFR binding site comprises a VH CDR3 sequence as depicted for MF3370 in FIG. 1, and wherein the variable domain comprising the cMET binding site comprises a VH CDR3 region as depicted for MF8230 in FIG. 8. The VH variable region comprising the EGFR binding site preferably comprises the sequence of the CDR1 region, CDR2 region and the CDR3 region of a VH chain as depicted for MF3370 in FIG. 1. The VH variable region comprising the cMET binding site preferably comprises the sequence of the CDR1 region, CDR2 region and the CDR3 region of a VH chain as depicted for MF8230 in FIG. 8. CDR grafting may also be used to produce a VH chain with the CDR regions of a VH of FIG. 7 or FIG. 8, but having a different framework. The different framework may be of another human VH, or of a different mammal.

An invention as disclosed herein therefore further provides a human or humanized bispecific antibody comprising a first antigen-binding site that binds EGFR and a second antigen-binding site that binds cMET, wherein the variable domain comprising the EGFR binding site comprises a VH CDR3 sequence as depicted for MF8233 in FIG. 7, and wherein the variable domain comprising the cMET binding site comprises a VH CDR3 region as depicted for MF4356 in FIG. 8. The VH variable region comprising the EGFR binding site preferably comprises the sequence of the CDR1 region, CDR2 region and the CDR3 region of a VH chain as depicted for MF8233 in FIG. 7. The VH variable region comprising the cMET binding site preferably comprises the sequence of the CDR1 region, CDR2 region and the CDR3 region of a VH chain as depicted for MF4356 in FIG. 8. CDR grafting may also be used to produce a VH chain with the CDR regions of a VH of FIG. 7 or FIG. 8, but having a different framework. The different framework may be of another human VH, or of a different mammal.

An invention as disclosed herein therefore further provides a human or humanized bispecific antibody comprising a first antigen-binding site that binds EGFR and a second antigen-binding site that binds cMET, wherein the variable domain comprising the EGFR binding site comprises a VH CDR3 sequence as depicted for MF8232 in FIG. 7, and wherein the variable domain comprising the cMET binding site comprises a VH CDR3 region as depicted for MF8230 in FIG. 8. The VH variable region comprising the EGFR binding site preferably comprises the sequence of the CDR1 region, CDR2 region and the CDR3 region of a VH chain as depicted for MF8232 in FIG. 7. The VH variable region comprising the cMET binding site preferably comprises the sequence of the CDR1 region, CDR2 region and the CDR3 region of a VH chain as depicted for MF8230 in FIG. 8. CDR grafting may also be used to produce a VH chain with the CDR regions of a VH of FIG. 7 or FIG. 8, but having a different framework. The different framework may be of another human VH, or of a different mammal.

An invention as disclosed herein therefore further provides a human or humanized bispecific antibody comprising a first antigen-binding site that binds EGFR and a second antigen-binding site that binds cMET, wherein the variable domain comprising the EGFR binding site comprises a VH CDR3 sequence as depicted for MF8232 in FIG. 7, and wherein the variable domain comprising the cMET binding site comprises a VH CDR3 region as depicted for MF4356 in FIG. 8. The VH variable region comprising the EGFR binding site preferably comprises the sequence of the CDR1 region, CDR2 region and the CDR3 region of a VH chain as depicted for MF8232 in FIG. 7. The VH variable region comprising the cMET binding site preferably comprises the sequence of the CDR1 region, CDR2 region and the CDR3 region of a VH chain as depicted for MF4356 in FIG. 8. CDR grafting may also be used to produce a VH chain with the CDR regions of a VH of FIG. 7 or FIG. 8, but having a different framework. The different framework may be of another human VH, or of a different mammal.

The invention further provides a human or humanized bispecific antibody comprising a first variable domain that binds EGFR and a second variable domain that binds cMET wherein the first variable domain comprises a heavy chain variable region with the amino acid sequence of MF3370 as depicted in FIG. 7 having at most 10, preferably 0, 1, 2, 3, 4, 5, 6, 7, 8, 9 or 10 and preferably having 0, 1, 2, 3, 4 or 5 amino acid insertions, deletions, substitutions or a combination thereof and wherein the second variable domain comprises a heavy chain variable region that comprises the amino acid sequence of MF4356 depicted in FIG. 8 (SEQ ID NO: 23) with 0-10 preferably 0-5 amino acid insertions, deletions, substitutions, additions or a combination thereof. The invention further provides a human or humanized bispecific antibody comprising a first variable domain that binds EGFR and a second variable domain that binds cMET wherein the first variable domain comprises a heavy chain variable region with the amino acid sequence of MF8233 as depicted in FIG. 7 having at most 10, preferably 0, 1, 2, 3, 4, 5, 6, 7, 8, 9 or 10 and preferably having 0, 1, 2, 3, 4 or 5 amino acid insertions, deletions, substitutions or a combination thereof and wherein the second variable domain comprises a heavy chain variable region that comprises the amino acid sequence of MF8230 depicted in FIG. 8 (SEQ ID NO: 13) with 0-10 preferably 0-5 amino acid insertions, deletions, substitutions, additions or a combination thereof. The invention further provides a human or humanized bispecific antibody comprising a first variable domain that binds EGFR and a second variable domain that binds cMET wherein the first variable domain comprises a heavy chain variable region with the amino acid sequence of MF3370 as depicted in FIG. 7 having at most 10, preferably 0, 1, 2, 3, 4, 5, 6, 7, 8, 9 or 10 and preferably having 0, 1, 2, 3, 4 or 5 amino acid insertions, deletions, substitutions or a combination thereof and wherein the second variable domain comprises a heavy chain variable region that comprises the amino acid sequence of MF8230 depicted in FIG. 8 (SEQ ID NO: 13) with 0-10 preferably 0-5 amino acid insertions, deletions, substitutions, additions or a combination thereof.

The invention further provides a human or humanized bispecific antibody comprising a first variable domain that binds EGFR and a second variable domain that binds cMET wherein the first variable domain comprises a heavy chain variable region with the amino acid sequence of MF8233 as depicted in FIG. 7 having at most 10, preferably 0, 1, 2, 3, 4, 5, 6, 7, 8, 9 or 10 and preferably having 0, 1, 2, 3, 4 or 5 amino acid insertions, deletions, substitutions or a combination thereof and wherein the second variable domain comprises a heavy chain variable region that comprises the amino acid sequence of MF4356 depicted in FIG. 8 (SEQ ID NO: 23) with 0-10 preferably 0-5 amino acid insertions, deletions, substitutions, additions or a combination thereof.

The invention further provides a human or humanized bispecific antibody comprising a first variable domain that binds EGFR and a second variable domain that binds cMET wherein the first variable domain comprises a heavy chain variable region with the amino acid sequence of MF8232 as depicted in FIG. 7 having at most 10, preferably 0, 1, 2, 3, 4, 5, 6, 7, 8, 9 or 10 and preferably having 0, 1, 2, 3, 4 or 5 amino acid insertions, deletions, substitutions or a combination thereof and wherein the second variable domain comprises a heavy chain variable region that comprises the amino acid sequence of MF4356 depicted in FIG. 8 (SEQ ID NO: 23) with 0-10 preferably 0-5 amino acid insertions, deletions, substitutions, additions or a combination thereof.

The invention further provides a human or humanized bispecific antibody comprising a first variable domain that binds EGFR and a second variable domain that binds cMET wherein the first variable domain comprises a heavy chain variable region with the amino acid sequence of MF8232 as depicted in FIG. 7 having at most 10, preferably 0, 1, 2, 3, 4, 5, 6, 7, 8, 9 or 10 and preferably having 0, 1, 2, 3, 4 or 5 amino acid insertions, deletions, substitutions or a combination thereof and wherein the second variable domain comprises a heavy chain variable region that comprises the amino acid sequence of MF8230 depicted in FIG. 8 (SEQ ID NO: 23) with 0-10 preferably 0-5 amino acid insertions, deletions, substitutions, additions or a combination thereof.

The mentioned at most 15, preferably 0, 1, 2, 3, 4, 5, 6, 7, 8, 9 or 10 and preferably 0, 1, 2, 3, 4 or 5 amino acid substitutions are preferably conservative amino acid substitutions, the insertions, deletions, substitutions or a combination thereof are preferably not in the CDR3 region of the VH chain, preferably not in the CDR1, CDR2 or CDR3 region of the VH chain and preferably not in the FR4 region.

Various methods are available to produce bispecific antibodies. One method involves the expression of two different heavy chains and two different light chains in a cell and collecting antibody that is produced by the cell. Antibody produced in this way will typically contain a collection of antibodies with different combinations of heavy and light chains, some of which are the desired bispecific antibody. The bispecific antibody can subsequently be purified from the collection. The ratio of bispecific to other antibodies that are produced by the cell can be increased in various ways. In a preferred embodiment, the ratio is increased by expressing not two different light chains but a common light chain in the cell. When a common light chain is expressed with the two different heavy chains, the ratio of bispecific antibody to other antibody that is produced by the cell is significantly improved over the expression of two different light chains.

The ratio of bispecific antibody that is produced by the cell can be further improved by stimulating the pairing of two different heavy chains with each other over the pairing of two identical heavy chains. Methods and means are disclosed for producing bispecific antibodies (from a single cell), whereby means are provided that favor the formation of bispecific antibodies over the formation of monospecific antibodies. These methods can also be favorably employed in the present invention. Thus an invention as disclosed herein in one aspect provides a method for producing a bispecific antibody from a single cell, wherein said bispecific antibody comprises two CH3 domains that are capable of forming an interface, said method comprising providing in said cell a) a first nucleic acid molecule encoding a 1st CH3 domain comprising heavy chain, b) a second nucleic acid molecule encoding a 2nd CH3 domain comprising heavy chain, wherein said nucleic acid molecules are provided with means for preferential pairing of said 1st and 2nd CH3 domain comprising heavy chains, said method further comprising the step of culturing said host cell and allowing for expression of said two nucleic acid molecules and harvesting said bispecific antibody from the culture. Said first and second nucleic acid molecules may be part of the same nucleic acid molecule, vector or gene delivery vehicle and may be integrated at the same site of the host cell's genome. Alternatively, said first and second nucleic acid molecules are separately provided to said cell.

A preferred embodiment provides a method for producing a bispecific antibody according to an invention as disclosed herein from a single cell, wherein said bispecific antibody comprises two CH3 domains that are capable of forming an interface, said method comprising providing:

a cell having a) a first nucleic acid molecule encoding a heavy chain comprising an antigen binding site that binds EGFR and that contains a 1st CH3 domain, and b) a second nucleic acid molecule encoding a heavy chain comprising an antigen-binding site that binds ErbB-3 and that contains a 2nd CH3 domain, wherein said nucleic acid molecules are provided with means for preferential pairing of said 1st and 2nd CH3 domains, said method further comprising the step of culturing said cell and allowing for expression of the proteins encoded by said two nucleic acid molecules and harvesting said bispecific IgG antibody from the culture. In a particularly preferred embodiment, said cell also has a third nucleic acid molecule encoding a common light chain. Said first, second and third nucleic acid molecule may be part of the same nucleic acid molecule, vector or gene delivery vehicle and may be integrated at the same site of the host cell's genome. Alternatively, said first, second and third nucleic acid molecules are separately provided to said cell. A preferred common light chain is based on O12, preferably it is the rearranged germline human kappa light chain IgV$_K$1 39*01/IGJ$_K$1*01, as described above. Means for preferential pairing of said 1st and said 2nd CH3 domain are preferably the corresponding mutations in the CH3 domain of the heavy chain coding regions. The preferred mutations to preferentially produce bispecific antibodies are the amino acid substitutions L351K and T366K (EU-numbering) in the first CH3 domain and the amino acid substitutions L351D and L368E in the second CH3 domain, or vice versa. Further provided is therefore a method according to an invention as disclosed herein for producing a bispecific antibody, wherein said first CH3 domain comprises the amino acid substitutions L351K and T366K (EU-numbering) and wherein said second CH3 domain comprises the amino acid substitutions L351D and L368E, said method further comprising the step of culturing said cell and allowing for expression of proteins encoded by said nucleic acid molecules and harvesting said bispecific antibody from the culture. Also provided is a method according to an invention as disclosed herein for producing a bispecific antibody, wherein said first CH3 domain comprises the amino acid substitutions L351D and L368E (EU-numbering) and wherein said second CH3 domain comprises the amino acid substitutions L351K and T366K, said method further comprising the step of culturing said cell and allowing for expression of said nucleic acid molecules and harvesting said bispecific antibody from the culture. Antibodies that can be produced by these methods are also part of the present invention. The CH3 hetero-dimerization domains are preferably IgG1 hetero-dimerization domains. The heavy chain constant regions comprising the CH3 hetero-dimerization domains are preferably IgG1 constant regions.

In one embodiment of the invention includes a nucleic acid molecule encoding an antibody heavy chain variable region. The nucleic acid molecule (typically an in vitro, isolated or recombinant nucleic acid molecule) preferably encodes a heavy chain variable region as depicted in FIG. 7 or FIG. 8, or a heavy chain variable region as depicted in FIG. 7 or FIG. 8 having 1, 2, 3, 4 or 5 amino acid insertions, deletions, substitutions or combination thereof. In a preferred embodiment the nucleic acid molecule comprises codon optimized nucleic acid sequence coding for an amino acid sequence as depicted in FIG. 7 or FIG. 8. The codon optimization is optimized for the species and/or the cell type of the antibody producing cell. For example, for CHO production the nucleic acid sequence of the molecule is codon optimized for Chinese hamster cells. The invention further provides a nucleic acid molecule encoding a heavy chain of FIG. 7 or FIG. 8.

A nucleic acid molecule as used in an invention as disclosed herein is typically but not exclusively a ribonucleic acid (RNA) or a deoxyribonucleic acid (DNA). Alternative nucleic acids are available for a person skilled in the art. A nucleic acid according to an invention as disclosed herein is for instance comprised in a cell. When said nucleic acid is expressed in said cell, said cell can produce an antibody according to an invention as disclosed herein. Therefore, in one embodiment of the invention includes a cell comprising an antibody according to invention as disclosed herein and/or a nucleic acid according to invention as disclosed herein. Said cell is preferably an animal cell, more preferably a mammal cell, more preferably a primate cell, most preferably a human cell. A suitable cell is any cell capable of comprising and preferably producing an antibody according to an invention as disclosed herein and/or a nucleic acid according to an invention as disclosed herein.

An invention as disclosed herein further provides a cell comprising an antibody according to an invention as disclosed herein. Preferably said cell (typically an in vitro, isolated or recombinant cell) produces said antibody. Said cell can also be a stored cell that is able to produce said antibody when taken out of storage and cultured. In a preferred embodiment said cell is a hybridoma cell, a Chinese hamster ovary (CHO) cell, an NS0 cell or a PER-C6™ cell. In a particularly preferred embodiment said cell is a CHO cell. Further provided is a cell culture comprising a cell according to an invention as disclosed herein. Various institutions and companies have developed cell lines for the large scale production of antibodies, for instance for clinical use. Non-limiting examples of such cell lines are CHO cells, NS0 cells or PER.C6™ cells. These cells are also used for other purposes such as the production of proteins. Cell lines developed for industrial scale production of proteins and antibodies are herein further referred to as industrial cell lines. Thus a preferred embodiment includes use of a cell line developed for the large scale production of antibody for the production of an antibody of an invention as disclosed herein, including preferably a cell for producing an antibody comprising a nucleic acid molecule that codes for a VH, a VL, and/or a heavy chain as depicted in FIG. 7 or FIG. 8.

The invention further provides a method for producing an antibody comprising culturing a cell of an invention as disclosed herein and harvesting said antibody from said culture. Preferably said cell is cultured in a serum free medium. Preferably said cell is adapted for suspension growth. Further provided is an antibody obtainable by a method for producing an antibody according to an invention as disclosed herein. The antibody is preferably purified from the medium of the culture. Preferably said antibody is affinity purified.

A cell of an invention as disclosed herein is for instance a hybridoma cell line, a CHO cell, a 293F cell, an NS0 cell or another cell type known for its suitability for antibody production for clinical purposes. In a particularly preferred embodiment said cell is a human cell. Preferably a cell that is transformed by an adenovirus E1 region or a functional equivalent thereof. A preferred example of such a cell line is the PER.C6™ cell line or equivalent thereof. In a particularly preferred embodiment said cell is a CHO cell or a variant thereof. Preferably a variant that makes use of a Glutamine synthetase (GS) vector system for expression of an antibody.

Antibodies of an invention as disclosed herein can be produced at levels>50 mg/L after transient transfection in suspension 293F cells. The bispecific antibodies can be purified to greater than 98% purity with yields>70%. Analytical characterization studies show bispecific IgG1 antibody profiles that are comparable to bivalent monospecific IgG1. In terms of functional activity a bispecific antibody of an invention as disclosed herein can demonstrate superior potency compared to cetuximab in vitro and in vivo.

The invention further provides a pharmaceutical composition comprising an antibody according to an invention as disclosed herein. The pharmaceutical composition preferably comprises a preferably pharmaceutically acceptable excipient or carrier.

An antibody can comprise a label, preferably a label for in vivo imaging. Such a label is typically not necessary for therapeutic applications. In for instance a diagnostic setting, a label can be helpful. For instance in visualizing target cells in the body. Various labels are suited and many are well known in the art. In a preferred embodiment the label is a radioactive label for detection. In another preferred embodiment, the label is an infrared label. Preferably the infrared label is suited for in vivo imaging. Various infrared labels are available to the person skilled in the art. Preferred infrared labels are for instance, IRDye 800; IRDye 680RD; IRDye 680LT; IRDye 750; IRDye 700DX; IRDye 800RS IRDye 650; IRDye 700 phosphoramidite; IRDye 800 phosphoramidite (LI-COR USA; 4647 Superior Street; Lincoln, Nebr.).

The invention further provides a method for the treatment of a subject that has a tumor or is at risk of having said tumor comprising administering to the subject in need thereof an antibody or pharmaceutical composition according to an invention as disclosed herein. The tumor is preferably an EGFR, cMET or EGFR/cMET positive tumor. Before start of said treatment, the method preferably further comprises determining whether said subject has such an EGFR, cMET or EGFR/cMET positive tumor. The invention further provides an antibody or pharmaceutical composition of an invention as disclosed herein for use in the treatment of a subject that has or is at risk of having an EGFR, cMET or EGFR/cMET positive tumor.

To establish whether a tumor is positive for EGFR the skilled person can for instance determine the EGFR amplification and/or immuno-histochemistry staining. At least 10% of the tumor cells in a biopsy should be positive. The biopsy can also contain 20%, 30% 40% 50% 60% 70% or more positive cells. To establish whether a tumor is positive for cMET the skilled person can for instance determine the cMET amplification and/or staining in immunohistochemistry. At least 10% of the tumor cells in a biopsy should be positive. The biopsy can also contain 20%, 30% 40% 50% 60% 70% or more positive cells.

The invention as disclosed herein can be applied to a wide range of cancers, like breast cancer, colon cancer, pancreatic cancer, gastric cancer, ovarian cancer, colorectal cancer, head- and neck cancer, lung cancer including non-small cell lung cancer, bladder cancer and the like. The tumor may be an EGFR, cMET or EGFR/cMET positive cancer. An embodiment of the invention may preferably treat a positive cancer that is a breast cancer, such as early-stage breast cancer. In another embodiment of the invention may preferably treat the EGFR, cMET or EGFR/cMET positive cancer that is colorectal cancer. The invention as disclosed herein can be applied to a wide range of EGFR, cMET or EGFR/cMET positive cancers, like breast cancer, colon cancer, pancreatic cancer, gastric cancer, ovarian cancer, colorectal cancer, head- and neck cancer, lung cancer including non-small cell lung cancer, bladder cancer and the like. The subject is preferably a human subject. The subject is preferably a subject eligible for antibody therapy using an EGFR specific antibody such as cetuximab. In a preferred embodiment the invention may preferably treat a subject that comprises a tumor, preferably an EGFR/cMET positive cancer, preferably a tumor/cancer with an EGFR RTK resistant phenotype, an EGFR monoclonal antibody resistant phenotype or a combination thereof.

The amount of antibody to be administered to a patient is typically in the therapeutic window, meaning that a sufficient quantity is used for obtaining a therapeutic effect, while the amount does not exceed a threshold value leading to an unacceptable extent of side-effects. The lower the amount of antibody needed for obtaining a desired therapeutic effect, the larger the therapeutic window will typically be. An antibody according to an invention as disclosed herein exerting sufficient therapeutic effects at low dosage is, therefore, preferred. The dosage can be in range of the dosing regimen of cetuximab. The dosage can also be lower.

A bispecific antibody according to an invention as disclosed herein preferably induces less skin toxicity as compared to cetuximab under otherwise similar conditions. A bispecific antibody according to an invention as disclosed herein preferably produces less proinflammatory chemokines, preferably of CXCL14 as compared to cetuximab under otherwise similar conditions. A bispecific antibody according to an invention as disclosed herein preferably induces less impairment of antimicrobial RNAses, preferably Rnase 7, as compared to cetuximab under otherwise similar conditions.

The present invention describes among others antibodies that target the EGFR and cMET receptors and result in potent proliferation inhibition of cancer cell lines in vitro and tumor growth inhibition in vivo. A bispecific antibody of an invention as disclosed herein can combine low toxicity profiles with high efficacy. An antibody of invention as disclosed herein can be useful in various types and lines of EGFR-targeted therapies. An antibody of an invention as disclosed herein can have an increased therapeutic window when compared to an antibody that binds the same antigen(s) with both arms. A bispecific antibody of an invention as disclosed herein can exhibit better growth inhibitory effects in vitro, in vivo or a combination thereof when compared to the cetuximab antibody.

The invention also provides a bispecific antibody of an invention as disclosed herein, for use in the treatment of subject that may have one or more of a variety of different kinds of tumors. The tumor may be an EGFR positive tumor, a cMET positive tumor or an EGFR and cMET positive tumor. The tumor may be a breast cancer; colon cancer, pancreatic cancer, gastric cancer, ovarian cancer, colorectal cancer, head- and neck cancer, lung cancer including non-small cell lung cancer or bladder cancer. The tumor may be resistant to treatment with an EGFR tyrosine kinase inhibitor. The EGFR tyrosine kinase inhibitor is preferably erlotinib, gefitinib, or afatinib, an analogue of erlotinib, gefitinib or afatinib or a combination of one or more of the respective compounds and/or analogues thereof. The treatment preferably further comprises treatment with an EGFR tyrosine kinase inhibitor. When co-treating with an EGFR tyrosine kinase inhibitor the tumor can be resistant to the treatment with the EGFR tyrosine kinase inhibitor. The co-treatment at least partly restores sensitivity of the tumor to the tyrosine kinase inhibitor. The EGFR tyrosine kinase inhibitor can be a first generation EGFR tyrosine kinase inhibitor. Examples of clinically relevant first generation EGFR tyrosine kinase inhibitors are erlotinib and gefitinib. In this and other embodiments the tumor may be an HGF-associated tumor.

An EGFR-positive tumor is typically a tumor that has an EGFR activating mutation. An EGFR activating mutation is a mutation of EGFR that results in activation of the EGF/EGFR signaling pathway. The EGFR activating mutation may be important for a cancerous state of the tumor. One of the ways in which such tumors can become insensitive to EGFR targeted therapy is by activation of the HGF/cMET signaling pathway. The tumor may be an HGF-associated tumor. Activation of the cMET/HGF signaling pathway is one of the ways in which an EGFR-positive tumor can escape treatment with an EGFR-targeted therapy. The cMET/HGF pathway can be activated in various ways. Various methods of activation are described in the art some of which are detailed herein. An antibody of an invention as disclosed herein is particularly suited for the treatment of tumors wherein activation of the cMET/HGF signaling pathway is associated with the presence of or excess of HGF. Such cMET positive tumors are referred to as HGF-associated tumors or HGF-dependent tumors. An antibody of an invention as disclosed herein can also be used to at least in part inhibit this possible escape mechanism of EGFR positive tumors. Such tumors can escape EGFR-targeted therapy through the selected outgrowth of tumor cells wherein, in addition, the cMET/HGF signaling pathway is activated. Such cells may be present at the start of the EGFR-targeted therapy. Such cells have a selective growth advantage over HGF/cMET signaling negative tumor cells. The tumor may be a tumor wherein the HGF/cMET signaling pathway is activated. The tumor may be a tumor that is associated with elevated levels of hepatocyte growth factor (HGF) or overexpression of the HGF receptor c-Met. The tumor may be a tumor wherein growth is driven by the EGF and/or HGF. A tumor is said to be driven by a certain growth factor if the signaling pathway is activated in cells of the tumor in response to the presence of the growth factor and removal of the growth factor results in inhibition of the growth of the cells of the tumor. Reduction can be measured by reduced cell division and/or induced cell kill such as apoptosis. A tumor is an HGF-associated tumor if under conditions that would otherwise be permissive for the growth of the tumor, the tumor growths or growths faster in the presence of HGF.

EGFR-targeted therapies for various tumors have been reviewed by Vecchione et al., EGFR-targeted therapy." Experimental cell research Vol 317 (2011): 2765-2771. In general EGFR-targeted therapy is a therapy with a molecule that interacts with EGFR and inhibits EGFR-mediated signaling in the cell.

The method of treatment or antibody for use in the treatment as indicated herein preferably further comprises the step of determining whether the tumor is an HGF-associated tumor.

An antibody of an invention as disclosed herein can inhibit growth of an HGF-associated tumor.

In some embodiments wherein a cMET binding variable domain is described to have a CDR2 sequence "WINTYTGDPTYAQGFTG" (SEQ ID NO: 29) the CDR2 sequence can also be "WINTYTGDPTYAQGFT" (SEQ ID NO: 45).

Where herein ranges are given as between number 1 and number 2, the range includes the number 1 and number 2. For instance a range of between 2-5 includes the number 2 and 5.

When herein reference is made to an affinity that is higher than another, the Kd=lower than the other Kd. For the avoidance of doubt a Kd of 10e-9 M is lower than a Kd of 10e-8 M. The affinity of an antibody with a Kd of 10e-9 M for a target is higher than when the Kd is 10e-8 M.

A reference herein to a patent document or other matter which is cited is not to be taken as an admission that that document or matter was known or that the information it contains was part of the common general knowledge as at the priority date of any of the claims.

For the purpose of clarity and a concise description, features are described herein as part of the same or separate embodiments, however, it will be appreciated that the scope of the invention as disclosed herein may include embodiments having combinations of all or some of the features described.

BRIEF DESCRIPTION OF THE DRAWINGS

FIG. 1. Amino acid sequence of the heavy chain variable regions of variable domains referred to in this application.

Cells were incubated either without (mock) or with 12.5 ng/ml EGF or 15 ng/ml HGF or a combination of HGF and EGF (15 ng/ml and 12.5 ng/ml) with addition of 5 individual cMET x EGFR bispecifics. As a control cetuximab in combination with 2994 Fab was included. The Y-axis depicts the percentage of wound closure measured by time-lapse microscopy.

Figure 4:
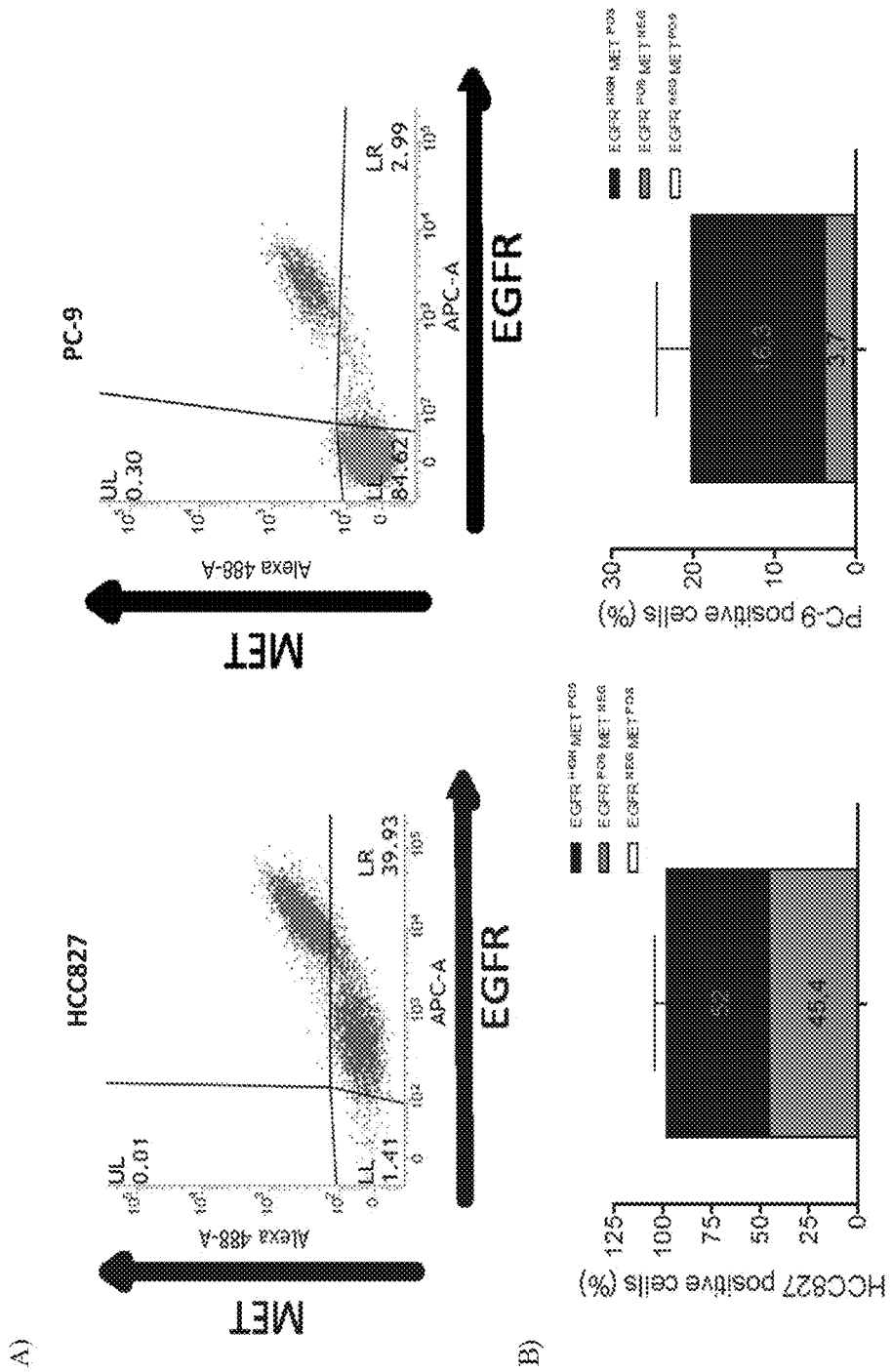

FIG. 4. FACS analysis on the EGFR and cMET expression analysis in the TKI resistant NSCLC cells, HCC827 and PC-9 cells.

(A) Both cells lines were characterized for the expression of EGFR (x-axis) and cMET (y-axis) using fluorescently labeled antibodies. All HCC827 cells show EGFR expression and can be subdivided into a EGFR$^{high}$, cMET$^{pos}$ population and a EGFR$^{pos}$, cMET$^{neg}$ population. PC-9 cells contain a small population of EGFR$^{high}$ and cMET$^{pos}$ cells and a minimal population of EGFR$^{pos}$ and cMET$^{neg}$ cells.

(B) Graph representing the distribution of the different cell populations in PC-9 and HCC827 cells.

Figure 5:
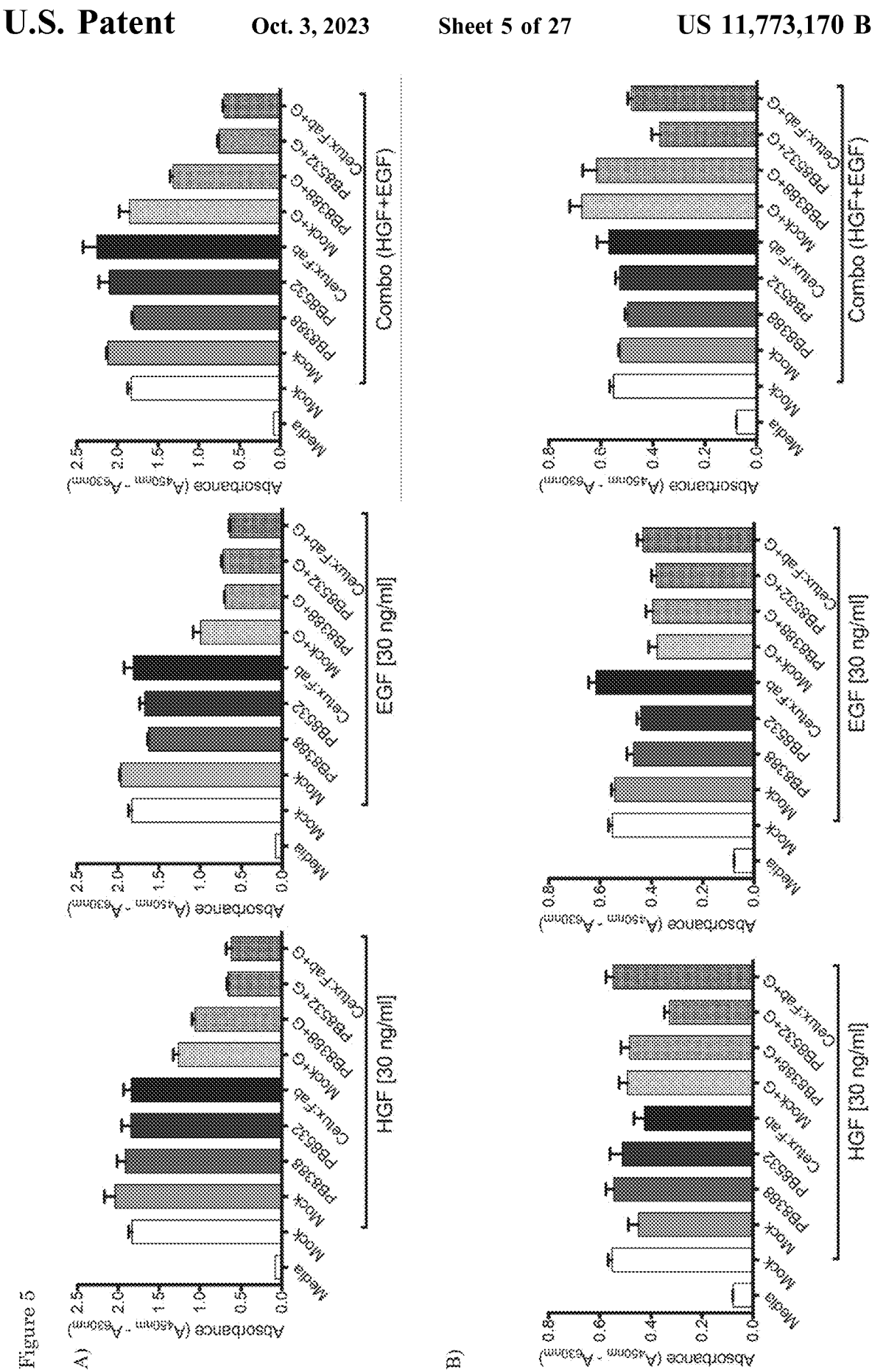

FIG. 5. Example of the effect of PB8532 and PB8388 on HGF induced resistance to TKI inhibitors in PC-9 (panel A) and HCC827 (panel B) cells.

Cells were pre-treated with bispecific PB8532, PB8388, or the cetuximab/5D5 Fab mixture and incubated with HGF and/or EGF in combination with a TKI inhibitor, after which the proliferation was measured. PB8532 inhibits HGF mediated and EGF mediated gefitinib resistance in PC-9 cells and HCC827 cells.

Figure 6:
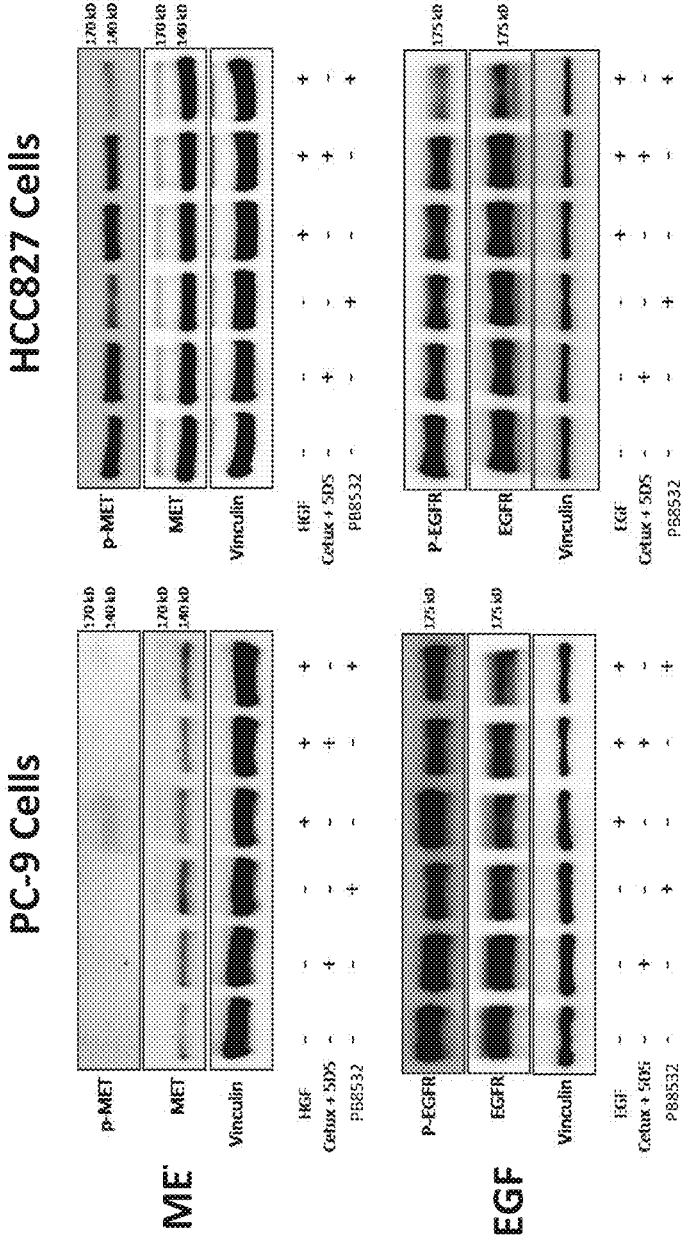

FIG. 6. Effect of treatment with the indicated antibodies on HGF induced cMET phosphorylation or EGF induced EGFR phosphorylation on PC-9 and HCC827 cells. Antibodies (100 nM) were incubated for 15 minutes at 37° C. where after cell extracts were generated and applied to Western Blot analysis for detection of (p)EGFR and (p)cMET. Anti-vinculin antibody was included as a protein loading control.

FIG. 7. MF3370 and variants thereof. The CDR1, CDR2 and CDR3 sequences in MF8226 are underlined from left to right. The CDRs in the other sequences are at the corresponding positions.

FIG. 8. MF4356 and variants thereof. The CDR1, CDR2 and CDR3 sequences in MF4356 are underlined from left to right. The CDRs in the other sequences are at the corresponding positions.

FIG. 9. Common light chain used in mono- and bispecific IgG.

FIG. 9A: Common light chain amino acid sequence. FIG. 9B: Common light chain variable domain DNA sequence and translation (IGKV1-39/jk1). FIG. 9C: Common light chain constant region DNA sequence and translation. FIG. 9D: IGKV1-39/jk5 common light chain variable domain translation. FIG. 9E: V-region IGKV1-39A.

FIG. 10. IgG heavy chains for the generation of bispecific molecules. FIG. 10A: CH1 region. FIG. 10B: hinge region. Figure C: CH2 region. FIG. 10D: CH2 containing L235G and G236R silencing substitutions. FIG. 10E: CH3 domain containing substitutions L351K and T366K (KK). FIG. 10F; CH3 domain containing substitutions L351D and L368E (DE).

Figure 11:
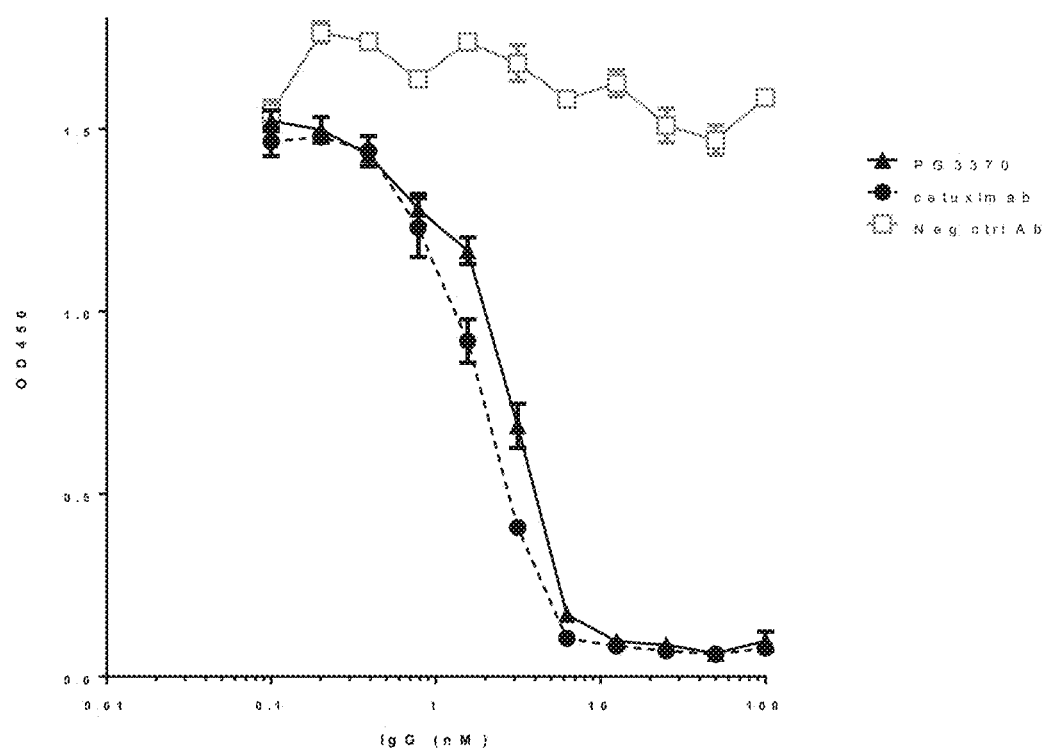

FIG. 11. Inhibition of EGF binding to recombinant EGFR in ELISA.

Biotinylated EGF was allowed to bind coated EGFR in the presence of a serial dilution of IgG. Cetuximab was used as a positive control and PG2708 as a negative control antibody (Neg ctrl Ab). EGF binding was detected by streptavidin HRP.

Figure 12:
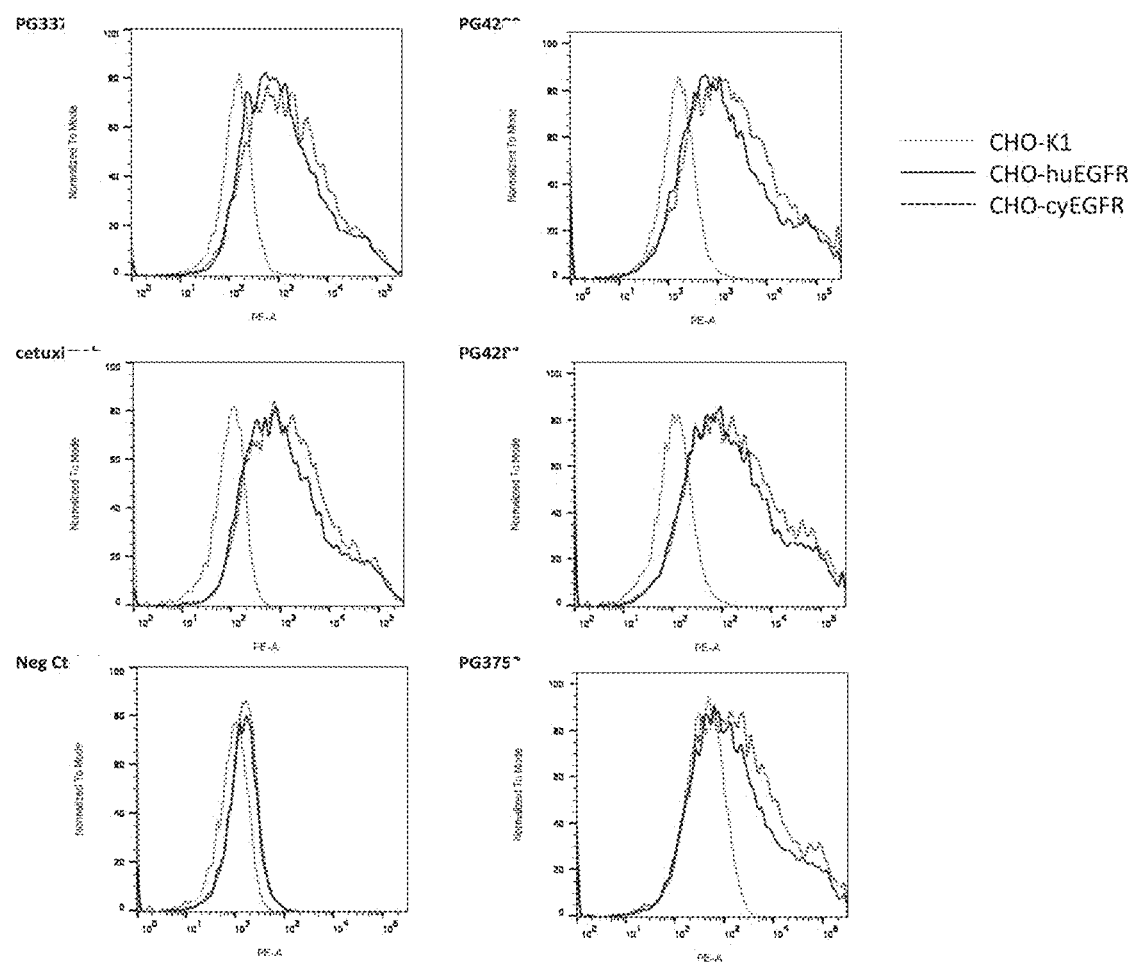

FIG. 12. Determination of cynomolgus EGFR cross reactivity by FACS analysis. CHO-K1 cells were transfected with human EGFR or cynomolgus EGFR constructs. Antibodies were allowed to bind the transfected cells and CHO-K1 cells at 5 µg/ml. Cetuximab was used as a positive control and PG2708 as a negative control antibody (Neg ctrl Ab). Bound antibodies were detected by a PE conjugated antibody.

Figure 13:
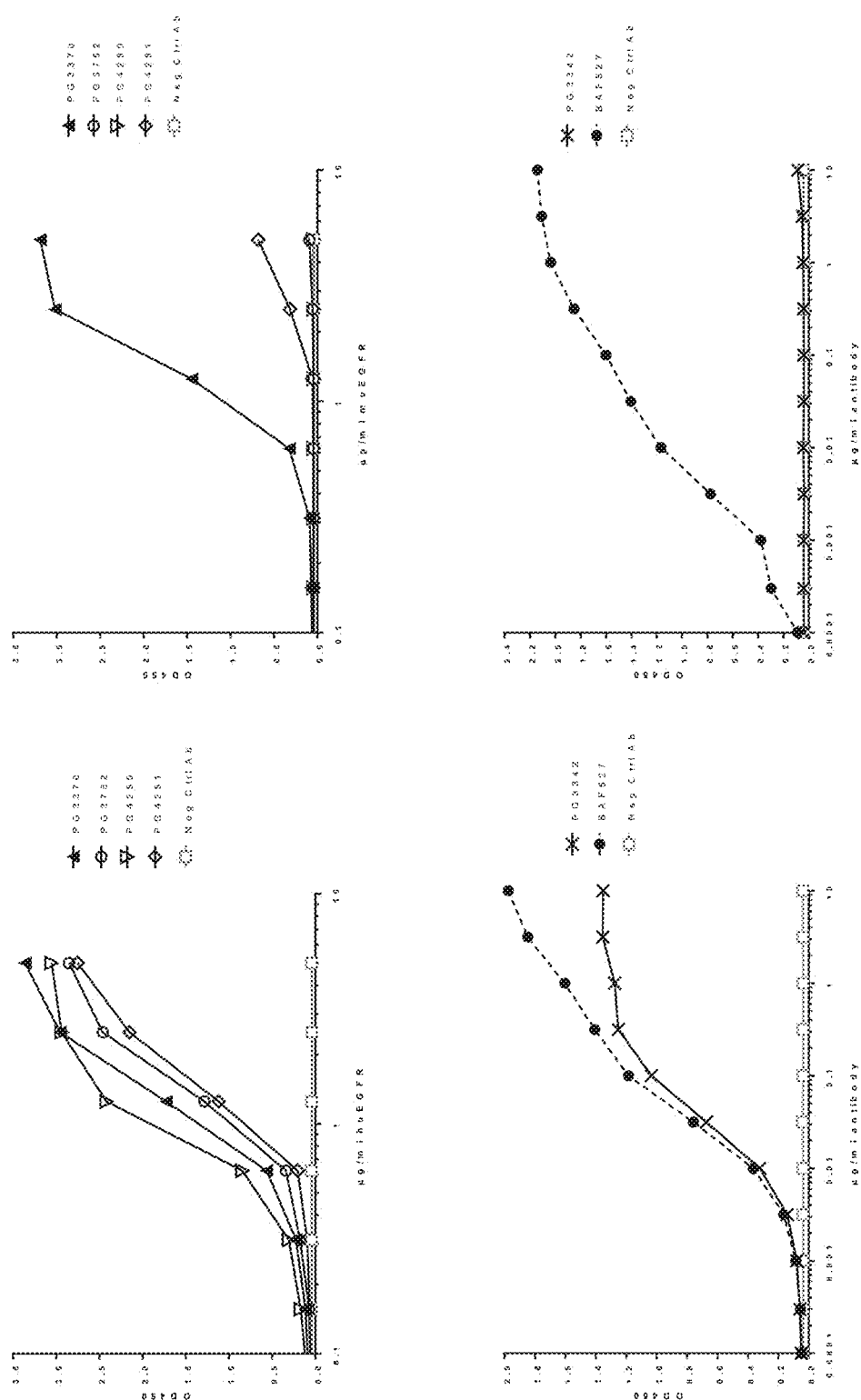

FIG. 13. Determination of mouse EGFR and cMET cross reactivity by ELISA. Upper panel; A fixed concentration of antibody (5 µg/ml) was tested in a serial titration in microtiter plates coated with mouse EGFR and human EGFR. Anti-EGFR antibodies and PG2708 (neg Ctrl Ab) were allowed to bind and detected by an HRP conjugated antibody. Lower panel; a serial titration of antibodies was allowed to bind coated human and mouse cMET. The human/mouse cross reactive antibody BAF527 was included as a positive control antibody and PG2708 was added as a negative control antibody (Neg Ctrl Ab). Bound antibodies were detected by streptavidin HRP.

Figure 14A:
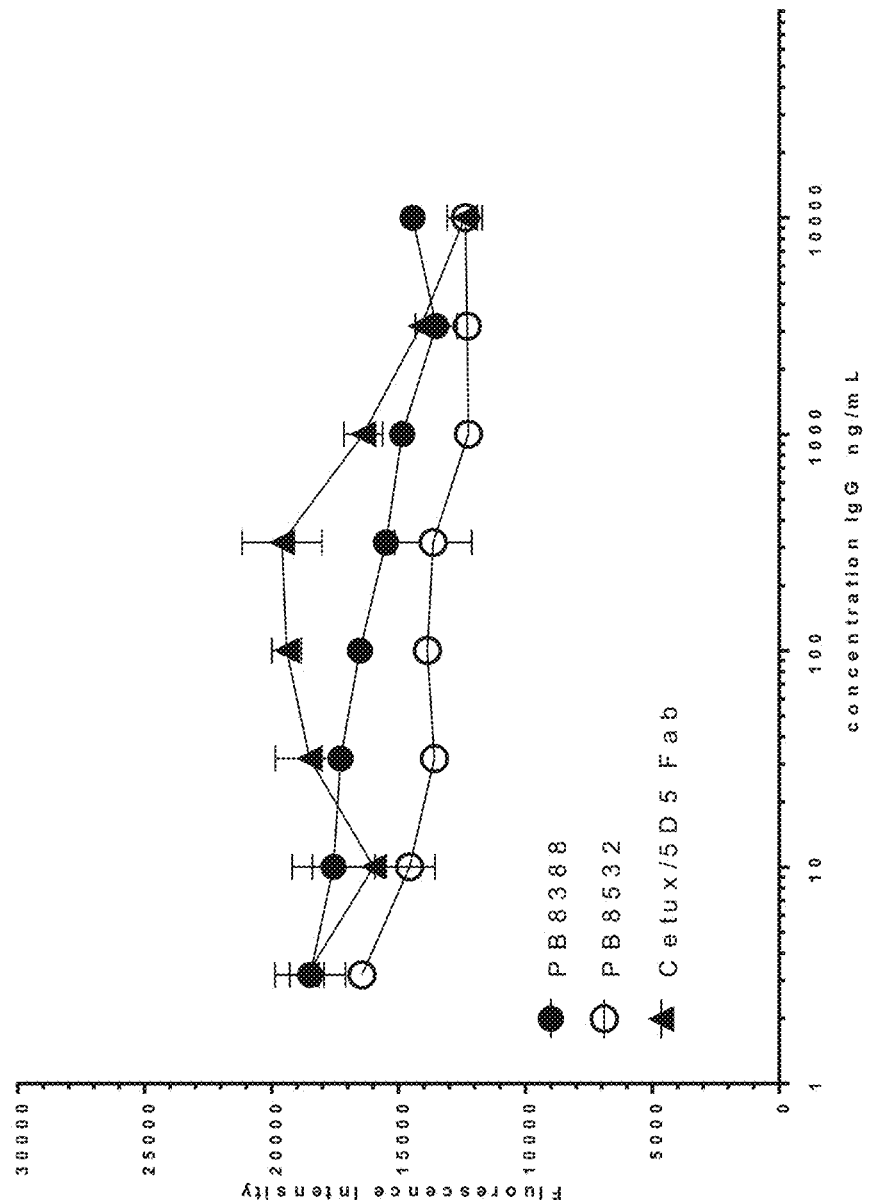
Figure 14B:
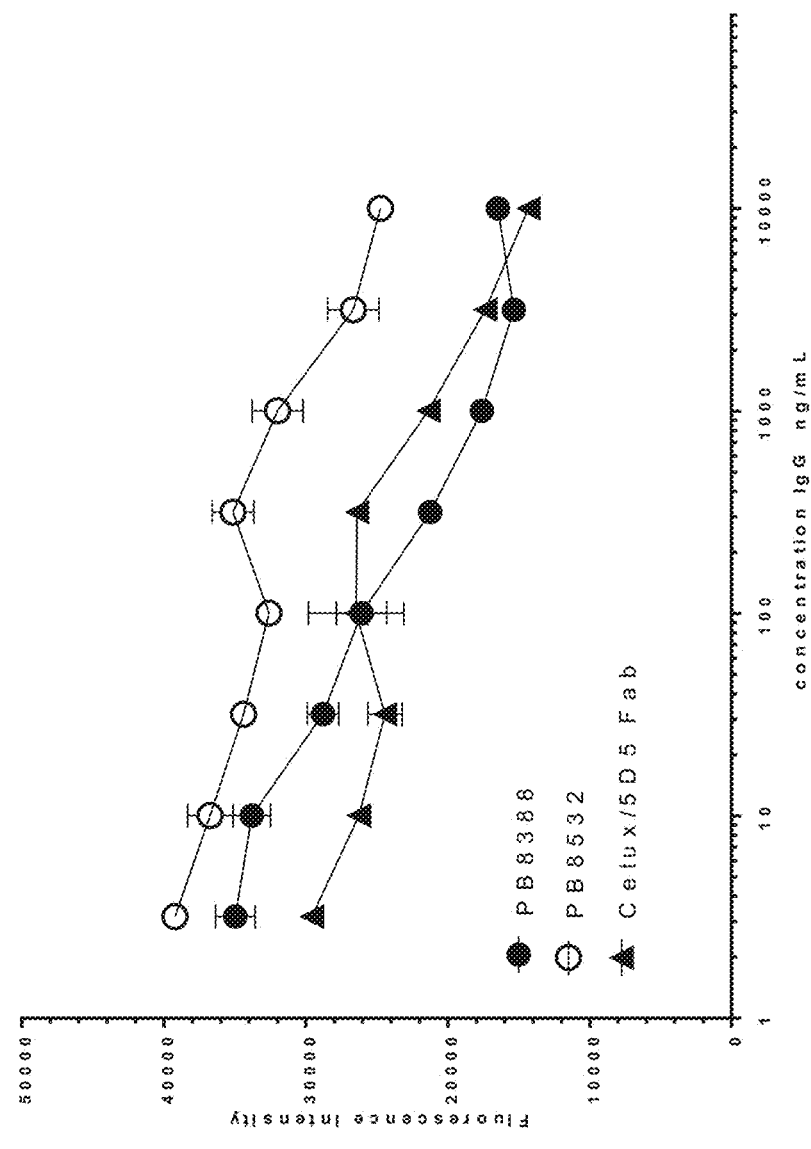
Figure 14C:
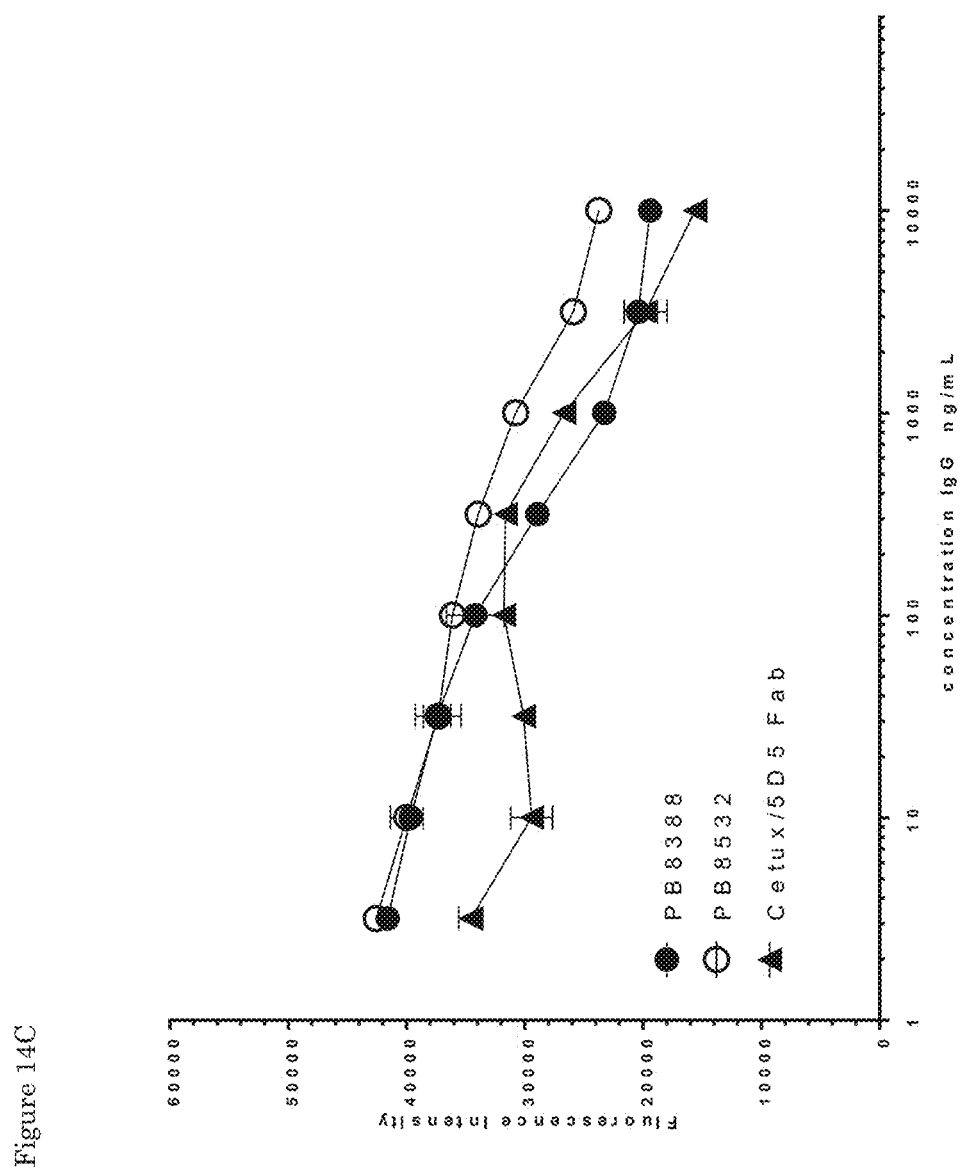

FIG. 14. Inhibition of ligand dependent N87 proliferation. A serial antibody titration was incubated with N87 cells in the presence of HGF(A), EGF (B) or EGF/HGF (C). Cell proliferation was measured by Alamar Blue. Fab 5D5/cetuximab in an equimolar concentration was included as a positive control antibody. The Y-axis represents the fluorescence intensity as an indicator of cell proliferation. The X-axis represents the different concentration of the tested antibodies.

Figure 15A:
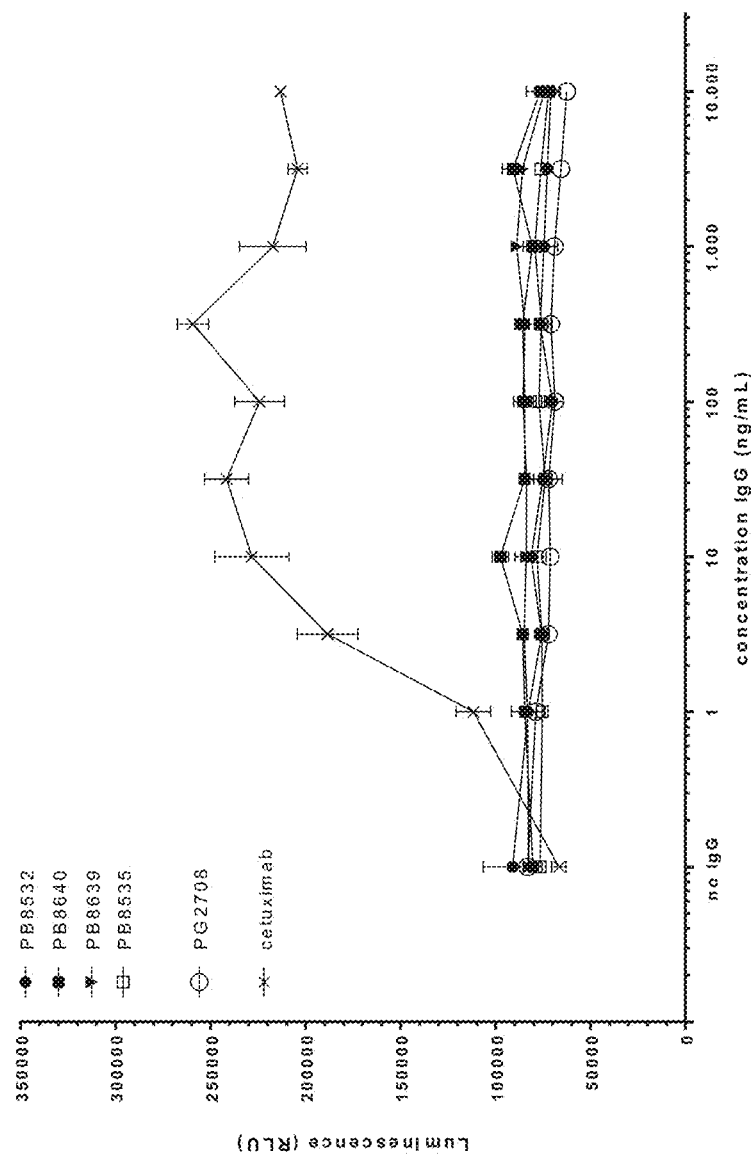
Figure 15B:
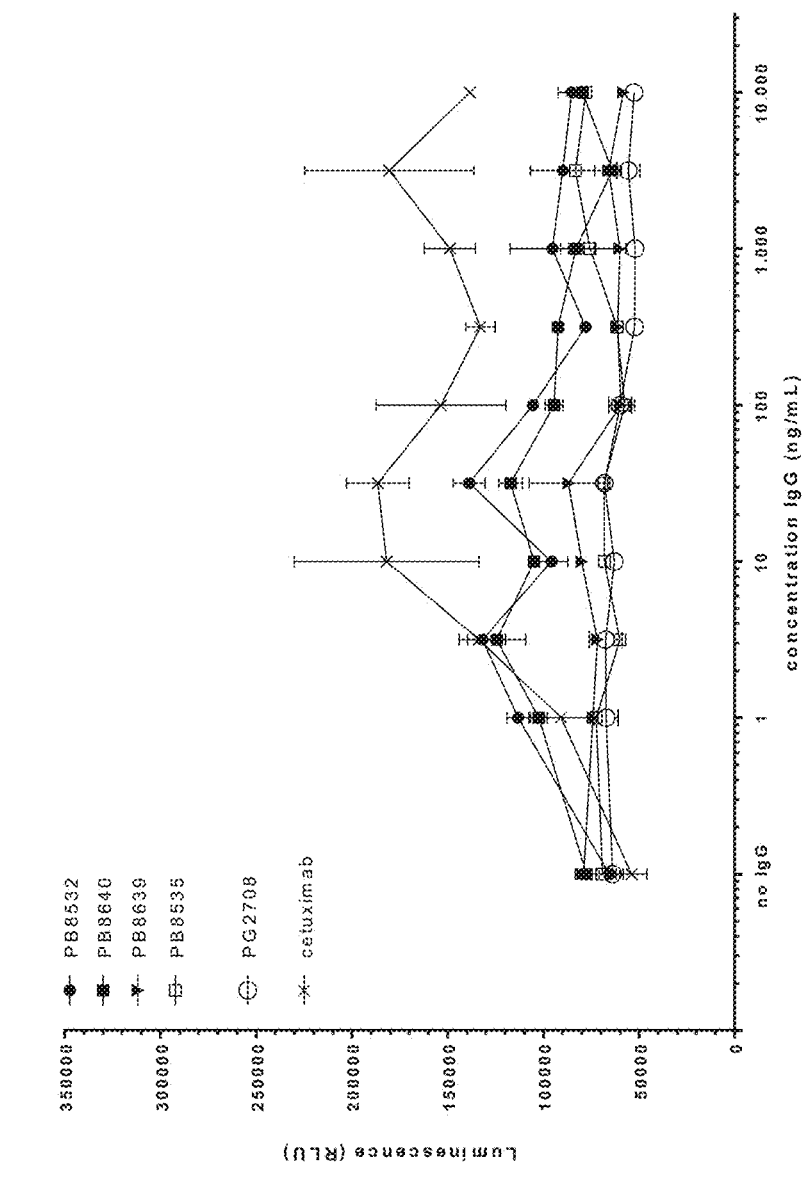

FIG. 15. An example of ADCC activity of cMETxEGFR bispecific antibodies in N87 cells (A) and MKN-45 cells (B) using the high affinity FcγRIIIa ADCC reporter assay. The X-axis represents the added antibody concentration. The Y-Axis represents the Luminescence (RLU) as a read out for ADCC activity. Anti-EGFR antibody cetuximab was included as a positive control antibody.

Figure 16A:
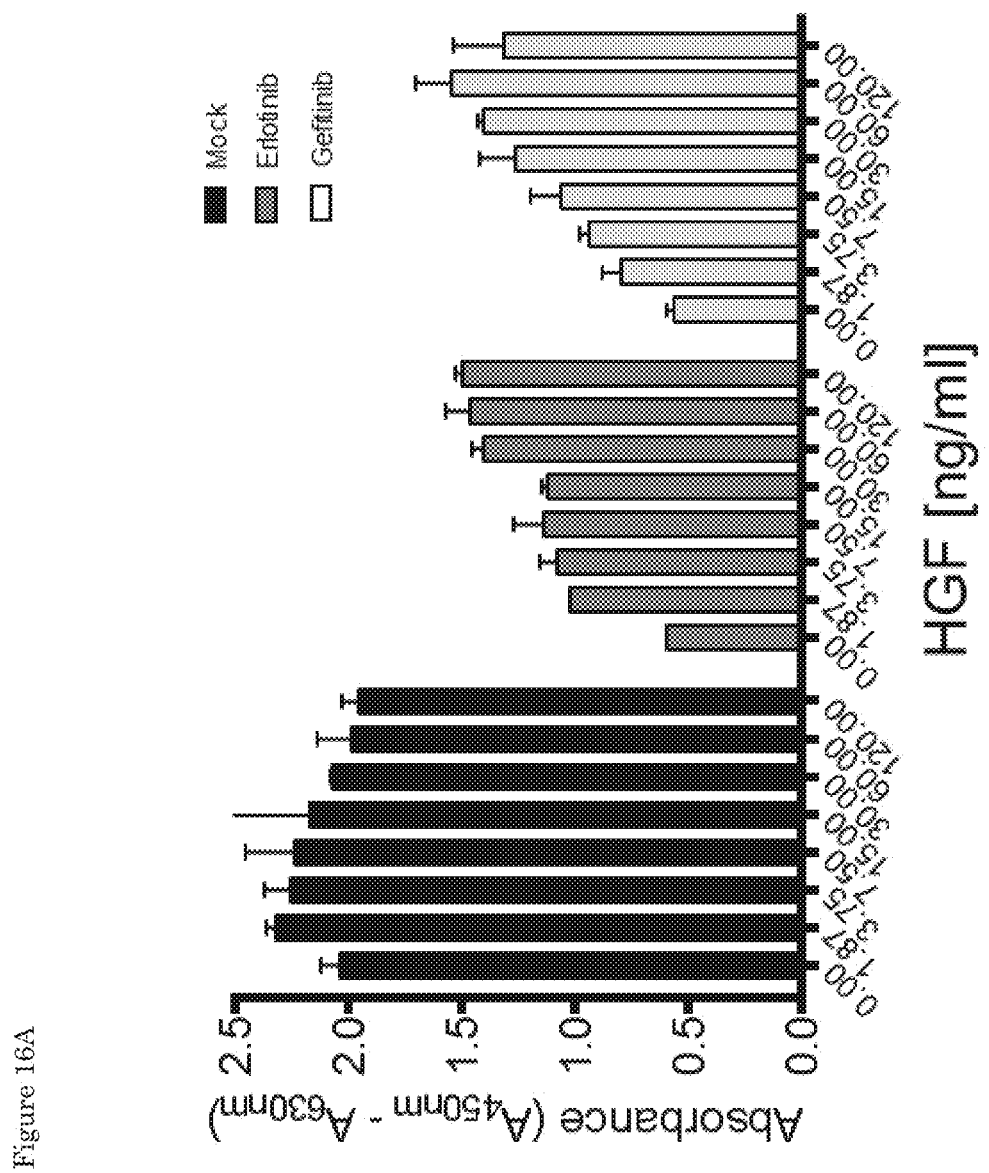
Figure 16B:
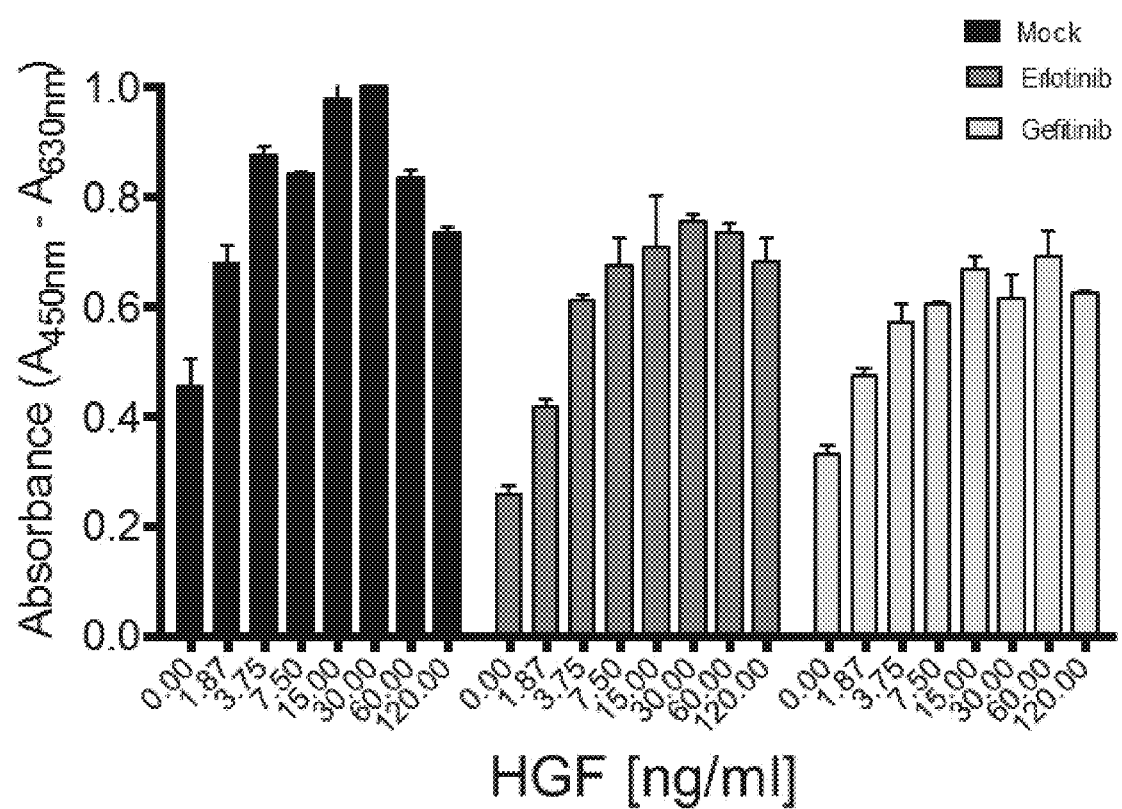

FIG. 16. The effect of HGF on the efficacy of the TKIs erlotinib and gefitinib in PC-9 (A) and HCC827 (B) cells. Cells were incubated with increasing concentrations of HGF (0 to 120 ng/mL) in combination with 300 nM erlotinib or gefitinib, after which cell proliferation was measured. In both cell lines HGF induced a dose-dependent resistance to the TKIs.

Figure 17A:
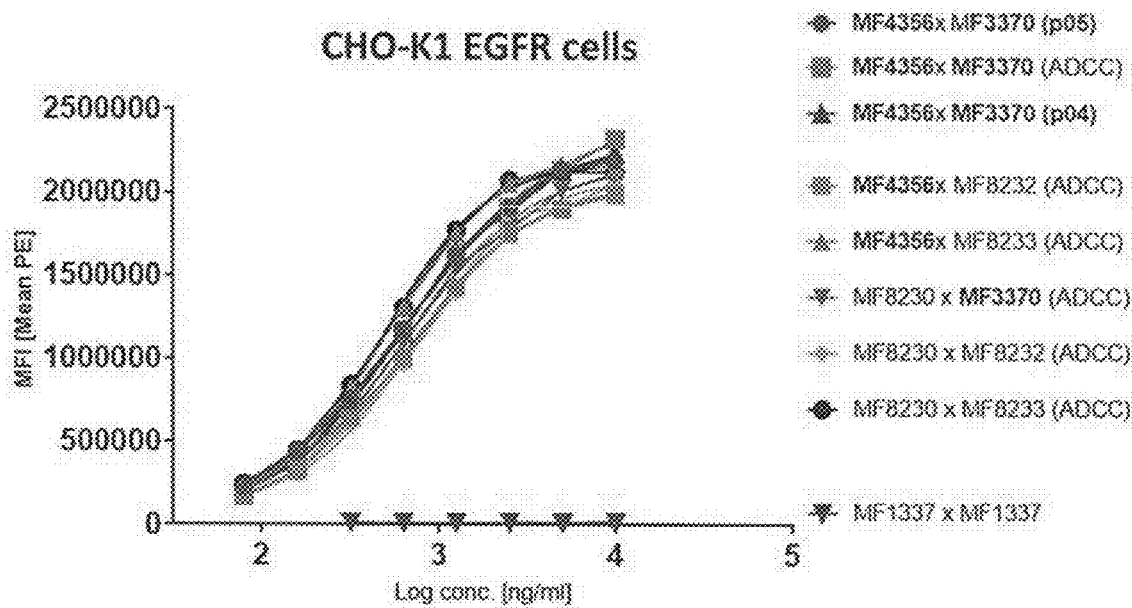
Figure 17B:
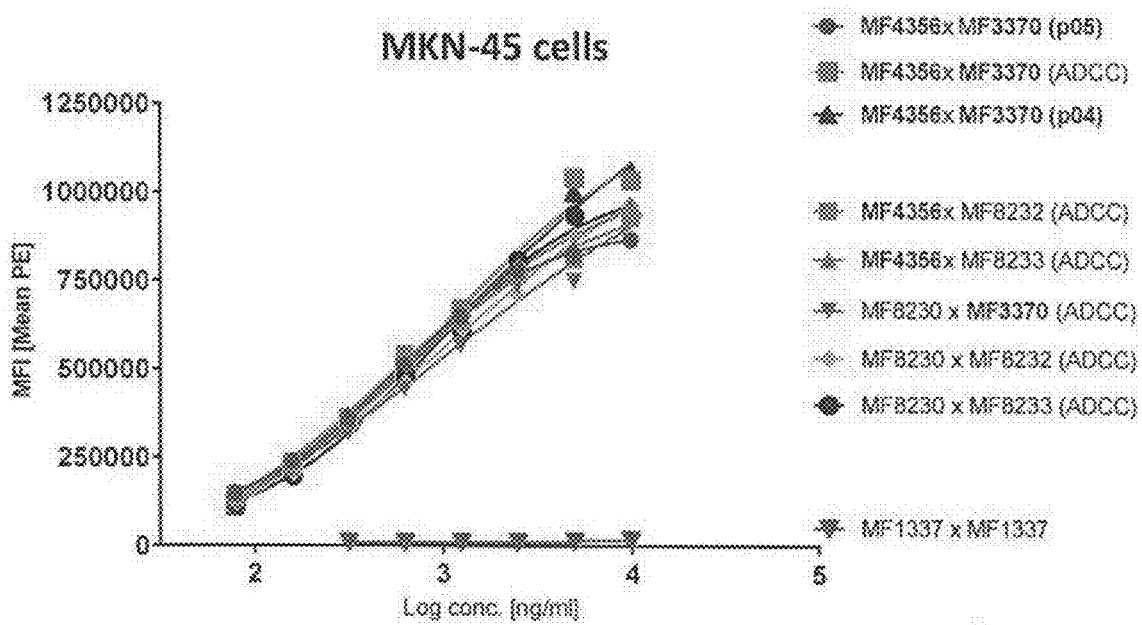

FIG. 17. Testing of affinity binding of ADCC-enhanced c-MET x EGFR variants. CHO-K1 cells stably expressing EGFR (A) or MKN-45 cells endogenously expressing c-MET (B) were incubated at 2×10⁵ cells/well with increasing concentrations of antibody as indicated. After washing, binding was detected with anti-human IgG-PE (3 µg/ml). Stained cells were analyzed on an iQue system and mean fluorescence intensity (MFI) was calculated. Control antibodies were MF1337xMF1337; TTxTT negative control; dark triangles at the bottom) and MF4356xMF3770 (PB8532p04; c-METxEGFR positive control for c-MET; black triangles). TT stands for tetanus toxoid. ADCC indicates antibodies with enhanced ADCC function through co-transfection with DNA encoding the RMD enzyme to remove a fucose residue from the Fc region of IgG1.

Figure 18:
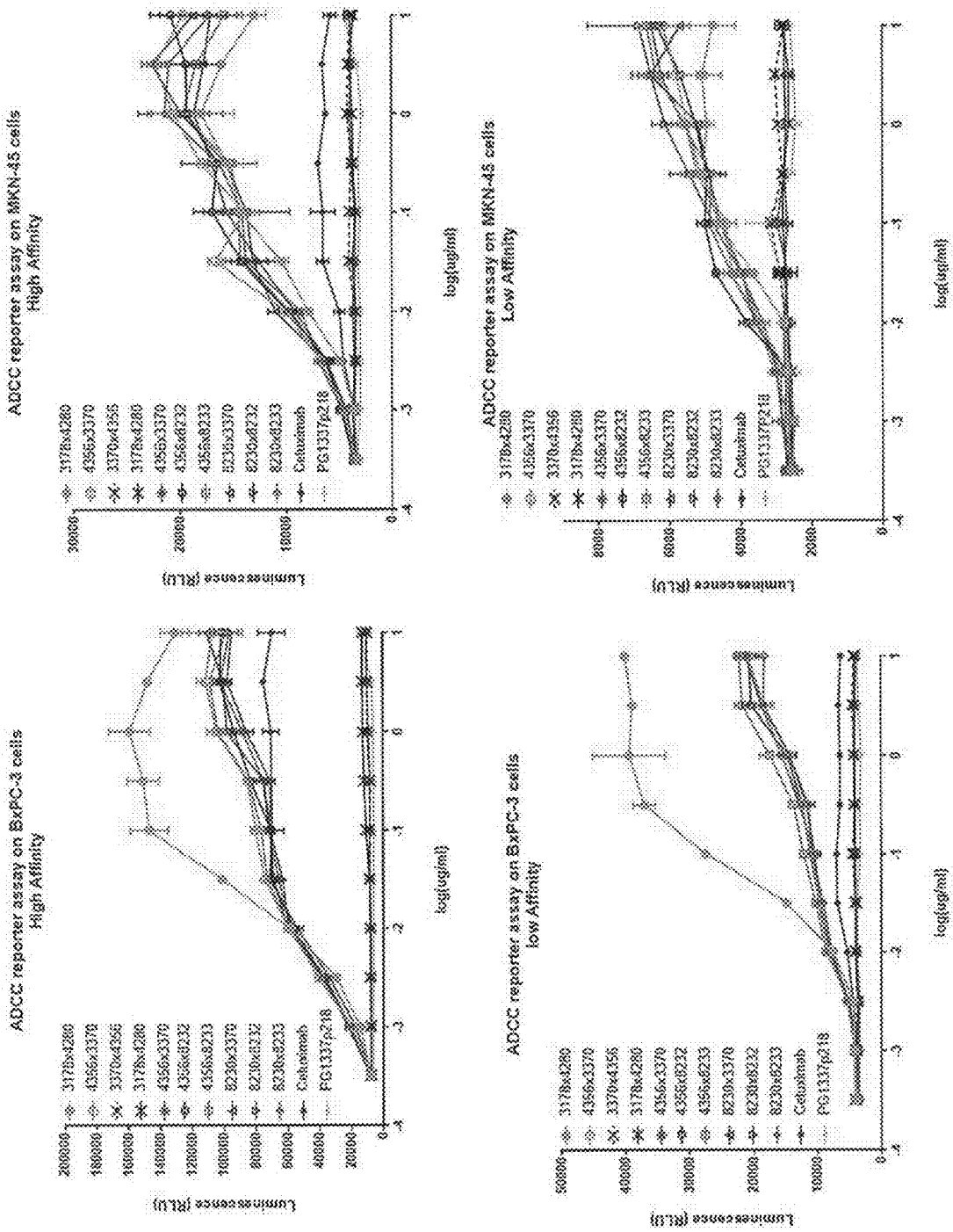

FIG. 18. Results of ADCC reporter assay to confirm enhanced ADCC effector function. EGFR-expressing BxPC-3 cells (left) or c-MET-expressing MKN-45 cells (right) were mixed with ADCC effector cells at an E:T ratio of 15:1, and incubated in the presence of a titration of test antibody (0.01 to 10 µg/ml). After 6 hours, Bio-Glo reagent was added and luminescence measured using a microplate reader. The greater the level of luminescence, the greater the degree of interaction between target and effector cells induced by the test antibody. Top panels show results of high-affinity assay and bottom panels those of low-affinity assay. The negative control antibody was PG1337p218 (anti-TT, light triangles at the bottom); the other control antibodies were 3178x4280 (HER3 x EGFR, ADCC-enhanced, light closed circles (at the top in the left hand top panel); 3178x4280 (HER3 x EGFR, non-ADCC-enhanced, black crosses, at the bottom); 4356x3370 (c-MET x EGFR, ADCC-enhanced, open light circles); 3370x4356 (EGFR x c-MET, non-ADCC-enhanced, black crosses and dashed lines); and Cetuximab (anti-EGFR, small black circles).

Figure 19:
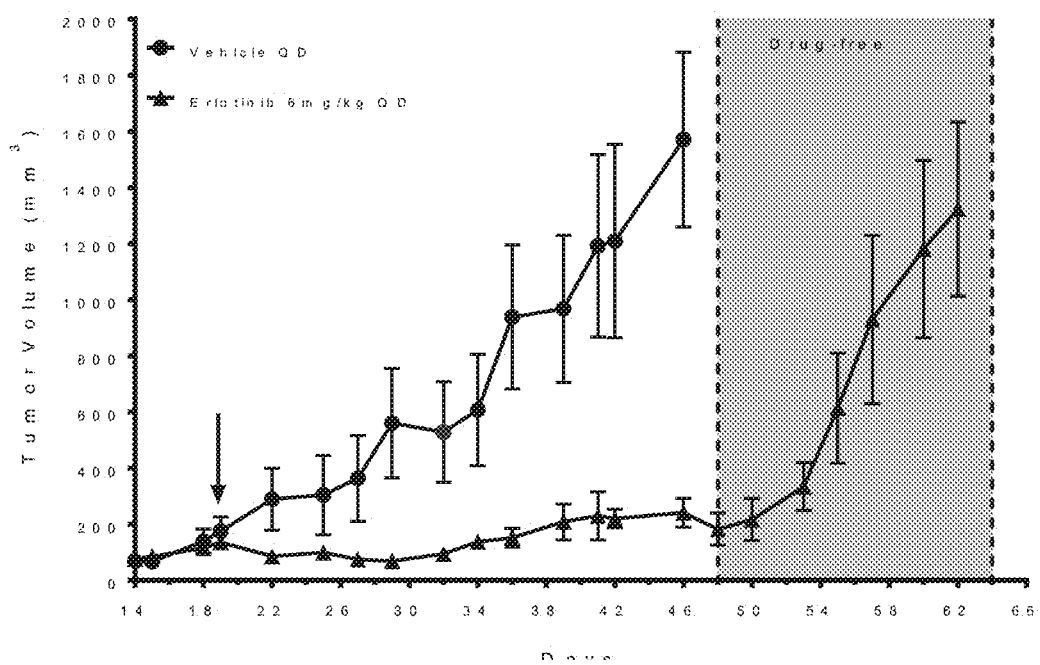

FIG. 19. Erlotinib induces an anti-tumor response in NGS-hHGFki mice engrafted with HCC827 cells as long as mice receive treatment. Black arrow indicates start of treatment.

Figure 20:
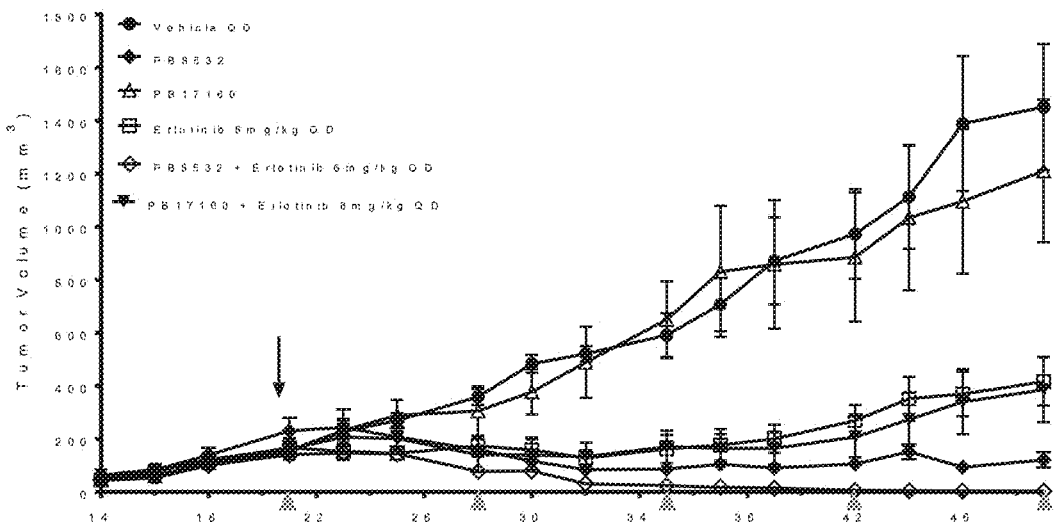

FIG. 20. PB8532 alone and in combination with erlotinib induces an anti-tumor response in NGS-hHGFki mice engrafted with HCC827 cells. Black arrow indicates start of treatment; grey arrows in the X-axis indicate weekly antibody treatments.

Figure 21:
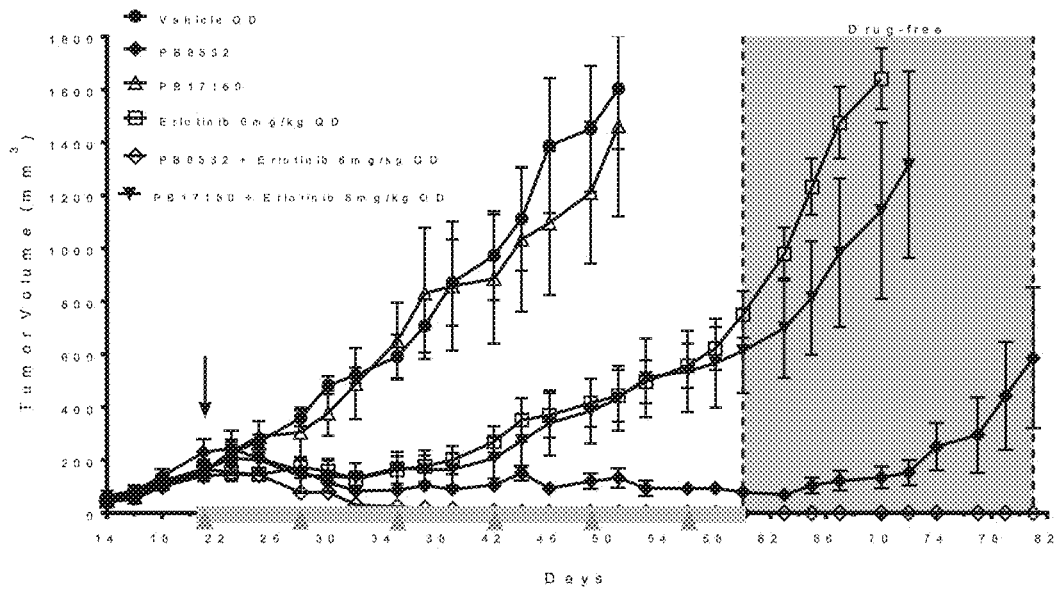

FIG. 21. The anti-tumor response induced by PB8532 alone and in combination with erlotinib is superior to that of erlotinib, even after treatment stops. Black arrow indicates start of treatment; grey arrows in the X-axis indicate weekly antibody treatments.

Figure 22:
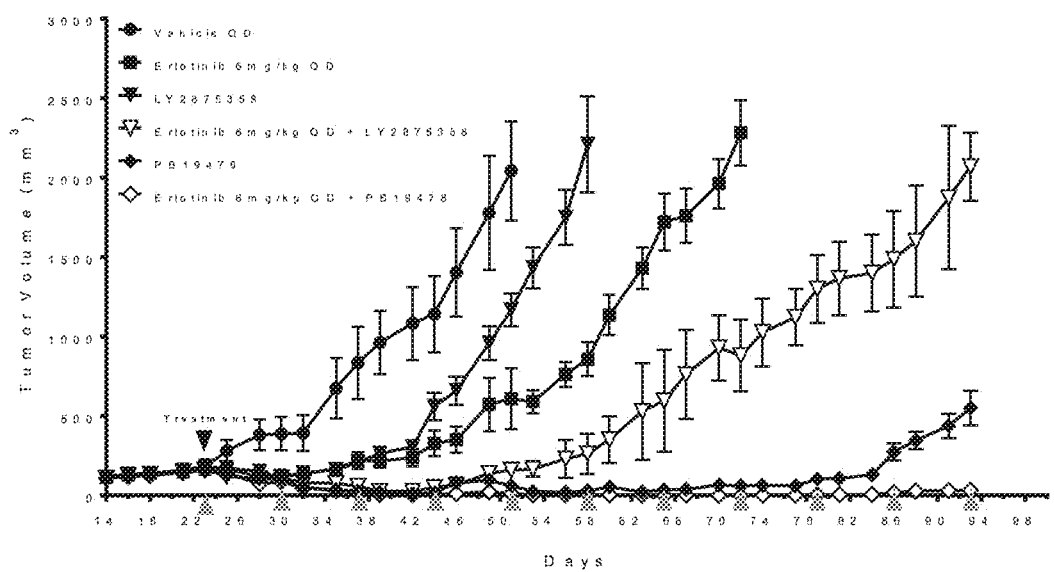

FIG. 22. The anti-tumor response induced by PB8532 alone and in combination with erlotinib is superior to that of erlotinib. Black arrow indicates start of treatment; grey arrows in the X-axis indicate weekly antibody treatments. Treatment with the cMET antibody LY2875358 with and without erlotinib treatment was less effective than PB8532 even without erlotinib treatment.

Figure 23:
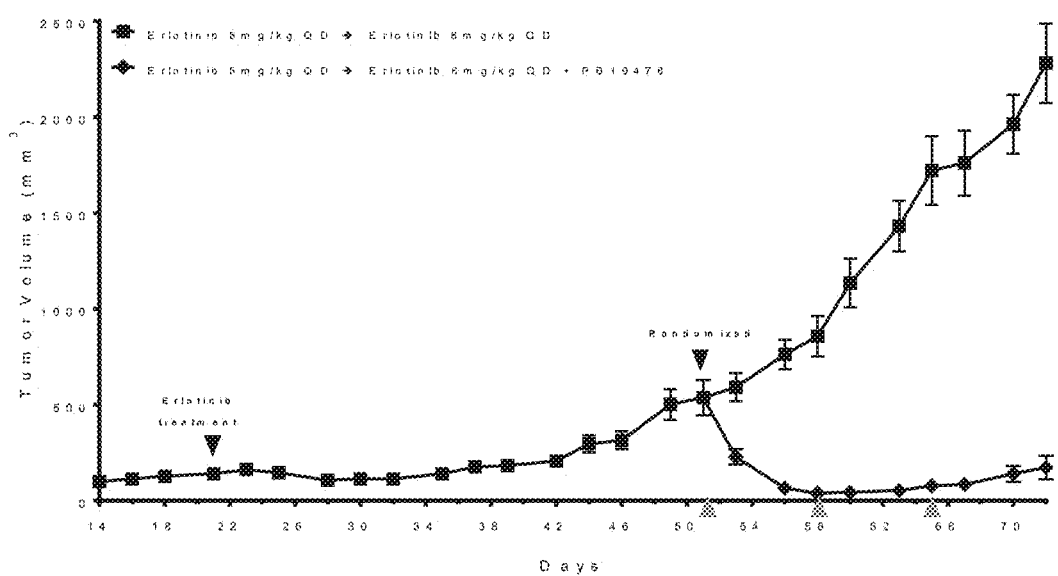

FIG. 23. The anti-tumor response induced by the cMETx-EGFR bispecific antibody PB19478 is effective also when the tumor develops resistance to erlotinib. Black arrows indicate the start of the erlotinib treatment and the start of the PB19478 treatment.

EXAMPLES

As used herein "MFXXXX" wherein X is independently a numeral 0-9, refers to a Fab comprising a variable domain wherein the VH has the amino acid sequence identified by the 4 digits. Unless otherwise indicated the light chain variable region of the variable domain typically has a sequence of FIG. 9A, typically 9B. "MFXXXX VH" refers to the amino acid sequence of the VH identified by the 4 digits. The MF further comprises a constant region of a light chain and a constant region of a heavy chain that normally interacts with a constant region of a light chain. PG refers to a monospecific antibody comprising identical heavy and light chains. PB refers to a bispecific antibody with two different heavy chains. The VH variable regions of the heavy chains differ and typically also the CH3 region, wherein one of the heavy chains has a KK mutation of its CH3 domain and the other has the complementing DE mutation of its CH3 domain (see for reference PCT/NL2013/050294 (published as WO2013/157954).

Example 1: Materials and Methods

Cell Lines:
EBC-1 [JCRB0820], PC-9 [RCB0446], H358 [ATCC® CRL-5807™], HCC827 [ATCC® CRL-2868™], MKN-45 [DSMZ ACC 409] N87 [ATCC®CRL-5822™] and A431 [ATCC® CRL-1555™] cell lines were purchased and routinely maintained in growth media supplemented with 10% heat inactivated fetal bovine serum (FBS). HEK293F Freestyle cells were obtained from Invitrogen and routinely maintained in 293 FreeStyle medium.

cDNA Constructs:

Generation of cMET and EGFR Expression Vectors for Generation of Stable Cell Lines (cMET and EGFR) and for Immunization (cMET)

Full length cDNA of each target including unique restriction sites for cloning and kozak consensus sequence for efficient translation was either synthetized, or obtained via PCR amplification on a commercially available expression construct, containing the target cDNA, with specific primers that introduced unique restriction sites for cloning and kozak consensus sequence for efficient translation. The full length cDNA of each target was cloned into a eukaryotic expression construct such as pcDNA3.1, whereas the extracellular domains were cloned into pVAX1 and pDisplay. The insert sequences were verified by comparison with NCBI Reference amino acid sequences.

Amino acid sequence full length human EGFR insert for expression on the cell surface (Identical to GenBank: NP_00533)

(SEQ ID NO: 42)
MRPSGTAGAALLALLAALCPASRALEEKKVCQGTSNKLTQLGTFEDHFLS

LQRMFNNCEVVLGNLEITYVQRNYDLSFLKTIQEVAGYVLIALNTVERIP

LENLQIIRGNMYYENSYALAVLSNYDANKTGLKELPMRNLQEILHGAVRF

SNNPALCNVESIQWRDIVSSDFLSNMSMDFQNHLGSCQKCDPSCPNGSCW

GAGEENCQKLTKIICAQQCSGRCRGKSPSDCCHNQCAAGCTGPRESDCLV

CRKFRDEATCKDTCPPLMLYNPTTYQMDVNPEGKYSFGATCVKKCPRNYV

VTDHGSCVRACGADSYEMEEDGVRKCKKCEGPCRKVCNGIGIGEFKDSLS

INATNIKHFKNCTSISGDLHILPVAFRGDSFTHTPPLDPQELDILKTVKE

ITGFLLIQAWPENRTDLHAFENLEIIRGRTKQHGQFSLAVVSLNITSLGL

RSLKEISDGDVIISGNKNLCYANTINWKKLFGTSGQKTKIISNRGENSCK

ATGQVCHALCSPEGCWGPEPRDCVSCRNVSRGRECVDKCNLLEGEPREFV

ENSECIQCHPECLPQAMNITCTGRGPDNCIQCAHYIDGPHCVKTCPAGVM

GENNTLVWKYADAGHVCHPLCHNCTYGCTGPGLEGCPTNGPKIPSIATGM

VGALLLLLVVALGIGLFMRRRHIVRKRTLRRLLQERELVEPLTPSGEAPN

QALLRILKETEFKKIKVLGSGAFGTVYKGLWIPEGEKVKIPVAIKELREA

TSPKANKEILDEAYVMASVDNPHVCRLLGICLTSTVQLITQLMPFGCLLD

YVREHKDNIGSQYLLNWCVQIAKGMNYLEDRRLVHRDLAARNVLVKTPQH

VKITDFGLAKLLGAEEKEYHAEGGKVPIKWMALESILHRIYTHQSDVWSY

GVTVWELMTFGSKPYDGIPASEISSILEKGERLPQPPICTIDVYMIMVKC

WMIDADSRPKFRELIIEFSKMARDPQRYLVIQGDERMHLPSPTDSNFYRA

LMDEEDMDDVVDADEYLIPQQGFFSSPSTSRTPLLSSLSATSNNSTVACI

DRNGLQSCPIKEDSFLQRYSSDPTGALTEDSIDDTFLPVPEYINQSVPKR

-continued

```
PAGSVQNPVYHNQPLNPAPSRDPHYQDPHSTAVGNPEYLNTVQPTCVNST
FDSPAHWAQKGSHQISLDNPDYQQDFFPKEAKPNGIFKGSTAENAEYLRV
APQSSEFIGA
```

Of which:

(SEQ ID NO: 141)
MRPSGTAGAALLALLAALCPASR: signal peptide.

(SEQ ID NO: 142)
```
ALEEKKVCQGTSNKLTQLGTFEDHFLSLQRMFNNCEVVLGNEITYVQRNY
DLSFLKTIQEVAGYVLIALNTVERIPLENLQIIRGNMYYENSYALAVLSN
YDANKTGLKELPMRNLQEILHGAVRFSNNPALCNVESIQWRDIVSSDFLS
NMSMDFQNHLGSCQKCDPSCPNGSCWGAGEENCQKLTKIICAQQCSGRCR
GKSPSDCCHNQCAAGCTGPRESDCLVCRKFRDEATCKDTCPPLMLYNPTT
YQMDVNPEGKYSFGATCVKKCPRNYVVTDHGSCVRACGADSYEMEEDGVR
KCKKCEGPCRKVCNGIGIGEFKDSLSINATNIKHPKNCTSISGDLHILPV
AFRGDSFTHTPPLDPQELDILKTVKEITGFLLIQAWPENRTDLHAFENLE
IIRGRTKQHGQFSLAVVSLNITSLGLRSLKEISDGDVIISGNKNLCYANT
INWKKLFSTSGQKTKIISNRGENSCKATGQVCHALCSPEGCWGPEPRDCV
SCRNVSRGRECVDKCNLLEGEPREFVENSECIQCHPECLPQAMNITCTGR
GPDNCIQCAHYIDGPHCVKTCPAGVMGENNTLVWKYADAGHVCHLCHPNC
TYGCTGPGLEGCPTNGPKIPS: ECD of human EGFR.
```

(SEQ ID NO: 143)
IATGMVGALLLLLVVALGIGLFM: predicted TM region.

(SEQ ID NO: 144)
```
RRRHIVRKRTLRRLLQERELVEPLTPSGEAPNQALLRILKETEFKKIKVL
GSGAFGTVYKGLWIPEGEKVKIPVAIKELREATSPKANKEILDEAYVMAS
VDNPHVCRLLGICLTSTVQLITQLMPFGCLLDYVREHKDNIGSQYLLNWC
VQIAKGMNYLEDRRLVHRDLAARNVLVKTPQHVKITDFGLAKLLGAEEKE
YHAEGGKVPIKWMALESILHRIYTHQSDVWSYGVTVWELMTFGSKPYDGI
PASEISSILEKGERLPQPPICTIDVYMIMVKCWMIDADSRPKFRELIIEF
SKMARDPQRYLVIQGDERMHLPSPTDSNFYRALMDEEDMDDVVDADEYLI
PQQGFFSSPSTSRTPLLSSLSATSNNSTVACIDRNGLQSCPIKEDSFLQR
YSSDPTGALTEDSIDDTFLPVPEYINQSVPKRPAGSVQNPVYHNQPLNPA
PSRDPHYQDPHSTAVGNPEYLNTVQPTCVNSTFDSPAHWAQKGSHQISLD
NPDYQQDFFPKEAKPNGIFKGSTAENAEYLRVAPQSSEFIGA:
intracellular tail.
```

Amino acid sequence of extracellular domain of human EGFRvarIII a natural occurring EGFR variant VAR_066493 [Ji H., Zhao X; PNAS 103:7817-7822(2006)] caused by an in-frame deletion of exons 2-7. The _ below indicates the location lacking amino acids 30-297

(SEQ ID NO: 43)
```
MRPSGTAGAALLALLAALCPASRALEEKK_GNYVVTDHGSCVRACGADSY
EMEEDGVRKCKKCEGPCRKVCNGIGIGEFKDSLSINATNIKHFKNCTSIS
GDLHILPVAFRGDSFTHTPPLDPQELDILKTVKEITGFLLIQAWPENRTD
LHAFENLEIIRGRTKQHGQFSLAVVSLNITSLGLRSLKEISDGDVIISGN
KNLCYANTINWKKLFGTSGQKTKIISNRGENSCKATGQVCHALCSPEGCW
GPEPRDCVSCRNVSRGRECVDKCNLLEGEPREFVENSECIQCHPECLPQA
MNITCTGRGPDNCIQCAHYIDGPHCVKTCPAGVMGENNTLVWKYADAGHV
CHLCHPNCTYGCTGPGLEGCPTNGPKIPS
```

Of which:

(SEQ ID NO: 145)
MRPSGTAGAALLALLAALCPASR: signal peptide.

(SEQ ID NO: 146)
```
ALEEKK_GNYVVTDHGSCVRACGADSYEMEEDGVRKCKKCEGPCRKVCNG
IGIGEFKDSLSINATNIKHFKNCTSISGDLHILPVAFRGDSFTHTPPLDP
QELDILKTVKEITGFLLIQAWPENRTDLHAFENLEIIRGRTKQHGQFSLA
VVSLNITSLGLRSLKEISDGDVIISGNKNLCYANTINWKKLFGTSGQKTK
IISNRGENSCKATGQVCHALCSPEGCWGPEPRDCVSCRNVSRGRECVDKC
NLLEGEPREFVENSECIQCHPECLPQAMNITCTGRGPDNCIQCAHYIDGP
HCVKTCPAGVMGENNTLVWKYADAGHVCHLCHPNCTYGCTGPGLEGCPTN
GPKIPS: ECD of EGFRvarIII
```

Amino acid sequence chimeric macaque (*Macaca mulatta*) extra cellular EGFR domain hybrid with human EGFR transmembrane and intracellular domain for expression on the cell surface (Identical to GenBank: XP_014988922.1. Human EGFR sequence underlined in the example below.

(SEQ ID NO: 44)
```
MGPSGTAGAALLALLAALCPASRALEEKKVCQGTSNKLTQLGTFEDHFLS
LQRMFNNCEVVLGNLEITYVQRNYDLSFLKTIQEVAGYVLIALNTVERIP
LENLQIIRGNMYYENSYALAVLSNYDANKTGLKELPMRNLQEILHGAVRF
SNNPALCNVESIQWRDIVSSEFLSNMSMDFQNHLGSCQKCDPSCPNGSCW
GAGEENCQKLTKIICAQQCSGRCRGKSPSDCCHNQCAAGCTGPRESDCLV
CRKFRDEATCKDTCPPLMLYNPTTYQMDVNPEGKYSFGATCVKKCPRNYV
VTDHGSCVRACGADSYEMEEDGVRKCKKCEGPCRKVCNGIGIGEFKDTLS
INATNIKHFKNCTSISGDLHILPVAFRGDSFTHTPPLDPQELDILKTVKE
ITGFLLIQAWPENRTDLHAFENLEIIRGRTKQHGQFSLAVVSLNITSLGL
RSLKEISDGDVIISGNKNLCYANTINWKKLFGTSSQKTKIISNRGENSCK
ATGQVCHALCSPEGCWGPEPRDCVSCQNVSPGRECVDKCNILEGEPREFV
ENSECIQCHPECLPQVMNITCTGRGPDNCIQCAHYIDGPHCVKTCPAGVM
GENNTLVWKYADAGHVCHLCHPNCTYGCTGPGLEGCARNGPKIPSIATGM
LGALLLLLVVALGIGLFMRRRHIVRKRTLRRLLQERELVEPLTPSGEAPN
QALLRILKETEFKKIKVLGSGAFGTVYKGLWIPEGEKVKIPVAIKELREA
TSPKANKEILDEAYVNASVDNPHVCRLLGICLTSTVQLITQLMPFGCLLD
YVREHKDNIGSQYLLNWCVQIAKGMNYLEDRRLVHRDLAARNVLVKTPQH
VKITDFGLAKLLGAEEKEYHAEGGKVPIKWMALESILHRIYTHQSDVWSY
```

-continued
GVTVWELMTFGSKPYDGIPASEISSILEKGERLPQPPICTIDVYMIMVKC
WMIDADSRPKFRELIIEFSKMARDPQRYLVIQGDERMHLPSPTDSNFYRA
LMDEEDMDDVVDADEYLIPQQGFFSSPSTSRTPLLSSLSATSNNSTVACI
DRNGLQSCPIKEDSFLQRYSSDPTGALTEDSIDDTFLPVPEYINQSVPKR
PAGSVQNPVYHNQPLNPAPSRDPHYQDPHSTAVGNPEYLNTVQPTCVNST
FDSPAHWAQKGSHQISLDNPDYQQDFFPKEAKPNGIFKGSTAENAEYLRV
APQSSEFIGA Of which:

(SEQ ID NO: 147)
MGPSGTAGAALLALLAALCPASR: signal peptide.

(SEQ ID NO: 148)
LEEKKVCQGTSNKLTQLGTFEDHFLSLQRMFNNCEVVLGNLEITYVQRNY
DLSFLKTIQEVAGYVLIALNTVERIPLENLQIIRGNMYYENSYALAVLSN
YDANKTGLKELPMRNLQEILHGAVRFSNNPALCNVESIQWRDIVSSDFLS
NMSMDFQNHLGSCQKCDPSCPNGSCWGAGEENCQKLTKIICAQQCSGRCR
GKSPSDCCHNQCAAGCTGPRESDCLVCRKFRDEATCKDTCPPLMLYNPTT
YQMDVNPEGKYSFGATCVKKCPRNYVVTDHGSCVRACGADSYEMEEDGVR
KCKKCEGPCRKVCNGIGIGEFKDSLSINATNIKHFKNCTSISGDLHILPV
AFRGDSFTHTPPLDPQELDILKTVKEITGFLLIQAWPENRTDLHAFENLE
IIRGRTKQHGQFSLAVVSLNITSLGLRSLKEISDGDVIISGNKNLCYANT
INWKKLFGTSGQKTKIISNRGENSCKATGQVCHALCSPEGCWGPEPRDCV
SCRNVSRGRECVDKCNLLEGEPREFVENSECIQCHPECLPQAMNITCTGR
GPDNCIQCAHYIDGPHCVKTGPAGVMGENNTLVWKYADAGHVCHLCHPNC
TYGCTGPGLEGCPTNGPKIPS: ECD of cyEGFR

Amino acid sequence full length human cMET insert for expression on the cell surface (Identical to GenBank: P08581-2). The sequence differs from the reference sequence at position with an insertion at 755-755: S→STWWKEPLNIVSFLFCFAS (SEQ ID NO: 46)
MKAPAVLAPGILVLLFTLVQRSNGECKEALAKSEMNVNMKYQLPNFTAET
PIQNVILHEHHIFLGATNYIYVLNEEDLQKVAEYKTGPVLEHPDCFPCQD
CSSKANLSGGVWKDNINMALVVDTYYDDQLISCGSVNRGTCQRHVFPHNH
TADIQSEVHCIFSPQIEEPSQCPDCVVSALGAKVLSSVKDRFINFFVGNT
INSSYFPDHPLHSIDVRRLKETKDGFMFLTDQSYIDVLPEFRDSYPIKYV
HAFESNNFIYFLTVQRETLDAQTFHTRIIRFCSINSGLHSYMEMPLECIL
TEKRKKRSTKKEVFNILQAAYVSKPGAQLARQIGASLNDDILFGVFAQSK
PDSAEPMDRSAMCAFPIHYVNDFFNKIVNKNNVRCLQHFYGPNHEHCFNR
TLLRNSSGCEARRDEYRTEFTTALQRVDLFMGQFSEVLLTSISTFIKGDL
TIANLGTSEGRFMQVVVSRSGPSTPHVNFLLDSHPVSPEVIVEHTLNQNG
YTLVITGKKITKIPLNGLGCRHFQSCSQCLSAPPFVQCGWCHDKCVRSEE
CLSGTWTQQICLPAIYKVFPNSAPLEGGTRLTICGWDFGFRRNNKFDLKK
TRVLLGNESCTLTLSESTMNTLKCTVGPAMNKHFNMSIIISNGHGTTQYS
TFSYVDPVITSISPKYGPMAGGTLLTLTGNYLNSGNSRHISIGGKTCTLK
SVSNSILECYTPAQTISTEFAVKLKIDLANRETSIFSYREDPIVYEIHPT
KSFISTWWKEPLNIVSFLFCFASGGSTITGVGKNLNSVSVPRMVINVHEA
GRNFTVACQHRSNSEIICCTTPSLQQLNLQLPLKTKAFFMLDGILSKYFD
LIYVHNPVFKPFEKPVMISMGNENVLEIKGNDIDPEAVKGEVLKVGNKSC
ENIHLHSEAVLCTVPNDLLKLNSELNIEWKQAISSTVLGKVIVQPDQNFT
GLIAGVVSISTALLLLLGFFLWLKKRKQIKDLGSELVRYDARVHTPHLDR
LVSARSVSPTTEMVSNESVDYRATFPEDQFPNSSQNGSCRQVQYPLTDMS
PILTSGDSDISSPLLQNTVHIDLSALNPELVQAVQHVVIGPSSLIVHFNE
VIGRGHFGCVYHGTLLDNDGKKIHCAVKSLNRITDIGEVSQFLTEGIIMK
DFSHPNVLSLLGICLRSEGSPLVVLPYMKHGDLRNFIRNETHNPTVKDLI
GFGLQVAKGMKYLASKKFVHRDLAARNCMLDEKFTVKVADFGLARDMYDK
EYYSVHNKTGAKLPVKWMALESLQTQKFTTKSDVWSFGVLLWELMTRGAP
PYPDVNTFDITVYLLQGRRLLQPEYCPDPLYEVMLKCWHPKAEMRPSFSE
LVSRISAIFSTFIGEHYVHVNATYVNVKCVAPYPSLLSSEDNADDEVDTR
PASFWETS Of which:

(SEQ ID NO: 148)
MKAPAVLAPGILVLLFTLVQRSNG: signal peptide (SEQ ID NO: 149)
ECKEALAKSEMNVNMKYQLPNFTAETPIQNVILHEHHIFLGATNYIYVLN
EEDLQKVAEYKTGPVLEHPDCFPCQDCSSKANLSGGVWKDNINMALVVDT
YYDDQLISCGSVNRGTCQRHVFPHNHTADIQSEVHCIFSPQIEEPSQCPD
CVVSALGAKVLSSVKDRFINFFVGNTINSSYFPDHPLHSISVRRLKETKD
GFMFLTDQSYIDVLPEFRDSYPIKYVHAFESNNFIYFLTVQRETLDAQTF
HTRIIRFCSINSGLHSYMEMPLECILTEKRKKRSTKKEVFNILQAAYVSK
PGAQLARQIGASLNDDILFGVFAQSKPDSAEPMDRSAMCAFPIKYVNDFF
NKIVNKNNVRCLQHFYGPNHEHCFNRTLLRNSSGCEARRDEYRTEFTTAL
QRVDLFMGQFSEVLLTSISTFIKGDLTIANLGTSEGRFMQVVVSRSGPST
PHVNFLLDSHPVSPEVIVEHTLNQNGYTLVITGKKITKIPLNGLGCRHFQ
SCSQCLSAPPFVQCGWCHDKCVRSEECLSGTWTQQICLPAIYKVFPNSAP
LEGGTRLTICGWDFGFRRNNKFDLKKTRVLLGNESCTLTLSESTMNTLKC
TVGPAMNKHFNMSIIISNGHGTTQYSTFSYVDPVITSISPKYGPMAGGTL
LTLTGNYLNSGNSRHISIGGKTCTLKSVSNSILECYTPAQTISTEFAVKL
KIDLANRETSIFSYREDPIVIEIHPTKSFISGGSTITGVGKNLNSVSVPR
MVINVHEAGRNFTVACQHRSNSEIICCTTPSLQQLNLQLPLKTKAFFMLD -continued

```
GILSKYFDLIYVHNPVFKPFEKPVMISMGNENVLEIKGNDIDPEAVKGEV

LKVGNKSCENIHLHSEAVLCTVPNDLLKLNSELNIEWKQAISSTVLGKVI

VQPDQNFT: ECD of human cMET (SEQ ID NO: 150)
GLIAGVVSISTALLLLLGFFWL: transmembrane region (SEQ ID NO: 151)
KKRKQIKDLGSELVRYDARVHTPHLDRLVSARSVSPTTEMVSNESVDYRA

TFPEDQFPNSSQNGSCRQVQYPLTDMSPILTSGDSDISSPLLQNTVHIDL

SALNPELVQAVQHVVIGPSSLIVHFNEVIGPGHFGCVYHGTLLDNDGKKI

HCAVKSLNRITDIGEVSQFLTEGIIMKDFSHPNVLSLLGICLRSEGSPLV

VLPYMKHGDLRNFIRNETHNPTVKDLIGFGLQVAKGMKYASKKFVHRDLA

ARNCMLDEKFTVKVADFGLARDMYDKEYYSVHNKTGAKLPVKWMALESLQ

TQKFTTKSDVWSFGVLLWELMTRGAPPYPDVNTFDITVYLLQGRRLLQPE

YCPDPLYEVMLKCWHPKAEMRPSFSELVSRISAIFSTFIGEHYVHVNATY

VNVKCVAPYPSLLSSEDNADDEVEDTRPASFWETS: intracellular region
```

Reference Antibodies

Anti-cMET Antibodies are known in the art (Table 1). Monospecific bivalent cMET antibodies were constructed according to published information and expressed in 293F Freestyle cell. Table 1 shows the related disclosed information. Monospecific bivalent antibodies directed against cMET were constructed according to published information and expressed in 293F Freestyle cells. For HGF ligand blocking assays VH- and VL-encoding gene segments of patent-derived anti-cMET antibodies were re-cloned in a phage display vector for display on filamentous bacteriophage.

Reference antibody cetuximab (Erbitux) was used as reference antibody for the EGFR Fab panel.

2994 Fab protein was generated from purified PG2994 IgG by papain digestion. Therefore PG2994 was incubated with papain coupled on beads (Pierce #44985), and allowed to digest for 5.5 hour at 37° C. under rotation. Fab fragments were purified from the digestion mixture by filtration over MabSelectSure LX. Flow through fractions containing Fab protein, concentrated to 3 ml using vivaspin20 10 kDa and further purified by gel filtration using a superdex75 16/600 column in PBS.

Example 2

Generation of Bivalent Monoclonal Antibodies and Antibody Characterization

VH genes of unique antibodies, as judged by VH gene sequence and some sequence variants thereof, were cloned in the backbone IgG1 vector. Suspension adapted 293F Freestyle cells were cultivated in T125 flasks at a shaker plateau until a density of $3.0 \times 10^6$ cells/ml. Cells were seeded at a density of $0.3$-$0.5 \times 10^6$ viable cells/ml in each well of a 24-deep well plate. The cells were transiently transfected with the individual sterile DNA:PEI mixture and further cultivated. Seven days after transfection, supernatant was harvested and filtrated through 0.22 μM (Sartorius) and purified on protein A beads using batch purification followed by a buffer exchange to PBS.

Inhibition of EGF Mediated Apoptosis

High (10 nM) concentrations of EGF induce (apoptotic) cell death in A431 cells [Gulli et al., 1996)]. This effect can be dose-dependently reverted by the addition of ligand-blocking anti-EGFR antibodies, such as cetuximab.

Figure 2:
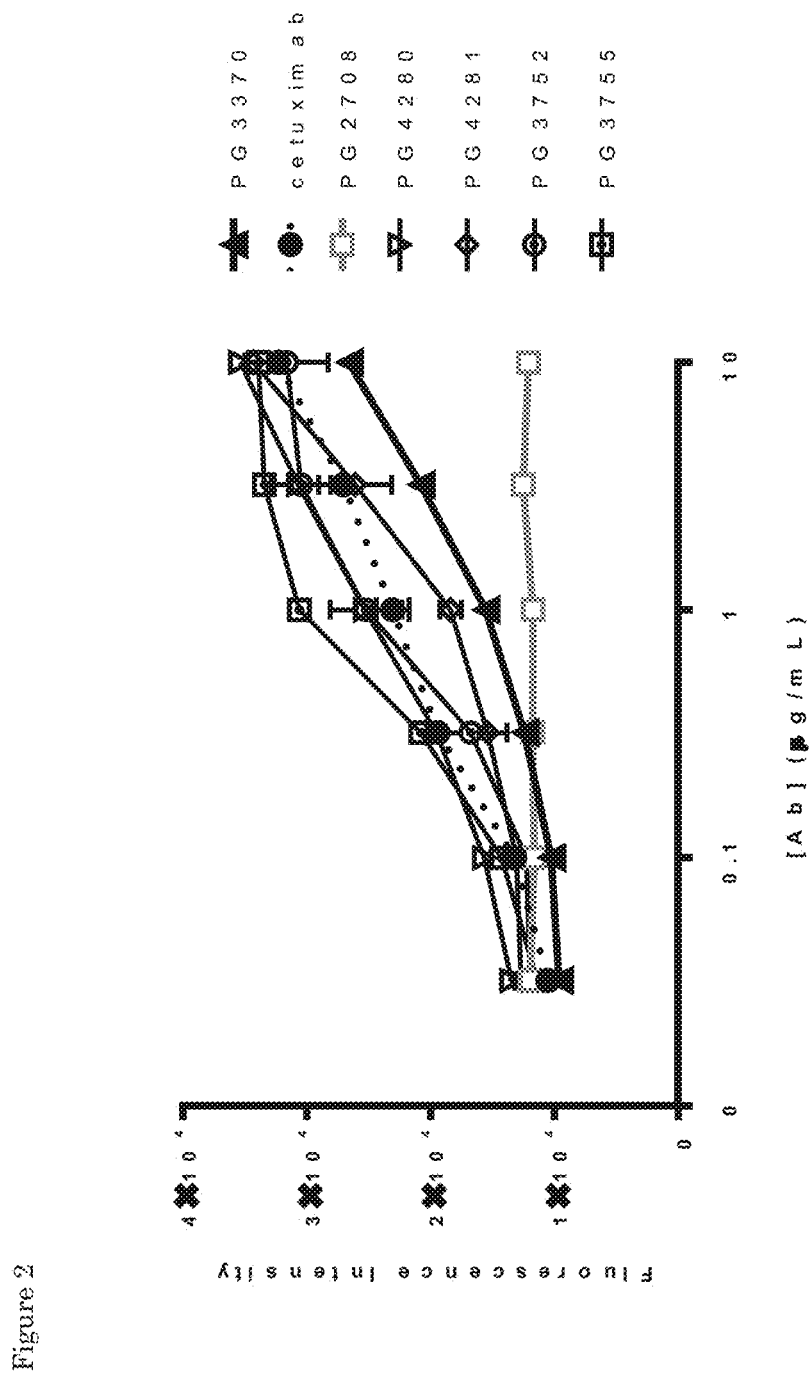
FIG. 2. Functionality of anti-EGFR cLC bivalent antibodies in inhibiting the EGF induced death of A431 cells. The Y axis (counts) shows the fluorescence readout of the assay, reminiscent of the number of metabolically active cells, as a function of the concentration of antibody used (X-axis). PG3370 is able to inhibit EGF-induced cell death and therefore shows enhanced growth of the cells with increasing antibody concentration. Molecules having variable region amino acid sequences of cetuximab/Erbitux, referred to herein as cetuximab or reference antibody cetuximab, were used in experiments as an internal standard (black dots).

To test the bivalent anti-EGFR IgG for their potency to inhibit EGF-induced cell death of A431 cells, antibodies were incubated in a serial titration—from 10 μg/ml onwards—in the presence of 10 nM EGF. Each assay plate contained a serial dilution of negative (Ctrl Ab; PG2708) and positive control antibody (cetuximab) that served as reference controls. On the third day, Alamar blue (Invitrogen, #DAL1100) was added (20 μl per well) and the fluorescence was measured after 6 hours of incubation (at 37° C.) with Alamar blue using 560 nm excitation and 590 nm readout on a Biotek Synergy 2 Multi-mode microplate reader. FIG. 2 shows the activity of the cLC EGFR antibodies compared to that of cetuximab and the control antibody. Antibodies PG4280, 3755 and 3752 were more potent in comparison to cetuximab whereas antibodies PG4281 and PG3370 showed less efficacy.

EGF Blocking ELISA

EGFR specific phages were tested for binding to recombinant EGFR in the absence and presence of a molar excess of ligand (EGF). Therefore 5 μg/ml of goat anti-human IgG was coated overnight to MAXISORP™ ELISA plates at 4° C. Wells of the ELISA plates were blocked with PBS (pH 7.2) containing 2% ELK for 1 h at RT while shaking (700 rpm). Next, 5 μg/ml recombinant human EGFR-Fc was allowed to incubate for 1H at RT. Meanwhile, IgG was mixed in a serial titration with human biotinylated EGF for 1 H at RT. After washing away unbound human EGFR-Fc, the antibody/EGF mixture was added and allowed to bind for 1H at RT. Bound EGF was detected by HRP-streptavidine for 1H at RT. As a control the procedure was performed simultaneously with an antibody specific for the coated antigens (not shown) and a negative control phage (Neg Ctrl Ab). Bound secondary antibody was visualized by TMB/$H_2O_2$ staining and staining was quantified by means of $OD_{450nm}$ measurement. FIG. 11 depicts that the PG3370 antibody, which is less potent in the inhibition of EGF mediated apoptosis, shows similar EGF blocking activity in comparison cetuximab.

Cynomolgus EGFR and Mouse EGFR Cross Reactivity Test

To test whether anti-EGFR IgGs were reactive with cynomolgus EGFR, the constructs encoding full-length human EGFR, as well as the expression construct encoding the ECD of cynomolgus fused to intracellular human EGFR, were both transfected in (antigen negative) CHO cells and cells were then stained with the anti-EGFR antibodies at 5 μg/ml and finally analysed by FACS. As a positive control for the staining, the clinically used antibody cetuximab was used, as this antibody is known to cross-react with cynomolgus EGFR. PG3370, PG3752, PG4280 and PG4281 were shown to be reactive with cynomolgus EGFR, as the staining of cells expressing human EGFR was virtually indistinguishable from that of cells expressing the chimeric receptor (FIG. 12).

To test anti-EGFR IgG for their cross-reactivity with murine EGFR, an ELISA was performed. A serial titration of recombinant mouse EGFR ECD-Fc, starting at 5 μg/ml and diluted until 0.038 μg/ml was coated overnight to MAXISORP™ ELISA plates at 4° C. Binding of the anti-EGFR IgG to this antigen was tested at a fixed concentration of 5 μg/ml and allowed to bind for 1H at RT. As a positive control for the immuno-reactivity of the antibodies, the same ELISA setup was performed using the human EGFR ECD-Fc fusion protein as antigen (R&D systems). Next, Goat anti-mouse IgG HRP conjugate, BD Biosciences) and was allowed to bind for 2 hours at RT. Bound IgG was detected by means of OD450 nm measurement. Antibody PG3370 was shown to recognize murine EGFR, as well as human EGFR with similar affinity (FIG. 13—Upper panel). Cetuximab does not recognize mouse EGFR (125084 Erbitux Pharmacology Review Part 2-FDA). PG3370 and cetuximab thus do not recognize the same epitope on human EGFR.

Mouse cMET Cross Reactivity Test

To test PG3342 for its cross-reactivity to murine cMET, an ELISA was performed. A fixed concentration of mouse HGF R/c-MET Fc (R&D systems) HGF R/c-MET Fc was diluted to 2.5 µg/ml in PBS and coated overnight to MAX-ISORP™ ELISA plates at 4° C. Binding of the anti-cMET IgG to this antigen was tested in a semi-log titration starting at 10 µg/ml. Antibodies were allowed to bind for 1H at RT. As a positive control for the immuno-reactivity of the antibodies, the same ELISA setup was performed using the human HGF R/c-MET Fc fusion protein as antigen (R&D systems). Next, Goat anti-mouse IgG HRP conjugate (BD Biosciences) was added and allowed to bind for 2 hours at RT. Bound IgG was detected by means of OD450 nm measurement. BAF527 an antigen affinity-purified Polyclonal Goat IgG directed against mouse cMET coupled to biotin was included as a positive control antibody. No cross reactivity to murine cMET was observed with the PG3342 antibody (FIG. 13 lower panel).

Cross Block Assay cMET Antibodies cMET specific phages were tested for competition with cMET reference antibodies in ELISA. Therefore 2.5 µg/ml of cMET-Fc fusion protein was coated overnight to MAX-ISORP™ ELISA plates at 4° C. Wells of the ELISA plates were blocked with PBS (pH 7.2) containing 2% ELK for 1 H at RT while shaking (700 rpm). Next reference or negative control IgG was added at a concentration of 5 µg/ml and allowed to bind for 15 min at RT at 700 rpm. Next, 5 µl of PEG precipitated phage was added and allowed to bind for 1H at RT at 700 rpm. Bound phages were detected with HRP labelled anti-M13 antibody for 1H at RT at 700 rpm. As a control the procedure was performed simultaneously with an antibody specific for the coated antigens and a negative control phage. Bound secondary antibody was visualized by TMB/H$_2$O$_2$ staining and staining was quantified by means of OD$_{450nm}$ measurement. Table 2 demonstrates that MF4040 and MF4356 show competition with the 5D5 reference antibody. MF4297 competes with 13.3.2 and C8H241 to a lesser extent. The positive control phages all show complete competition with the corresponding IgG, whereas the no antibody control, does not influence the competition assay.

Generation of Bispecific Antibodies

Bispecific antibodies were generated by transient co-transfection of two plasmids encoding IgG with different VH domains, using a proprietary CH3 engineering technology to ensure efficient heterodimerisation and formation of bispecific antibodies. The common light chain is also co-transfected in the same cell, either on the same plasmid or on another plasmid. In our co-pending applications (e.g. WO2013/157954 and WO2013/157953; incorporated herein by reference) we have disclosed methods and means for producing bispecific antibodies from a single cell, whereby means are provided that favor the formation of bispecific antibodies over the formation of monospecific antibodies. These methods can also be favorably employed in the present invention. Specifically, preferred mutations to produce essentially only bispecific full length IgG molecules are amino acid substitutions at positions 351 and 366, e.g. L351K and T366K (numbering according to EU numbering) in the first CH3 domain (the 'KK-variant' heavy chain) and amino acid substitutions at positions 351 and 368, e.g. L351D and L368E in the second CH3 domain (the 'DE-variant' heavy chain), or vice versa. It was previously demonstrated in our co-pending applications that the negatively charged DE-variant heavy chain and positively charged KK-variant heavy chain preferentially pair to form heterodimers (so-called 'DEKK' bispecific molecules). Homodimerization of DE-variant heavy chains (DE-DE homodimers) or KK-variant heavy chains (KK-KK homodimers) are disfavored due to strong repulsion between the charged residues in the CH3-CH3 interface between identical heavy chains.

cMET and EGFR Fab arms were cloned in the appropriate KK and DE vectors (Table 3). After production, bispecific IgG were purified by protein-A batch purification and the buffer was exchanged to PBS. Successful productions resulted in an IgG1 full length antibody, with a minimal concentration of 0.1 mg/ml, which were assigned a unique code (PBnnnnn; where nnnnn represents a randomly generated number) to identify the specific combination of 2 different target binding Fab fragments.

Successfully produced bispecific IgG were tested for binding to their respective targets in ELISA.

Example 3

Screening of c MET x EGFR Bispecific Antibodies in an EGF/HGF and HGF and EGF Proliferation Assay The potency of a panel of cMET x EGFR bispecific antibodies was tested in N87 cells using an HGF/EGF, HGF and EGF assays. The N87 cell line, official name NCI-N87, is a gastric carcinoma cell line derived from a metastatic site and has high EGFR expression levels and intermediate cMET expression levels (Zhang et al, 2010). Antibodies were tested in an 8 steps semi-log titration ranging from 10 µg/ml to 3.16 ng/ml. Each antibody was tested in duplicate. The anti-RSV-G antibody PG2708 was used as negative control. The reference antibody 2994 Fab was used as positive control for the HGF assay and the reference antibody cetuximab was used as positive control for the EGF assay.

An equimolar 1:1 cetuximab/5D5 Fab was used as positive control for the EGF, HGF and EGF/HGF assays.

Wells with either one, or a combination of ligand, as well as medium control were included to determine the assay window. Antibodies were diluted in chemically defined starvation medium (CDS: RPMI1640 medium, containing 80 U penicillin and 80 µg of streptomycin per ml, 0.05% (w/v) BSA and 10 µg/ml holo-transferrin) and 50 µl of diluted antibody was added to the wells of a 96 wells black well clear bottom plate (Costar). Ligand was added (50 µl per well of a stock solution containing 400 ng/ml HGF and 4 ng/ml of EGF, and a EGF/HGF concentration of 4 ng/ml EGF/400 ng/ml HGF diluted in CDS: R&D systems, cat. nr. 396-HB and 236-EG). N87 cells were trypsinised, harvested and counted and 8000 cells in 100 µl of CDS were added to each well of the plate. To avoid edge effects, plates were left for an hour at RT before being put in a container inside a 37° C. cell culture incubator for three days. On the fourth day, Alamar blue (Invitrogen, #DAL1100) was added (20 µl per well) and the fluorescence was measured after 6 hours of incubation (at 37° C.) with Alamar blue using 560 nm excitation and 590 nm readout on a Biotek Synergy 2 Multi-mode microplate reader. Fluorescence values were normalised to uninhibited growth (no antibody, but both ligands added). An example of an HGF, EGF and EGF/HGF proliferation assay is shown in FIG. 14 (FIGS. 14A, B and C respectively).

Table 4 lists the results of the various experiments. In the N87 HGF/EGF assay, fourteen different cMETxEGFR bispecifics with potency comparable to the reference monospecific antibodies (equimolar mix of cetuximab and 5D5 Fab) were identified: PB7679, PB7686, PB8218, PB8244, PB8292, PB8316, PB8340, PB8364, PB8388, PB8511, PB8535, PB8583, PB8607 and PB8640.

In the N87 EGF assay, eleven different cMETxEGFR bispecifics with potency comparable to monospecific cetuximab were identified: PB7679, PB8244, PB8292, PB8340, PB8364, PB8388, PB8511, PB8535, PB8583, PB8607 and PB8640. They all contain the EGFR Fab arm MF3755. In the HGF N87 assay nine bispecifics were identified that showed a higher potency compared to the monospecific 5D5 Fab reference antibody: PB8218, PB8388, PB8511, PB8532, PB8535, PB8545, PB8583, PB8639 and PB8640. They contain six different cMET Fab arms MF4040, MF4297, MF4301, MF4356, MF4491 and MF4506.

ADCC Activity

The ADCC activity of the 24 cMetxEGFR bispecifics was tested to the tumor cell lines N87 (EGFR-high, cMET-low) and MKN-45 (EGFR-low, cMET-amplified). The ADCC assay was performed using the Promega ADCC Bioassay kit in 384-well plate format. Antibodies were tested in duplicate at 9 different concentrations in semi-log serial dilutions ranging from 10 µg/ml to 1 ng/ml.

The reference cetuximab antibody was included as a positive control for the assay and PG2708 was used as negative control antibody. Antibodies or assay medium control (no IgG) were incubated for 6 hours of induction at 37° C. with ADCC effector cells, and target cells (N87 or MKN-45). Luciferase activity was quantified using Bio-Glo luciferase reagent.

An example of the ADCC assay is shown in FIG. 15. None of the cMETxEGFR bispecifics showed a significant ADCC activity in both cell lines. The positive control reference cetuximab antibody showed a dose-dependent ADCC activity to both cell lines.

Five bispecifics composed of EGFR and cMet arms which did show high efficacy in the N87 HGF/EGF assay and showed high sequence diversity (Table 5) were selected for further analysis. Two from the five bispecifics contain MF4356, which competes with 5D5 for binding to cMET (Table 2). Table 5 summarizes the characteristics of the selected candidates.

Wound Healing Cell Migration Assay

Two NSCLC cell lines were tested in the wound healing assay; EBC-1 and H358. These cell lines were chosen since they express high levels of EGFR and c-Met (Zhang et al, 2010; Fong et al., 2013). The assay was performed using the CytoSelect™ 24-well plate wound healing assay (Cell Biolabs, CBA-120) according to the manufacturer's instructions. Briefly, 2.5-4×10$^5$ cancer cells were seeded in each well and incubated overnight at 37° C. to form a monolayer. Well inserts were then removed to create a wound field of 0.9-mm After washing with PBS to remove dead cells and debris in the wound area, cells were incubated for 15 minutes at 37° C. with complete media (0.5% FBS) containing bispecifics (100 nM) or cetuximab:Fab2994 control antibody mixture (100 nM, 1:1 molar ratio). Each well was then supplemented with growth factors: HGF (15 ng/ml), EGF (12.5 ng/ml) or a combination of both (15 and 12.5 ng/ml). Time-lapse monitoring of the wound closure was performed for 14 h at 37° C. with a confocal microscope (Zeiss LSM780). The extent (%) of wound closure is shown relative to untreated controls.

Figure 3:
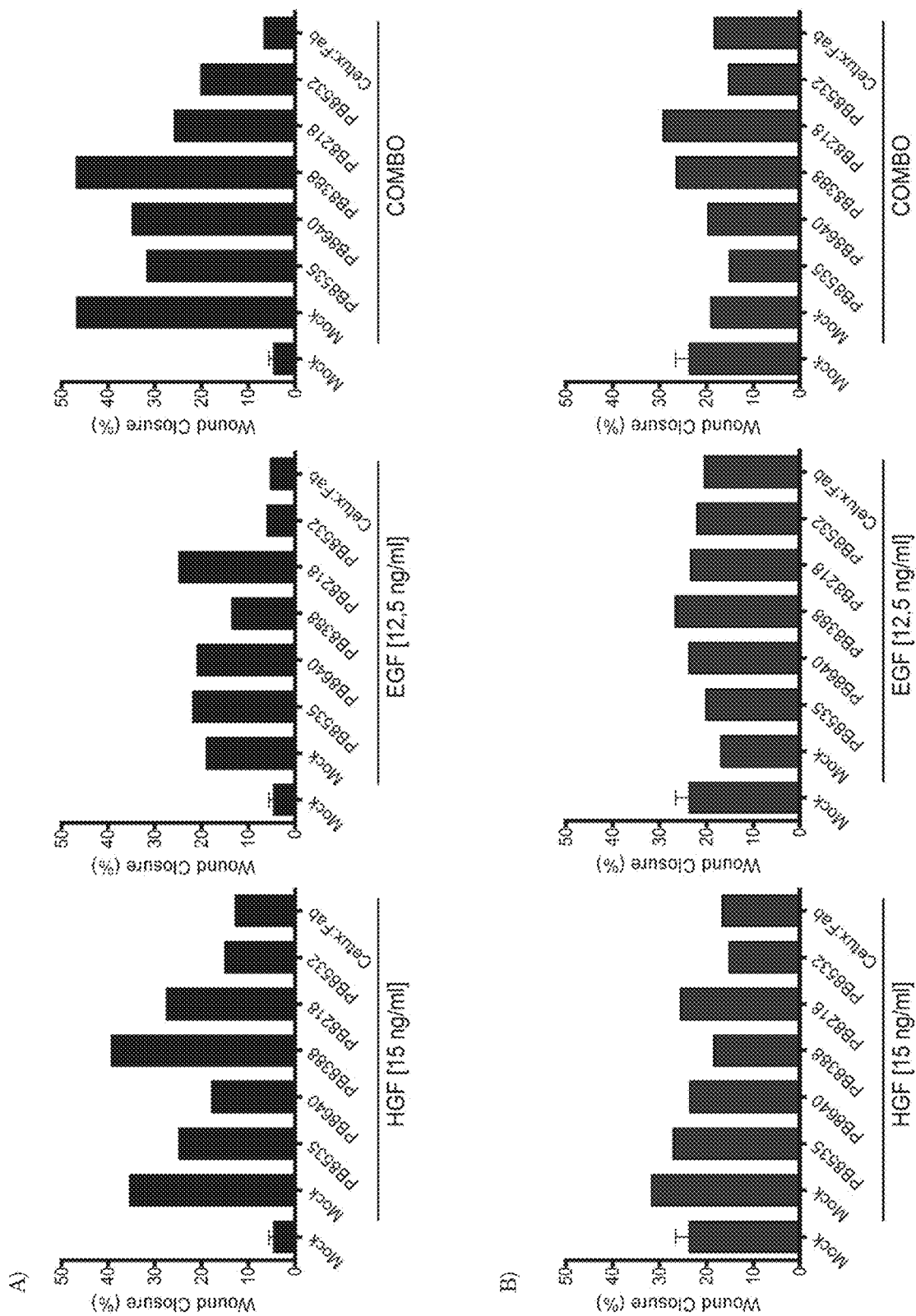
FIG. 3. The effect of cMET x EGFR bispecifics on wound healing in H385 cells (panel A) and EBC-1 cells (panel B).

H358 cells showed in an increase in migration (percentage wound closure) upon exposure to either HGF or EGF alone, which was most effective by a combination of HGF and EGF (FIG. 3). This increased migration was abrogated by the addition of the majority of the bispecifics and was most pronounced with PB8532. This inhibition was comparable to the cetuximab and 5D5 Fab combination except for the inhibition migration in the presence of EGF/HGF.

EBC-1 cells showed a slight increase in migration by addition of HGF; and no increase in migration in the presence of EGF or the combination of EGF/HGF. However wound closure could be inhibited in all assay conditions by the bispecifics in particular by PB8532. PB8532 was as effective or more effective (EGF/HGF) than the combination of cetuximab/5D5 Fab.

Analysis of EGFR and cMET Expression on PC-9 and HCC827 Cells by Flow Cytometry

Acquired resistance to erlotinib can result from aberrant activation of HGF mediated c-MET activation. The NSCLC cell lines PC-9 and HCC827 were selected to investigate the ability of the cMET xEGFR bispecific antibodies to inhibit ligand mediated proliferation in a tyrosine kinase inhibitor (TKI) resistant setting. Both cell lines do not harbor EGFR mutations and are resistant in the presence of HGF to both erlotinib and gefitinib or a combination of gefinitib and erlotinib (PC-9 only). In PC-9 cells, it has been reported that the HGF-induced erlotinib resistance can be abrogated by a cMET inhibitor (Nakade et al., 2014) and the gefitinib resistance can be abrogated by an anti-HGF antibody (Yano, 2008). PC-9 and HCC827 were characterized for the expression of cMET and EGFR by FACS analysis, using fluorescently labeled antibodies. Cells were harvested with PBS 2 mM EDTA. Single-cell suspensions (10e6 cells in 50 µl) were incubated with fluorescently labelled antibodies on ice for 20 min in staining buffer (PBS 2% FBS 2 mM EDTA). The following antibodies were used alone or in combination: Met Alexa Fluor 488 conjugate (Clone D1C2, Cell Signaling, 1:50 dilution); EGF Receptor Alexa Fluor 647 conjugate (Clone D38B1, Cell Signaling, 1:50 dilution). After incubation, cells were washed with staining buffer and FACS analysis was performed on a BD FACSVerse flow cytometer.

All HCC827 cells show EGFR expression and can be subdivided into a EGFR$^{high}$, cMET$^{pos}$ population and a EGFR$^{pos}$, cMET$^{neg}$ population (FIG. 4). PC-9 cells contain a small population of EGFR$^{high}$ and cMET$^{pos}$ cells and a minimal population of EGFR$^{pos}$ and cMET$^{neg}$ cells.

PC-9 and HCC827 Proliferation Assay

Initial experiments were performed to determine the concentration of HGF establishing erlotinib and gefitinib resistance in PC-9 and HCC827 cells. Upon overnight starvation in media containing 0.5% FBS, cells were incubated with increasing concentrations of HGF, ranging from 0 to 120 ng/mL supplemented with 300 nM erlotinib or gefitinib, in 10% FBS. After 72 hours of incubation, cell proliferation was assessed using the WST-1 reagent according to the manufacture's instructions. The absorbance was measured with a microplate reader at test and reference wavelengths of 450 and 630 nm, respectively. In both PC-9 (FIG. 16A) and HCC287 (FIG. 16B) the addition of HGF induced resistance to TKIs in a dose-dependent manner.

PB8532 and PB8388 were tested for their efficacy in a TKI resistance setting. 4×10$^3$ cancer cells were seeded in 96-well plates in 100 µL complete RPMI 1640 (10% FBS).

Upon overnight starvation in media containing 0.5% FBS, cells were pre-incubated for 15 minutes at 37° C. with Biclonics® (100 nM) or cetuximab:Fab2994 control monospecific antibody mixture (100 nM, 1:1 molar ratio). Each well was then supplemented with complete media (10% FBS) containing gefitinib or erlotinib (300 nM) with or w/o HGF (30 ng/ml), EGF (30 ng/ml) or a combination of both (at 30 ng/ml). After 72 hours of incubation, cell proliferation was assessed using the WST-1 method.

FIG. 5 shows that PB8532 can inhibit HGF mediated and EGF mediated gefitinib resistance in PC-9 cells. In HCC827 cells PB8532 inhibited HGF mediated TKI resistance, and was more potent than the combination of administering dual monospecific cetuximab 5D5 Fab. Comparable results were obtained with the TKI erlotinib.

Example 4 PB8532 Inhibition of EGF and cMET Phosphorylation

Following overnight starvation in media without FBS, cells were incubated for 15 minutes at 37° C. with media (0.5% FBS) containing PB8532 (100 nM) or cetuximab:Fab2994 control monospecific antibody mixture (100 nM, 1:1 molar ratio). The cells were then stimulated with growth factors: HGF (30 ng/ml) or EGF (50 ng/ml) for 15 minutes at 37° C. After stimulation, cells were washed with PBS in presence of 1 mM orthovanadate (Sigma-Aldrich). Protein extraction was performed using RIPA lysis buffer (50 mM Tris HCl pH 8, 150 mM NaCl, 1% Triton X-100, 0.5% sodium deoxycholate, 0.1% SDS) supplemented with Complete Protease Inhibitor Cocktail (Roche), PhosSTOP phosphatase inhibitor (Roche) and orthovanadate (1 mM, Sigma-Aldrich). Lysates were incubated on ice for 30 minutes before centrifuging 15 minutes at 4° C. to remove cellular debris. After centrifugation, the supernatant was collected and protein concentrations were determined using bicinchoninic acid (BCA) reagent (Pierce) according to the manufacturer's instructions. Protein samples were denaturated by adding loading buffer 6× (β-mercaptoethanol 0.6 M; SDS 8%; Tris-HCl 0.25 M pH 6.8; glycerol 40%; Bromophenol Blue 0.2%) and incubating at 95° C. for 5 minutes. After electrophoresis, proteins were transferred onto a nitrocellulose membrane using the Trans-Blot® Turbo™ Blotting System (Bio-Rad). The membranes were blocked for non-specific binding in 5% non-fatty dry milk in Tris Buffered Saline-Tween 0.1% (50 mM Tris HCl ph 7.6, 150 mM NaCl, 0.1% Tween; TBS-T) for 1 h at room temperature (RT) and incubated with primary antibody overnight (ON) at 4° C. The following primary antibodies were used: Phospho-Met (Tyr1234/1235, Clone D26, Cell Signaling) 1:500 in TBS-T 5% BSA; Met (Clone D1C2, Cell Signaling) 1:1000 in TBS-T 5% BSA; Phospho-EGF Receptor (Tyr1068, Clone D7A5, Cell Signaling) 1:1000 in TBS-T 5% non-fatty dry milk; EGF Receptor (Clone D38B1, Cell Signaling) 1:1000 in TBS-T 5% BSA; Vinculin (Monoclonal anti-Vinculin, V9131, SIGMA Aldrich) 1:4000 in TBS-T 5% non-fatty dry milk. After incubation with the indicated primary antibodies, the membranes were washed for 15 minutes in TBS-T and incubated with secondary antibody (1:5000 in TBS-T 5% non-fatty dry milk) for 1 H at RT. The following secondary antibodies were used: goat anti-rabbit IgG-HRP (sc-2004, Santa Cruz biotechnology); goat anti-mouse IgG-HRP (sc-2005, Santa Cruz biotechnology). The signal was visualized with Enhanced Chemiluminescent Reagents (ECL; Invitrogen) or SuperSignal West Femto Chemiluminescent Substrate (Thermo Scientific) with a digital imager (ImageQuant LAS 4000, GE Health Care Life Science Technologies).

FIG. 6 shows a Western blot analysis of the performed experiment.

In PC-9 cells, PB8532 and 5D5/cetuximab were able to reduce HGF induced phosphorylation. In addition both antibodies slightly reduced EGF phosphorylation in the absence and presence of EGF.

In HCC827 cells PB8532 reduced phosphorylation of cMET in the presence and absence of HGF. No effect was observed by the combination 5D5/cetuximab. Furthermore, in this cell line PB8532 reduced EGF induced phosphorylation of EGFR in contrast to the combination of 5D5 with cetuximab.

Example 5

FIG. 7 depicts various sequences for alternative variable regions of the heavy chain of an EGFR binding variable domain as disclosed herein. FIG. 8 depicts various sequences for alternative variable regions of the heavy chain of a cMET binding variable domain as disclosed herein. The heavy chain variable regions were used to create a number of different cMET x EGFR bispecific antibodies. The light chain in these antibodies has the sequence as depicted in FIG. 9B. Bispecific antibodies were produced as described in example 1. The antibodies were also produced as an ADCC enhanced version. ADCC enhanced versions were produced by including in the co-transfection of the antibody constructs, a DNA encoding a reductase enzyme that removes a fucose residue from the Fc region of IgG1.

FIG. 17 depicts a titration of various produced bispecific antibodies on CHO-K1 EGFR cells described in example 2 (panel A) and on MKN-45 cells that endogenously express c-MET (panel B). The cells were incubated at $2 \times 10^5$ cells/well with increasing concentrations of antibody as indicated. After washing, binding was detected with anti-human IgG-PE (3 μg/ml). Stained cells were analyzed on an iQue system and mean fluorescence intensity (MFI) and area under the curve (AUC) calculated. Control antibodies were MF1337xMF1337 (PG1337p218; TTxTT negative control; dark triangles at the bottom) and MF4356xMF3770 (PB8532p04; c-METxEGFR positive control; black triangles). TT stands for tetanus toxoid, A variable domain comprising the VH of MF1337 (see FIG. 1) and a common light chain as described herein, binds to Tetanus Toxoid and is thus not expected to bind to the CHO-K1 EGFR cells and MKN-45 cells. The note (ADCC) indicates that the antibodies are produced with enhanced ADCC function through co-transfection with DNA encoding the RMD enzyme to remove a fucose residue from the Fc region of IgG1. See table 6 for a list of the bispecific antibodies used and their PB coding.

ADCC Reporter Assay

An ADCC reporter assay was performed to determine whether co-transfection of RMD-encoding DNA successfully enhanced ADCC effector function. All samples were tested in duplo on BxPC3 cells (which express EGFR) and MKN-45 cells (which express c-MET) using both the high-affinity and low-affinity assay. The assay's high-affinity effector cells express the V-variant of the human FcγRIIIa and the low-affinity effector cells express the F-variant.

Briefly, the BxPC3 and MKN-45 target cells were harvested and plated at 1000 cells/well in 30 μL and incubated overnight at 37° C., 5% CO2, 95% relative humidity. The next day, medium was removed and 10 μL antibody dilution added to each well (antibody dilution 1.5×; 9-step serial titration with semi-log dilution steps resulting in assay concentration of 1 ng/ml to 10 µg/ml). On the same day, effector cells were thawed at 37° C., and 630 µL added to 3.6 ml assay buffer in a 15-ml tube and mixed by inversion; 5 µL of this solution (15,000 cells) was then added to the wells of the assay plate. The plate was incubated for 6 hours at 37° C., 5% CO2, 95% relative humidity before the addition of 15 µL Bio-Glo reagent to assay wells. Luminescence was measured using an EnVision plate reader.

A list of samples tested is provided in Table 6 and the results of the assays are provided in FIG. 18. The non-ADCC-enhanced anti-HER3 x EGFR control antibody (batch PB4522p25; MF4280xMF3178 described in WO2015/130172) was negative in all four assays (indicated by black crosses and solid lines (4th from above) in FIG. 18). In contrast, the ADCC-enhanced version of this antibody (PB4522p34) was positive in all four assays (indicated by solid orange circles). Similarly, the non-ADCC-enhanced anti-c-MET x EGFR control antibody (PB8532p04) was negative in all four assays (indicated by black crosses and dashed lines in FIG. 18), as was the PB8532p05 batch was also non-ADCC-enhanced (indicated by green asterisks). The three lines with asterisks are all at the bottom of the four panels. However, the ADCC-enhanced p06 variant (PB8532p06) was positive in all assays (indicated by open orange circles). Enhanced ADCC effector function similar to that of PB8532p06 was also seen for the 5 bispecifics (PB19474 to PB19478). This meant that co-transfection of RMD-encoding DNA successfully enhanced ADCC effector function.

Example 6

The heavy chain variable region (VH) of the cMET variable domain of PB8532 comprises the amino acid of MF4356 as depicted for instance in FIG. 8. The VH of the cMET variable domain of PB19748 comprises the amino acid sequence of MF8230 (see FIG. 8). The VH of the EGFR variable domain of PB8532 comprises the amino acid of MF3370 as depicted for instance in FIG. 7. The VH of the EGFR variable domain of PB19748 comprises the amino acid sequence of MF8233 of FIG. 7. The light chain in PB8532 and PB19748 is the same and is depicted in FIG. 9B. The cMET antibody LY2875358 antibody is among other described in Kim and Kim 2017. The capacity of the cMETxEGFR bispecific antibody PB8532 or PB19748 to inhibit tumor growth in vivo was tested alone and in combination with the receptor tyrosine kinase inhibitor erlotinib in a xenograft mouse model. In the chosen model, HCC827 tumor cells are engrafted into immunodeficient NOD SCID gamma (NSG) human hepatocyte growth factor knock-in (hHGFki) mice, that express human HGF (ligand for cMET) in place of endogenous mouse HGF. The NSG-hHGFki mice are known in full as NOD.Cg-Hgf$^{tm1.1(HGF)Aveo}$ Prk$^{dcscid}$ $^{Il2rgtm}$ $^{1Wjl/J}$ (stk #014553) (NOD.Cg-Hgftm1.1(HGF)Aveo Prkdcscid Il2rgtm 1Wjl/J). They have no T or B cells, lack functional NK cells, and are deficient in cytokine signaling, which allows for better tumor engraftment. HCC827 is an established human non-small-cell lung carcinoma (NSCLC) cell line that expresses EGFR and cMET and is known to be resistant to erlotinib in the presence of HGF.

To establish the effect of erlotinib on tumor growth in this model, a first experiment was done with two groups of mice. Prior to tumor cell engraftment, the cell cycle of HCC827 cells was boosted by culturing the cells overnight in medium supplemented with 20% fetal bovine serum (FBS) at confluency not exceeding 80%. The next day, NSG-hHGFki mice (The Jackson Laboratory) were inoculated subcutaneously with 17×10e6 HCC827 tumor cells suspended in 300 µl PBS plus 30% matrigel containing a high concentration of basement membrane matrix. The resulting tumors were measured twice each week using calipers. When the mean tumor volume reached approximately 200 mm$^3$, the mice were randomized into two groups (4-7 mice per group depending on tumor growth and volume) and drug treatment was started.

A fine suspension of erlotinib was prepared freshly every week in 0.05% hydroxypropyl methylcellulose (HPMC) and 0.2% Tween-80 in water by sonication.

From day 19, the erlotinib solution was used to treat 5 mice once daily (QD) via gavage at a dose of 6 mg/kg (n=5), and a group of 4 mice was given once daily gavage with 200 µl vehicle (0.05% HPMC and 0.1% Tween 80 in water). Tumor volume was measured twice each week using calipers, and mean tumor volume (and SEM) calculated for each group. When tumor sizes reached 1500 mm$^3$ mice were euthanized. Treatment was stopped after day 48, and tumor volume in surviving mice was measured up to day 62.

In a second experiment that tested the capacity of the PB8532 bispecific antibody to inhibit tumor growth in this model (alone and in combination with erlotinib), NSG-hHGFki mice with tumors (generated as described above) were given one of six treatments or combination treatments, whereby antibody was given weekly by intraperitoneal (i.p.) injection and erlotinib or vehicle was given once a day (QD) by gavage. As a negative control, mice were also treated with PB17160, a bispecific antibody made up of the same anti-cMET Fab arm as in PB8532, in combination with a Fab arm specific for an irrelevant target. An irrelevant target is for instance a target that is not present in the mouse and tumor. Often a tetanus toxoid specific variable domain is used. A suitable tetanus toxoid binding variable domain has the VH of MF1337 (see FIG. 1) and a common light as disclosed herein, preferably a sequence of FIG. 9. Bispecific antibodies with a targeting arm and a non-targeting (TT) arm are among others described in WO2017/069628, see MF1337, which is incorporated by reference herein. Another irrelevant target is RSV-G. A suitable RSV-G variable domain has the VH of MF2708 of FIG. 1 and a common light chain, preferably one of FIG. 9, preferably 9B.

On day 21, when the mean tumor volume had reached approximately 200 mm$^3$, the mice were randomized into six groups (5-7 mice per group depending on tumor growth and volume) and drug treatment was started: daily gavage with vehicle alone (n=5); weekly i.p. injections of 25 mg/kg PB8532 antibody plus daily gavage with vehicle (n=7); weekly i.p. injections of 25 mg/kg PB17160 antibody plus daily oral gavage with vehicle (n=6); daily oral gavage with 6 mg/kg erlotinib (n=7); weekly i.p. injections of 25 mg/kg PB8532 antibody plus daily oral gavage with 6 mg/kg erlotinib (n=7); or weekly i.p. injections of 25 mg/kg PB17160 antibody plus daily oral gavage with 6 mg/kg erlotinib (n=7). As before, tumor volume was monitored and mean tumor volume (and SEM) calculated in each group. All treatments were stopped after day 60, and tumor volume in surviving mice was measured up to day 82.

In a third experiment the capacity of the PB19478 bispecific antibody to inhibit tumor growth in this model (alone and in combination with erlotinib) was tested. NSG-hHGFki mice with tumors (generated as described above) were given one of six treatments or combination treatments, whereby antibody was given weekly by intraperitoneal (i.p.) injection and erlotinib or vehicle was given once a day (QD) by gavage.

On day 23, when the mean tumor volume had reached approximately 200 mm$^3$, the mice were randomized into six groups (5-6 mice per group depending on tumor growth and volume) and drug treatment was started: daily gavage with vehicle alone (n=5); weekly i.p. injections of 25 mg/kg PB19478 antibody plus daily gavage with vehicle (n=5); daily oral gavage with 6 mg/kg erlotinib (n=6); weekly i.p. injections of 25 mg/kg PB19478 antibody plus daily oral gavage with 6 mg/kg erlotinib (n=4, one mouse died during the experiment); weekly i.p. injections of 25 mg/kg LY2875358 antibody plus daily gavage with vehicle (n=5); weekly i.p. injections of 25 mg/kg LY2875358 antibody plus daily oral gavage with 6 mg/kg erlotinib (n=3, two mice died during the experiment). As before, tumor volume was monitored and mean tumor volume (and SEM) calculated in each group. All treatments were stopped after day 93, and tumor volume in surviving mice was measured up to day 93.

In a fourth experiment the effect of a later administration of PB19478 was tested. NSG-hHGFki mice with tumors (generated as described above) were given one of two treatments, whereby antibody was given weekly by intraperitoneal (i.p.) injection and erlotinib or vehicle was given once a day (QD) by gavage.

On day 21, when the mean tumor volume had reached approximately 200 mm$^3$, all 14 mice were started on a daily oral gavage treatment with 6 mg/kg erlotinib. On day 51 when the mean tumor volume had clearly passed the 500 mm$^3$ mark the mice were randomized into two groups. One group of six were treated with daily oral gavage with 6 mg/kg erlotinib and a group of 8 received weekly i.p. injections of 25 mg/kg PB19478 antibody plus daily gavage with 6 mg/kg erlotinib. As before, tumor volume was monitored and mean tumor volume (and SEM) calculated in each group. All treatments were stopped after day 72.

The results of the first experiment demonstrate that erlotinib was able to induce an anti-tumor response in NGS-hHGFki mice engrafted with HCC827 cells, but only for as long as the mice were receiving treatment (FIG. 19). In the drug-free period that commenced after about 4 weeks of treatment, tumor volume clearly increased in the mice that had been treated with erlotinib.

The anti-cMETxEGFR bispecific antibody PB8532 was also able to induce an anti-tumor response in NGS-hHGFki mice engrafted with HCC827 cells (FIG. 20). This effect was greater when the antibody was given in combination with daily doses of erlotinib. Within 2.5 weeks all tumors disappeared from the combination of PB8532 with erlotinib. The control antibody PB17160 targeting cMet with one Fab arm induced no anti-tumor response, either with or without erlotinib. Thus, the specific targeting of the cMet Fab arm by combination with an EGFR targeting Fab arm in bispecific antibody PB8532 can overcome HGF mediated erlotinib resistance.

In the drug-free period that commenced after about 5½ weeks of treatment, PB8532 was clearly more effective than erlotinib in reducing tumor volume (FIG. 21) and no tumor regrowth was observed in the PB8532+erlotinib combination group.

The anti-cMETxEGFR bispecific antibody PB19478 was also able to induce an anti-tumor response in NGS-hHGFki mice engrafted with HCC827 cells (FIG. 22). This effect was greater when the antibody was given in combination with daily doses of erlotinib. Within 2 weeks all tumors disappeared from the combination of PB19478 with or without erlotinib. With erlotinib the tumor did not reappear in the test period. Without erlotinib the tumor reappeared shortly around day 50 and stayed at the detection level until it finally grew further at day 80 onwards. The humanized monoclonal antibody emibetuzumab (LY3875358) was less effective, also when combined with the EGFR inhibitor erlotinib. Thus, the specific targeting of the cMet Fab arm by combination with an EGFR targeting Fab arm in bispecific antibody PB8532 or PB19478 can overcome HGF mediated erlotinib resistance.

FIG. 23 shows that when you treat tumors at a time point where erlotinib resistance starts to develop there is an immediate effect of the bispecific antibody PB19478.

Taken together, the data from this xenograft model of HCC827 tumor cells engrafted into immunodeficient NSG-hHGFki mice show that PB8532, PB19478 and antibodies having the similar VH sequences given in FIGS. 7 and 8 have the capacity to overcome HGF-mediated erlotinib resistance in vivo. The combination treatment continues to be effective after stopping treatment.

CITED ART

Ahmed, M et al. Lack of in Vivo Antibody Dependent Cellular Cytotoxicity with Antibody containing gold particles/Bioconjugate chemistry (2015): 26 812-816. DOI: 10.1021/acs.bioconjchem.5b00139.

Buday L, Downward J. Epidermal growth factor regulates p21ras through the formation of a complex of receptor, Grb2 adapter protein, and Sos nucleotide exchange factor. Cell 1993; 73: 611-20.

Castoldi, R., et al. "A novel bispecific EGFR/Met antibody blocks tumor-promoting phenotypic effects induced by resistance to EGFR inhibition and has potent antitumor activity." Oncogene 32.50 (2013): 5593-5601.

Chen et al., MET activation mediates resistance to lapatinib inhibition of HER2-amplified gastric cancer cells. *Mol Cancer Ther* 2012; 11(3):650-669

Ferguson K M. Structure-based view of epidermal growth factor receptor regulation. Annu Rev Biophys 2008; 37: 353-73.

Fong J T, et al., Alternative signaling pathways as potential therapeutic targets for overcoming EGFR and c-Met inhibitor resistance in non-small cell lung cancer. PLoS One. 2013 Nov. 4; 8(11):e78398.

Gale N W, Kaplan S, Lowenstein E J, Schlessinger J, Bar-Sagi D. Grb2 mediates the EGF-dependent activation of guanine nucleotide exchange on Ras. Nature 1993; 363:88-92.

Gulli LF1, Palmer K C, Chen Y Q, Reddy K B. 1996. Epidermal growth factor-induced apoptosis in A431 cells can be reversed by reducing the tyrosine kinase activity. Cell Growth Differ. February; 7(2):173-8.

Jorissen R N, Walker F, Pouliot N, Garrett T P, Ward C W, Burgess A W. Epidermal growth factor receptor: mechanisms of activation and signalling. Exp Cell Res 2003; 284:31-53.

Kim, George P., and Axel Grothey. "Targeting colorectal cancer with human anti-EGFR monoclonal antibodies: focus on panitumumab." Biologics 2.2 (2008): 223-228.

Kim, Ki-Hyun and Kim, Hyori. Progress of antibody-based inhibitors of the HGF-cMET axis in cancer therapy. Experimental & Molecular medicine (2017), e307; doi: 10.1038/emm.2017.17)

Morgillo F, et al. ESMO Open 2016; 1:e000060.doi: 10.1136/esmoopen-2016-000060

Moores, Sheri L., et al. "A novel bispecific antibody targeting EGFR and cMet is effective against EGFR inhibitor-resistant lung tumors." Cancer research 76.13 (2016): 3942-3953.

Nakade et al. Triple inhibition of EGFR, Met, and VEGF suppresses regrowth of HGF-triggered, erlotinib-resistant lung cancer harboring an EGFR mutation. *J Thorac Oncol* 2014, 9(6):775-83.

Prigent S A, Gullick W J. Identification of cErbB-3 binding sites for phosphatidylinositol 30-kinase and SHC using an EGF receptor/c-ErbB-3 chimera. EMBO J 1994; 13:2831-41.

Robertson S C, Tynan J, Donoghue D J. RTK mutations and human syndromes: when good receptors turn bad. Trends Genet 2000; 16:368.

Soltoff S P, Carraway K L, III, Prigent S A, Gullick W G, Cantley L C. ErbB3 is involved in activation of phosphatidylinositol 3-kinase by epidermal growth factor. Mol Cell Biol 1994; 14:3550-8.

Yano et al. Hepatocyte growth factor induces gefitinib resistance of lung adenocarcinoma with epidermal growth factor receptor-activating mutations. *Cancer Res.* 2008, 15; 68(22):9479-87.

Yarden Y. The EGFR family and its ligands in human cancer. Signalling mechanisms and therapeutic opportunities. Eur J Cancer 2001; 37 (Suppl 4):S3-S8.

Zhang et al., MET kinase inhibitor SGX523 synergizes with epidermal growth factor receptor inhibitor erlotinib in a hepatocyte growth factor-dependent fashion to suppress carcinoma growth. *Cancer Res* 2010, 70:6880-6890.

US20120107234A1_Symphogen patent "PAN HER antibody composition". 125084 Erbitux Pharmacology Review Part 2-FDA.

TABLE 1

Reference antibodies with reported specificities against cMET extracellular domains.

| Name | INN name | Epitope | MOA |
|---|---|---|---|
| 5D5 | MetMAb | Sema Domain | HGF block |
| 13.3.2 | | | |
| 224G11 | | | |
| C8-H241 | LY-2875358 | | HGF block, |
| R13 | 13-MET | | internalization |

TABLE 2

Competition of cMet reference antibodies with cMET cLC antibodies. Shown are OD450 values. OD450 values indicate the existence or lack of competition with the stated antibody. MF4506 was not tested.

| | Competition of phages with reference antibodies | | | | | | |
|---|---|---|---|---|---|---|---|
| MF tested | no IgG | 13.3.2 | 5D5 | R13 | 224G11 | C8H241 | R28 |
| 4040 | 1.915 | 1.818 | 0.066 | 1.608 | 1.907 | 1.979 | 1.787 |
| 4297 | 1.769 | 0.072 | 1.499 | 1.332 | 1.955 | 1.031 | 1.885 |
| 4356 | 2.380 | 2.541 | 0.088 | 2.231 | 2.170 | 1.806 | 1.825 |
| 13.3.2 | 2.172 | 0.311 | 1.934 | 1.988 | 2.221 | 1.893 | 2.129 |
| 5D5 | 1.868 | 1.773 | 0.164 | 1.660 | 2.025 | 2.054 | 2.035 |
| R13 | 1.693 | 1.590 | 1.549 | 0.090 | 1.878 | 0.078 | 1.794 |

TABLE 3

List of the 24 cMETxEGFR bispecifics antibodies selected after dose dependent titration experiments in a N87 HGF/EGF proliferation assay. The MF number of the EGFR and cMET arms in each individual PB as well as the their HCDR3 sequence are indicated.

| | PBs MF'S | | | |
|---|---|---|---|---|
| PBs | | EGFR | | cMET |
| PB7678 | MF4280 | EGYYETTTYYYNLFDS (SEQ ID NO: 47) | MF4298 | KLEPTGYYYYMDV (SEQ ID NO: 52) |
| PB7679 | MF3755 | ERFLEWLHFDY (SEQ ID NO: 48) | MF4487 | KTSRYSGYHYYMDV (SEQ ID NO: 53) |
| PB7686 | MF3755 | ERFLEWLHFDY (SEQ ID NO: 48) | MF4507 | AHYDILTG (SEQ ID NO: 54) |
| PB8021 | MF3755 | ERFLEWLHFDY (SEQ ID NO: 48) | MF3462 | GKSHYSWDAFDY (SEQ ID NO: 55) |
| PB8218 | MF3752 | DRNWGWDFDY (SEQ ID NO: 49) | MF4040 | GTYYYGSGSFSTRVFDAFDV (SEQ ID NO: 56) |
| PB8244 | MF3755 | ERFLEWLHFDY (SEQ ID NO: 48) | MF4044 | QSRRYSGYASYFDY (SEQ ID NO: 57) |
| PB8292 | MF3755 | ERFLEWLHFDY (SEQ ID NO: 48) | MF4130 | QRRAYSGYNWYFDL (SEQ ID NO: 58) |
| PB8301 | MF4280 | EGYYETTTYYYNLFDS (SEQ ID NO: 47) | MF4130 | QRRAYSGYNWYFDL (SEQ ID NO: 58) |
| PB8316 | MF3755 | ERFLEWLHFDY (SEQ ID NO: 48) | MF4293 | RNDFWSGYLFDY (SEQ ID NO: 59) |
| PB8339 | MF3752 | DRNWGWDFDY (SEQ ID NO: 49) | MF4294 | KTTVGYYYYMDV (SEQ ID NO: 60) |

TABLE 3-continued

List of the 24 cMETxEGFR bispecifics antibodies selected after dose dependent titration experiments in a N87 HGF/EGF proliferation assay. The MF number of the EGFR and cMET arms in each individual PB as well as the their HCDR3 sequence are indicated.

| PBs | PBs MF'S | | | |
|---|---|---|---|---|
| | EGFR | | cMET | |
| PB8340 | MF3755 | ERFLEWLHFDY (SEQ ID NO: 48) | MF4294 | KTTVGYYYYYMDV (SEQ ID NO: 60) |
| PB8364 | MF3755 | ERFLEWLHFDY (SEQ ID NO: 48) | MF4296 | GPELGYYYYYMDI (SEQ ID NO: 61) |
| PB8388 | MF3755 | ERFLEWLHFDY (SEQ ID NO: 48) | MF4297 | ASSMITFGGVIVSWFDP (SEQ ID NO: 62) |
| PB8511 | MF3755 | ERFLEWLHFDY (SEQ ID NO: 48) | MF4301 | RVNRYSGYATYFDL (SEQ ID NO: 63) |
| PB8532 | MF3370 | DRHWHWWLDAFDY (SEQ ID NO: 37) | MF4356 | ETYYYDRGGYPFDP (SEQ ID NO: 30) |
| PB8535 | MF3755 | ERFLEWLHFDY (SEQ ID NO: 48) | MF4356 | ETYYYDRGGYPFDP (SEQ ID NO: 30) |
| PB8545 | MF4281 | GDLFITGTLDY (SEQ ID NO: 51) | MF4356 | ETYYYDRGGYPFDP (SEQ ID NO: 30) |
| PB8582 | MF3752 | DRNWGWDFDY (SEQ ID NO: 49) | MF4491 | RTSRYSGYHYYLDV (SEQ ID NO: 65) |
| PB8583 | MF3755 | ERFLEWLHFDY (SEQ ID NO: 48) | MF4491 | RTSRYSGYHYYLDV (SEQ ID NO: 65) |
| PB8607 | MF3755 | ERFLEWLHFDY (SEQ ID NO: 48) | MF4505 | LLYDLFDL (SEQ ID NO: 66) |
| PB8639 | MF3752 | DRNWGWDFDY (SEQ ID NO: 49) | MF4506 | SIDMATITDAFDI (SEQ ID NO: 67) |
| PB8640 | MF3755 | ERFLEWLHFDY (SEQ ID NO: 48) | MF4506 | SIDMATITDAFDI (SEQ ID NO: 67) |
| PB8687 | MF3752 | DRNWGWDFDY (SEQ ID NO: 49) | MF4508 | GTTGNPYYFYYYMDV (SEQ ID NO: 68) |
| PB8688 | MF3755 | ERFLEWLHFDY (SEQ ID NO: 48) | MF4508 | GTTGNPYYFYYYMDV (SEQ ID NO: 68) |

TABLE 4

Summary of the antibody titration experiments done using N87 HGF/EGF, HGF and EGF proliferation assays with the 24 cMETxEGFR bispecific antibodies. Bispecifics are indicated as PBXXXX and the different Fab arms with MGXXXX. The activity of the bispecifics in the individual assays is indicated as: − no effect; + inhibition, of proliferation lower than positive control; ++ = inhibition of proliferation comparable to positive control antibody 5D5 Fab; +++ = Inhibition of proliferation higher than positive control antibody 5D5 Fab.

| PBs | PBs MF's | | N87 proliferation assays | | |
|---|---|---|---|---|---|
| | EGFR | cMET | HGF/EGF | HGF | EGF |
| PB7678 | MF4280 | MF4298 | + | + | + |
| PB7679 | MF3755 | MF4487 | ++ | − | ++ |
| PB7686 | MF3755 | MF4507 | ++ | + | + |
| PB8021 | MF3755 | MF3462 | + | + | + |
| PB8218 | MF3732 | MF4040 | ++ | +++ | + |
| PB8244 | MF3755 | MF4044 | ++ | + | ++ |
| PB8292 | MF3755 | MF4130 | ++ | + | ++ |
| PB8301 | MF4280 | MF4130 | + | ++ | + |
| PB8316 | MF3755 | MF4293 | ++ | + | + |
| PB8339 | MF3752 | MF4294 | + | + | + |
| PB8340 | MF3755 | MF4294 | ++ | + | ++ |
| PB8364 | MF3755 | MF4296 | ++ | + | ++ |
| PB8388 | MF3755 | MF4297 | ++ | +++ | ++ |
| PB8511 | MF3755 | MF4301 | ++ | +++ | ++ |

TABLE 4-continued

Summary of the antibody titration experiments done using N87 HGF/EGF, HGF and EGF proliferation assays with the 24 cMETxEGFR bispecific antibodies. Bispecifics are indicated as PBXXXX and the different Fab arms with MGXXXX. The activity of the bispecifics in the individual assays is indicated as: − no effect; + inhibition, of proliferation lower than positive control; ++ = inhibition of proliferation comparable to positive control antibody 5D5 Fab; +++ = Inhibition of proliferation higher than positive control antibody 5D5 Fab.

|  | PBs MF's |  | N87 proliferation assays | | |
|---|---|---|---|---|---|
| PBs | EGFR | cMET | HGF/EGF | HGF | EGF |
| PB8532 | MF3370 | MF4358 | + | +++ | + |
| PB8535 | MF3755 | MF4358 | ++ | +++ | ++ |
| PB8545 | ME4281 | MF4358 | + | +++ | + |
| PB8582 | MF3752 | MF4491 | + | − | + |
| PB8583 | MF3755 | MF4491 | ++ | +++ | ++ |
| PB8607 | MF3755 | MF4505 | ++ | − | ++ |
| PB8639 | MF3752 | MF4506 | + | +++ | + |
| PB8640 | MF3755 | MF4508 | ++ | +++ | ++ |
| PB8687 | MF3752 | MF4508 | + | ++ | + |
| PB8688 | MF3755 | MF4508 | + | − | + |

TABLE 5

Composition of the most potent EQFRxcMET bispecific antibodies and their competition with reference antibodies.

| Bispecific antibody | EGFR arm | EGFE blocking compared to cetux (based on IC50) | cMET arm | Cross reference antibody blocking |
|---|---|---|---|---|
| PB8535 | MF3753 | 100% | MF4358 | 5D5 |
| PB8640 | MF3755 | 100% | MF4506 | ND |
| PB8388 | MF3755 | 100% | MF4297 | 13.3.2 |
| PB8218 | MF3752 | 80% | MF4040 | 5D5 |
| PB8532 | MF3370 | 80% | MF4358 | 5D5 |

TABLE 6

Composition of bispecific antibodies. The pXX number indicates the number of the production run and can be used to identify whether the antibody was produced in an ADCC version or not.

| Bispecific antibody | cMET arm | EGFE arm | ADCC enhanced |
|---|---|---|---|
| Cetuximab | — | — | — |
| PB8532p05 | MF4356 | MF3378 | No |
| PB19474p01 | MF4356 | MF8232 | Yes |
| PB19475p01 | MF4356 | MF8233 | Yes |
| PB19476p01 | MF8230 | MF3370 | Yes |
| PB19477p01 | MF8230 | MF8232 | Yes |
| PB19478p01 | MF8230 | MF8233 | Yes |
| PB8532p06 | MF4358 | MF3370 | Yes |
| PB8532p04 | MF4356 | MF3370 | No |
|  | HER-3 arm | EGFR arm |  |
| PB4522p34 | MF3178 | MF4280 | Yes |
| PB4522p25 | MF3178 | MF4280 | No |
|  | TT arm | TT arm |  |
| PG1337p218 | MF1337 | MF1337 | No |

The invention claimed is:

1. A bispecific antibody that comprises a first variable domain that can bind an extracellular part of human epidermal growth factor receptor (EGFR) and a second variable domain that can bind an extracellular part of human MET Proto-Oncogene, Receptor Tyrosine Kinase (cMET);

wherein the first variable domain comprises a heavy chain variable region with a CDR1 sequence SYGIS (SEQ ID NO: 24); a CDR2 sequence WISAY-NANTNYAQKLQG (SEQ ID NO:155) and a CDR3 comprising the sequence DRHWHWWLDA (SEQ ID NO:139) and wherein the second variable domain comprises a heavy chain variable region with a CDR1 sequence TYSMN (SEQ ID NO: 152); a CDR2 sequence WINTYTGDPTYAQGFTG (SEQ ID NO:157) and a CDR3 comprising the sequence ETYFYDRGGYPFDP (SEQ ID NO: 31);

wherein the first variable domain comprises a heavy chain variable region with a CDR1 sequence SYGIS (SEQ ID NO: 24); a CDR2 sequence WISAY-NANTNYAQKLQG (SEQ ID NO:155) and a CDR3 comprising the sequence DRHWHWWLDAFDY (SEQ ID NO:37) and wherein the second variable domain comprises a heavy chain variable region with a CDR1 sequence TYSMN (SEQ ID NO: 152); a CDR2 sequence WINTYTGDPTYAQGFTG (SEQ ID NO:157) and a CDR3 comprising the sequence ETYFYDRGGYPFDP (SEQ ID NO: 31);

wherein the first variable domain comprises a heavy chain variable region with a CDR1 sequence SYGIS (SEQ ID NO: 24); a CDR2 sequence WISAY-SGNTNYAQKLQG (SEQ ID NO:140) and a CDR3 comprising the sequence DRHWHWWLDA (SEQ ID NO:139) and wherein the second variable domain comprises a heavy chain variable region with a CDR1 sequence TYSMN (SEQ ID NO: 152); a CDR2 sequence WINTYTGDPTYAQGFTG (SEQ ID NO:157) and a CDR3 comprising the sequence ETYFYDRGGYPFDP (SEQ ID NO: 31);

wherein the first variable domain comprises a heavy chain variable region with a CDR1 sequence SYGIS (SEQ ID NO: 24); a CDR2 sequence WISAY-SGNTNYAQKLQG (SEQ ID NO:140) and a CDR3 comprising the sequence DRHWHWWLDA (SEQ ID NO:139) and wherein the second variable domain comprises a heavy chain variable region with a CDR1 sequence SYSMN (SEQ ID NO: 28); a CDR2 sequence WINTYTGDPTYAQGFTG (SEQ ID NO: 157) and a CDR3 sequence ETYYYDRGGYPFDP (SEQ ID NO: 30);

wherein the first variable domain comprises a heavy chain variable region with a CDR1 sequence SYGIS (SEQ ID NO: 24); a CDR2 sequence WISAY-SGNTNYAQKLQG (SEQ ID NO:140) and a CDR3 comprising the sequence DRHWHWWLDAFDY (SEQ ID NO:37) and wherein the second variable domain comprises a heavy chain variable region with a CDR1 sequence SYSMN (SEQ ID NO: 28); a CDR2 sequence WINTYTGDPTYAQGFTG (SEQ ID NO: 157) and a CDR3 sequence ETYYYDRGGYPFDP (SEQ ID NO: 30);

wherein the first variable domain comprises a heavy chain variable region with a CDR1 sequence SYGIS (SEQ ID NO: 24); a CDR2 sequence WISAY-NANTNYAQKLQG (SEQ ID NO:155) and a CDR3 comprising the sequence DRHWHWWLDAFDY (SEQ ID NO: 37) and wherein the second variable domain comprises a heavy chain variable region with a CDR1 sequence SYSMN (SEQ ID NO: 28); a CDR2 sequence WINTYTGDPTYAQGFTG (SEQ ID NO: 157) and a CDR3 sequence ETYYYDRGGYPFDP (SEQ ID NO: 30);

wherein the first variable domain comprises a heavy chain variable region with a CDR1 sequence SYGIS (SEQ ID NO: 24); a CDR2 sequence WISAYN-GNTNYAQKLQG (SEQ ID NO:113) and a CDR3 comprising the sequence DRHWHWWLDAFDY (SEQ ID NO: 37) and wherein the second variable domain comprises a heavy chain variable region with a CDR1 sequence TYSMN (SEQ ID NO: 152); a CDR2 sequence WINTYTGDPTYAQGFTG (SEQ ID NO:157) and a CDR3 comprising the sequence ETYFYDRGGYPFDP (SEQ ID NO: 31); or wherein the first variable domain comprises a heavy chain variable region with a CDR1 sequence SYGIS (SEQ ID NO: 24); a CDR2 sequence WISAYN-GNTNYAQKLQG (SEQ ID NO:113) and a CDR3 comprising the sequence DRHWHWWLDAFDY (SEQ ID NO: 37) and wherein the second variable domain comprises a heavy chain variable region with a CDR1 sequence SYSMN (SEQ ID NO: 28); a CDR2 sequence WINTYTGDPTYAQGFTG (SEQ ID NO: 157) and a CDR3 sequence ETYYYDRGGYPFDP (SEQ ID NO: 30); and wherein the first and second variable domains further comprise the common light chain variable domain comprising a CDR1 sequence QSISSY (SEQ ID NO:38), a CDR2 sequence AAS, and a CDR3 sequence QQSYSTP (SEQ ID NO: 39).

2. The bispecific antibody of claim 1, that is an IgG1 format antibody having an anti-EGFR, anti-cMET stoichiometry of 1:1.

3. The bispecific antibody of claim 1, wherein the amino acids at positions 405 and 409 in one CH3 domain are the same as the amino acids at the corresponding positions in the other CH3 domain (EU-numbering).

4. The bispecific antibody of claim 1, wherein the heavy chain variable region of the second variable domain comprises the amino acid sequence of one of the sequences of SEQ ID NO: 13 or 23.

5. The bispecific antibody of claim 1, wherein the heavy chain variable region of the second variable domain comprises the amino acid sequence of one of the sequences of SEQ ID NO: 2; 7; 8; 10; 13 or 23.

6. The bispecific antibody of claim 1, wherein the first variable domain comprises a heavy chain variable region with a CDR1 sequence SYGIS (SEQ ID NO: 24); a CDR2 sequence WISAYNANTNYAQKLQG (SEQ ID NO:155) and a CDR3 comprising the sequence DRHWHWWLDA (SEQ ID NO:139) and wherein the second variable domain comprises a heavy chain variable region with a CDR1 sequence TYSMN (SEQ ID NO: 152); a CDR2 sequence WINTYTGDPTYAQGFTG (SEQ ID NO:157) and a CDR3 comprising the sequence ETYFYDRGGYPFDP (SEQ ID NO: 31).

7. The bispecific antibody of claim 1, wherein the first variable domain comprises a heavy chain variable region with a CDR1 sequence SYGIS (SEQ ID NO: 24); a CDR2 sequence WISAYNANTNYAQKLQG (SEQ ID NO:155) and a CDR3 comprising the sequence DRHWHWWLDAFDY (SEQ ID NO: 37) and wherein the second variable domain comprises a heavy chain variable region with a CDR1 sequence TYSMN (SEQ ID NO: 152); a CDR2 sequence WINTYTGDPTYAQGFTG (SEQ ID NO:157) and a CDR3 comprising the sequence ETYFYDRGGYPFDP (SEQ ID NO: 31).

8. The bispecific antibody of claim 1, wherein the first variable domain comprises a heavy chain variable region with a CDR1 sequence SYGIS (SEQ ID NO: 24); a CDR2 sequence WISAYSGNTNYAQKLQG (SEQ ID NO: 140) and a CDR3 comprising the sequence DRHWHWWLDA (SEQ ID NO: 139) and wherein the second variable domain comprises a heavy chain variable region with a CDR1 sequence TYSMN (SEQ ID NO: 152); a CDR2 sequence WINTYTGDPTYAQGFTG (SEQ ID NO:157) and a CDR3 comprising the sequence ETYFYDRGGYPFDP (SEQ ID NO: 31).

9. The bispecific antibody of claim 1, wherein the first variable domain comprises a heavy chain variable region with a CDR1 sequence SYGIS (SEQ ID NO: 24); a CDR2 sequence WISAYSGNTNYAQKLQG (SEQ ID NO: 140) and a CDR3 comprising the sequence DRHWHWWLDA (SEQ ID NO: 139) and wherein the second variable domain comprises a heavy chain variable region with a CDR1 sequence SYSMN (SEQ ID NO: 28); a CDR2 sequence WINTYTGDPTYAQGFTG (SEQ ID NO:157) and a CDR3 sequence ETYYYDRGGYPFDP (SEQ ID NO: 30).

10. The bispecific antibody of claim 1, wherein the first variable domain comprises a heavy chain variable region comprising the amino acid sequence of SEQ ID NO:79 and the second variable domain comprising the amino acid sequence of SEQ ID NO:13.

11. The bispecific antibody of claim 1, wherein the first variable domain comprises a heavy chain variable region comprising the amino acid sequence of SEQ ID NO:80 and the second variable domain comprising the amino acid sequence of SEQ ID NO:13.

12. The bispecific antibody of claim 1, wherein the first variable domain comprises a heavy chain variable region comprising the amino acid sequence of SEQ ID NO:78 and the second variable domain comprising the amino acid sequence of SEQ ID NO:13.

13. The bispecific antibody of claim 1, wherein the first variable domain comprises a heavy chain variable region with a CDR1 sequence SYGIS (SEQ ID NO: 24); a CDR2 sequence WISAYSGNTNYAQKLQG (SEQ ID NO:140) and a CDR3 comprising the sequence DRHWHWWLDAFDY (SEQ ID NO:37) and wherein the second variable domain comprises a heavy chain variable region with a CDR1 sequence SYSMN (SEQ ID NO: 28); a CDR2 sequence WINTYTGDPTYAQGFTG (SEQ ID NO: 157) and a CDR3 sequence ETYYYDRGGYPFDP (SEQ ID NO: 30).

14. The bispecific antibody of claim 1, wherein the first variable domain comprises a heavy chain variable region with a CDR1 sequence SYGIS (SEQ ID NO: 24); a CDR2 sequence WISAYNANTNYAQKLQG (SEQ ID NO:155) and a CDR3 comprising the sequence DRHWHWWLDAFDY (SEQ ID NO: 37) and wherein the second variable domain comprises a heavy chain variable region with a CDR1 sequence SYSMN (SEQ ID NO: 28); a CDR2 sequence WINTYTGDPTYAQGFTG (SEQ ID NO: 157) and a CDR3 sequence ETYYYDRGGYPFDP (SEQ ID NO: 30).

15. The bispecific antibody of claim 1, wherein the first variable domain comprises a heavy chain variable region with a CDR1 sequence SYGIS (SEQ ID NO: 24); a CDR2 sequence WISAYNGNTNYAQKLQG (SEQ ID NO:113) and a CDR3 comprising the sequence DRHWHWWLDAFDY (SEQ ID NO: 37) and wherein the second variable domain comprises a heavy chain variable region with a CDR1 sequence TYSMN (SEQ ID NO: 152); a CDR2 sequence WINTYTGDPTYAQGFTG (SEQ ID NO:157) and a CDR3 comprising the sequence ETYFYDRGGYPFDP (SEQ ID NO: 31).

16. The bispecific antibody of claim 1, wherein the first variable domain comprises a heavy chain variable region with a CDR1 sequence SYGIS (SEQ ID NO: 24); a CDR2 sequence WISAYNGNTNYAQKLQG (SEQ ID NO:113) and a CDR3 comprising the sequence DRHWHWWLDAFDY (SEQ ID NO: 37) and wherein the second variable domain comprises a heavy chain variable region with a CDR1 sequence SYSMN (SEQ ID NO: 28); a CDR2 sequence WINTYTGDPTYAQGFTG (SEQ ID NO: 157) and a CDR3 sequence ETYYYDRGGYPFDP (SEQ ID NO: 30).

* * * * *

SEQUENCE LISTING

```
<160> NUMBER OF SEQ ID NOS: 159

<210> SEQ ID NO 1
<211> LENGTH: 123
<212> TYPE: PRT
<213> ORGANISM: Artificial Sequence
<220> FEATURE:
<223> OTHER INFORMATION: MF8225

<400> SEQUENCE: 1

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Tyr
            20                  25                  30

Ser Leu Asn Trp Val Arg Gln Ala Pro Gly Gln Gly Leu Glu Trp Met
        35                  40                  45

Gly Trp Ile Asn Thr Tyr Thr Gly Asn Pro Thr Tyr Ala Gln Gly Phe
    50                  55                  60

Thr Gly Arg Phe Val Phe Phe Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95
```

Ala Arg Glu Thr Tyr Tyr Tyr Asp Ser Ser Gly Tyr Pro Phe Asp Pro
            100                 105                 110

Trp Gly Gln Gly Thr Leu Val Thr Val Ser Ser
            115                 120

<210> SEQ ID NO 2
<211> LENGTH: 123
<212> TYPE: PRT
<213> ORGANISM: Artificial Sequence
<220> FEATURE:
<223> OTHER INFORMATION: MF8243

<400> SEQUENCE: 2

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Thr Tyr Tyr Tyr Asp Arg Gly Tyr Pro Phe Asp Pro
            100                 105                 110

Trp Gly Gln Gly Thr Leu Val Thr Val Ser Ser
            115                 120

<210> SEQ ID NO 3
<211> LENGTH: 123
<212> TYPE: PRT
<213> ORGANISM: Artificial Sequence
<220> FEATURE:
<223> OTHER INFORMATION: MF8224

<400> SEQUENCE: 3

Gln Val Gln Leu Met Gln Ser Gly Ser Glu Leu Lys Lys Pro Gly Ala
1               5                   10                  15

Ser Val Lys Val Ser Cys Lys Ala Ser Gly Tyr Thr Phe Thr Thr Tyr
            20                  25                  30

Ser Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Asp Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Thr Tyr Tyr Tyr Asp Ser Ser Gly Tyr Pro Phe Asp Pro
            100                 105                 110

Trp Gly Gln Gly Thr Leu Val Thr Val Ser Ser
            115                 120

<210> SEQ ID NO 4
<211> LENGTH: 123
<212> TYPE: PRT
<213> ORGANISM: Artificial Sequence

<220> FEATURE:
<223> OTHER INFORMATION: MF8239

<400> SEQUENCE: 4

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ala Met Asn Trp Val Arg Gln Val Pro Gly Gln Gly Leu Glu Trp Met
        35                  40                  45

Gly Trp Ile Asn Thr Tyr Thr Gly Asn Pro Thr Tyr Val Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Thr Tyr Tyr Tyr Asp Ser Ser Gly Phe Pro Phe Asp Pro
            100                 105                 110

Trp Gly Gln Gly Thr Leu Val Thr Val Ser Ser
        115                 120

<210> SEQ ID NO 5
<211> LENGTH: 123
<212> TYPE: PRT
<213> ORGANISM: Artificial Sequence
<220> FEATURE:
<223> OTHER INFORMATION: MF8242

<400> SEQUENCE: 5

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Pro Leu Asp Thr Ser Val Ser Thr Thr Tyr
65                  70                  75                  80

Leu Gln Ile Ser Ser Leu Lys Ala Glu Asp Thr Ala Val Tyr Tyr Cys
                85                  90                  95

Ala Arg Glu Thr Tyr Tyr Tyr Gln Ser Ser Gly Tyr Leu Phe Asp Pro
            100                 105                 110

Trp Gly Gln Gly Thr Leu Val Thr Val Ser Ser
        115                 120

<210> SEQ ID NO 6
<211> LENGTH: 123
<212> TYPE: PRT
<213> ORGANISM: Artificial Sequence
<220> FEATURE:
<223> OTHER INFORMATION: MF8237

<400> SEQUENCE: 6

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Phe
            20                  25                  30

Gly Met Ser Trp Val Arg Gln Ala Pro Gly Gln Gly Leu Glu Trp Met
         35                  40                  45

Gly Trp Ile Asn Thr Asn Thr Gly Asn Pro Thr Tyr Ala Gln Gly Phe
 50                  55                  60

Thr Gly Arg Phe Val Phe Ser Leu Asp Thr Ser Val Ser Thr Ala Tyr
 65                  70                  75                  80

Leu Gln Ile Asn Ser Leu Lys Ala Glu Asp Thr Ala Val Tyr Tyr Cys
                 85                  90                  95

Ala Arg Glu Ser Tyr Tyr Asp Arg Asn Asp Tyr Pro Phe Asp Pro
                100                 105                 110

Trp Gly Gln Gly Thr Leu Val Thr Val Ser Ser
            115                 120

<210> SEQ ID NO 7
<211> LENGTH: 123
<212> TYPE: PRT
<213> ORGANISM: Artificial Sequence
<220> FEATURE:
<223> OTHER INFORMATION: MF8240

<400> SEQUENCE: 7

Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Thr Tyr
                 20                  25                  30

Ser Met Asn Trp Val Arg Gln Ala Pro Gly Gln Gly Leu Glu Trp Met
             35                  40                  45

Gly Trp Ile Asn Thr Asn Thr Gly Asn Pro Thr Tyr Ala Gln Gly Phe
 50                  55                  60

Thr Gly Arg Phe Val Phe Ser Leu Asp Thr Ser Val Ser Thr Ala Tyr
 65                  70                  75                  80

Leu Gln Ile Ser Ser Leu Asn Thr Glu Asp Thr Ala Val Tyr Tyr Cys
                 85                  90                  95

Ala Arg Glu Thr Tyr Tyr Asp Val Gly Tyr Pro Phe Asp Pro
                100                 105                 110

Trp Gly Gln Gly Thr Leu Val Thr Val Ser Ser
            115                 120

<210> SEQ ID NO 8
<211> LENGTH: 123
<212> TYPE: PRT
<213> ORGANISM: Artificial Sequence
<220> FEATURE:
<223> OTHER INFORMATION: MF8234

<400> SEQUENCE: 8

Gln Val Gln Leu Val Gln Ser Gly Ser Glu Leu Glu Lys Pro Gly Ala
 1               5                  10                  15

Ser Val Lys Val Ser Cys Lys Ala Ser Gly Tyr Thr Phe Ile Ser Tyr
                 20                  25                  30

Ala Met Asn Trp Val Arg Gln Ala Pro Gly Gln Gly Leu Glu Trp Met
             35                  40                  45

Gly Trp Ile Asn Thr Tyr Thr Gly Asn Pro Thr Tyr Ala Gln Gly Phe
 50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

-continued

Ala Arg Glu Thr Tyr Tyr Tyr Asp Ser Gly Gly Tyr Pro Phe Asp Pro
            100                 105                 110

Trp Gly Gln Gly Thr Leu Val Thr Val Ser Ser
        115                 120

<210> SEQ ID NO 9
<211> LENGTH: 123
<212> TYPE: PRT
<213> ORGANISM: Artificial Sequence
<220> FEATURE:
<223> OTHER INFORMATION: MF8245

<400> SEQUENCE: 9

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
                20                  25                  30

Ala Val Asn Trp Val Arg Gln Ala Pro Gly Gln Gly Leu Glu Trp Met
            35                  40                  45

Gly Trp Ile Asn Thr Tyr Thr Gly Asn Pro Thr Tyr Ala Gln Gly Phe
        50                  55                  60

Thr Gly Arg Phe Val Phe Ser Ser Asp Thr Ser Val Asn Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Thr Tyr Phe Tyr Asp Ser Ser Gly Tyr Pro Phe Asp Pro
            100                 105                 110

Trp Gly Gln Gly Thr Leu Val Thr Val Ser Ser
        115                 120

<210> SEQ ID NO 10
<211> LENGTH: 123
<212> TYPE: PRT
<213> ORGANISM: Artificial Sequence
<220> FEATURE:
<223> OTHER INFORMATION: MF8231

<400> SEQUENCE: 10

Gln Val Gln Val Val Gln Ser Gly Ser Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Ser Met Asn Trp Val Arg Gln Ala Pro Gly Gln Gly Leu Glu Trp Met
            35                  40                  45

Gly Trp Ile Asn Thr Tyr Thr Gly Asp Pro Thr Tyr Val Gln Gly Phe
        50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Thr Tyr Phe Tyr Asp Arg Gly Gly Tyr Pro Phe Asp Pro
            100                 105                 110

Trp Gly Gln Gly Thr Leu Val Thr Val Ser Ser
        115                 120

<210> SEQ ID NO 11
<211> LENGTH: 123
<212> TYPE: PRT

```
<213> ORGANISM: Artificial Sequence
<220> FEATURE:
<223> OTHER INFORMATION: MF8247

<400> SEQUENCE: 11

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
                20                  25                  30

Ala Met Asn Trp Val Arg Gln Ala Pro Gly Gln Gly Leu Glu Trp Met
            35                  40                  45

Gly Trp Ile Asn Thr Tyr Thr Gly Asn Pro Thr Tyr Val Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Thr Tyr Tyr Tyr Asp Ser Ser Ala Tyr Pro Phe Asp Pro
                100                 105                 110

Trp Gly Gln Gly Thr Leu Val Thr Val Ser Ser
            115                 120

<210> SEQ ID NO 12
<211> LENGTH: 123
<212> TYPE: PRT
<213> ORGANISM: Artificial Sequence
<220> FEATURE:
<223> OTHER INFORMATION: MF8238

<400> SEQUENCE: 12

Gln Val Gln Leu Val Gln Ser Gly Ser Glu Leu Glu Lys Pro Gly Ala
1               5                   10                  15

Ser Val Lys Val Ser Cys Lys Ala Ser Gly Tyr Thr Phe Thr Thr Tyr
                20                  25                  30

Ser Met Asn Trp Val Arg Gln Ala Pro Gly Gln Gly Leu Glu Trp Met
            35                  40                  45

Gly Trp Ile Asn Thr Tyr Thr Gly Ser Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Ile Tyr Tyr Cys
                85                  90                  95

Ala Arg Glu Thr Phe Tyr Phe Asp Ser Gly Gly Tyr Pro Phe Asp Pro
                100                 105                 110

Trp Gly Gln Gly Thr Leu Val Thr Val Ser Ser
            115                 120

<210> SEQ ID NO 13
<211> LENGTH: 123
<212> TYPE: PRT
<213> ORGANISM: Artificial Sequence
<220> FEATURE:
<223> OTHER INFORMATION: MF8230

<400> SEQUENCE: 13

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Tyr
                20                  25                  30
```

Ser Met Asn Trp Val Arg Gln Ala Pro Gly Gln Gly Leu Glu Trp Met
        35                  40                  45

Gly Trp Ile Asn Thr Tyr Thr Gly Asp Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Thr Tyr Phe Tyr Asp Arg Gly Tyr Pro Phe Asp Pro
            100                 105                 110

Trp Gly Gln Gly Thr Leu Val Thr Val Ser Ser
            115                 120

<210> SEQ ID NO 14
<211> LENGTH: 123
<212> TYPE: PRT
<213> ORGANISM: Artificial Sequence
<220> FEATURE:
<223> OTHER INFORMATION: MF8248

<400> SEQUENCE: 14

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Tyr
            20                  25                  30

Ala Ile Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala His
65                  70                  75                  80

Leu Gln Ile Ser Ser Leu Lys Ala Glu Asp Thr Ala Val Tyr Tyr Cys
                85                  90                  95

Ala Arg Glu Thr Tyr Tyr Tyr Ala Thr Ser Gly Tyr Pro Phe Asp Pro
            100                 105                 110

Trp Gly Gln Gly Ala Leu Val Thr Val Ser Ser
            115                 120

<210> SEQ ID NO 15
<211> LENGTH: 123
<212> TYPE: PRT
<213> ORGANISM: Artificial Sequence
<220> FEATURE:
<223> OTHER INFORMATION: MF8246

<400> SEQUENCE: 15

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Tyr
            20                  25                  30

Ala Met Asn Trp Val Arg Gln Ala Pro Gly Gln Gly Leu Glu Trp Met
        35                  40                  45

Gly Trp Ile Asn Thr Tyr Thr Gly Asp Pro Thr Tyr Ala Gln Gly Phe
    50                  55                  60

Thr Gly Arg Phe Val Phe Ser Leu Asp Thr Ser Val Asn Thr Ala Tyr
65                  70                  75                  80

Leu Gln Ile Ser Ser Leu Lys Ala Glu Asp Thr Ala Val Tyr Tyr Cys

```
                    85                  90                  95
Ala Arg Glu Thr Ser Tyr Tyr Asp Arg Thr Gly Tyr Pro Phe Asp Pro
                100                 105                 110
Trp Gly Gln Gly Thr Leu Val Thr Val Ser Ser
        115                 120

<210> SEQ ID NO 16
<211> LENGTH: 123
<212> TYPE: PRT
<213> ORGANISM: Artificial Sequence
<220> FEATURE:
<223> OTHER INFORMATION: MF8223

<400> SEQUENCE: 16

Gln Val Gln Leu Val Gln Ser Gly Ser Glu Leu Lys Lys Pro Gly Ala
1               5                   10                  15
Ser Val Lys Val Ser Cys Lys Ala Ser Gly Tyr Thr Phe Thr Thr Tyr
                20                  25                  30
Ala Met Asn Trp Val Arg Gln Ala Pro Gly Gln Gly Leu Glu Trp Met
            35                  40                  45
Gly Trp Ile Asn Thr Asn Thr Gly Asn Pro Thr Tyr Ala Gln Gly Phe
    50                  55                  60
Thr Gly Arg Phe Val Phe Ser Leu Asp Thr Ser Asp Ser Thr Ala Phe
65                  70                  75                  80
Leu Gln Ile Ser Ser Leu Lys Ala Glu Asp Thr Ala Val Tyr Tyr Cys
                85                  90                  95
Ala Arg Glu Thr Tyr Tyr Tyr Asp Ser Ser Gly Tyr Pro Phe Asp Pro
                100                 105                 110
Trp Gly Gln Gly Thr Leu Val Thr Val Ser Ser
        115                 120

<210> SEQ ID NO 17
<211> LENGTH: 123
<212> TYPE: PRT
<213> ORGANISM: Artificial Sequence
<220> FEATURE:
<223> OTHER INFORMATION: MF8222

<400> SEQUENCE: 17

Gln Val Glu Leu Val Gln Ser Gly Ser Glu Leu Lys Lys Pro Gly Ala
1               5                   10                  15
Ser Val Lys Val Ser Cys Lys Ala Ser Gly Tyr Thr Phe Thr Thr Tyr
                20                  25                  30
Ser Met Asn Trp Val Arg Gln Ala Pro Gly Gln Gly Leu Glu Trp Met
            35                  40                  45
Gly Trp Ile Asn Thr Asn Thr Gly Thr Pro Thr Tyr Ala Gln Gly Phe
    50                  55                  60
Thr Gly Arg Phe Val Phe Ser Leu Asp Thr Ser Val Ser Thr Ala Tyr
65                  70                  75                  80
Leu Gln Ile Ser Ser Leu Lys Ala Glu Asp Thr Ala Val Tyr Tyr Cys
                85                  90                  95
Ala Arg Glu Thr Tyr Tyr Tyr Asp Ser Ser Gly Tyr Pro Phe Asp Pro
                100                 105                 110
Trp Gly Gln Gly Thr Leu Val Thr Val Ser Ser
        115                 120

<210> SEQ ID NO 18
<211> LENGTH: 123
```

```
<212> TYPE: PRT
<213> ORGANISM: Artificial Sequence
<220> FEATURE:
<223> OTHER INFORMATION: MF8235

<400> SEQUENCE: 18

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Tyr
            20                  25                  30

Ser Met Asn Trp Val Arg Gln Ala Pro Gly Gln Gly Leu Glu Trp Met
        35                  40                  45

Gly Trp Ile Asn Thr Asn Thr Gly Thr Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Thr Tyr Tyr Tyr Gly Ser Ser Gly Tyr Pro Phe Ala Pro
            100                 105                 110

Trp Gly Gln Gly Thr Leu Val Thr Val Ser Ser
        115                 120

<210> SEQ ID NO 19
<211> LENGTH: 123
<212> TYPE: PRT
<213> ORGANISM: Artificial Sequence
<220> FEATURE:
<223> OTHER INFORMATION: MF8236

<400> SEQUENCE: 19

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Tyr
            20                  25                  30

Ser Met Asn Trp Val Arg Gln Ala Pro Gly Gln Gly Leu Glu Trp Met
        35                  40                  45

Gly Trp Ile Asn Thr Tyr Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Thr Thr Glu Asp Thr Ala Val Tyr Tyr Cys
                85                  90                  95

Ala Arg Glu Thr Tyr Tyr Tyr Glu Ser Ser Gly Tyr Pro Phe Asp Pro
            100                 105                 110

Trp Gly Gln Gly Thr Leu Val Thr Val Ser Ser
        115                 120

<210> SEQ ID NO 20
<211> LENGTH: 123
<212> TYPE: PRT
<213> ORGANISM: Artificial Sequence
<220> FEATURE:
<223> OTHER INFORMATION: MF8241

<400> SEQUENCE: 20

Gln Val Gln Leu Val Gln Ser Gly Ser Glu Leu Glu Lys Pro Gly Ala
1               5                   10                  15

Ser Val Lys Val Ser Cys Lys Ala Ser Gly Tyr Thr Phe Thr Thr Tyr
```

```
            20                  25                  30
Ser Met Asn Trp Val Arg Gln Ala Pro Gly Gln Gly Leu Glu Trp Met
        35                  40                  45

Gly Trp Ile Asn Thr Tyr Thr Gly Ser Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Thr Tyr Tyr Phe Asp Ser Gly Asp Tyr Pro Phe Asp Pro
            100                 105                 110

Trp Gly Gln Gly Thr Leu Val Thr Val Ser Ser
        115                 120

<210> SEQ ID NO 21
<211> LENGTH: 123
<212> TYPE: PRT
<213> ORGANISM: Artificial Sequence
<220> FEATURE:
<223> OTHER INFORMATION: MF8244

<400> SEQUENCE: 21

Gln Val Gln Leu Val Gln Ser Gly Ser Glu Leu Glu Lys Pro Gly Ala
1               5                   10                  15

Ser Val Lys Val Ser Cys Lys Ala Ser Gly Tyr Thr Phe Thr Thr Tyr
            20                  25                  30

Ser Met Asn Trp Val Arg Gln Ala Pro Gly Gln Gly Leu Glu Trp Met
        35                  40                  45

Gly Trp Ile Asn Thr Tyr Thr Gly Ser Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Thr Tyr Tyr Phe Asp Ser Gly Gly Tyr Pro Phe Asp Pro
            100                 105                 110

Trp Gly Gln Gly Thr Leu Val Thr Val Ser Ser
        115                 120

<210> SEQ ID NO 22
<211> LENGTH: 123
<212> TYPE: PRT
<213> ORGANISM: Artificial Sequence
<220> FEATURE:
<223> OTHER INFORMATION: MF8221

<400> SEQUENCE: 22

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ala Met Asn Trp Val Arg Gln Ala Pro Gly Gln Gly Leu Glu Trp Met
        35                  40                  45

Gly Trp Ile Asn Thr Tyr Thr Gly Asn Pro Thr Tyr Val Gln Gly Phe
    50                  55                  60

Thr Gly Arg Phe Val Phe Ser Leu Asp Thr Ser Val Ser Thr Ala Tyr
65                  70                  75                  80
```

```
Leu Gln Ile Ser Ser Leu Lys Ala Glu Asp Thr Ala Val Tyr Tyr Cys
                85                  90                  95

Ala Arg Glu Thr Tyr Tyr Tyr Asp Ser Ser Gly Tyr Pro Phe Asp Pro
            100                 105                 110

Trp Gly Gln Gly Thr Leu Val Thr Val Ser Ser
        115                 120
```

<210> SEQ ID NO 23
<211> LENGTH: 123
<212> TYPE: PRT
<213> ORGANISM: Artificial Sequence
<220> FEATURE:
<223> OTHER INFORMATION: MF4356

<400> SEQUENCE: 23

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
                20                  25                  30

Ser Met Asn Trp Val Arg Gln Ala Pro Gly Gln Gly Leu Glu Trp Met
            35                  40                  45

Gly Trp Ile Asn Thr Tyr Thr Gly Asp Pro Thr Tyr Ala Gln Gly Phe
    50                  55                  60

Thr Gly Arg Tyr Val Phe Ser Leu Asp Thr Ser Val Asn Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Thr Tyr Tyr Tyr Asp Arg Gly Gly Tyr Pro Phe Asp Pro
            100                 105                 110

Trp Gly Gln Gly Thr Leu Val Thr Val Ser Ser
        115                 120
```

<210> SEQ ID NO 24
<211> LENGTH: 5
<212> TYPE: PRT
<213> ORGANISM: Artificial Sequence
<220> FEATURE:
<223> OTHER INFORMATION: CDR1

<400> SEQUENCE: 24

```
Ser Tyr Gly Ile Ser
1               5
```

<210> SEQ ID NO 25
<211> LENGTH: 17
<212> TYPE: PRT
<213> ORGANISM: Artificial Sequence
<220> FEATURE:
<223> OTHER INFORMATION: CDR2
<220> FEATURE:
<221> NAME/KEY: VARIANT
<222> LOCATION: (6)..(6)
<223> OTHER INFORMATION: May also be S
<220> FEATURE:
<221> NAME/KEY: VARIANT
<222> LOCATION: (7)..(7)
<223> OTHER INFORMATION: May also be G

<400> SEQUENCE: 25

```
Trp Ile Ser Ala Tyr Asn Ala Asn Thr Asn Tyr Ala Gln Lys Leu Gln
1               5                   10                  15

Gly
```

```
<210> SEQ ID NO 26
<211> LENGTH: 10
<212> TYPE: PRT
<213> ORGANISM: Artificial Sequence
<220> FEATURE:
<223> OTHER INFORMATION: CDR3
<220> FEATURE:
<221> NAME/KEY: VARIANT
<222> LOCATION: (1)..(1)
<223> OTHER INFORMATION: May also be G
<220> FEATURE:
<221> NAME/KEY: VARIANT
<222> LOCATION: (2)..(2)
<223> OTHER INFORMATION: May also be S or Y
<220> FEATURE:
<221> NAME/KEY: VARIANT
<222> LOCATION: (3)..(3)
<223> OTHER INFORMATION: May also be L or Y
<220> FEATURE:
<221> NAME/KEY: VARIANT
<222> LOCATION: (4)..(4)
<223> OTHER INFORMATION: May also be W
<220> FEATURE:
<221> NAME/KEY: VARIANT
<222> LOCATION: (10)..(10)
<223> OTHER INFORMATION: May also be G

<400> SEQUENCE: 26

Asp Arg His Asp His Trp Trp Leu Asp Ala
1               5                   10

<210> SEQ ID NO 27
<211> LENGTH: 5
<212> TYPE: PRT
<213> ORGANISM: Artificial Sequence
<220> FEATURE:
<223> OTHER INFORMATION: preferred option for C-terminal part of CDR3

<400> SEQUENCE: 27

Asp Arg His Trp Asp
1               5

<210> SEQ ID NO 28
<211> LENGTH: 5
<212> TYPE: PRT
<213> ORGANISM: Artificial Sequence
<220> FEATURE:
<223> OTHER INFORMATION: CDR1

<400> SEQUENCE: 28

Ser Tyr Ser Met Asn
1               5

<210> SEQ ID NO 29
<211> LENGTH: 17
<212> TYPE: PRT
<213> ORGANISM: Artificial Sequence
<220> FEATURE:
<223> OTHER INFORMATION: CDR2

<400> SEQUENCE: 29

Trp Ile Asn Thr Tyr Thr Gly Asp Pro Thr Tyr Ala Gln Gly Phe Thr
1               5                   10                  15

Gly

<210> SEQ ID NO 30
<211> LENGTH: 14
<212> TYPE: PRT
<213> ORGANISM: Artificial Sequence
```

<220> FEATURE:
<223> OTHER INFORMATION: CDR3

<400> SEQUENCE: 30

Glu Thr Tyr Tyr Tyr Asp Arg Gly Gly Tyr Pro Phe Asp Pro
1               5                   10

<210> SEQ ID NO 31
<211> LENGTH: 14
<212> TYPE: PRT
<213> ORGANISM: Artificial Sequence
<220> FEATURE:
<223> OTHER INFORMATION: CDR3

<400> SEQUENCE: 31

Glu Thr Tyr Phe Tyr Asp Arg Gly Gly Tyr Pro Phe Asp Pro
1               5                   10

<210> SEQ ID NO 32
<211> LENGTH: 12
<212> TYPE: PRT
<213> ORGANISM: Artificial Sequence
<220> FEATURE:
<223> OTHER INFORMATION: CDR3 variant
<220> FEATURE:
<221> NAME/KEY: VARIANT
<222> LOCATION: (1)..(1)
<223> OTHER INFORMATION: Can also be G
<220> FEATURE:
<221> NAME/KEY: VARIANT
<222> LOCATION: (2)..(2)
<223> OTHER INFORMATION: Can also be S or Y
<220> FEATURE:
<221> NAME/KEY: VARIANT
<222> LOCATION: (3)..(3)
<223> OTHER INFORMATION: Can also be L or Y
<220> FEATURE:
<221> NAME/KEY: VARIANT
<222> LOCATION: (4)..(4)
<223> OTHER INFORMATION: Can also be W
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: VARIANT
<222> LOCATION: (10)..(10)
<223> OTHER INFORMATION: Can also be G

<400> SEQUENCE: 32

Asp Arg His Asp Xaa His Trp Trp Leu Asp Ala Phe
1               5                   10

<210> SEQ ID NO 33
<211> LENGTH: 13
<212> TYPE: PRT
<213> ORGANISM: Artificial Sequence
<220> FEATURE:
<223> OTHER INFORMATION: CDR3 variant
<220> FEATURE:
<221> NAME/KEY: VARIANT
<222> LOCATION: (1)..(1)
<223> OTHER INFORMATION: Can also be G
<220> FEATURE:
<221> NAME/KEY: VARIANT
<222> LOCATION: (2)..(2)
<223> OTHER INFORMATION: Can also be S or Y
<220> FEATURE:
<221> NAME/KEY: VARIANT
<222> LOCATION: (3)..(3)
<223> OTHER INFORMATION: Can also be L or Y
<220> FEATURE:
<221> NAME/KEY: VARIANT

```
<222> LOCATION: (4)..(4)
<223> OTHER INFORMATION: Can also be W
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: VARIANT
<222> LOCATION: (10)..(10)
<223> OTHER INFORMATION: Can also be G

<400> SEQUENCE: 33

Asp Arg His Asp Xaa His Trp Trp Leu Asp Ala Phe Asp
1               5                   10

<210> SEQ ID NO 34
<211> LENGTH: 14
<212> TYPE: PRT
<213> ORGANISM: Artificial Sequence
<220> FEATURE:
<223> OTHER INFORMATION: CDR3 variant
<220> FEATURE:
<221> NAME/KEY: VARIANT
<222> LOCATION: (1)..(1)
<223> OTHER INFORMATION: Can also be G
<220> FEATURE:
<221> NAME/KEY: VARIANT
<222> LOCATION: (2)..(2)
<223> OTHER INFORMATION: Can also be S or Y
<220> FEATURE:
<221> NAME/KEY: VARIANT
<222> LOCATION: (3)..(3)
<223> OTHER INFORMATION: Can also be L or Y
<220> FEATURE:
<221> NAME/KEY: VARIANT
<222> LOCATION: (4)..(4)
<223> OTHER INFORMATION: Can also be W
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: VARIANT
<222> LOCATION: (10)..(10)
<223> OTHER INFORMATION: Can also be G

<400> SEQUENCE: 34

Asp Arg His Asp Xaa His Trp Trp Leu Asp Ala Phe Asp Tyr
1               5                   10

<210> SEQ ID NO 35
<211> LENGTH: 11
<212> TYPE: PRT
<213> ORGANISM: Artificial Sequence
<220> FEATURE:
<223> OTHER INFORMATION: CDR3

<400> SEQUENCE: 35

Asp Arg His Trp His Trp Trp Leu Asp Ala Phe
1               5                   10

<210> SEQ ID NO 36
<211> LENGTH: 12
<212> TYPE: PRT
<213> ORGANISM: Artificial Sequence
<220> FEATURE:
<223> OTHER INFORMATION: CDR3

<400> SEQUENCE: 36

Asp Arg His Trp His Trp Trp Leu Asp Ala Phe Asp
1               5                   10
```

```
<210> SEQ ID NO 37
<211> LENGTH: 13
<212> TYPE: PRT
<213> ORGANISM: Artificial Sequence
<220> FEATURE:
<223> OTHER INFORMATION: CDR3

<400> SEQUENCE: 37

Asp Arg His Trp His Trp Trp Leu Asp Ala Phe Asp Tyr
1               5                   10

<210> SEQ ID NO 38
<211> LENGTH: 6
<212> TYPE: PRT
<213> ORGANISM: Artificial Sequence
<220> FEATURE:
<223> OTHER INFORMATION: CDR1-tail

<400> SEQUENCE: 38

Gln Ser Ile Ser Ser Tyr
1               5

<210> SEQ ID NO 39
<211> LENGTH: 7
<212> TYPE: PRT
<213> ORGANISM: Artificial Sequence
<220> FEATURE:
<223> OTHER INFORMATION: CDR3-tail

<400> SEQUENCE: 39

Gln Gln Ser Tyr Ser Thr Pro
1               5

<210> SEQ ID NO 40
<211> LENGTH: 107
<212> TYPE: PRT
<213> ORGANISM: Artificial Sequence
<220> FEATURE:
<223> OTHER INFORMATION: light chain variable region

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
            100                 105

<210> SEQ ID NO 41
<211> LENGTH: 108
<212> TYPE: PRT
<213> ORGANISM: Artificial Sequence
<220> FEATURE:
<223> OTHER INFORMATION: light chain variable region

<400> SEQUENCE: 41
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

<210> SEQ ID NO 42
<211> LENGTH: 1210
<212> TYPE: PRT
<213> ORGANISM: Homo sapiens
<220> FEATURE:
<221> NAME/KEY: SIGNAL
<222> LOCATION: (1)..(23)
<220> FEATURE:
<221> NAME/KEY: DOMAIN
<222> LOCATION: (24)..(645)
<223> OTHER INFORMATION: ECD
<220> FEATURE:
<221> NAME/KEY: DOMAIN
<222> LOCATION: (646)..(668)
<223> OTHER INFORMATION: predicted TM
<220> FEATURE:
<221> NAME/KEY: DOMAIN
<222> LOCATION: (669)..(1210)
<223> OTHER INFORMATION: intracellular tail

<400> SEQUENCE: 42

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
```

```
            180                 185                 190
Ser Cys Pro Asn Gly Ser Cys Trp Gly Ala Gly Glu Glu Asn Cys Gln
            195                 200                 205
Lys Leu Thr Lys Ile Ile Cys Ala Gln Gln Cys Ser Gly Arg Cys Arg
            210                 215                 220
Gly Lys Ser Pro Ser Asp Cys Cys His Asn Gln Cys Ala Ala Gly Cys
225                 230                 235                 240
Thr Gly Pro Arg Glu Ser Asp Cys Leu Val Cys Arg Lys Phe Arg Asp
                245                 250                 255
Glu Ala Thr Cys Lys Asp Thr Cys Pro Pro Leu Met Leu Tyr Asn Pro
                260                 265                 270
Thr Thr Tyr Gln Met Asp Val Asn Pro Glu Gly Lys Tyr Ser Phe Gly
                275                 280                 285
Ala Thr Cys Val Lys Lys Cys Pro Arg Asn Tyr Val Val Thr Asp His
            290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
                325                 330                 335
Cys Asn Gly Ile Gly Ile Gly Glu Phe Lys Asp Ser Leu Ser Ile Asn
                340                 345                 350
Ala Thr Asn Ile Lys His Phe Lys Asn Cys Thr Ser Ile Ser Gly Asp
                355                 360                 365
Leu His Ile Leu Pro Val Ala Phe Arg Gly Asp Ser Phe Thr His Thr
            370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
                420                 425                 430
His Gly Gln Phe Ser Leu Ala Val Val Ser Leu Asn Ile Thr Ser Leu
            435                 440                 445
Gly Leu Arg Ser Leu Lys Glu Ile Ser Asp Gly Asp Val Ile Ile Ser
            450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
                500                 505                 510
Glu Gly Cys Trp Gly Pro Glu Pro Arg Asp Cys Val Ser Cys Arg Asn
            515                 520                 525
Val Ser Arg Gly Arg Glu Cys Val Asp Lys Cys Asn Leu Leu Glu Gly
            530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
                580                 585                 590
Lys Thr Cys Pro Ala Gly Val Met Gly Glu Asn Asn Thr Leu Val Trp
                595                 600                 605
```

-continued

```
Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
            645                 650                 655

Leu Leu Val Val Ala Leu Gly Ile Gly Leu Phe Met Arg Arg His
        660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe
    1010                1015                1020
```

-continued

```
Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 43
<211> LENGTH: 378
<212> TYPE: PRT
<213> ORGANISM: Homo sapiens
<220> FEATURE:
<221> NAME/KEY: SIGNAL
<222> LOCATION: (1)..(23)
<220> FEATURE:
<221> NAME/KEY: DOMAIN
<222> LOCATION: (24)..(378)
<223> OTHER INFORMATION: ECD

<400> SEQUENCE: 43

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Gly Asn Tyr
            20                  25                  30

Val Val Thr Asp His Gly Ser Cys Val Arg Ala Cys Gly Ala Asp Ser
        35                  40                  45

Tyr Glu Met Glu Glu Asp Gly Val Arg Lys Cys Lys Lys Cys Glu Gly
    50                  55                  60

Pro Cys Arg Lys Val Cys Asn Gly Ile Gly Ile Gly Glu Phe Lys Asp
65                  70                  75                  80

Ser Leu Ser Ile Asn Ala Thr Asn Ile Lys His Phe Lys Asn Cys Thr
                85                  90                  95

Ser Ile Ser Gly Asp Leu His Ile Leu Pro Val Ala Phe Arg Gly Asp
            100                 105                 110

Ser Phe Thr His Thr Pro Pro Leu Asp Pro Gln Glu Leu Asp Ile Leu
        115                 120                 125

Lys Thr Val Lys Glu Ile Thr Gly Phe Leu Leu Ile Gln Ala Trp Pro
```

```
                130                 135                 140
Glu Asn Arg Thr Asp Leu His Ala Phe Glu Asn Leu Glu Ile Ile Arg
145                 150                 155                 160

Gly Arg Thr Lys Gln His Gly Gln Phe Ser Leu Ala Val Val Ser Leu
                165                 170                 175

Asn Ile Thr Ser Leu Gly Leu Arg Ser Leu Lys Glu Ile Ser Asp Gly
            180                 185                 190

Asp Val Ile Ile Ser Gly Asn Lys Asn Leu Cys Tyr Ala Asn Thr Ile
                195                 200                 205

Asn Trp Lys Lys Leu Phe Gly Thr Ser Gly Gln Lys Thr Lys Ile Ile
            210                 215                 220

Ser Asn Arg Gly Glu Asn Ser Cys Lys Ala Thr Gly Gln Val Cys His
225                 230                 235                 240

Ala Leu Cys Ser Pro Glu Gly Cys Trp Gly Pro Glu Pro Arg Asp Cys
                245                 250                 255

Val Ser Cys Arg Asn Val Ser Arg Gly Arg Glu Cys Val Asp Lys Cys
            260                 265                 270

Asn Leu Leu Glu Gly Glu Pro Arg Glu Phe Val Glu Asn Ser Glu Cys
            275                 280                 285

Ile Gln Cys His Pro Glu Cys Leu Pro Gln Ala Met Asn Ile Thr Cys
        290                 295                 300

Thr Gly Arg Gly Pro Asp Asn Cys Ile Gln Cys Ala His Tyr Ile Asp
305                 310                 315                 320

Gly Pro His Cys Val Lys Thr Cys Pro Ala Gly Val Met Gly Glu Asn
                325                 330                 335

Asn Thr Leu Val Trp Lys Tyr Ala Asp Ala Gly His Val Cys His Leu
            340                 345                 350

Cys His Pro Asn Cys Thr Tyr Gly Cys Thr Gly Pro Gly Leu Glu Gly
                355                 360                 365

Cys Pro Thr Asn Gly Pro Lys Ile Pro Ser
            370                 375

<210> SEQ ID NO 44
<211> LENGTH: 1210
<212> TYPE: PRT
<213> ORGANISM: Macaca mulatta
<220> FEATURE:
<221> NAME/KEY: SIGNAL
<222> LOCATION: (1)..(23)
<220> FEATURE:
<221> NAME/KEY: DOMAIN
<222> LOCATION: (24)..(641)
<223> OTHER INFORMATION: ECD

<400> SEQUENCE: 44

Met Gly Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95
```

```
Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
        130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Glu Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Thr Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Ser Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510
```

```
Glu Gly Cys Trp Gly Pro Glu Pro Arg Asp Cys Val Ser Cys Gln Asn
            515                 520                 525
Val Ser Arg Gly Arg Glu Cys Val Asp Lys Cys Asn Ile Leu Glu Gly
        530                 535                 540
Glu Pro Arg Glu Phe Val Glu Asn Ser Glu Cys Ile Gln Cys His Pro
545                 550                 555                 560
Glu Cys Leu Pro Gln Val Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
        595                 600                 605
Lys Tyr Ala Asp Ala Gly His Val Cys His Leu Cys His Pro Asn Cys
610                 615                 620
Thr Tyr Gly Cys Thr Gly Pro Gly Leu Glu Gly Cys Ala Arg Asn Gly
625                 630                 635                 640
Pro Lys Ile Pro Ser Ile Ala Thr Gly Met Leu Gly Ala Leu Leu Leu
                645                 650                 655
Leu Leu Val Val Ala Leu Gly Ile Gly Leu Phe Met Arg Arg Arg His
                660                 665                 670
Ile Val Arg Lys Arg Thr Leu Arg Arg Leu Leu Gln Glu Arg Glu Leu
            675                 680                 685
Val Glu Pro Leu Thr Pro Ser Gly Glu Ala Pro Asn Gln Ala Leu Leu
            690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
                740                 745                 750
Pro Lys Ala Asn Lys Glu Ile Leu Asp Glu Ala Tyr Val Met Ala Ser
                755                 760                 765
Val Asp Asn Pro His Val Cys Arg Leu Leu Gly Ile Cys Leu Thr Ser
770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                805                 810                 815
Trp Cys Val Gln Ile Ala Lys Gly Met Asn Tyr Leu Glu Asp Arg Arg
                820                 825                 830
Leu Val His Arg Asp Leu Ala Ala Arg Asn Val Leu Val Lys Thr Pro
            835                 840                 845
Gln His Val Lys Ile Thr Asp Phe Gly Leu Ala Lys Leu Leu Gly Ala
        850                 855                 860
Glu Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                885                 890                 895
Val Trp Ser Tyr Gly Val Thr Val Trp Glu Leu Met Thr Phe Gly Ser
                900                 905                 910
Lys Pro Tyr Asp Gly Ile Pro Ala Ser Glu Ile Ser Ser Ile Leu Glu
            915                 920                 925
Lys Gly Glu Arg Leu Pro Gln Pro Pro Ile Cys Thr Ile Asp Val Tyr
```

```
                930             935             940
Met Ile Met Val Lys Cys Trp Met Ile Asp Ala Asp Ser Arg Pro Lys
945             950             955             960

Phe Arg Glu Leu Ile Ile Glu Phe Ser Lys Met Ala Arg Asp Pro Gln
            965             970             975

Arg Tyr Leu Val Ile Gln Gly Asp Glu Arg Met His Leu Pro Ser Pro
            980             985             990

Thr Asp Ser Asn Phe Tyr Arg Ala Leu Met Asp Glu Glu Asp Met Asp
        995            1000            1005

Asp Val Val Asp Ala Asp Glu Tyr Leu Ile Pro Gln Gln Gly Phe
    1010            1015            1020

Phe Ser Ser Pro Ser Thr Ser Arg Thr Pro Leu Leu Ser Ser Leu
    1025            1030            1035

Ser Ala Thr Ser Asn Asn Ser Thr Val Ala Cys Ile Asp Arg Asn
    1040            1045            1050

Gly Leu Gln Ser Cys Pro Ile Lys Glu Asp Ser Phe Leu Gln Arg
    1055            1060            1065

Tyr Ser Ser Asp Pro Thr Gly Ala Leu Thr Glu Asp Ser Ile Asp
    1070            1075            1080

Asp Thr Phe Leu Pro Val Pro Glu Tyr Ile Asn Gln Ser Val Pro
    1085            1090            1095

Lys Arg Pro Ala Gly Ser Val Gln Asn Pro Val Tyr His Asn Gln
    1100            1105            1110

Pro Leu Asn Pro Ala Pro Ser Arg Asp Pro His Tyr Gln Asp Pro
    1115            1120            1125

His Ser Thr Ala Val Gly Asn Pro Glu Tyr Leu Asn Thr Val Gln
    1130            1135            1140

Pro Thr Cys Val Asn Ser Thr Phe Asp Ser Pro Ala His Trp Ala
    1145            1150            1155

Gln Lys Gly Ser His Gln Ile Ser Leu Asp Asn Pro Asp Tyr Gln
    1160            1165            1170

Gln Asp Phe Phe Pro Lys Glu Ala Lys Pro Asn Gly Ile Phe Lys
    1175            1180            1185

Gly Ser Thr Ala Glu Asn Ala Glu Tyr Leu Arg Val Ala Pro Gln
    1190            1195            1200

Ser Ser Glu Phe Ile Gly Ala
    1205            1210

<210> SEQ ID NO 45
<211> LENGTH: 16
<212> TYPE: PRT
<213> ORGANISM: Artificial Sequence
<220> FEATURE:
<223> OTHER INFORMATION: CDR2

<400> SEQUENCE: 45

Trp Ile Asn Thr Tyr Thr Gly Asp Pro Thr Tyr Ala Gln Gly Phe Thr
1               5                   10                  15

<210> SEQ ID NO 46
<211> LENGTH: 1408
<212> TYPE: PRT
<213> ORGANISM: Homo sapiens
<220> FEATURE:
<221> NAME/KEY: SIGNAL
<222> LOCATION: (1)..(24)
<220> FEATURE:
<221> NAME/KEY: DOMAIN
```

```
<222> LOCATION: (25)..(950)
<223> OTHER INFORMATION: ECD
<220> FEATURE:
<221> NAME/KEY: DOMAIN
<222> LOCATION: (951)..(973)
<223> OTHER INFORMATION: TM
<220> FEATURE:
<221> NAME/KEY: DOMAIN
<222> LOCATION: (974)..(1408)
<223> OTHER INFORMATION: intracellular tail

<400> SEQUENCE: 46

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350
```

```
Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Thr Trp Trp Lys Glu Pro Leu Asn Ile Val Ser Phe Leu
        755                 760                 765

Phe Cys Phe Ala Ser Gly Gly Ser Thr Ile Thr Gly Val Gly Lys Asn
```

```
              770             775             780
Leu Asn Ser Val Ser Val Pro Arg Met Val Ile Asn Val His Glu Ala
785             790             795             800

Gly Arg Asn Phe Thr Val Ala Cys Gln His Arg Ser Asn Ser Glu Ile
            805             810             815

Ile Cys Cys Thr Thr Pro Ser Leu Gln Gln Leu Asn Leu Gln Leu Pro
            820             825             830

Leu Lys Thr Lys Ala Phe Phe Met Leu Asp Gly Ile Leu Ser Lys Tyr
            835             840             845

Phe Asp Leu Ile Tyr Val His Asn Pro Val Phe Lys Pro Phe Glu Lys
850             855             860

Pro Val Met Ile Ser Met Gly Asn Glu Asn Val Leu Glu Ile Lys Gly
865             870             875             880

Asn Asp Ile Asp Pro Glu Ala Val Lys Gly Glu Val Leu Lys Val Gly
            885             890             895

Asn Lys Ser Cys Glu Asn Ile His Leu His Ser Glu Ala Val Leu Cys
            900             905             910

Thr Val Pro Asn Asp Leu Leu Lys Leu Asn Ser Glu Leu Asn Ile Glu
            915             920             925

Trp Lys Gln Ala Ile Ser Ser Thr Val Leu Gly Lys Val Ile Val Gln
            930             935             940

Pro Asp Gln Asn Phe Thr Gly Leu Ile Ala Gly Val Val Ser Ile Ser
945             950             955             960

Thr Ala Leu Leu Leu Leu Leu Gly Phe Phe Leu Trp Leu Lys Lys Arg
            965             970             975

Lys Gln Ile Lys Asp Leu Gly Ser Glu Leu Val Arg Tyr Asp Ala Arg
            980             985             990

Val His Thr Pro His Leu Asp Arg Leu Val Ser Ala Arg Ser Val Ser
            995            1000            1005

Pro Thr Thr Glu Met Val Ser Asn Glu Ser Val Asp Tyr Arg Ala
           1010            1015            1020

Thr Phe Pro Glu Asp Gln Phe Pro Asn Ser Ser Gln Asn Gly Ser
           1025            1030            1035

Cys Arg Gln Val Gln Tyr Pro Leu Thr Asp Met Ser Pro Ile Leu
           1040            1045            1050

Thr Ser Gly Asp Ser Asp Ile Ser Ser Pro Leu Leu Gln Asn Thr
           1055            1060            1065

Val His Ile Asp Leu Ser Ala Leu Asn Pro Glu Leu Val Gln Ala
           1070            1075            1080

Val Gln His Val Val Ile Gly Pro Ser Ser Leu Ile Val His Phe
           1085            1090            1095

Asn Glu Val Ile Gly Arg Gly His Phe Gly Cys Val Tyr His Gly
           1100            1105            1110

Thr Leu Leu Asp Asn Asp Gly Lys Lys Ile His Cys Ala Val Lys
           1115            1120            1125

Ser Leu Asn Arg Ile Thr Asp Ile Gly Glu Val Ser Gln Phe Leu
           1130            1135            1140

Thr Glu Gly Ile Ile Met Lys Asp Phe Ser His Pro Asn Val Leu
           1145            1150            1155

Ser Leu Leu Gly Ile Cys Leu Arg Ser Glu Gly Ser Pro Leu Val
           1160            1165            1170

Val Leu Pro Tyr Met Lys His Gly Asp Leu Arg Asn Phe Ile Arg
           1175            1180            1185
```

```
Asn Glu Thr His Asn Pro Thr Val Lys Asp Leu Ile Gly Phe Gly
    1190            1195                1200

Leu Gln Val Ala Lys Gly Met Lys Tyr Leu Ala Ser Lys Lys Phe
    1205            1210                1215

Val His Arg Asp Leu Ala Ala Arg Asn Cys Met Leu Asp Glu Lys
    1220            1225                1230

Phe Thr Val Lys Val Ala Asp Phe Gly Leu Ala Arg Asp Met Tyr
    1235            1240                1245

Asp Lys Glu Tyr Tyr Ser Val His Asn Lys Thr Gly Ala Lys Leu
    1250            1255                1260

Pro Val Lys Trp Met Ala Leu Glu Ser Leu Gln Thr Gln Lys Phe
    1265            1270                1275

Thr Thr Lys Ser Asp Val Trp Ser Phe Gly Val Leu Leu Trp Glu
    1280            1285                1290

Leu Met Thr Arg Gly Ala Pro Pro Tyr Pro Asp Val Asn Thr Phe
    1295            1300                1305

Asp Ile Thr Val Tyr Leu Leu Gln Gly Arg Arg Leu Leu Gln Pro
    1310            1315                1320

Glu Tyr Cys Pro Asp Pro Leu Tyr Glu Val Met Leu Lys Cys Trp
    1325            1330                1335

His Pro Lys Ala Glu Met Arg Pro Ser Phe Ser Glu Leu Val Ser
    1340            1345                1350

Arg Ile Ser Ala Ile Phe Ser Thr Phe Ile Gly Glu His Tyr Val
    1355            1360                1365

His Val Asn Ala Thr Tyr Val Asn Val Lys Cys Val Ala Pro Tyr
    1370            1375                1380

Pro Ser Leu Leu Ser Ser Glu Asp Asn Ala Asp Asp Glu Val Asp
    1385            1390                1395

Thr Arg Pro Ala Ser Phe Trp Glu Thr Ser
    1400            1405

<210> SEQ ID NO 47
<211> LENGTH: 16
<212> TYPE: PRT
<213> ORGANISM: Artificial Sequence
<220> FEATURE:
<223> OTHER INFORMATION: EFGR CDR3

<400> SEQUENCE: 47

Glu Gly Tyr Tyr Glu Thr Thr Thr Tyr Tyr Asn Leu Phe Asp Ser
1               5                   10                  15

<210> SEQ ID NO 48
<211> LENGTH: 11
<212> TYPE: PRT
<213> ORGANISM: Artificial Sequence
<220> FEATURE:
<223> OTHER INFORMATION: EGFR CDR3

<400> SEQUENCE: 48

Glu Arg Phe Leu Glu Trp Leu His Phe Asp Tyr
1               5                   10

<210> SEQ ID NO 49
<211> LENGTH: 10
<212> TYPE: PRT
<213> ORGANISM: Artificial Sequence
<220> FEATURE:
<223> OTHER INFORMATION: EGFR CDR3
```

```
<400> SEQUENCE: 49

Asp Arg Asn Trp Gly Trp Asp Phe Asp Tyr
1               5                   10

<210> SEQ ID NO 50
<211> LENGTH: 13
<212> TYPE: PRT
<213> ORGANISM: Artificial Sequence
<220> FEATURE:
<223> OTHER INFORMATION: EGFR CDR3

<400> SEQUENCE: 50

Asp Arg His Trp His Trp Trp Leu Asp Ala Phe Asp Tyr
1               5                   10

<210> SEQ ID NO 51
<211> LENGTH: 11
<212> TYPE: PRT
<213> ORGANISM: Artificial Sequence
<220> FEATURE:
<223> OTHER INFORMATION: EGFR CDR3

<400> SEQUENCE: 51

Gly Asp Leu Phe Ile Thr Gly Thr Leu Asp Tyr
1               5                   10

<210> SEQ ID NO 52
<211> LENGTH: 14
<212> TYPE: PRT
<213> ORGANISM: Artificial Sequence
<220> FEATURE:
<223> OTHER INFORMATION: c-MET CDR3

<400> SEQUENCE: 52

Lys Leu Glu Pro Thr Gly Tyr Tyr Tyr Tyr Tyr Met Asp Val
1               5                   10

<210> SEQ ID NO 53
<211> LENGTH: 14
<212> TYPE: PRT
<213> ORGANISM: Artificial Sequence
<220> FEATURE:
<223> OTHER INFORMATION: c-MET CDR3

<400> SEQUENCE: 53

Lys Thr Ser Arg Tyr Ser Gly Tyr His Tyr Tyr Met Asp Val
1               5                   10

<210> SEQ ID NO 54
<211> LENGTH: 8
<212> TYPE: PRT
<213> ORGANISM: Artificial Sequence
<220> FEATURE:
<223> OTHER INFORMATION: c-MET CDR3

<400> SEQUENCE: 54

Ala His Tyr Asp Ile Leu Thr Gly
1               5

<210> SEQ ID NO 55
<211> LENGTH: 12
<212> TYPE: PRT
<213> ORGANISM: Artificial Sequence
<220> FEATURE:
<223> OTHER INFORMATION: c-MET CDR3
```

```
<400> SEQUENCE: 55

Gly Lys Ser His Tyr Ser Trp Asp Ala Phe Asp Tyr
1               5                   10

<210> SEQ ID NO 56
<211> LENGTH: 20
<212> TYPE: PRT
<213> ORGANISM: Artificial Sequence
<220> FEATURE:
<223> OTHER INFORMATION: c-MET CDR3

<400> SEQUENCE: 56

Gly Thr Tyr Tyr Tyr Gly Ser Gly Ser Phe Ser Thr Arg Val Phe Asp
1               5                   10                  15

Ala Phe Asp Val
            20

<210> SEQ ID NO 57
<211> LENGTH: 14
<212> TYPE: PRT
<213> ORGANISM: Artificial Sequence
<220> FEATURE:
<223> OTHER INFORMATION: c-MET CDR3

<400> SEQUENCE: 57

Gln Ser Arg Arg Tyr Ser Gly Tyr Ala Ser Tyr Phe Asp Tyr
1               5                   10

<210> SEQ ID NO 58
<211> LENGTH: 14
<212> TYPE: PRT
<213> ORGANISM: Artificial Sequence
<220> FEATURE:
<223> OTHER INFORMATION: c-MET CDR3

<400> SEQUENCE: 58

Gln Arg Arg Ala Tyr Ser Gly Tyr Asn Trp Tyr Phe Asp Leu
1               5                   10

<210> SEQ ID NO 59
<211> LENGTH: 12
<212> TYPE: PRT
<213> ORGANISM: Artificial Sequence
<220> FEATURE:
<223> OTHER INFORMATION: c-MET CDR3

<400> SEQUENCE: 59

Arg Asn Asp Phe Trp Ser Gly Tyr Leu Phe Asp Tyr
1               5                   10

<210> SEQ ID NO 60
<211> LENGTH: 13
<212> TYPE: PRT
<213> ORGANISM: Artificial Sequence
<220> FEATURE:
<223> OTHER INFORMATION: c-MET CDR3

<400> SEQUENCE: 60

Lys Thr Thr Val Gly Tyr Tyr Tyr Tyr Tyr Met Asp Val
1               5                   10

<210> SEQ ID NO 61
<211> LENGTH: 13
<212> TYPE: PRT
<213> ORGANISM: Artificial Sequence
<220> FEATURE:
```

```
<223> OTHER INFORMATION: c-MET CDR3

<400> SEQUENCE: 61

Gly Pro Glu Leu Gly Tyr Tyr Tyr Tyr Met Asp Ile
1               5                   10

<210> SEQ ID NO 62
<211> LENGTH: 17
<212> TYPE: PRT
<213> ORGANISM: Artificial Sequence
<220> FEATURE:
<223> OTHER INFORMATION: c-MET CDR3

<400> SEQUENCE: 62

Ala Ser Ser Met Ile Thr Phe Gly Gly Val Ile Val Ser Trp Phe Asp
1               5                   10                  15

Pro

<210> SEQ ID NO 63
<211> LENGTH: 14
<212> TYPE: PRT
<213> ORGANISM: Artificial Sequence
<220> FEATURE:
<223> OTHER INFORMATION: c-MET CDR3

<400> SEQUENCE: 63

Arg Val Asn Arg Tyr Ser Gly Tyr Ala Thr Tyr Phe Asp Leu
1               5                   10

<210> SEQ ID NO 64
<211> LENGTH: 14
<212> TYPE: PRT
<213> ORGANISM: Artificial Sequence
<220> FEATURE:
<223> OTHER INFORMATION: c-MET CDR3

<400> SEQUENCE: 64

Glu Thr Tyr Tyr Tyr Asp Arg Gly Gly Tyr Pro Phe Asp Pro
1               5                   10

<210> SEQ ID NO 65
<211> LENGTH: 14
<212> TYPE: PRT
<213> ORGANISM: Artificial Sequence
<220> FEATURE:
<223> OTHER INFORMATION: c-MET CDR3

<400> SEQUENCE: 65

Arg Thr Ser Arg Tyr Ser Gly Tyr His Tyr Tyr Leu Asp Val
1               5                   10

<210> SEQ ID NO 66
<211> LENGTH: 8
<212> TYPE: PRT
<213> ORGANISM: Artificial Sequence
<220> FEATURE:
<223> OTHER INFORMATION: c-MET CDR3

<400> SEQUENCE: 66

Leu Leu Tyr Asp Leu Phe Asp Leu
1               5

<210> SEQ ID NO 67
<211> LENGTH: 13
<212> TYPE: PRT
<213> ORGANISM: Artificial Sequence
```

```
<220> FEATURE:
<223> OTHER INFORMATION: c-MET CDR3

<400> SEQUENCE: 67

Ser Ile Asp Met Ala Thr Ile Thr Asp Ala Phe Asp Ile
1               5                   10

<210> SEQ ID NO 68
<211> LENGTH: 15
<212> TYPE: PRT
<213> ORGANISM: Artificial Sequence
<220> FEATURE:
<223> OTHER INFORMATION: c-MET CDR3

<400> SEQUENCE: 68

Gly Thr Thr Gly Asn Pro Tyr Tyr Phe Tyr Tyr Tyr Met Asp Val
1               5                   10                  15

<210> SEQ ID NO 69
<211> LENGTH: 127
<212> TYPE: PRT
<213> ORGANISM: Artificial Sequence
<220> FEATURE:
<223> OTHER INFORMATION: heavy chain variable region
<220> FEATURE:
<221> NAME/KEY: DOMAIN
<222> LOCATION: (1)..(30)
<223> OTHER INFORMATION: FR1
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (36)..(49)
<223> OTHER INFORMATION: FR2
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (67)..(97)
<223> OTHER INFORMATION: FR3
<220> FEATURE:
<221> NAME/KEY: DOMAIN
<222> LOCATION: (98)..(116)
<223> OTHER INFORMATION: CDR3
<220> FEATURE:
<221> NAME/KEY: DOMAIN
<222> LOCATION: (117)..(127)
<223> OTHER INFORMATION: FR4

<400> SEQUENCE: 69

Glu Val Gln Leu Val Glu Thr Gly Ala Glu Val Lys Lys Pro Gly Ala
1               5                   10                  15

Ser Val Lys Val Ser Cys Lys Ala Ser Asp Tyr Ile Phe Thr Lys Tyr
            20                  25                  30

Asp Ile Asn Trp Val Arg Gln Ala Pro Gly Gln Gly Leu Glu Trp Met
        35                  40                  45

Gly Trp Met Ser Ala Asn Thr Gly Asn Thr Gly Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Ser Ser Leu Thr Ser Gly Asp Thr Ala Val Tyr Phe Cys
                85                  90                  95

Ala Arg Ser Ser Leu Phe Lys Thr Glu Thr Ala Pro Tyr Tyr His Phe
            100                 105                 110
```

Ala Leu Asp Val Trp Gly Gln Gly Thr Thr Val Thr Val Ser Ser
            115                 120                 125

<210> SEQ ID NO 70
<211> LENGTH: 122
<212> TYPE: PRT
<213> ORGANISM: Artificial Sequence
<220> FEATURE:
<223> OTHER INFORMATION: heavy chain variable region
<220> FEATURE:
<221> NAME/KEY: DOMAIN
<222> LOCATION: (1)..(30)
<223> OTHER INFORMATION: FR1
<220> FEATURE:
<221> NAME/KEY: DOMAIN
<222> LOCATION: (31)..(35)
<223> OTHER INFORMATION: CR1
<220> FEATURE:
<221> NAME/KEY: DOMAIN
<222> LOCATION: (36)..(49)
<223> OTHER INFORMATION: FR2
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (67)..(97)
<223> OTHER INFORMATION: FR3
<220> FEATURE:
<221> NAME/KEY: DOMAIN
<222> LOCATION: (98)..(111)
<223> OTHER INFORMATION: CDR3
<220> FEATURE:
<221> NAME/KEY: DOMAIN
<222> LOCATION: (112)..(122)
<223> OTHER INFORMATION: FR4

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Lys Asp Arg His Trp His Trp Trp Leu Asp Ala Phe Asp Tyr Trp
            100                 105                 110

Gly Gln Gly Thr Leu Val Thr Val Ser Ser
        115                 120

<210> SEQ ID NO 71
<211> LENGTH: 120
<212> TYPE: PRT
<213> ORGANISM: Artificial Sequence
<220> FEATURE:
<223> OTHER INFORMATION: heavy chain variable region
<220> FEATURE:
<221> NAME/KEY: DOMAIN
<222> LOCATION: (1)..(30)
<223> OTHER INFORMATION: FR1
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (36)..(49)
<223> OTHER INFORMATION: FR2
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (67)..(97)
<223> OTHER INFORMATION: FR3
<220> FEATURE:
<221> NAME/KEY: DOMAIN
<222> LOCATION: (98)..(109)
<223> OTHER INFORMATION: CDR3
<220> FEATURE:
<221> NAME/KEY: DOMAIN
<222> LOCATION: (110)..(120)
<223> OTHER INFORMATION: FR4

<400> SEQUENCE: 71

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Asp Phe Thr Asn Tyr
            20                  25                  30

Ala Met Asn Trp Val Arg Gln Ala Pro Gly His Gly Leu Glu Trp Met
        35                  40                  45

Gly Trp Ile Asn Ala Asn Thr Gly Asp Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Ser Ala Val Tyr Tyr Cys
                85                  90                  95

Thr Arg Glu Arg Phe Leu Glu Trp Leu His Phe Asp Tyr Trp Gly Gln
            100                 105                 110

Gly Thr Leu Val Thr Val Ser Ser
        115                 120

<210> SEQ ID NO 72
<211> LENGTH: 128
<212> TYPE: PRT
<213> ORGANISM: Artificial Sequence
<220> FEATURE:
<223> OTHER INFORMATION: heavy chain variable region
<220> FEATURE:
<221> NAME/KEY: DOMAIN
<222> LOCATION: (1)..(30)
<223> OTHER INFORMATION: FR1
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (36)..(49)
<223> OTHER INFORMATION: FR2
<220> FEATURE:
<221> NAME/KEY: DOMAIN
<222> LOCATION: (50)..(67)
<223> OTHER INFORMATION: CDR2
<220> FEATURE:
<221> NAME/KEY: DOMAIN
<222> LOCATION: (68)..(100)
<223> OTHER INFORMATION: FR3
<220> FEATURE:
<221> NAME/KEY: DOMAIN
<222> LOCATION: (101)..(117)

<223> OTHER INFORMATION: CDR3
<220> FEATURE:
<221> NAME/KEY: DOMAIN
<222> LOCATION: (118)..(128)
<223> OTHER INFORMATION: FR4

<400> SEQUENCE: 72

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Lys Ala
            20                  25                  30

Trp Met Asn Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
            85                  90                  95

Tyr Cys Thr Thr Ala Ser Ser Met Ile Thr Phe Gly Gly Val Ile Val
            100                 105                 110

Ser Trp Phe Asp Pro Trp Gly Gln Gly Thr Leu Val Thr Val Ser Ser
        115                 120                 125

<210> SEQ ID NO 73
<211> LENGTH: 123
<212> TYPE: PRT
<213> ORGANISM: Artificial Sequence
<220> FEATURE:
<223> OTHER INFORMATION: heavy chain variable region
<220> FEATURE:
<221> NAME/KEY: DOMAIN
<222> LOCATION: (1)..(30)
<223> OTHER INFORMATION: FR1
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (36)..(49)
<223> OTHER INFORMATION: FR2
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (67)..(97)
<223> OTHER INFORMATION: FR3
<220> FEATURE:
<221> NAME/KEY: DOMAIN
<222> LOCATION: (98)..(112)
<223> OTHER INFORMATION: CDR3
<220> FEATURE:
<221> NAME/KEY: DOMAIN
<222> LOCATION: (113)..(123)
<223> OTHER INFORMATION: FR4

<400> SEQUENCE: 73

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ser Met Asn Trp Val Arg Gln Ala Pro Gly Gln Gly Leu Glu Trp Met
        35                  40                  45

Gly Trp Ile Asn Thr Tyr Thr Gly Asp Pro Thr Tyr Ala Gln Gly Phe
    50              55                  60

Thr Gly Arg Tyr Val Phe Ser Leu Asp Thr Ser Val Asn Thr Ala Tyr
65              70                  75                  80

Leu Gln Ile Ser Ser Leu Lys Ala Glu Asp Thr Ala Val Tyr Tyr Cys
                85                  90                  95

Ala Arg Glu Thr Tyr Tyr Tyr Asp Arg Gly Gly Tyr Pro Phe Asp Pro
            100                 105                 110

Trp Gly Gln Gly Thr Leu Val Thr Val Ser Ser
        115                 120

<210> SEQ ID NO 74
<211> LENGTH: 125
<212> TYPE: PRT
<213> ORGANISM: Artificial Sequence
<220> FEATURE:
<223> OTHER INFORMATION: heavy chain variable region
<220> FEATURE:
<221> NAME/KEY: DOMAIN
<222> LOCATION: (1)..(30)
<223> OTHER INFORMATION: FR1
<220> FEATURE:
<221> NAME/KEY: DOMAIN
<222> LOCATION: (31)..(35)
<223> OTHER INFORMATION: CDR1
<220> FEATURE:
<221> NAME/KEY: DOMAIN
<222> LOCATION: (36)..(49)
<223> OTHER INFORMATION: FR2
<220> FEATURE:
<221> NAME/KEY: DOMAIN
<222> LOCATION: (50)..(66)
<223> OTHER INFORMATION: CDR2
<220> FEATURE:
<221> NAME/KEY: DOMAIN
<222> LOCATION: (67)..(97)
<223> OTHER INFORMATION: FR3
<220> FEATURE:
<221> NAME/KEY: DOMAIN
<222> LOCATION: (98)..(114)
<223> OTHER INFORMATION: CDR3
<220> FEATURE:
<221> NAME/KEY: DOMAIN
<222> LOCATION: (115)..(125)
<223> OTHER INFORMATION: FR4

<400> SEQUENCE: 74

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Thr Lys Tyr Ser Ala Asp Ser Leu
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Asp Thr Ala Val Tyr Tyr Cys
                85                  90                  95

Ala Lys Glu Gly Trp Ser Phe Asp Ser Ser Gly Tyr Arg Ser Trp Phe
            100                 105                 110

Asp Ser Trp Gly Gln Gly Thr Leu Val Thr Val Ser Ser
        115                 120                 125

<210> SEQ ID NO 75

```
<211> LENGTH: 122
<212> TYPE: PRT
<213> ORGANISM: Artificial Sequence
<220> FEATURE:
<223> OTHER INFORMATION: MF3353

<400> SEQUENCE: 75

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Tyr Trp His Trp Trp Leu Gly Ala Phe Asp Tyr Trp
            100                 105                 110

Gly Gln Gly Thr Leu Val Thr Val Ser Ser
        115                 120

<210> SEQ ID NO 76
<211> LENGTH: 122
<212> TYPE: PRT
<213> ORGANISM: Artificial Sequence
<220> FEATURE:
<223> OTHER INFORMATION: MF8229

<400> SEQUENCE: 76

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Ala Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Tyr Trp His Trp Trp Leu Gly Ala Phe Asp Tyr Trp
            100                 105                 110

Gly Gln Gly Thr Leu Val Thr Val Ser Ser
        115                 120

<210> SEQ ID NO 77
<211> LENGTH: 122
<212> TYPE: PRT
<213> ORGANISM: Artificial Sequence
<220> FEATURE:
<223> OTHER INFORMATION: MF8228

<400> SEQUENCE: 77

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Tyr Trp His Trp Trp Leu Gly Ala Phe Asp Tyr Trp
            100                 105                 110

Gly Gln Gly Thr Leu Val Thr Val Ser Ser
        115                 120

<210> SEQ ID NO 78
<211> LENGTH: 122
<212> TYPE: PRT
<213> ORGANISM: Artificial Sequence
<220> FEATURE:
<223> OTHER INFORMATION: MF3370

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Lys Asp Arg His Trp His Trp Trp Leu Asp Ala Phe Asp Tyr Trp
            100                 105                 110

Gly Gln Gly Thr Leu Val Thr Val Ser Ser
        115                 120

<210> SEQ ID NO 79
<211> LENGTH: 122
<212> TYPE: PRT
<213> ORGANISM: Artificial Sequence
<220> FEATURE:
<223> OTHER INFORMATION: MF8233

<400> SEQUENCE: 79

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Ala Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80
```

Met Glu Leu Arg Ser Leu Arg Ser Asp Asp Thr Ala Val Tyr Tyr Cys
                85                  90                  95

Ala Lys Asp Arg His Trp His Trp Trp Leu Asp Ala Phe Asp Tyr Trp
            100                 105                 110

Gly Gln Gly Thr Leu Val Thr Val Ser Ser
        115                 120

<210> SEQ ID NO 80
<211> LENGTH: 122
<212> TYPE: PRT
<213> ORGANISM: Artificial Sequence
<220> FEATURE:
<223> OTHER INFORMATION: MF8232

<400> SEQUENCE: 80

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Lys Asp Arg His Trp His Trp Trp Leu Asp Ala Phe Asp Tyr Trp
            100                 105                 110

Gly Gln Gly Thr Leu Val Thr Val Ser Ser
        115                 120

<210> SEQ ID NO 81
<211> LENGTH: 122
<212> TYPE: PRT
<213> ORGANISM: Artificial Sequence
<220> FEATURE:
<223> OTHER INFORMATION: MF3393

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Leu Asp His Trp Trp Leu Gly Ala Phe Asp Tyr Trp
            100                 105                 110

Gly Gln Gly Thr Leu Val Thr Val Ser Ser
        115                 120

-continued

```
<210> SEQ ID NO 82
<211> LENGTH: 122
<212> TYPE: PRT
<213> ORGANISM: Artificial Sequence
<220> FEATURE:
<223> OTHER INFORMATION: MF8227

<400> SEQUENCE: 82

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Ala Asn Thr Asn Tyr Ala Gln Lys Leu
        50                  55                  60

Gln Gly Arg Val Thr Met Thr Thr Asp Thr Ser Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Leu Asp His Trp Trp Leu Gly Ala Phe Asp Tyr Trp
            100                 105                 110

Gly Gln Gly Thr Leu Val Thr Val Ser Ser
        115                 120

<210> SEQ ID NO 83
<211> LENGTH: 122
<212> TYPE: PRT
<213> ORGANISM: Artificial Sequence
<220> FEATURE:
<223> OTHER INFORMATION: MF8226

<400> SEQUENCE: 83

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Ser Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Leu Asp His Trp Trp Leu Gly Ala Phe Asp Tyr Trp
            100                 105                 110

Gly Gln Gly Thr Leu Val Thr Val Ser Ser
        115                 120

<210> SEQ ID NO 84
<211> LENGTH: 107
<212> TYPE: PRT
<213> ORGANISM: Artificial Sequence
<220> FEATURE:
<223> OTHER INFORMATION: common light chain

<400> SEQUENCE: 84

Asp Ile Gln Met Thr Gln Ser Pro Ser Ser Leu Ser Ala Ser Val Gly
1               5                   10                  15
```

-continued

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
            100                 105

<210> SEQ ID NO 85
<211> LENGTH: 107
<212> TYPE: PRT
<213> ORGANISM: Artificial Sequence
<220> FEATURE:
<223> OTHER INFORMATION: common light chain

<400> SEQUENCE: 85

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 86
<211> LENGTH: 321
<212> TYPE: DNA
<213> ORGANISM: Artificial Sequence
<220> FEATURE:
<223> OTHER INFORMATION: common light chain
<220> FEATURE:
<221> NAME/KEY: CDS
<222> LOCATION: (1)..(321)

<400> SEQUENCE: 86 gac atc cag atg acc cag tct cca tcc tcc ctg tct gca tct gta gga      48
Asp Ile Gln Met Thr Gln Ser Pro Ser Ser Leu Ser Ala Ser Val Gly
1               5                   10                  15 gac aga gtc acc atc act tgc cgg gca agt cag agc att agc agc tac      96
Asp Arg Val Thr Ile Thr Cys Arg Ala Ser Gln Ser Ile Ser Ser Tyr
            20                  25                  30 tta aat tgg tat cag cag aaa cca ggg aaa gcc cct aag ctc ctg atc     144
Leu Asn Trp Tyr Gln Gln Lys Pro Gly Lys Ala Pro Lys Leu Leu Ile
        35                  40                  45 tat gct gca tcc agt ttg caa agt ggg gtc cca tca agg ttc agt ggc     192
Tyr Ala Ala Ser Ser Leu Gln Ser Gly Val Pro Ser Arg Phe Ser Gly
    50                  55                  60

```
agt gga tct ggg aca gat ttc act ctc acc atc agc agt ctg caa cct      240
Ser Gly Ser Gly Thr Asp Phe Thr Leu Thr Ile Ser Ser Leu Gln Pro
 65                  70                  75                  80 gaa gat ttt gca act tac tac tgt caa cag agt tac agt acc cct cca      288
Glu Asp Phe Ala Thr Tyr Tyr Cys Gln Gln Ser Tyr Ser Thr Pro Pro
                 85                  90                  95 acg ttc ggc caa ggg acc aag gtg gag atc aaa                          321
Thr Phe Gly Gln Gly Thr Lys Val Glu Ile Lys
             100                 105
```

<210> SEQ ID NO 87
<211> LENGTH: 107
<212> TYPE: PRT
<213> ORGANISM: Artificial Sequence
<220> FEATURE:
<223> OTHER INFORMATION: Synthetic Construct

<400> SEQUENCE: 87

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

Thr Phe Gly Gln Gly Thr Lys Val Glu Ile Lys
             100                 105
```

<210> SEQ ID NO 88
<211> LENGTH: 324
<212> TYPE: DNA
<213> ORGANISM: Artificial Sequence
<220> FEATURE:
<223> OTHER INFORMATION: common light chain
<220> FEATURE:
<221> NAME/KEY: CDS
<222> LOCATION: (1)..(324)

<400> SEQUENCE: 88

```
cga act gtg gct gca cca tct gtc ttc atc ttc ccg cca tct gat gag       48
Arg Thr Val Ala Ala Pro Ser Val Phe Ile Phe Pro Pro Ser Asp Glu
 1               5                  10                  15 cag ttg aaa tct gga act gcc tct gtt gtg tgc ctg ctg aat aac ttc       96
Gln Leu Lys Ser Gly Thr Ala Ser Val Val Cys Leu Leu Asn Asn Phe
             20                  25                  30 tat ccc aga gag gcc aaa gta cag tgg aag gtg gat aac gcc ctc caa      144
Tyr Pro Arg Glu Ala Lys Val Gln Trp Lys Val Asp Asn Ala Leu Gln
         35                  40                  45 tcg ggt aac tcc cag gag agt gtc aca gag cag gac agc aag gac agc      192
Ser Gly Asn Ser Gln Glu Ser Val Thr Glu Gln Asp Ser Lys Asp Ser
 50                  55                  60 acc tac agc ctc agc agc acc ctg acg ctg agc aaa gca gac tac gag      240
Thr Tyr Ser Leu Ser Ser Thr Leu Thr Leu Ser Lys Ala Asp Tyr Glu
 65                  70                  75                  80 aaa cac aaa gtc tac gcc tgc gaa gtc acc cat cag ggc ctg agc tcg      288
Lys His Lys Val Tyr Ala Cys Glu Val Thr His Gln Gly Leu Ser Ser
                 85                  90                  95
```

```
        ccc gtc aca aag agc ttc aac agg gga gag tgt tag              324
        Pro Val Thr Lys Ser Phe Asn Arg Gly Glu Cys
                100                 105
```

<210> SEQ ID NO 89
<211> LENGTH: 107
<212> TYPE: PRT
<213> ORGANISM: Artificial Sequence
<220> FEATURE:
<223> OTHER INFORMATION: Synthetic Construct

<400> SEQUENCE: 89

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 90
<211> LENGTH: 108
<212> TYPE: PRT
<213> ORGANISM: Artificial Sequence
<220> FEATURE:
<223> OTHER INFORMATION: GKV1-39/jk5 common light chain

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 91
<211> LENGTH: 95
<212> TYPE: PRT
<213> ORGANISM: Artificial Sequence
<220> FEATURE:
<223> OTHER INFORMATION: V-region IGKV1-39A

<400> SEQUENCE: 91

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 92
<211> LENGTH: 294
<212> TYPE: DNA
<213> ORGANISM: Artificial Sequence
<220> FEATURE:
<223> OTHER INFORMATION: CH1 region
<220> FEATURE:
<221> NAME/KEY: CDS
<222> LOCATION: (1)..(294)

<400> SEQUENCE: 92 gct agc acc aag ggc cca tcg gtc ttc ccc ctg gca ccc tcc tcc aag      48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac      96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc     144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc     192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acc cag acc     240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag     288
Tyr Ile Cys Asn Val Asn His Lys Pro Ser Asn Thr Lys Val Asp Lys
                85                  90                  95 aga gtt                                                              294
Arg Val <210> SEQ ID NO 93
<211> LENGTH: 98
<212> TYPE: PRT
<213> ORGANISM: Artificial Sequence
<220> FEATURE:
<223> OTHER INFORMATION: Synthetic Construct

<400> SEQUENCE: 93

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
```

```
                65                  70                  75                  80
Tyr Ile Cys Asn Val Asn His Lys Pro Ser Asn Thr Lys Val Asp Lys
                    85                  90                  95

Arg Val

<210> SEQ ID NO 94
<211> LENGTH: 45
<212> TYPE: DNA
<213> ORGANISM: Artificial Sequence
<220> FEATURE:
<223> OTHER INFORMATION: hinge
<220> FEATURE:
<221> NAME/KEY: CDS
<222> LOCATION: (1)..(45)

<400> SEQUENCE: 94 gag ccc aaa tct tgt gac aaa act cac aca tgc cca ccg tgc cca        45
Glu Pro Lys Ser Cys Asp Lys Thr His Thr Cys Pro Pro Cys Pro
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Synthetic Construct

<400> SEQUENCE: 95

Glu Pro Lys Ser Cys Asp Lys Thr His Thr Cys Pro Pro Cys Pro
1               5                   10                  15

<210> SEQ ID NO 96
<211> LENGTH: 330
<212> TYPE: DNA
<213> ORGANISM: Artificial Sequence
<220> FEATURE:
<223> OTHER INFORMATION: CH2 region
<220> FEATURE:
<221> NAME/KEY: CDS
<222> LOCATION: (1)..(330)

<400> SEQUENCE: 96 gca cct gaa ctc ctg ggg gga ccg tca gtc ttc ctc ttc ccc cca aaa    48
Ala Pro Glu Leu Leu Gly Gly Pro Ser Val Phe Leu Phe Pro Pro Lys
1               5                   10                  15 ccc aag gac acc ctc atg atc tcc cgg acc cct gag gtc aca tgc gtg    96
Pro Lys Asp Thr Leu Met Ile Ser Arg Thr Pro Glu Val Thr Cys Val
                20                  25                  30 gtg gtg gac gtg agc cac gaa gac cct gag gtc aag ttc aac tgg tac   144
Val Val Asp Val Ser His Glu Asp Pro Glu Val Lys Phe Asn Trp Tyr
            35                  40                  45 gtg gac ggc gtg gag gtg cat aat gcc aag aca aag ccg cgg gag gag   192
Val Asp Gly Val Glu Val His Asn Ala Lys Thr Lys Pro Arg Glu Glu
        50                  55                  60 cag tac aac agc acg tac cgt gtg gtc agc gtc ctc acc gtc ctg cac   240
Gln Tyr Asn Ser Thr Tyr Arg Val Val Ser Val Leu Thr Val Leu His
65                  70                  75                  80 cag gac tgg ctg aat ggc aag gag tac aag tgc aag gtc tcc aac aaa   288
Gln Asp Trp Leu Asn Gly Lys Glu Tyr Lys Cys Lys Val Ser Asn Lys
                85                  90                  95 gcc ctc cca gcc ccc atc gag aaa acc atc tcc aaa gcc aaa           330
Ala Leu Pro Ala Pro Ile Glu Lys Thr Ile Ser Lys Ala Lys
            100                 105                 110
```

```
<210> SEQ ID NO 97
<211> LENGTH: 110
<212> TYPE: PRT
<213> ORGANISM: Artificial Sequence
<220> FEATURE:
<223> OTHER INFORMATION: Synthetic Construct

<400> SEQUENCE: 97

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 98
<211> LENGTH: 330
<212> TYPE: DNA
<213> ORGANISM: Artificial Sequence
<220> FEATURE:
<223> OTHER INFORMATION: CH2 containing L235G and G236R silencing
      substitutions:
<220> FEATURE:
<221> NAME/KEY: CDS
<222> LOCATION: (1)..(330)

<400> SEQUENCE: 98 gca cct gaa ctc ggc agg gga ccg tca gtc ttc ctc ttc ccc cca aaa        48
Ala Pro Glu Leu Gly Arg Gly Pro Ser Val Phe Leu Phe Pro Pro Lys
1               5                   10                  15 ccc aag gac acc ctc atg atc tcc cgg acc cct gag gtc aca tgc gtg        96
Pro Lys Asp Thr Leu Met Ile Ser Arg Thr Pro Glu Val Thr Cys Val
            20                  25                  30 gtg gtg gac gtg agc cac gaa gac cct gag gtc aag ttc aac tgg tac       144
Val Val Asp Val Ser His Glu Asp Pro Glu Val Lys Phe Asn Trp Tyr
        35                  40                  45 gtg gac ggc gtg gag gtg cat aat gcc aag aca aag ccg cgg gag gag       192
Val Asp Gly Val Glu Val His Asn Ala Lys Thr Lys Pro Arg Glu Glu
    50                  55                  60 cag tac aac agc acg tac cgt gtg gtc agc gtc ctc acc gtc ctg cac       240
Gln Tyr Asn Ser Thr Tyr Arg Val Val Ser Val Leu Thr Val Leu His
65                  70                  75                  80 cag gac tgg ctg aat ggc aag gag tac aag tgc aag gtc tcc aac aaa       288
Gln Asp Trp Leu Asn Gly Lys Glu Tyr Lys Cys Lys Val Ser Asn Lys
                85                  90                  95 gcc ctc cca gcc ccc atc gag aaa acc atc tcc aaa gcc aaa               330
Ala Leu Pro Ala Pro Ile Glu Lys Thr Ile Ser Lys Ala Lys
            100                 105                 110

<210> SEQ ID NO 99
<211> LENGTH: 110
<212> TYPE: PRT
<213> ORGANISM: Artificial Sequence
<220> FEATURE:
<223> OTHER INFORMATION: Synthetic Construct
```

```
<400> SEQUENCE: 99

Ala Pro Glu Leu Gly Arg Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 100
<211> LENGTH: 321
<212> TYPE: DNA
<213> ORGANISM: Artificial Sequence
<220> FEATURE:
<223> OTHER INFORMATION: CH3: KK of DEKK
<220> FEATURE:
<221> NAME/KEY: CDS
<222> LOCATION: (1)..(321)

<400> SEQUENCE: 100 ggg cag ccc cga gaa cca cag gtg tac acc aag ccc cca tcc cgg gag      48
Gly Gln Pro Arg Glu Pro Gln Val Tyr Thr Lys Pro Pro Ser Arg Glu
1               5                   10                  15 gag atg acc aag aac cag gtc agc ctg aag tgc ctg gtc aaa ggc ttc      96
Glu Met Thr Lys Asn Gln Val Ser Leu Lys Cys Leu Val Lys Gly Phe
            20                  25                  30 tat ccc agc gac atc gcc gtg gag tgg gag agc aat ggg cag ccg gag     144
Tyr Pro Ser Asp Ile Ala Val Glu Trp Glu Ser Asn Gly Gln Pro Glu
        35                  40                  45 aac aac tac aag acc acg cct ccc gtg ctg gac tcc gac ggc tcc ttc     192
Asn Asn Tyr Lys Thr Thr Pro Pro Val Leu Asp Ser Asp Gly Ser Phe
    50                  55                  60 ttc ctc tat agc aag ctc acc gtg gac aag agc agg tgg cag cag ggg     240
Phe Leu Tyr Ser Lys Leu Thr Val Asp Lys Ser Arg Trp Gln Gln Gly
65                  70                  75                  80 aac gtc ttc tca tgc tcc gtg atg cat gag gct ctg cac aac cac tac     288
Asn Val Phe Ser Cys Ser Val Met His Glu Ala Leu His Asn His Tyr
                85                  90                  95 acg cag aag agc ctc tcc ctg tct ccg ggt tga                         321
Thr Gln Lys Ser Leu Ser Leu Ser Pro Gly
            100                 105

<210> SEQ ID NO 101
<211> LENGTH: 106
<212> TYPE: PRT
<213> ORGANISM: Artificial Sequence
<220> FEATURE:
<223> OTHER INFORMATION: Synthetic Construct

<400> SEQUENCE: 101

Gly Gln Pro Arg Glu Pro Gln Val Tyr Thr Lys Pro Pro Ser Arg Glu
1               5                   10                  15

Glu Met Thr Lys Asn Gln Val Ser Leu Lys Cys Leu Val Lys Gly Phe
```

```
                20                  25                  30
Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 102
<211> LENGTH: 321
<212> TYPE: DNA
<213> ORGANISM: Artificial Sequence
<220> FEATURE:
<223> OTHER INFORMATION: CH3: DE of DEKK
<220> FEATURE:
<221> NAME/KEY: CDS
<222> LOCATION: (1)..(321)

<400> SEQUENCE: 102 ggg cag ccc cga gaa cca cag gtg tac acc gac ccc tcc cgg gag      48
Gly Gln Pro Arg Glu Pro Gln Val Tyr Thr Asp Pro Ser Arg Glu
 1               5                  10                  15 gag atg acc aag aac cag gtc agc ctg acc tgc gag gtc aaa ggc ttc  96
Glu Met Thr Lys Asn Gln Val Ser Leu Thr Cys Glu Val Lys Gly Phe
                20                  25                  30 tat ccc agc gac atc gcc gtg gag tgg gag agc aat ggg cag ccg gag 144
Tyr Pro Ser Asp Ile Ala Val Glu Trp Glu Ser Asn Gly Gln Pro Glu
            35                  40                  45 aac aac tac aag acc acg cct ccc gtg ctg gac tcc gac ggc tcc ttc 192
Asn Asn Tyr Lys Thr Thr Pro Pro Val Leu Asp Ser Asp Gly Ser Phe
        50                  55                  60 ttc ctc tat agc aag ctc acc gtg gac aag agc agg tgg cag cag ggg 240
Phe Leu Tyr Ser Lys Leu Thr Val Asp Lys Ser Arg Trp Gln Gln Gly
 65                  70                  75                  80 aac gtc ttc tca tgc tcc gtg atg cat gag gct ctg cac aac cac tac 288
Asn Val Phe Ser Cys Ser Val Met His Glu Ala Leu His Asn His Tyr
                85                  90                  95 acg cag aag agc ctc tcc ctg tct ccg ggt tga                     321
Thr Gln Lys Ser Leu Ser Leu Ser Pro Gly
            100                 105

<210> SEQ ID NO 103
<211> LENGTH: 106
<212> TYPE: PRT
<213> ORGANISM: Artificial Sequence
<220> FEATURE:
<223> OTHER INFORMATION: Synthetic Construct

<400> SEQUENCE: 103

Gly Gln Pro Arg Glu Pro Gln Val Tyr Thr Asp Pro Ser Arg Glu
 1               5                  10                  15

Glu Met Thr Lys Asn Gln Val Ser Leu Thr Cys Glu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60
```

```
Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105
```

<210> SEQ ID NO 104
<211> LENGTH: 30
<212> TYPE: PRT
<213> ORGANISM: Artificial Sequence
<220> FEATURE:
<223> OTHER INFORMATION: FR1

<400> SEQUENCE: 104

```
Glu Val Gln Leu Val Glu Thr Gly Ala Glu Val Lys Lys Pro Gly Ala
1               5                   10                  15

Ser Val Lys Val Ser Cys Lys Ala Ser Asp Tyr Ile Phe Thr
            20                  25                  30
```

<210> SEQ ID NO 105
<211> LENGTH: 5
<212> TYPE: PRT
<213> ORGANISM: Artificial Sequence
<220> FEATURE:
<223> OTHER INFORMATION: CDR1

<400> SEQUENCE: 105

```
Lys Tyr Asp Ile Asn
1               5
```

<210> SEQ ID NO 106
<211> LENGTH: 14
<212> TYPE: PRT
<213> ORGANISM: Artificial Sequence
<220> FEATURE:
<223> OTHER INFORMATION: FR2

<400> SEQUENCE: 106

```
Trp Val Arg Gln Ala Pro Gly Gln Gly Leu Glu Trp Met Gly
1               5                   10
```

<210> SEQ ID NO 107
<211> LENGTH: 17
<212> TYPE: PRT
<213> ORGANISM: Artificial Sequence
<220> FEATURE:
<223> OTHER INFORMATION: CDR2

<400> SEQUENCE: 107

```
Trp Met Ser Ala Asn Thr Gly Asn Thr Gly Tyr Ala Gln Lys Phe Gln
1               5                   10                  15

Gly
```

<210> SEQ ID NO 108
<211> LENGTH: 32
<212> TYPE: PRT
<213> ORGANISM: Artificial Sequence
<220> FEATURE:
<223> OTHER INFORMATION: FR3

<400> SEQUENCE: 108

```
Arg Val Thr Met Thr Arg Asp Thr Ser Ile Asn Thr Ala Tyr Met Glu
1               5                   10                  15
```

-continued

Leu Ser Ser Leu Thr Ser Gly Asp Thr Ala Val Tyr Phe Cys Ala Arg
            20                  25                  30

<210> SEQ ID NO 109
<211> LENGTH: 18
<212> TYPE: PRT
<213> ORGANISM: Artificial Sequence
<220> FEATURE:
<223> OTHER INFORMATION: CDR3

<400> SEQUENCE: 109

Ser Ser Leu Phe Lys Thr Glu Thr Ala Pro Tyr Tyr His Phe Ala Leu
1               5                   10                  15

Asp Val

<210> SEQ ID NO 110
<211> LENGTH: 11
<212> TYPE: PRT
<213> ORGANISM: Artificial Sequence
<220> FEATURE:
<223> OTHER INFORMATION: FR4

<400> SEQUENCE: 110

Trp Gly Gln Gly Thr Thr Val Thr Val Ser Ser
1               5                   10

<210> SEQ ID NO 111
<211> LENGTH: 30
<212> TYPE: PRT
<213> ORGANISM: Artificial Sequence
<220> FEATURE:
<223> OTHER INFORMATION: FR1

<400> SEQUENCE: 111

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 112
<211> LENGTH: 14
<212> TYPE: PRT
<213> ORGANISM: Artificial Sequence
<220> FEATURE:
<223> OTHER INFORMATION: FR2

<400> SEQUENCE: 112

Trp Val Arg Gln Ala Pro Gly Gln Gly Leu Glu Trp Met Gly
1               5                   10

<210> SEQ ID NO 113
<211> LENGTH: 17
<212> TYPE: PRT
<213> ORGANISM: Artificial Sequence
<220> FEATURE:
<223> OTHER INFORMATION: CDR2

<400> SEQUENCE: 113

Trp Ile Ser Ala Tyr Asn Gly Asn Thr Asn Tyr Ala Gln Lys Leu Gln
1               5                   10                  15

Gly

<210> SEQ ID NO 114
<211> LENGTH: 32

```
<212> TYPE: PRT
<213> ORGANISM: Artificial Sequence
<220> FEATURE:
<223> OTHER INFORMATION: FR3

<400> SEQUENCE: 114

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Lys
            20                  25                  30

<210> SEQ ID NO 115
<211> LENGTH: 11
<212> TYPE: PRT
<213> ORGANISM: Artificial Sequence
<220> FEATURE:
<223> OTHER INFORMATION: FR4

<400> SEQUENCE: 115

Trp Gly Gln Gly Thr Leu Val Thr Val Ser Ser
1               5                   10

<210> SEQ ID NO 116
<211> LENGTH: 30
<212> TYPE: PRT
<213> ORGANISM: Artificial Sequence
<220> FEATURE:
<223> OTHER INFORMATION: FR1

<400> SEQUENCE: 116

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Asp Phe Thr
            20                  25                  30

<210> SEQ ID NO 117
<211> LENGTH: 5
<212> TYPE: PRT
<213> ORGANISM: Artificial Sequence
<220> FEATURE:
<223> OTHER INFORMATION: CDR1

<400> SEQUENCE: 117

Asn Tyr Ala Met Asn
1               5

<210> SEQ ID NO 118
<211> LENGTH: 14
<212> TYPE: PRT
<213> ORGANISM: Artificial Sequence
<220> FEATURE:
<223> OTHER INFORMATION: FR2

<400> SEQUENCE: 118

Trp Val Arg Gln Ala Pro Gly His Gly Leu Glu Trp Met Gly
1               5                   10

<210> SEQ ID NO 119
<211> LENGTH: 17
<212> TYPE: PRT
<213> ORGANISM: Artificial Sequence
<220> FEATURE:
<223> OTHER INFORMATION: CDR2

<400> SEQUENCE: 119

Trp Ile Asn Ala Asn Thr Gly Asp Pro Thr Tyr Ala Gln Gly Phe Thr
```

Gly

```
<210> SEQ ID NO 120
<211> LENGTH: 32
<212> TYPE: PRT
<213> ORGANISM: Artificial Sequence
<220> FEATURE:
<223> OTHER INFORMATION: FR3

<400> SEQUENCE: 120
```

Arg Phe Val Phe Ser Leu Asp Thr Ser Val Ser Thr Ala Tyr Leu Gln
1               5                   10                  15

Ile Ser Ser Leu Lys Ala Glu Asp Ser Ala Val Tyr Tyr Cys Thr Arg
                20                  25                  30

```
<210> SEQ ID NO 121
<211> LENGTH: 11
<212> TYPE: PRT
<213> ORGANISM: Artificial Sequence
<220> FEATURE:
<223> OTHER INFORMATION: FR4

<400> SEQUENCE: 121
```

Trp Gly Gln Gly Thr Leu Val Thr Val Ser Ser
1               5                   10

```
<210> SEQ ID NO 122
<211> LENGTH: 30
<212> TYPE: PRT
<213> ORGANISM: Artificial Sequence
<220> FEATURE:
<223> OTHER INFORMATION: FR1

<400> SEQUENCE: 122
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
                20                  25                  30

```
<210> SEQ ID NO 123
<211> LENGTH: 5
<212> TYPE: PRT
<213> ORGANISM: Artificial Sequence
<220> FEATURE:
<223> OTHER INFORMATION: CDR1

<400> SEQUENCE: 123
```

Lys Ala Trp Met Asn
1               5

```
<210> SEQ ID NO 124
<211> LENGTH: 14
<212> TYPE: PRT
<213> ORGANISM: Artificial Sequence
<220> FEATURE:
<223> OTHER INFORMATION: FR2

<400> SEQUENCE: 124
```

Trp Val Arg Gln Ala Pro Gly Lys Gly Leu Glu Trp Val Gly
1               5                   10

```
<210> SEQ ID NO 125
<211> LENGTH: 19
<212> TYPE: PRT
```

```
<213> ORGANISM: Artificial Sequence
<220> FEATURE:
<223> OTHER INFORMATION: CDR2

<400> SEQUENCE: 125

Arg Ile Lys Ser Lys Thr Asp Gly Gly Thr Thr Asp Tyr Ala Ala Pro
1               5                   10                  15

Val Lys Gly

<210> SEQ ID NO 126
<211> LENGTH: 32
<212> TYPE: PRT
<213> ORGANISM: Artificial Sequence
<220> FEATURE:
<223> OTHER INFORMATION: FR3

<400> SEQUENCE: 126

Arg Phe Thr Ile Ser Arg Asp Asp Ser Lys Asn Thr Leu Tyr Leu Gln
1               5                   10                  15

Met Asn Ser Leu Lys Thr Glu Asp Thr Ala Val Tyr Tyr Cys Thr Thr
            20                  25                  30

<210> SEQ ID NO 127
<211> LENGTH: 11
<212> TYPE: PRT
<213> ORGANISM: Artificial Sequence
<220> FEATURE:
<223> OTHER INFORMATION: FR4

<400> SEQUENCE: 127

Trp Gly Gln Gly Thr Leu Val Thr Val Ser Ser
1               5                   10

<210> SEQ ID NO 128
<211> LENGTH: 30
<212> TYPE: PRT
<213> ORGANISM: Artificial Sequence
<220> FEATURE:
<223> OTHER INFORMATION: FR1

<400> SEQUENCE: 128

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr
            20                  25                  30

<210> SEQ ID NO 129
<211> LENGTH: 14
<212> TYPE: PRT
<213> ORGANISM: Artificial Sequence
<220> FEATURE:
<223> OTHER INFORMATION: FR2

<400> SEQUENCE: 129

Trp Val Arg Gln Ala Pro Gly Gln Gly Leu Glu Trp Met Gly
1               5                   10

<210> SEQ ID NO 130
<211> LENGTH: 32
<212> TYPE: PRT
<213> ORGANISM: Artificial Sequence
<220> FEATURE:
<223> OTHER INFORMATION: FR3

<400> SEQUENCE: 130
```

Arg Tyr Val Phe Ser Leu Asp Thr Ser Val Asn Thr Ala Tyr Leu Gln
1               5                   10                  15

Ile Ser Ser Leu Lys Ala Glu Asp Thr Ala Val Tyr Tyr Cys Ala Arg
            20                  25                  30

<210> SEQ ID NO 131
<211> LENGTH: 11
<212> TYPE: PRT
<213> ORGANISM: Artificial Sequence
<220> FEATURE:
<223> OTHER INFORMATION: FR4

<400> SEQUENCE: 131

Trp Gly Gln Gly Thr Leu Val Thr Val Ser Ser
1               5                   10

<210> SEQ ID NO 132
<211> LENGTH: 30
<212> TYPE: PRT
<213> ORGANISM: Artificial Sequence
<220> FEATURE:
<223> OTHER INFORMATION: FR1

<400> SEQUENCE: 132

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30

<210> SEQ ID NO 133
<211> LENGTH: 5
<212> TYPE: PRT
<213> ORGANISM: Artificial Sequence
<220> FEATURE:
<223> OTHER INFORMATION: CDR1

<400> SEQUENCE: 133

Asn Tyr Gly Met His
1               5

<210> SEQ ID NO 134
<211> LENGTH: 14
<212> TYPE: PRT
<213> ORGANISM: Artificial Sequence
<220> FEATURE:
<223> OTHER INFORMATION: FR2

<400> SEQUENCE: 134

Trp Val Arg Gln Ala Pro Gly Lys Gly Leu Glu Trp Val Ala
1               5                   10

<210> SEQ ID NO 135
<211> LENGTH: 17
<212> TYPE: PRT
<213> ORGANISM: Artificial Sequence
<220> FEATURE:
<223> OTHER INFORMATION: CDR2

<400> SEQUENCE: 135

Val Ile Ser Tyr Asp Gly Ser Thr Lys Tyr Ser Ala Asp Ser Leu Lys
1               5                   10                  15

Gly

<210> SEQ ID NO 136
<211> LENGTH: 32

```
<212> TYPE: PRT
<213> ORGANISM: Artificial Sequence
<220> FEATURE:
<223> OTHER INFORMATION: FR3

<400> SEQUENCE: 136

Arg Phe Thr Ile Ser Arg Asp Asn Ser Lys Asn Thr Leu Tyr Leu Gln
1               5                   10                  15

Met Asn Ser Leu Arg Ala Asp Asp Thr Ala Val Tyr Tyr Cys Ala Lys
            20                  25                  30

<210> SEQ ID NO 137
<211> LENGTH: 16
<212> TYPE: PRT
<213> ORGANISM: Artificial Sequence
<220> FEATURE:
<223> OTHER INFORMATION: CDR3

<400> SEQUENCE: 137

Glu Gly Trp Ser Phe Asp Ser Ser Gly Tyr Arg Ser Trp Phe Asp Ser
1               5                   10                  15

<210> SEQ ID NO 138
<211> LENGTH: 11
<212> TYPE: PRT
<213> ORGANISM: Artificial Sequence
<220> FEATURE:
<223> OTHER INFORMATION: FR4

<400> SEQUENCE: 138

Trp Gly Gln Gly Thr Leu Val Thr Val Ser Ser
1               5                   10

<210> SEQ ID NO 139
<211> LENGTH: 10
<212> TYPE: PRT
<213> ORGANISM: Artificial Sequence
<220> FEATURE:
<223> OTHER INFORMATION: CDR3

<400> SEQUENCE: 139

Asp Arg His Trp His Trp Trp Leu Asp Ala
1               5                   10

<210> SEQ ID NO 140
<211> LENGTH: 17
<212> TYPE: PRT
<213> ORGANISM: Artificial Sequence
<220> FEATURE:
<223> OTHER INFORMATION: CDR2

<400> SEQUENCE: 140

Trp Ile Ser Ala Tyr Ser Gly Asn Thr Asn Tyr Ala Gln Lys Leu Gln
1               5                   10                  15

Gly

<210> SEQ ID NO 141
<211> LENGTH: 23
<212> TYPE: PRT
<213> ORGANISM: Artificial Sequence
<220> FEATURE:
<223> OTHER INFORMATION: signal peptide

<400> SEQUENCE: 141

Met Arg Pro Ser Gly Thr Ala Gly Ala Ala Leu Leu Ala Leu Leu Ala
1               5                   10                  15
```

```
Ala Leu Cys Pro Ala Ser Arg
            20

<210> SEQ ID NO 142
<211> LENGTH: 622
<212> TYPE: PRT
<213> ORGANISM: Artificial Sequence
<220> FEATURE:
<223> OTHER INFORMATION: ECD of human EGFR

<400> SEQUENCE: 142

Ala Leu Glu Glu Lys Lys Val Cys Gln Gly Thr Ser Asn Lys Leu Thr
1               5                   10                  15

Gln Leu Gly Thr Phe Glu Asp His Phe Leu Ser Leu Gln Arg Met Phe
            20                  25                  30

Asn Asn Cys Glu Val Val Leu Gly Asn Leu Glu Ile Thr Tyr Val Gln
        35                  40                  45

Arg Asn Tyr Asp Leu Ser Phe Leu Lys Thr Ile Gln Glu Val Ala Gly
    50                  55                  60

Tyr Val Leu Ile Ala Leu Asn Thr Val Glu Arg Ile Pro Leu Glu Asn
65                  70                  75                  80

Leu Gln Ile Ile Arg Gly Asn Met Tyr Tyr Glu Asn Ser Tyr Ala Leu
                85                  90                  95

Ala Val Leu Ser Asn Tyr Asp Ala Asn Lys Thr Gly Leu Lys Glu Leu
            100                 105                 110

Pro Met Arg Asn Leu Gln Glu Ile Leu His Gly Ala Val Arg Phe Ser
        115                 120                 125

Asn Asn Pro Ala Leu Cys Asn Val Glu Ser Ile Gln Trp Arg Asp Ile
    130                 135                 140

Val Ser Ser Asp Phe Leu Ser Asn Met Ser Met Asp Phe Gln Asn His
145                 150                 155                 160

Leu Gly Ser Cys Gln Lys Cys Asp Pro Ser Cys Pro Asn Gly Ser Cys
                165                 170                 175

Trp Gly Ala Gly Glu Glu Asn Cys Gln Lys Leu Thr Lys Ile Ile Cys
            180                 185                 190

Ala Gln Gln Cys Ser Gly Arg Cys Arg Gly Lys Ser Pro Ser Asp Cys
        195                 200                 205

Cys His Asn Gln Cys Ala Ala Gly Cys Thr Gly Pro Arg Glu Ser Asp
    210                 215                 220

Cys Leu Val Cys Arg Lys Phe Arg Asp Glu Ala Thr Cys Lys Asp Thr
225                 230                 235                 240

Cys Pro Pro Leu Met Leu Tyr Asn Pro Thr Thr Tyr Gln Met Asp Val
                245                 250                 255

Asn Pro Glu Gly Lys Tyr Ser Phe Gly Ala Thr Cys Val Lys Lys Cys
            260                 265                 270

Pro Arg Asn Tyr Val Val Thr Asp His Gly Ser Cys Val Arg Ala Cys
        275                 280                 285

Gly Ala Asp Ser Tyr Glu Met Glu Glu Asp Gly Val Arg Lys Cys Lys
    290                 295                 300

Lys Cys Glu Gly Pro Cys Arg Lys Val Cys Asn Gly Ile Gly Ile Gly
305                 310                 315                 320

Glu Phe Lys Asp Ser Leu Ser Ile Asn Ala Thr Asn Ile Lys His Phe
                325                 330                 335

Lys Asn Cys Thr Ser Ile Ser Gly Asp Leu His Ile Leu Pro Val Ala
            340                 345                 350
```

```
Phe Arg Gly Asp Ser Phe Thr His Thr Pro Pro Leu Asp Pro Gln Glu
            355                 360                 365

Leu Asp Ile Leu Lys Thr Val Lys Glu Ile Thr Gly Phe Leu Leu Ile
        370                 375                 380

Gln Ala Trp Pro Glu Asn Arg Thr Asp Leu His Ala Phe Glu Asn Leu
385                 390                 395                 400

Glu Ile Ile Arg Gly Arg Thr Lys Gln His Gly Gln Phe Ser Leu Ala
                405                 410                 415

Val Val Ser Leu Asn Ile Thr Ser Leu Gly Leu Arg Ser Leu Lys Glu
            420                 425                 430

Ile Ser Asp Gly Asp Val Ile Ile Ser Gly Asn Lys Asn Leu Cys Tyr
        435                 440                 445

Ala Asn Thr Ile Asn Trp Lys Lys Leu Phe Gly Thr Ser Gly Gln Lys
450                 455                 460

Thr Lys Ile Ile Ser Asn Arg Gly Glu Asn Ser Cys Lys Ala Thr Gly
465                 470                 475                 480

Gln Val Cys His Ala Leu Cys Ser Pro Glu Gly Cys Trp Gly Pro Glu
                485                 490                 495

Pro Arg Asp Cys Val Ser Cys Arg Asn Val Ser Arg Gly Arg Glu Cys
            500                 505                 510

Val Asp Lys Cys Asn Leu Leu Glu Gly Glu Pro Arg Glu Phe Val Glu
        515                 520                 525

Asn Ser Glu Cys Ile Gln Cys His Pro Glu Cys Leu Pro Gln Ala Met
530                 535                 540

Asn Ile Thr Cys Thr Gly Arg Gly Pro Asp Asn Cys Ile Gln Cys Ala
545                 550                 555                 560

His Tyr Ile Asp Gly Pro His Cys Val Lys Thr Cys Pro Ala Gly Val
                565                 570                 575

Met Gly Glu Asn Asn Thr Leu Val Trp Lys Tyr Ala Asp Ala Gly His
            580                 585                 590

Val Cys His Leu Cys His Pro Asn Cys Thr Tyr Gly Cys Thr Gly Pro
        595                 600                 605

Gly Leu Glu Gly Cys Pro Thr Asn Gly Pro Lys Ile Pro Ser
610                 615                 620

<210> SEQ ID NO 143
<211> LENGTH: 23
<212> TYPE: PRT
<213> ORGANISM: Artificial Sequence
<220> FEATURE:
<223> OTHER INFORMATION: predicted TM region

<400> SEQUENCE: 143

Ile Ala Thr Gly Met Val Gly Ala Leu Leu Leu Leu Leu Val Val Ala
1               5                   10                  15

Leu Gly Ile Gly Leu Phe Met
            20

<210> SEQ ID NO 144
<211> LENGTH: 542
<212> TYPE: PRT
<213> ORGANISM: Artificial Sequence
<220> FEATURE:
<223> OTHER INFORMATION: intracellular tail

<400> SEQUENCE: 144

Arg Arg Arg His Ile Val Arg Lys Arg Thr Leu Arg Arg Leu Leu Gln
```

-continued

```
1               5                   10                  15
Glu Arg Glu Leu Val Glu Pro Leu Thr Pro Ser Gly Glu Ala Pro Asn
                20                  25                  30

Gln Ala Leu Leu Arg Ile Leu Lys Glu Thr Glu Phe Lys Lys Ile Lys
                35                  40                  45

Val Leu Gly Ser Gly Ala Phe Gly Thr Val Tyr Lys Gly Leu Trp Ile
 50                      55                  60

Pro Glu Gly Glu Lys Val Lys Ile Pro Val Ala Ile Lys Glu Leu Arg
 65                  70                  75                  80

Glu Ala Thr Ser Pro Lys Ala Asn Lys Glu Ile Leu Asp Glu Ala Tyr
                 85                  90                  95

Val Met Ala Ser Val Asp Asn Pro His Val Cys Arg Leu Leu Gly Ile
                100                 105                 110

Cys Leu Thr Ser Thr Val Gln Leu Ile Thr Gln Leu Met Pro Phe Gly
                115                 120                 125

Cys Leu Leu Asp Tyr Val Arg Glu His Lys Asp Asn Ile Gly Ser Gln
                130                 135                 140

Tyr Leu Leu Asn Trp Cys Val Gln Ile Ala Lys Gly Met Asn Tyr Leu
145                 150                 155                 160

Glu Asp Arg Arg Leu Val His Arg Asp Leu Ala Ala Arg Asn Val Leu
                165                 170                 175

Val Lys Thr Pro Gln His Val Lys Ile Thr Asp Phe Gly Leu Ala Lys
                180                 185                 190

Leu Leu Gly Ala Glu Glu Lys Glu Tyr His Ala Glu Gly Gly Lys Val
                195                 200                 205

Pro Ile Lys Trp Met Ala Leu Glu Ser Ile Leu His Arg Ile Tyr Thr
210                 215                 220

His Gln Ser Asp Val Trp Ser Tyr Gly Val Thr Val Trp Glu Leu Met
225                 230                 235                 240

Thr Phe Gly Ser Lys Pro Tyr Asp Gly Ile Pro Ala Ser Glu Ile Ser
                245                 250                 255

Ser Ile Leu Glu Lys Gly Glu Arg Leu Pro Gln Pro Pro Ile Cys Thr
                260                 265                 270

Ile Asp Val Tyr Met Ile Met Val Lys Cys Trp Met Ile Asp Ala Asp
                275                 280                 285

Ser Arg Pro Lys Phe Arg Glu Leu Ile Ile Glu Phe Ser Lys Met Ala
                290                 295                 300

Arg Asp Pro Gln Arg Tyr Leu Val Ile Gln Gly Asp Glu Arg Met His
305                 310                 315                 320

Leu Pro Ser Pro Thr Asp Ser Asn Phe Tyr Arg Ala Leu Met Asp Glu
                325                 330                 335

Glu Asp Met Asp Asp Val Val Asp Ala Asp Glu Tyr Leu Ile Pro Gln
                340                 345                 350

Gln Gly Phe Phe Ser Ser Pro Ser Thr Ser Arg Thr Pro Leu Leu Ser
                355                 360                 365

Ser Leu Ser Ala Thr Ser Asn Asn Ser Thr Val Ala Cys Ile Asp Arg
                370                 375                 380

Asn Gly Leu Gln Ser Cys Pro Ile Lys Glu Asp Ser Phe Leu Gln Arg
385                 390                 395                 400

Tyr Ser Ser Asp Pro Thr Gly Ala Leu Thr Glu Asp Ser Ile Asp Asp
                405                 410                 415

Thr Phe Leu Pro Val Pro Glu Tyr Ile Asn Gln Ser Val Pro Lys Arg
                420                 425                 430
```

```
Pro Ala Gly Ser Val Gln Asn Pro Val Tyr His Asn Gln Pro Leu Asn
            435                 440                 445

Pro Ala Pro Ser Arg Asp Pro His Tyr Gln Asp Pro His Ser Thr Ala
    450                 455                 460

Val Gly Asn Pro Glu Tyr Leu Asn Thr Val Gln Pro Thr Cys Val Asn
465                 470                 475                 480

Ser Thr Phe Asp Ser Pro Ala His Trp Ala Gln Lys Gly Ser His Gln
                485                 490                 495

Ile Ser Leu Asp Asn Pro Asp Tyr Gln Gln Asp Phe Phe Pro Lys Glu
            500                 505                 510

Ala Lys Pro Asn Gly Ile Phe Lys Gly Ser Thr Ala Glu Asn Ala Glu
        515                 520                 525

Tyr Leu Arg Val Ala Pro Gln Ser Ser Glu Phe Ile Gly Ala
    530                 535                 540
```

<210> SEQ ID NO 145
<211> LENGTH: 23
<212> TYPE: PRT
<213> ORGANISM: Artificial Sequence
<220> FEATURE:
<223> OTHER INFORMATION: signal peptide

<400> SEQUENCE: 145

```
Met Arg Pro Ser Gly Thr Ala Gly Ala Ala Leu Leu Ala Leu Leu Ala
1               5                   10                  15

Ala Leu Cys Pro Ala Ser Arg
            20
```

<210> SEQ ID NO 146
<211> LENGTH: 355
<212> TYPE: PRT
<213> ORGANISM: Artificial Sequence
<220> FEATURE:
<223> OTHER INFORMATION: ECD of EGFRvarIII

<400> SEQUENCE: 146

```
Ala Leu Glu Glu Lys Lys Gly Asn Tyr Val Val Thr Asp His Gly Ser
1               5                   10                  15

Cys Val Arg Ala Cys Gly Ala Asp Ser Tyr Glu Met Glu Glu Asp Gly
                20                  25                  30

Val Arg Lys Cys Lys Lys Cys Glu Gly Pro Cys Arg Lys Val Cys Asn
            35                  40                  45

Gly Ile Gly Ile Gly Glu Phe Lys Asp Ser Leu Ser Ile Asn Ala Thr
    50                  55                  60

Asn Ile Lys His Phe Lys Asn Cys Thr Ser Ile Ser Gly Asp Leu His
65                  70                  75                  80

Ile Leu Pro Val Ala Phe Arg Gly Asp Ser Phe Thr His Thr Pro Pro
                85                  90                  95

Leu Asp Pro Gln Glu Leu Asp Ile Leu Lys Thr Val Lys Glu Ile Thr
            100                 105                 110

Gly Phe Leu Leu Ile Gln Ala Trp Pro Glu Asn Arg Thr Asp Leu His
        115                 120                 125

Ala Phe Glu Asn Leu Glu Ile Ile Arg Gly Arg Thr Lys Gln His Gly
    130                 135                 140

Gln Phe Ser Leu Ala Val Val Ser Leu Asn Ile Thr Ser Leu Gly Leu
145                 150                 155                 160

Arg Ser Leu Lys Glu Ile Ser Asp Gly Asp Val Ile Ile Ser Gly Asn
```

-continued

```
                165                 170                 175
Lys Asn Leu Cys Tyr Ala Asn Thr Ile Asn Trp Lys Lys Leu Phe Gly
            180                 185                 190

Thr Ser Gly Gln Lys Thr Lys Ile Ile Ser Asn Arg Gly Glu Asn Ser
        195                 200                 205

Cys Lys Ala Thr Gly Gln Val Cys His Ala Leu Cys Ser Pro Glu Gly
    210                 215                 220

Cys Trp Gly Pro Glu Pro Arg Asp Cys Val Ser Cys Arg Asn Val Ser
225                 230                 235                 240

Arg Gly Arg Glu Cys Val Asp Lys Cys Asn Leu Leu Glu Gly Glu Pro
                245                 250                 255

Arg Glu Phe Val Glu Asn Ser Glu Cys Ile Gln Cys His Pro Glu Cys
            260                 265                 270

Leu Pro Gln Ala Met Asn Ile Thr Cys Thr Gly Arg Gly Pro Asp Asn
        275                 280                 285

Cys Ile Gln Cys Ala His Tyr Ile Asp Gly Pro His Cys Val Lys Thr
    290                 295                 300

Cys Pro Ala Gly Val Met Gly Glu Asn Asn Thr Leu Val Trp Lys Tyr
305                 310                 315                 320

Ala Asp Ala Gly His Val Cys His Leu Cys His Pro Asn Cys Thr Tyr
                325                 330                 335

Gly Cys Thr Gly Pro Gly Leu Glu Gly Cys Pro Thr Asn Gly Pro Lys
            340                 345                 350

Ile Pro Ser
        355

<210> SEQ ID NO 147
<211> LENGTH: 23
<212> TYPE: PRT
<213> ORGANISM: Artificial Sequence
<220> FEATURE:
<223> OTHER INFORMATION: signal peptide

<400> SEQUENCE: 147

Met Gly Pro Ser Gly Thr Ala Gly Ala Ala Leu Leu Ala Leu Leu Ala
1               5                   10                  15

Ala Leu Cys Pro Ala Ser Arg
            20

<210> SEQ ID NO 148
<211> LENGTH: 621
<212> TYPE: PRT
<213> ORGANISM: Artificial Sequence
<220> FEATURE:
<223> OTHER INFORMATION: ECD of cyEGFR

<400> SEQUENCE: 148

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80
```

-continued

```
Gln Ile Ile Arg Gly Asn Met Tyr Tyr Glu Asn Ser Tyr Ala Leu Ala
                 85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
        275                 280                 285

Ala Asp Ser Tyr Glu Met Glu Glu Asp Gly Val Arg Lys Cys Lys Lys
    290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
            340                 345                 350

Arg Gly Asp Ser Phe Thr His Thr Pro Pro Leu Asp Pro Gln Glu Leu
        355                 360                 365

Asp Ile Leu Lys Thr Val Lys Glu Ile Thr Gly Phe Leu Leu Ile Gln
    370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Ser Leu Asn Ile Thr Ser Leu Gly Leu Arg Ser Leu Lys Glu Ile
            420                 425                 430

Ser Asp Gly Asp Val Ile Ile Ser Gly Asn Lys Asn Leu Cys Tyr Ala
        435                 440                 445

Asn Thr Ile Asn Trp Lys Lys Leu Phe Gly Thr Ser Gly Gln Lys Thr
    450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
                485                 490                 495

Arg Asp Cys Val Ser Cys Arg Asn Val Ser Arg Gly Arg Glu Cys Val
```

```
                    500                 505                 510
Asp Lys Cys Asn Leu Glu Gly Glu Pro Arg Glu Phe Val Glu Asn
            515                 520                 525

Ser Glu Cys Ile Gln Cys His Pro Glu Cys Leu Pro Gln Ala Met Asn
        530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
                565                 570                 575

Gly Glu Asn Asn Thr Leu Val Trp Lys Tyr Ala Asp Ala Gly His Val
            580                 585                 590

Cys His Leu Cys His Pro Asn Cys Thr Tyr Gly Cys Thr Gly Pro Gly
        595                 600                 605

Leu Glu Gly Cys Pro Thr Asn Gly Pro Lys Ile Pro Ser
    610                 615                 620

<210> SEQ ID NO 149
<211> LENGTH: 908
<212> TYPE: PRT
<213> ORGANISM: Artificial Sequence
<220> FEATURE:
<223> OTHER INFORMATION: ECD of human cMET

<400> SEQUENCE: 149

Glu Cys Lys Glu Ala Leu Ala Lys Ser Glu Met Asn Val Asn Met Lys
1               5                   10                  15

Tyr Gln Leu Pro Asn Phe Thr Ala Glu Thr Pro Ile Gln Asn Val Ile
            20                  25                  30

Leu His Glu His His Ile Phe Leu Gly Ala Thr Asn Tyr Ile Tyr Val
        35                  40                  45

Leu Asn Glu Glu Asp Leu Gln Lys Val Ala Glu Tyr Lys Thr Gly Pro
    50                  55                  60

Val Leu Glu His Pro Asp Cys Phe Pro Cys Gln Asp Cys Ser Ser Lys
65                  70                  75                  80

Ala Asn Leu Ser Gly Gly Val Trp Lys Asp Asn Ile Asn Met Ala Leu
                85                  90                  95

Val Val Asp Thr Tyr Tyr Asp Asp Gln Leu Ile Ser Cys Gly Ser Val
            100                 105                 110

Asn Arg Gly Thr Cys Gln Arg His Val Phe Pro His Asn His Thr Ala
        115                 120                 125

Asp Ile Gln Ser Glu Val His Cys Ile Phe Ser Pro Gln Ile Glu Glu
    130                 135                 140

Pro Ser Gln Cys Pro Asp Cys Val Val Ser Ala Leu Gly Ala Lys Val
145                 150                 155                 160

Leu Ser Ser Val Lys Asp Arg Phe Ile Asn Phe Phe Val Gly Asn Thr
                165                 170                 175

Ile Asn Ser Ser Tyr Phe Pro Asp His Pro Leu His Ser Ile Ser Val
            180                 185                 190

Arg Arg Leu Lys Glu Thr Lys Asp Gly Phe Met Phe Leu Thr Asp Gln
        195                 200                 205

Ser Tyr Ile Asp Val Leu Pro Glu Phe Arg Asp Ser Tyr Pro Ile Lys
    210                 215                 220

Tyr Val His Ala Phe Glu Ser Asn Asn Phe Ile Tyr Phe Leu Thr Val
225                 230                 235                 240

Gln Arg Glu Thr Leu Asp Ala Gln Thr Phe His Thr Arg Ile Ile Arg
```

-continued

```
                245                 250                 255
Phe Cys Ser Ile Asn Ser Gly Leu His Ser Tyr Met Glu Met Pro Leu
                260                 265                 270
Glu Cys Ile Leu Thr Glu Lys Arg Lys Lys Arg Ser Thr Lys Lys Glu
                275                 280                 285
Val Phe Asn Ile Leu Gln Ala Ala Tyr Val Ser Lys Pro Gly Ala Gln
                290                 295                 300
Leu Ala Arg Gln Ile Gly Ala Ser Leu Asn Asp Asp Ile Leu Phe Gly
305                 310                 315                 320
Val Phe Ala Gln Ser Lys Pro Asp Ser Ala Glu Pro Met Asp Arg Ser
                325                 330                 335
Ala Met Cys Ala Phe Pro Ile Lys Tyr Val Asn Asp Phe Phe Asn Lys
                340                 345                 350
Ile Val Asn Lys Asn Asn Val Arg Cys Leu Gln His Phe Tyr Gly Pro
                355                 360                 365
Asn His Glu His Cys Phe Asn Arg Thr Leu Leu Arg Asn Ser Ser Gly
                370                 375                 380
Cys Glu Ala Arg Arg Asp Glu Tyr Arg Thr Glu Phe Thr Thr Ala Leu
385                 390                 395                 400
Gln Arg Val Asp Leu Phe Met Gly Gln Phe Ser Glu Val Leu Leu Thr
                405                 410                 415
Ser Ile Ser Thr Phe Ile Lys Gly Asp Leu Thr Ile Ala Asn Leu Gly
                420                 425                 430
Thr Ser Glu Gly Arg Phe Met Gln Val Val Ser Arg Ser Gly Pro
                435                 440                 445
Ser Thr Pro His Val Asn Phe Leu Leu Asp Ser His Pro Val Ser Pro
                450                 455                 460
Glu Val Ile Val Glu His Thr Leu Asn Gln Asn Gly Tyr Thr Leu Val
465                 470                 475                 480
Ile Thr Gly Lys Lys Ile Thr Lys Ile Pro Leu Asn Gly Leu Gly Cys
                485                 490                 495
Arg His Phe Gln Ser Cys Ser Gln Cys Leu Ser Ala Pro Pro Phe Val
                500                 505                 510
Gln Cys Gly Trp Cys His Asp Lys Cys Val Arg Ser Glu Glu Cys Leu
                515                 520                 525
Ser Gly Thr Trp Thr Gln Gln Ile Cys Leu Pro Ala Ile Tyr Lys Val
                530                 535                 540
Phe Pro Asn Ser Ala Pro Leu Glu Gly Gly Thr Arg Leu Thr Ile Cys
545                 550                 555                 560
Gly Trp Asp Phe Gly Phe Arg Arg Asn Asn Lys Phe Asp Leu Lys Lys
                565                 570                 575
Thr Arg Val Leu Leu Gly Asn Glu Ser Cys Thr Leu Thr Leu Ser Glu
                580                 585                 590
Ser Thr Met Asn Thr Leu Lys Cys Thr Val Gly Pro Ala Met Asn Lys
                595                 600                 605
His Phe Asn Met Ser Ile Ile Ile Ser Asn Gly His Gly Thr Thr Gln
                610                 615                 620
Tyr Ser Thr Phe Ser Tyr Val Asp Pro Val Ile Thr Ser Ile Ser Pro
625                 630                 635                 640
Lys Tyr Gly Pro Met Ala Gly Gly Thr Leu Leu Thr Leu Thr Gly Asn
                645                 650                 655
Tyr Leu Asn Ser Gly Asn Ser Arg His Ile Ser Ile Gly Gly Lys Thr
                660                 665                 670
```

```
Cys Thr Leu Lys Ser Val Ser Asn Ser Ile Leu Glu Cys Tyr Thr Pro
            675                 680                 685

Ala Gln Thr Ile Ser Thr Glu Phe Ala Val Lys Leu Lys Ile Asp Leu
    690                 695                 700

Ala Asn Arg Glu Thr Ser Ile Phe Ser Tyr Arg Glu Asp Pro Ile Val
705                 710                 715                 720

Tyr Glu Ile His Pro Thr Lys Ser Phe Ile Ser Gly Ser Thr Ile
                725                 730                 735

Thr Gly Val Gly Lys Asn Leu Asn Ser Val Ser Val Pro Arg Met Val
            740                 745                 750

Ile Asn Val His Glu Ala Gly Arg Asn Phe Thr Val Ala Cys Gln His
            755                 760                 765

Arg Ser Asn Ser Glu Ile Ile Cys Cys Thr Thr Pro Ser Leu Gln Gln
770                 775                 780

Leu Asn Leu Gln Leu Pro Leu Lys Thr Lys Ala Phe Phe Met Leu Asp
785                 790                 795                 800

Gly Ile Leu Ser Lys Tyr Phe Asp Leu Ile Tyr Val His Asn Pro Val
                805                 810                 815

Phe Lys Pro Phe Glu Lys Pro Val Met Ile Ser Met Gly Asn Glu Asn
                820                 825                 830

Val Leu Glu Ile Lys Gly Asn Asp Ile Asp Pro Glu Ala Val Lys Gly
            835                 840                 845

Glu Val Leu Lys Val Gly Asn Lys Ser Cys Glu Asn Ile His Leu His
        850                 855                 860

Ser Glu Ala Val Leu Cys Thr Val Pro Asn Asp Leu Leu Lys Leu Asn
865                 870                 875                 880

Ser Glu Leu Asn Ile Glu Trp Lys Gln Ala Ile Ser Ser Thr Val Leu
                885                 890                 895

Gly Lys Val Ile Val Gln Pro Asp Gln Asn Phe Thr
            900                 905

<210> SEQ ID NO 150
<211> LENGTH: 23
<212> TYPE: PRT
<213> ORGANISM: Artificial Sequence
<220> FEATURE:
<223> OTHER INFORMATION: transmembrane region

<400> SEQUENCE: 150

Gly Leu Ile Ala Gly Val Val Ser Ile Ser Thr Ala Leu Leu Leu Leu
1               5                   10                  15

Leu Gly Phe Phe Leu Trp Leu
            20

<210> SEQ ID NO 151
<211> LENGTH: 434
<212> TYPE: PRT
<213> ORGANISM: Artificial Sequence
<220> FEATURE:
<223> OTHER INFORMATION: intracellular region

<400> SEQUENCE: 151

Lys Lys Arg Lys Gln Ile Lys Asp Leu Gly Ser Glu Leu Val Arg Tyr
1               5                   10                  15

Asp Ala Arg Val His Thr Pro His Leu Asp Arg Leu Val Ser Ala Arg
            20                  25                  30

Ser Val Ser Pro Thr Thr Glu Met Val Ser Asn Glu Ser Val Asp Tyr
```

```
            35                  40                  45
Arg Ala Thr Phe Pro Glu Asp Gln Phe Pro Asn Ser Ser Gln Asn Gly
 50                  55                  60

Ser Cys Arg Gln Val Gln Tyr Pro Leu Thr Asp Met Ser Pro Ile Leu
 65                  70                  75                  80

Thr Ser Gly Asp Ser Asp Ile Ser Ser Pro Leu Leu Gln Asn Thr Val
                 85                  90                  95

His Ile Asp Leu Ser Ala Leu Asn Pro Glu Leu Val Gln Ala Val Gln
            100                 105                 110

His Val Val Ile Gly Pro Ser Ser Leu Ile Val His Phe Asn Glu Val
            115                 120                 125

Ile Gly Arg Gly His Phe Gly Cys Val Tyr His Gly Thr Leu Leu Asp
            130                 135                 140

Asn Asp Gly Lys Lys Ile His Cys Ala Val Lys Ser Leu Asn Arg Ile
145                 150                 155                 160

Thr Asp Ile Gly Glu Val Ser Gln Phe Leu Thr Glu Gly Ile Ile Met
                165                 170                 175

Lys Asp Phe Ser His Pro Asn Val Leu Ser Leu Leu Gly Ile Cys Leu
            180                 185                 190

Arg Ser Glu Gly Ser Pro Leu Val Val Leu Pro Tyr Met Lys His Gly
            195                 200                 205

Asp Leu Arg Asn Phe Ile Arg Asn Glu Thr His Asn Pro Thr Val Lys
            210                 215                 220

Asp Leu Ile Gly Phe Gly Leu Gln Val Ala Lys Gly Met Lys Tyr Ala
225                 230                 235                 240

Ser Lys Lys Phe Val His Arg Asp Leu Ala Ala Arg Asn Cys Met Leu
                245                 250                 255

Asp Glu Lys Phe Thr Val Lys Val Ala Asp Phe Gly Leu Ala Arg Asp
            260                 265                 270

Met Tyr Asp Lys Glu Tyr Tyr Ser Val His Asn Lys Thr Gly Ala Lys
            275                 280                 285

Leu Pro Val Lys Trp Met Ala Leu Glu Ser Leu Gln Thr Gln Lys Phe
            290                 295                 300

Thr Thr Lys Ser Asp Val Trp Ser Phe Gly Val Leu Leu Trp Glu Leu
305                 310                 315                 320

Met Thr Arg Gly Ala Pro Pro Tyr Pro Asp Val Asn Thr Phe Asp Ile
                325                 330                 335

Thr Val Tyr Leu Leu Gln Gly Arg Arg Leu Leu Gln Pro Glu Tyr Cys
            340                 345                 350

Pro Asp Pro Leu Tyr Glu Val Met Leu Lys Cys Trp His Pro Lys Ala
            355                 360                 365

Glu Met Arg Pro Ser Phe Ser Glu Leu Val Ser Arg Ile Ser Ala Ile
            370                 375                 380

Phe Ser Thr Phe Ile Gly Glu His Tyr Val His Val Asn Ala Thr Tyr
385                 390                 395                 400

Val Asn Val Lys Cys Val Ala Pro Tyr Pro Ser Leu Leu Ser Ser Glu
                405                 410                 415

Asp Asn Ala Asp Asp Glu Val Asp Thr Arg Pro Ala Ser Phe Trp Glu
            420                 425                 430

Thr Ser

<210> SEQ ID NO 152
<211> LENGTH: 5
```

```
<212> TYPE: PRT
<213> ORGANISM: Artificial Sequence
<220> FEATURE:
<223> OTHER INFORMATION: CDR1

<400> SEQUENCE: 152

Thr Tyr Ser Met Asn
1               5

<210> SEQ ID NO 153
<211> LENGTH: 10
<212> TYPE: PRT
<213> ORGANISM: Artificial Sequence
<220> FEATURE:
<223> OTHER INFORMATION: synthetic construct

<400> SEQUENCE: 153

Asp Ser Tyr Trp His Trp Trp Leu Gly Ala
1               5                   10

<210> SEQ ID NO 154
<211> LENGTH: 10
<212> TYPE: PRT
<213> ORGANISM: Artificial Sequence
<220> FEATURE:
<223> OTHER INFORMATION: CDR3

<400> SEQUENCE: 154

Gly Tyr Leu Asp His Trp Trp Leu Gly Ala
1               5                   10

<210> SEQ ID NO 155
<211> LENGTH: 17
<212> TYPE: PRT
<213> ORGANISM: Artificial Sequence
<220> FEATURE:
<223> OTHER INFORMATION: MF8233_CDR2

<400> SEQUENCE: 155

Trp Ile Ser Ala Tyr Asn Ala Asn Thr Asn Tyr Ala Gln Lys Leu Gln
1               5                   10                  15

Gly

<210> SEQ ID NO 156
<211> LENGTH: 13
<212> TYPE: PRT
<213> ORGANISM: Artificial Sequence
<220> FEATURE:
<223> OTHER INFORMATION: MF8233_CDR3

<400> SEQUENCE: 156

Asp Arg His Trp His Trp Trp Leu Asp Ala Phe Asp Tyr
1               5                   10

<210> SEQ ID NO 157
<211> LENGTH: 17
<212> TYPE: PRT
<213> ORGANISM: Artificial Sequence
<220> FEATURE:
<223> OTHER INFORMATION: MF8230_CDR2

<400> SEQUENCE: 157

Trp Ile Asn Thr Tyr Thr Gly Asp Pro Thr Tyr Ala Gln Gly Phe Thr
1               5                   10                  15

Gly
```

```
<210> SEQ ID NO 158

<400> SEQUENCE: 158

000

<210> SEQ ID NO 159
<211> LENGTH: 13
<212> TYPE: PRT
<213> ORGANISM: Artificial Sequence
<220> FEATURE:
<223> OTHER INFORMATION: CDR3

<400> SEQUENCE: 159

Gly Tyr Leu Asp His Trp Trp Leu Gly Ala Phe Asp Tyr
1               5                   10
```